United States Patent
Hrusovsky et al.

(10) Patent No.: US 12,130,294 B2
(45) Date of Patent: Oct. 29, 2024

(54) QUANTIFICATION OF BIOMARKERS PRESENT IN PHYSIOLOGICAL SAMPLES

(71) Applicant: QUANTERIX CORPORATION, Lexington, MA (US)

(72) Inventors: Edward Kevin Hrusovsky, Hopkinton, MA (US); David Wilson, Boxborough, MA (US); Dandan Shan, Acton, MA (US); Lei Chang, Winchester, MA (US); Linan Song, Waltham, MA (US); Andreas Jeromin, Alachua, FL (US); Carmen Ioana Tobos, Farmington Hills, MI (US); Purvish Prahlad Patel, Medford, MA (US)

(73) Assignee: QUANTERIX CORPORATION, Lexington, MA (US)

( * ) Notice: Subject to any disclaimer, the term of this patent is extended or adjusted under 35 U.S.C. 154(b) by 391 days.

(21) Appl. No.: 17/046,119

(22) PCT Filed: Apr. 9, 2019

(86) PCT No.: PCT/US2019/026640
§ 371 (c)(1),
(2) Date: Oct. 8, 2020

(87) PCT Pub. No.: WO2019/199869
PCT Pub. Date: Oct. 17, 2019

(65) Prior Publication Data
US 2021/0102959 A1    Apr. 8, 2021

Related U.S. Application Data

(60) Provisional application No. 62/789,067, filed on Jan. 7, 2019, provisional application No. 62/655,738, filed on Apr. 10, 2018.

(51) Int. Cl.
*G01N 33/68* (2006.01)
*A61B 5/00* (2006.01)
*G01N 1/38* (2006.01)
*G01N 33/58* (2006.01)

(52) U.S. Cl.
CPC ....... *G01N 33/6896* (2013.01); *A61B 5/0071* (2013.01); *A61B 5/0075* (2013.01); *A61B 5/0082* (2013.01); *A61B 5/4064* (2013.01); *G01N 1/38* (2013.01); *G01N 33/582* (2013.01); *G01N 2001/386* (2013.01); *G01N 2800/28* (2013.01); *G01N 2800/2821* (2013.01); *G01N 2800/285* (2013.01)

(58) Field of Classification Search
CPC .... G01N 33/6896; G01N 1/38; G01N 33/582; G01N 2001/386; G01N 2800/28; G01N 2800/2821; G01N 2800/285; A61B 5/0071; A61B 5/0075; A61B 5/0082; A61B 5/4064
See application file for complete search history.

(56) References Cited

U.S. PATENT DOCUMENTS

| | | |
|---|---|---|
| 2007/0003564 A1 | 1/2007 | Hurley et al. |
| 2010/0124552 A1 | 5/2010 | Klein et al. |
| 2011/0039278 A1 | 2/2011 | Pieribone |
| 2012/0070379 A1 | 3/2012 | Black et al. |
| 2013/0165342 A1 | 6/2013 | Rissin et al. |
| 2014/0086836 A1 | 3/2014 | Burnham et al. |
| 2015/0038355 A1 | 2/2015 | Tan et al. |
| 2015/0185232 A1 | 7/2015 | Keane et al. |
| 2015/0355182 A1 | 12/2015 | Rissin et al. |
| 2017/0044264 A1 | 2/2017 | Fricke et al. |
| 2017/0160292 A1 | 6/2017 | Wilson et al. |
| 2018/0080945 A1 | 3/2018 | Goetzl et al. |
| 2018/0195124 A1 | 7/2018 | Gonzalez et al. |
| 2021/0096140 A1 | 4/2021 | Hrusovsky et al. |
| 2022/0229073 A1 | 7/2022 | Hrusovsky et al. |

FOREIGN PATENT DOCUMENTS

| | | |
|---|---|---|
| EP | 2324360 B1 | 1/2018 |
| PT | 95669 A | 9/1991 |
| WO | WO 2013103475 A2 | 7/2013 |
| WO | WO 2013103475 A3 | 7/2013 |
| WO | WO 2014027899 A1 | 2/2014 |
| WO | WO 2015066211 A1 | 5/2015 |
| WO | WO 2016207253 A1 | 12/2016 |
| WO | WO 2019199865 A1 | 10/2019 |
| WO | WO 2019199871 A1 | 10/2019 |

OTHER PUBLICATIONS

Korley et al., 2018, "Performance Evaluation of a Multiplex Assay for Simultaneous Detection of Four Clinically Relevant Traumatic Brain Injury Biomarkers," J Neurotrauma, 36(1):182-187.

Wilson et al., 2016, "The Simoa HD-1 Analyzer: A Novel Fully Automated Digital Immunoassay Analyzer with Single-Molecule Sensitivity and Multiplexing," J Lab Autom, 21(4):533-547 (Epub 2015).

International Search Report and Written Opinion for International Patent Application No. PCT/US2019/026636 (Pub No. WO 2019199865) mailed Aug. 27, 2019 (12 pages).

International Search Report and Written Opinion for International Patent Application No. PCT/US2019/026640 (Pub No. WO 2019199869) mailed Jun. 18, 2019 (12 pages).

International Search Report and Written Opinion for International Patent Application No. PCT/US2019/026642 (Pub No. WO 2019199871) mailed Jun. 18, 2019 (12 pages).

(Continued)

*Primary Examiner* — Olga N Chernyshev
(74) *Attorney, Agent, or Firm* — JONES DAY

(57) ABSTRACT

The present disclosure relates to immunoassays for NF-L, GFAP, UCH L1, and Tau performed on liquid samples derived from physiological fluids such as venous blood to detect the presence or absence of a physiological condition by quantifying one or a combination of NF-L, GFAP, UCH L1, and Tau at concentrations indicative of the condition.

16 Claims, 12 Drawing Sheets

(56) References Cited

OTHER PUBLICATIONS

Hampel et al., 2004, "Total and phosphorylated tau proteins: evaluation as core biomarker candidates in frontotemporal dementia," Dement. Geriatr. Cogn. Disord., 17(4):350-354.
Thomann et al., 2009, "Association of total tau and phosphorylated tau 181 protein levels in cerebrospinal fluid with cerebral atrophy in mild cognitive impairment and Alzheimer disease," J. Psychiatry Neurosci., 34(2):136-142.
Arrambide et al., 2016, "Neurofilament light chain level is a weak risk factor for the development of MS," Neurology, 87(11):1076-1084.
Edwards et al., 2003, "The remarkable flexibility of the human antibody repertoire; isolation of over one thousand different antibodies to a single protein, BLyS," J. Mol. Biol., 334(1):103-118.
Khalil et al., 2018, "Neurofilaments as biomarkers in neurological disorders," Nat. Rev. Neurol., 14(10):577-589.
Kuhle et al., 2016, "Comparison of three analytical platforms for quantification of the neurofilament light chain in blood samples: ELISA, electrochemiluminescence immunoassay and Simoa," Clin. Chem. Lab Med., 54(10):1655-1661.
Kuhle et al., 2017, "Serum neurofilament is associated with progression of brain atrophy and disability in early MS," Neurology, 88(9):826-831.
Lloyd et al., 2009, "Modelling the human immune response: performance of a 1011 human antibody repertoire against a broad panel of therapeutically relevant antigens," Protein Eng. Des. Sel., 22(3):159-168.
Nimer et al., 2015, "Comparative Assessment of the Prognostic Value of Biomarkers in Traumatic Brain Injury Reveals an Independent Role for Serum Levels of Neurofilament Light," PLoS One, 10(7):e0132177 (19 pages).
Shahim et al., 2016, "Serum neurofilament light protein predicts clinical outcome in traumatic brain injury," Sci. Rep., 6:36791 (9 pages).
Uman Diagnostics, a Quanterix Company, 2017, "NF-light™M Serum ELISA (RUO)," 20-8002 (2 pages).
Shahim et al., 2016, "Serum neurofilament light protein predicts clinical outcome in traumatic brain injury," Sci. Rep., 6:36791 and Supplementary Material (15 pages).
Andersen et al., 2016, "Elimination of erroneous results in flow cytometry caused by antibody binding to Fc receptors on human monocytes and macrophages," Cytometry A, 89(11): 1001-1009.

QUANTIFICATION OF BIOMARKERS PRESENT IN PHYSIOLOGICAL SAMPLES

CROSS REFERENCE TO RELATED APPLICATION

This application is a U.S. National Stage Application under 35 U.S.C. § 371 of International Patent Application No. PCT/US2019/026640, filed Apr. 9, 2019, which claims the benefit of U.S. Provisional Application No. 62/789,067, filed Jan. 7, 2019, and U.S. Provisional Application No. 62/655,738, filed Apr. 10, 2018, the disclosure of each of which is incorporated by reference herein in its entirety.

FIELD OF THE INVENTION

The present disclosure relates to multiplex immunoassays for quantifying a plurality of biomarkers present in a physiological sample to detect the presence or absence of a physiological condition.

BACKGROUND OF THE INVENTION

Recent advances in digital and spotted well immunoassay technologies are closing in on next-generation capabilities to rapidly diagnosis serious physiological conditions that, even today, frequently go undiagnosed and untreated with potentially tragic consequences. As but one example, digital immunoassays have been shown, at least in principle, to quantify subtle changes in biomarkers indicative of traumatic brain injury (TBI) at very low concentrations that elude most other assay technologies. A brain injury in a human may be caused by any number of events or conditions. In some cases, a brain injury may be caused by external mechanical force, such as rapid acceleration or deceleration, impact, blast waves, or penetration by a projectile. This type of acquired brain injury is generally known as TBI. In the United States, more than 2.5 million people seek medical care for TBI each year. Nonetheless, as of 2015, no therapeutic has been approved by the U.S. Food and Drug Administration to treat acute TBI, due, at least in part, to the inability to precisely diagnose TBI.

Digital and spotted well immunoassays have also shown potential for detection of antigens indicative of crippling neurodegenerative disorders. For example, neurofilament light chain has the potential for detection of multiple sclerosis which affects more than 350,000 people in the U.S. and 2.5 million worldwide. In the U.S., prevalence estimates vary between 5 and 119 per 100,000 and healthcare costs are estimated to be more than $10 billion annually. It is the most common neurological disease in young adults, with the risk of subsequent chronic functional impairment and disability after 10-15% of disease duration. While a physician may diagnose multiple sclerosis in some patients soon after the onset of the illness, in other cases doctors may not be able to readily identify the cause of the symptoms, leading to years of uncertainty and multiple diagnoses. Unfortunately, no single laboratory test is yet available to prove or rule out multiple sclerosis.

Certain existing methods and kits directed to measuring biomarkers relevant to brain injury fail to target the correct biomarkers or fail to include a sufficient number of biomarkers for providing relevant information about the presence or severity of these conditions. Also, many conventional assays lack the sensitivity to determine levels of potential clinical relevance. Accordingly, improved methods, tests, assays, kits, and systems for measuring biomarkers relevant to such conditions are needed.

BRIEF SUMMARY OF THE INVENTION

Certain embodiments may provide, for example, a test for a neurological condition (for example a neural injury, defect, disorder, or disease) in a subject. In certain embodiments, for example, the test may comprise providing a liquid sample derived from a sample of physiological fluid. In certain embodiments, for example, the test may comprise obtaining, via a single multiplex immunoassay (for example a digital multiplex immunoassay or a multiplex spotted well immunoassay), concentrations of neurofilament light chain (NF-L), glial fibrillary acidic protein (GFAP), ubiquitin carboxyl-terminal hydrolase L1 (UCH L1), and Tau in the liquid sample. In certain embodiments, for example, the test may comprise calculating at least one classification value based on a multivariate classification model using the concentrations as inputs to the multivariate classification model. In certain embodiments, for example, the test may comprise assigning a risk (for example a risk of occurrence or presence) of the neurological condition, comprising: comparing the at least one classification value to at least one threshold value.

A. In certain embodiments, for example, the multivariate classification model may be a function of at least two biomarker concentrations, the at least two biomarkers selected from the group consisting of NF-L, GFAP, UCH L1, and Tau. In certain embodiments, for example, the multivariate classification model may be further a function of at least one demographic parameter (for example age, gender, and/or ethnicity). In certain embodiments, for example, the multivariate classification model may be a logistic regression. In certain embodiments, for example, the multivariate classification model may be a neural network. In certain embodiments, for example, the multivariate classification model may provide a receiver operating characteristic (ROC) curve having an area under the curve (AUC) of at least 0.7 (for example an AUC of at least 0.8 or at least 0.9). In certain embodiments, for example, the multivariate classification model may be characterized by at least one p-value (for example at least one p-value of less than 0.01, less than 0.001, or less than 0.0001).

In certain embodiments, for example, the multivariate classification model may require a baseline concentration of at least one of NF-L, GFAP, UCH L1, and Tau from the subject (for example a baseline concentration obtained from the subject prior to occurrence or suspected occurrence of the neurological condition) as an input to the multivariate classification model. In certain embodiments, for example, the classification value may be based at least on the concentrations of at least three biomarkers selected from the group consisting of NF-L, GFAP, UCH L1, and Tau. In certain embodiments, for example, one value of the at least one classification value may comprise a ratio of the concentrations of a first biomarker and a second biomarker determined from the single multiplex immunoassay, the first biomarker and the second biomarker selected from the group consisting of NF-L, GFAP, UCH L1, and Tau. In certain embodiments, for example, the at least one classification value may comprise a ratio of the concentration of a first biomarker selected from the group consisting of NF-L, GFAP, UCH L1, and Tau and a second biomarker selected from the group consisting of NF-L, GFAP, UCH L1, and Tau.

In certain embodiments, for example, the test may further comprise: normalizing one or more of the concentrations based at least on a sample age of the physiological fluid. In certain embodiments, for example, the test may further comprise: normalizing one or more of the concentrations based at least on a sample size of the sample of physiological fluid. In certain embodiments, for example, the test may further comprise: normalizing one or more of the concentrations based at least on sample age of the sample of physiological fluid. In certain embodiments, for example, the test may further comprise: normalizing one or more of the concentrations based at least on one or more demographic characteristics of a subject from which the sample of physiological fluid was taken. In certain embodiments, for example, the one or more demographic characteristics may comprise age. In certain embodiments, for example, the one or more demographic characteristics may comprise ethnicity. In certain embodiments, for example, the one or more demographic characteristics may comprise gender.

B. In certain embodiments, for example, a low risk of the neurological condition may be assigned if the at least one classification value is less than at least one threshold value (for example if the at least one classification value is a plurality of classification values (for example 2 classification values, 3 classification values, 4 classification values, or more than 4 classification values) that have lower values than corresponding threshold values for each of the plurality of classification values). In certain embodiments, for example, the method may further comprise: assigning an indeterminate risk of the neurological condition if one of the at least one classification value exceeds the at least one threshold value.

C. In certain embodiments, for example, the test may further comprise: indicating a neuroimaging study if the at least one classification value is greater than the at least one threshold value. In certain embodiments, for example, the test may further comprise: indicating a neuroimaging study if the at least one classification value is less than the at least one threshold value. In certain embodiments, for example, the test may further comprise: indicating subject observation if the at least one classification value is greater than the at least one threshold value. In certain embodiments, for example, the test may further comprise: indicating subject observation without a neuroimaging study if the at least one classification value is greater than a first value of the at least one threshold value and the at least one classification value is less than a second value of the at least one threshold value. In certain embodiments, for example, the test may further comprise: indicating a change in a course of therapy (for example as an indication of a change in the neurological condition) if the at least one classification value is greater than the at least one threshold value. In certain embodiments, for example, the test may further comprise: indicating a change of therapy treatment (for example as an indication of progress of the neurological condition) if the at least one classification value is less than the at least one threshold value.

D. In certain embodiments, for example, the sample of physiological fluid may be obtained from a subject within 24 hours after a medical procedure is performed on a subject. In certain embodiments, for example, the physiological fluid may be venous blood. In certain embodiments, for example, the sample of physiological fluid may not be used to derive the liquid sample until after an initial diagnosis of the neurological condition. In certain embodiments, for example, the sample of physiological fluid may be taken from a subject while the subject is under continual care of one or more healthcare providers during and following a medical procedure.

E. In certain embodiments, for example, the neurological condition may be a TBI. In certain embodiments, for example, the neurological condition may be an acquired brain injury. In certain embodiments, for example, the neurological condition may be collateral to trauma. In certain embodiments, for example, the neurological condition may be collateral to ischemia. In certain embodiments, for example, the neurological condition may be collateral to toxic exposure. In certain embodiments, for example, the neurological condition may be collateral to neurological disease. In certain embodiments, for example, the neurological condition may be collateral to heart attack. In certain embodiments, for example, the neurological condition may be collateral to child birth. In certain embodiments, for example, the neurological condition may be collateral to oxygen deprivation. In certain embodiments, for example, the neurological condition may be collateral to a vehicular accident. In certain embodiments, for example, the neurological condition may be collateral to a fall. In certain embodiments, for example, the neurological condition may be collateral to an assault. In certain embodiments, for example, the neurological condition may be collateral to being struck by an object. In certain embodiments, for example, the neurological condition may be neurodegenerative disease. In certain embodiments, for example, the neurodegenerative disease may be a multiple sclerosis (MS) (for example relapse-remitting MS, primary progressive MS, progressive relapsing MS, and/or secondary progressive MS). In certain embodiments, for example, the neurodegenerative disease may be an Alzheimer's disease.

F. In certain embodiments, for example, the test may be indicated by independent evidence of the neurological condition. In certain embodiments, for example, the test may be indicated by a lawsuit alleging the neurological condition. In certain embodiments, for example, the test may be performed in conjunction with (or indicated by) a positive computerized tomography (CT) scan. In certain embodiments, for example, the test may be performed in conjunction with (or indicated by) a positive MRI scan. In certain embodiments, for example, the test may be performed after an initial diagnosis of the neurological condition.

G. In certain embodiments, for example, the single multiplex immunoassay may be a digital assay. In certain embodiments, for example, the single multiplex immunoassay may be a multiplex spotted well assay.

Certain embodiments may provide, for example, a single-sample test for a neurological condition (for example a TBI or MS). In certain embodiments, for example, the single-sample test may comprise providing a liquid sample derived from a single sample of physiological fluid from a subject. In certain embodiments, for example, the single-sample test may comprise obtaining, via at least one immunoassay, concentrations of NF-L, GFAP, UCH L1, and Tau in the liquid sample. In certain embodiments, for example, the single-sample test may comprise assigning a risk of the neurological condition in the subject. In certain embodiments, for example, the assigning a risk of the neurological condition in the subject may comprise determining at least one measure of significance of differences between the concentrations of NF-L, GFAP, UCH L1, and Tau in the liquid sample and concentrations of NF-L, GFAP, UCH L1, and Tau in a group of healthy donors.

A. In certain embodiments, for example, the subject may be a neonate. In certain embodiments, for example, the subject may be a child. In certain embodiments, for example, the subject may be a toddler. In certain embodiments, for example, the subject may be a teenager. In certain embodiments, for example, the subject may be an adult. In certain embodiments, for example, the subject may be at least 50 years old (for example at least 60 years old, at least 70 years old, or at least 80 years old).

B. In certain embodiments, for example, the single sample of physiological fluid may be obtained within 12 hours of an event suspected of causing the neurological condition in the subject. In certain embodiments, for example, the single sample of physiological fluid may be obtained within 24 hours of an event suspected of causing the neurological condition in the subject.

C. In certain embodiments, for example, the at least one measure of significance of differences may be derived from a classification model (for example a statistical model). In certain embodiments, for example, the classification model may be a function of (or utilize as an input) concentrations for at least one biomarker in the liquid sample and in the group of healthy donors, the at least one biomarker selected from the group consisting of NF-L, GFAP, UCH L1, and Tau. In certain embodiments, for example, the classification model may be further a function of (or utilize as an input) at least one demographic parameter (for example age, gender, and/or ethnicity). In certain embodiments, for example, the classification model may be a logistic regression. In certain embodiments, for example, the classification model may be a neural network. In certain embodiments, for example, the classification model may provide an ROC curve having an AUC of at least 0.7. In certain embodiments, for example, the determining may comprise calculating at least one classification value based on a classification model; and comparing the at least one classification value to at least one threshold value. In certain embodiments, for example, the determining may comprise computing a statistical measure, the statistical measure may comprise a statistic obtained from an analysis of variance (ANOVA). In certain embodiments, for example, the ANOVA may be a one-way ANOVA. In certain embodiments, for example, the ANOVA may be a one-way ANOVA on ranks. In certain embodiments, for example, the ANOVA may be non-parametric. In certain embodiments, for example, the ANOVA may comprise a Kruskal-Wallis test. In certain embodiments, for example, the ANOVA may comprise a Mann-Whitney test. In certain embodiments, for example, the at least one measure of significance of differences may be based on at least three differences between the concentrations of NF-L, GFAP, UCH L1, and Tau in the liquid sample and concentrations of NF-L, GFAP, UCH L1, and Tau in a group of healthy donors.

Certain embodiments may provide, for example, a protocol indicated by potential neurological condition (for example a potential neural injury, potential defect, potential disorder, or potential disease). In certain embodiments, for example, the protocol indicated by the potential neurological condition may comprise a CT scan positive for the neurological condition. In certain embodiments, for example, the protocol may further comprise by one of the single-sample tests for the neurological condition disclosed herein if the CT scan is positive for the neurological condition. In certain embodiments, for example, the protocol may be exclusive of a magnetic resonance imaging (MRI) scan. In certain embodiments, for example, the protocol may be a modification of another protocol to replace an MRI scan with one of the single-sample tests for the neurological condition disclosed herein.

Certain embodiments may provide, for example, a modified protocol indicated by a potential neurological condition. In certain embodiments, for example, the modified protocol indicated by the potential neurological condition may comprise a protocol for detection of a neurological condition comprising a CT scan and in which an MRI scan is replaced by one of the single-sample tests for the neurological condition disclosed herein. In certain embodiments, for example, the at least one immunoassay may be a digital assay. In certain embodiments, for example, the at least one immunoassay may be a multiplex spotted well assay. In certain embodiments, for example, the physiological fluid may be derived from venous blood. In certain embodiments, for example, the physiological fluid may be a serum. In certain embodiments, for example, the physiological fluid may be a plasma. In certain embodiments, for example, the physiological fluid may be whole blood.

Certain embodiments may provide, for example, a single-assay test for a neurological condition (for example a neural injury, defect, disorder, or disease). In certain embodiments, for example, the single-assay test may comprise providing at least one liquid sample derived from a single sample of physiological fluid from a subject. In certain embodiments, for example, the single-assay test may comprise obtaining, via an immunoassay, concentrations of NF-L, GFAP, UCH L1, and Tau in the at least one liquid sample. In certain embodiments, for example, the single-assay test may comprise assigning a risk of the neurological condition (for example a TBI or MS) in the subject, comprising: determining at least one measure of significance of differences between the concentrations of NF-L, GFAP, UCH L1, and Tau in the liquid sample and concentrations of NF-L, GFAP, UCH L1, and Tau in a group of healthy donors. In certain embodiments, for example, the immunoassay may be a multiplex digital immunoassay. In certain embodiments, for example, the immunoassay may be a multiplex spotted well assay.

Certain embodiments may provide, for example, a dual-sample test for a neurological condition. In certain embodiments, for example, the dual-sample test may comprise providing, from a subject: a) a first liquid sample derived from a sample of a first physiological fluid taken at a first time; and b) a second liquid sample derived from a sample of a second physiological fluid taken at a second time. In certain embodiments, for example, the dual-sample test may comprise obtaining, via immunoassay, concentrations of NF-L, GFAP, UCH L1, and Tau in the first liquid sample and in the second liquid sample. In certain embodiments, for example, the dual-sample test may comprise assigning a risk of the neurological condition in the subject, comprising: determining at least one measure of significance of differences between the concentrations of NF-L, GFAP, UCH L1, and Tau in the first liquid sample and the concentrations of NF-L, GFAP, UCH L1, and Tau in the second liquid sample.

A. In certain embodiments, for example, the second time may be later than the first time. In certain embodiments, for example, the first time may be within 3 hours (for example within 6 hours, within 12 hours, within 1 day, or within 7 days) of an event suspected of causing an occurrence of the neurological condition. In certain embodiments, for example, the second time may be at least 2 hours (for example at least 12 hours, at least 1 day, at least 7 days, at least 8 days, at least 9 days, at least 10 days, at least 11 days, or at least 12 days) after the first time. In certain embodiments, for example, the second time may be at least 2 hours (for example at least 12 hours, at least 1 day, at least 7 days, at least 8 days, at least 9 days, at least 10 days, at least 11 days, or at least 12 days) after an event suspected of causing an occurrence of the neurological condition.

Certain embodiments may provide, for example, a dual-sample test for a neurological condition (for example a neural injury, defect, disorder, or disease). In certain embodiments, for example, the dual-sample test may comprise providing, from a subject: a) a first liquid sample derived from a first physiological fluid sample taken at a first time; and b) at least a second liquid sample derived from at least a second physiological fluid sample taken at least a second time. In certain embodiments, for example, the dual-sample test may comprise obtaining, via immunoassay, concentrations of NF-L, GFAP, UCH L1, and Tau in the first liquid sample and in the at least the second liquid sample. In certain embodiments, for example, the dual-sample test may comprise assigning a risk of the neurological condition (for example a TBI or a MS) in the subject, comprising: determining at least one measure of significance of differences between the concentrations of NF-L, GFAP, UCH L1, and Tau in the first liquid sample and the concentrations NF-L, GFAP, UCH L1, and Tau in the at least the second liquid sample.

Certain embodiments may provide, for example, a method to distinguish between types of neurological conditions (for example a neural injury, defect, disorder, or disease). In certain embodiments, for example, the method may comprise providing a liquid sample derived from a sample of physiological fluid from a subject. In certain embodiments, for example, the method may comprise obtaining, via at least one immunoassay, concentrations of NF-L, GFAP, UCH L1, and Tau in the liquid sample. In certain embodiments, for example, the method may comprise distinguishing between types of neurological conditions, comprising: a) classifying as statistically significant a difference between at least a first biomarker concentration of the concentrations of NF-L, GFAP, UCH L1, and Tau in the liquid sample and concentrations of NF-L, GFAP, UCH L1, and Tau in a group of healthy donors; and b) determining that a difference between at least a second biomarker concentration of the concentrations of the NF-L, GFAP, UCH L1, and Tau in the liquid sample and the concentrations of NF-L, GFAP, UCH L1, and Tau in the group of healthy donors is statistically insignificant.

A. In certain embodiments, for example, the method may distinguish between mild TBI and severe TBI. In certain embodiments, for example, the at least a first biomarker may comprise GFAP and the at least a first biomarker may be exclusive of NF-L. In certain embodiments, for example, the at least a second biomarker may comprise NF-L.

In certain embodiments, for example, the method may distinguish between a neurological condition arising from isolated contusion (or diffuse axonal injury) and at least one other type of neurological condition. In certain embodiments, for example, the at least a first biomarker may comprise GFAP, UCH L1, and NF-L and may be exclusive of Tau.

In certain embodiments, for example, the method may distinguish between astrocytic injury and neuronal/axonal injury. In certain embodiments, for example, the at least a first biomarker may comprise GFAP. In certain embodiments, for example, the at least a second biomarker may comprise UCH L1 and/or NF-L. In certain embodiments, for example, the method may distinguish between a neurological condition with intracranial hemorrhage and a neurological condition without intracranial hemorrhage. In certain embodiments, for example, the at least a first biomarker may comprise NF-L.

In certain embodiments, for example, the method may distinguish between a first type of MS and a second type of MS. In certain embodiments, for example, the first type of MS and the second type of MS may be selected from the group consisting of relapsing-remitting MS, primary progressive MS, progressive relapsing MS, and secondary progressive MS. In certain embodiments, for example, the at least a first biomarker may comprise GFAP. In certain embodiments, for example, the at least a second biomarker may comprise UCH L1 or NF-L. In certain embodiments, for example, the at least a second biomarker may be at least two biomarkers, the at least two biomarkers comprising UCH L1 and NF-L.

B. In certain embodiments, for example, the at least one difference may be classified using a classification model (for example a statistical model such as a train statistical model). In certain embodiments, for example, the classification model may be a function of (or utilizes as inputs) concentrations for at least one biomarker in the liquid sample and in the group of healthy donor, the at least one biomarker selected from the group consisting of NF-L, GFAP, UCH L1, and Tau.

Certain embodiments may provide, for example, a test for a neurological condition (for example a neural injury, defect, disorder, or disease). In certain embodiments, for example, the test may comprise providing a sample of venous blood plasma or serum from a subject. In certain embodiments, for example, the test may comprise diluting the sample with a diluent to form a liquid sample, the diluent comprising a predetermined concentration of at least one heterophilic interference inhibitor for at least one biomarker, the at least one biomarker selected from the group consisting of NF-L, GFAP, UCH L1, and Tau. In certain embodiments, for example, the test may comprise obtaining, via digital immunoassay, signal readings for NF-L, GFAP, UCH L1, and Tau in the liquid sample. In certain embodiments, for example, the test may comprise computing concentrations for NF-L, GFAP, UCH L1, and Tau in the liquid sample based on a standard curve, the standard curve derived from a plurality of calibration solutions, the calibration solutions exclusive of the heterophilic interference inhibitor.

A. In certain embodiments, for example, the at least one heterophilic interference inhibitor may be configured to increase at least one detectable signal of the immunoassay. In certain embodiments, for example, one of the at least one detectable signal may be associated with NF-L. In certain embodiments, for example, the at least one heterophilic interference inhibitor may comprise an immunoglobulin. In certain embodiments, for example, the immunoglobulin may be a human (or humanized) immunoglobulin. In certain embodiments, for example, the immunoglobulin may be an IgG. In certain embodiments, for example, the immunoglobulin may be a human IgG. In certain embodiments, for example, the at least one heterophilic interference inhibitor may be exclusive of non-human immunoglobulin.

B. In certain embodiments, for example, the sample diluent may comprise phosphate, NaCl, KCl, bovine serum albumin (BSA), $MgCl_2$, dextrose, bovine gamma globulin (BgG), urea, the non-ionic surfactant sold under the trademark Triton™ X-100, the immunoassay blocker sold under the trademark TRU Block™, the heterophile blocking agent sold under the trademark Superchemiblock™, human IgG, the preservative sold under the trademark ProClin™ 300, or a combination of two or more of the foregoing. In certain embodiments, for example, the sample diluent further may comprise 50 mM phosphate, 137 mM NaCl, 2.7 mM KCl, 0.02% BSA, 1 mM $MgCl_2$, 0.06% dextrose, 0.01% BgG, 5 mM urea, 0.5% Triton™ X-100, 10 mcg/mL TRU Block™, 50 mcg/mL Superchemiblock™, 5 mg/mL human IgG, and 0.05% ProClin™ 300.

C. In certain embodiments, for example, the standard curve may be used to compute a spike recovery for at least one of NF-L, GFAP, Tau, and UCH L1 (for example at least two of NF-L, GFAP, Tau, and UCH L1, at least three of NF-L, GFAP, Tau, and UCH L1, or each of NF-L, GFAP, Tau, and UCH L1) of between 80% and 120% (for example of between 95% and 105%) in the liquid sample (for example when the liquid sample is spiked with NF-L at a concentration of between 5 pg/mL and 1000 pg/mL, for example between 5 pg/mL and 100 pg/mL, between 5 pg/mL and 50 pg/mL, between 5 pg/mL and 10 pg/mL, between 10 pg/mL and 100 pg/mL, between 10 pg/mL and 50 pg/mL, 5 pg/mL 5 pg/mL, 10 pg/mL, 50 pg/mL, 100 pg/mL, or 1000 pg/mL; for example when the liquid sample is spiked with NF-L and GFAP at concentrations of between 5 pg/mL and 1000 pg/mL, for example between 5 pg/mL and 100 pg/mL, between 5 pg/mL and 50 pg/mL, between 5 pg/mL and 10 pg/mL, between 10 pg/mL and 100 pg/mL, between 10 pg/mL and 50 pg/mL, 5 pg/mL 5 pg/mL, 10 pg/mL, 50 pg/mL, 100 pg/mL, or 1000 pg/mL; for example when the liquid sample is spiked with NF-L, GFAP, and Tau at concentrations of between 5 pg/mL and 1000 pg/mL, for example between 5 pg/mL and 100 pg/mL, between 5 pg/mL and 50 pg/mL, between 5 pg/mL and 10 pg/mL, between 10 pg/mL and 100 pg/mL, between 10 pg/mL and 50 pg/mL, 5 pg/mL 5 pg/mL, 10 pg/mL, 50 pg/mL, 100 pg/mL, or 1000 pg/mL; for example when the liquid sample is spiked with the at least one of NF-L, GFAP, Tau, and UCH L1 at a concentrations of between 5 pg/mL and 1000 pg/mL, for example between 5 pg/mL and 100 pg/mL, between 5 pg/mL and 50 pg/mL, between 5 pg/mL and 10 pg/mL, between 10 pg/mL and 100 pg/mL, between 10 pg/mL and 50 pg/mL, 5 pg/mL 5 pg/mL, 10 pg/mL, 50 pg/mL, 100 pg/mL, or 1000 pg/mL; or for example when the liquid sample is spiked with the at least one of NF-L, GFAP, Tau, and UCH L1 at a concentration for each of the at least at least one of NF-L, GFAP, Tau, and UCH L1 of between 5 pg/mL and 1000 pg/mL, for example between 5 pg/mL and 100 pg/mL, between 5 pg/mL and 50 pg/mL, between 5 pg/mL and 10 pg/mL, between 10 pg/mL and 100 pg/mL, between 10 pg/mL and 50 pg/mL, 5 pg/mL 5 pg/mL, 10 pg/mL, 50 pg/mL, 100 pg/mL, or 1000 pg/mL). In certain embodiments, for example, the standard curve may be used to compute a series of concentrations for at least one of NF-L, GFAP, Tau, and UCH L1 (for example at least two of NF-L, GFAP, Tau, and UCH L1, at least three of NF-L, GFAP, Tau, and UCH L1, or each of NF-L, GFAP, Tau, and UCH L1) that are between 80% and 140% (for example between 80% and 125% or between 90% and 115%) proportional to one another when the liquid sample (for example a serum sample, plasma sample, or CSF sample) is diluted by between 2 times and 128 times (for example between 4 times and 64 times, such as 4 times, 8 times, 16 times, 32 times, and 64 times diluted) by the sample diluent.

Certain embodiments may provide, for example, an assay indicated by a traumatic event. In certain embodiments, for example, the assay may comprise providing a first liquid sample, the first liquid sample derived from first physiological fluid taken from a subject within 24 hours of the event. In certain embodiments, for example, the assay may comprise exposing at least a portion of the liquid sample to a plurality of capture objects, the plurality of capture objects comprising binding surfaces having affinity for a plurality of biomarkers, the plurality of biomarkers comprising: NF-L, GFAP, UCH L1, and Tau. In certain embodiments, for example, the assay may comprise binding at least one capture object of the plurality of capture objects to at least one biomarker of the plurality of biomarkers. In certain embodiments, for example, the assay may comprise verifying that a statistically significant proportion of the exposed plurality of capture objects are not bound to any of the at least two biomarkers. In certain embodiments, for example, the assay may comprise quantifying first concentrations of the plurality of biomarkers. In certain embodiments, for example, the assay may comprise applying a statistical test to the first concentrations at a p-value of less than 0.05 (for example less than 0.01, 0.001, or 0.0001) to assess a risk of a neurological condition (for example a TBI).

A. In certain embodiments, for example, the statistical test may utilize biomarker concentrations obtained for a group of healthy donors as inputs. In certain embodiments, for example, the statistical test may utilize second biomarker concentrations, the second biomarker concentrations quantified from a second liquid sample, the second liquid sample derived from second physiological fluid taken from the subject.

B. In certain embodiments, for example, the second physiological fluid may be taken from the subject at a different time from the time which the first physiological fluid is taken.

C. In certain embodiments, for example, at least one concentration of the first concentrations may be indicative of the neurological condition at a level of less than 1 pmol/L. In certain embodiments, for example, the event may be child birth resulting in a neonate. In certain embodiments, for example, the neonate may be at risk of hypoxia during child birth.

Certain embodiments may provide, for example, a method to detect a neurological condition in a subject. In certain embodiments, for example, the method may comprise performing the assay of indicated by a traumatic event, comprising: i) providing a first liquid sample, the first liquid sample derived from first physiological fluid taken from a subject within 24 hours of the event; ii) exposing at least a portion of the liquid sample to a plurality of capture objects, the plurality of capture objects comprising binding surfaces having affinity for a plurality of biomarkers, the plurality of biomarkers comprising: NF-L, GFAP, UCH L1, and Tau; iii) binding at least one capture object of the plurality of capture objects to at least one biomarker of the plurality of biomarkers; iv) verifying that a statistically significant proportion of the exposed plurality of capture objects are not bound to any of the at least two biomarkers; and v) quantifying first concentrations of the plurality of biomarkers; and vi) applying a statistical test to the first concentrations at a p-value of less than 0.05 to assess a risk of the neurological condition (for example a TBI or MS). In certain embodiments, for example, the method may comprise calculating at least one classification value based on a classification model of the first concentrations. In certain embodiments, for example, the method may comprise assigning a risk of the neurological condition, comprising: comparing the at least one classification value to at least one threshold value.

Certain embodiments may provide, for example, a method for detecting a neurological condition (for example a TBI or MS). In certain embodiments, for example, the method may comprise providing a liquid sample derived from a sample of physiological fluid taken from a subject. In certain embodiments, for example, the method may comprise diluting the liquid sample to adjust the liquid sample to within a working range in a digital immunoassay, the working range comprising: a) a plurality of biomarkers comprising NF-L, GFAP, UCH L1, and Tau, at least one biomarker of the plurality of biomarkers present at a concentration that is greater than a corresponding at least one limit of quantification of the digital immunoassay; and b) at least one threshold indicative of the neurological condition that is greater than the at least one corresponding limit of quantification. In certain embodiments, for example, the method may comprise quantifying concentrations NF-L, GFAP, UCH L1, and Tau via the digital immunoassay. In certain embodiments, for example, the digital immunoassay may be a multiplex immunoassay for NF-L, GFAP, UCH L1, and Tau.

Certain embodiments may provide, for example, a method for detecting a neurological condition. In certain embodiments, for example, the method may comprise providing a liquid sample derived from a sample of physiological fluid taken from a subject. In certain embodiments, for example, the method may comprise diluting a portion of the liquid sample to align concentrations of at least two biomarkers with a classification model for determining a risk of the neurological condition, the at least two biomarkers selected from the group consisting of NF-L, GFAP, UCH L1, and Tau. In certain embodiments, for example, the method may comprise quantifying the at least two biomarkers concentrations via a digital immunoassay for NF-L, GFAP, UCH L1, and Tau. In certain embodiments, for example, the classification model may be calibrated to a standard curve.

Certain embodiments may provide, for example, a dual-test method to detect a neurological condition. In certain embodiments, for example, the dual-test method may comprise a first assessment for the neurological condition in a subject. In certain embodiments, for example, the dual-test method may comprise performing, in response to the first assessment, a second assessment for the neurological condition, which second assessment is a multiplex immunoassay for NF-L, GFAP, UCH L1, and Tau on a fluid sample derived from the subject. In certain embodiments, for example, the first assessment may comprise a CT scan. In certain embodiments, for example, the first assessment may comprise an MRI scan.

Certain embodiments may provide, for example, a method to screen for a neurological condition. In certain embodiments, for example, the method may comprise providing a liquid sample derived from a sample of physiological fluid taken from a subject. In certain embodiments, for example, the method may comprise quantifying a first component in a first portion of the liquid sample. In certain embodiments, for example, the method may comprise computing a dilution factor based on the quantified first component. In certain embodiments, for example, the method may comprise diluting a second portion of the liquid sample by the dilution factor. In certain embodiments, for example, the method may comprise quantifying NF-L, GFAP, UCH L1, and Tau in the second portion of the liquid sample. In certain embodiments, for example, the first component concentration may be insensitive to changes in central nervous system (CNS) function associated with onset of one or more neurological conditions.

Certain embodiments may provide, for example, a method to detect a neurological condition. In certain embodiments, for example, the method may comprise: diluting a sample of physiological fluid in a diluent to form a diluted sample. In certain embodiments, for example, the method may comprise: performing a multiplex immunoassay on the diluted sample to obtain a plurality of measured parameters. In certain embodiments, for example, the method may comprise: obtaining concentration values for NF-L, GFAP, UCH L1, and Tau, comprising: inputting at least four of the plurality of measured parameters into a multivariate calibration model.

A. In certain embodiments, for example, the diluent may comprise human IgG.

B. In certain embodiments, for example, the multivariate calibration model may be derived from (for example may be fitted to) results of a series of multiplex calibration immunoassays. In certain embodiments, for example, the series of multiplex calibration immunoassays may comprise: i) a first calibration assay performed on a first calibration solution, the first calibration solution comprising NF-L at a first NF-L concentration, GFAP at a first GFAP concentration, UCH L1 at a first UCH L1 concentration, and Tau at a first Tau concentration; and ii) at least a second calibration assay performed on an at least second calibration solution, the at least second calibration solution comprising NF-L at an at least second NF-L concentration, GFAP at an at least second GFAP concentration, UCH L1 at an at least second UCH L1 concentration, and Tau at an at least second Tau concentration. In certain embodiments, for example, the series of multiplex immunoassays may comprise a calibration assay on a calibration solution that is exclusive of NF-L, GFAP, UCH L1, and Tau.

Certain embodiments may provide, for example, a kit. In certain embodiments, for example, the kit may comprise: a plurality of capture agents configured to separately bind to two or more (for example three or more) types of analytes selected from the group consisting of NF-L, GFAP, UCH L1, and Tau. In certain embodiments, for example, the kit may comprise: a plurality of detection agents configured to separately bind to the selected two or more types of analytes. In certain embodiments, for example, the kit may comprise: a sample diluent. In certain embodiments, for example, the kit may comprise: at least one calibration solution comprising at least first predetermined concentrations of the selected two or more types of analytes.

A. In certain embodiments, for example, at least one of the plurality of capture agents may comprise a bead (for example a paramagnetic bead configured for use in a multiplex digital immunoassay). In certain embodiments, for example, at least one of the plurality of capture agents may comprise a tag. In certain embodiments, for example, the kit may further comprise at least one bead, the at least one bead configured to selectively bind to the tag.

B. In certain embodiments, for example, the sample diluent may comprise human IgG.

C. In certain embodiments, for example, the at least one calibration solution may be a concentrate. In certain embodiments, for example, the at least one calibration solution may be pre-diluted to a working concentration for one or more analytes.

Certain embodiments may provide, for example, a kit. In certain embodiments, for example, the kit may comprise: a plurality of capture agents configured to separately bind to two or more (for example three or more) types of analytes selected from the group consisting of NF-L, GFAP, UCH L1, and Tau. In certain embodiments, for example, the kit may comprise: a plurality of detection agents configured to separately bind to the selected two or more types of analytes. In certain embodiments, for example, the kit may comprise: a sample diluent comprising human IgG. In certain embodiments, for example, the kit may comprise: a plurality of calibration solutions comprising a plurality of predetermined concentrations of the selected two or more types of analytes.

A. In certain embodiments, for example, the human IgG may be present in the sample diluent at a concentration of between 0.1 mg/mL and 25 mg/mL, for example between 0.25 mg/mL and 15 mg/mL, between 0.25 mg/mL and 1.0 mg/mL, between 1 mg/mL and 10 mg/mL, between 1 mg/mL and 3 mg/mL, between 3 mg/mL and 5 mg/mL, between 5 mg/mL and 7 mg/mL, between 7 mg/mL and 9 mg/mL, between 9 mg/mL and 11 mg/mL, between 11 mg/mL and 13 mg/mL, or the human IgG may be present in the diluent at a concentration of between 13 mg/mL and 15 mg/mL. In certain embodiments, for example, the human IgG may be present in the sample diluent at a concentration of 5 mg/mL. In certain embodiments, for example, the human IgG may be present in the sample diluent at a concentration of between 0.1 mcg/mL and 25 mcg/mL, for example between 0.25 mcg/mL and 15 mcg/mL, between 0.25 mcg/mL and 1.0 mcg/mL, between 1 mcg/mL and 10 mcg/mL, between 1 mcg/mL and 3 mcg/mL, between 3 mcg/mL and 5 mcg/mL, between 5 mcg/mL and 7 mcg/mL, between 7 mcg/mL and 9 mcg/mL, between 9 mcg/mL and 11 mcg/mL, between 11 mcg/mL and 13 mcg/mL, or the human IgG may be present in the diluent at a concentration of between 13 mcg/mL and 15 mcg/mL. In certain embodiments, for example, the human IgG may be present in the sample diluent at a concentration of 5 mcg/mL. In certain embodiments, for example, the sample diluent may further comprise at least one heterophile blocking agent exclusive of the human IgG. In certain embodiments, for example, the at least one heterophile blocking agent may be present in the sample diluent at a concentration of at least 1 mcg/mL, for example at least 5 mcg/mL, at least 10 mcg/mL, at least 15 mcg/mL, at least 20 mcg/mL, at least 25 mcg/mL or the at least one heterophile blocking agent may be present in the sample diluent at a concentration of at least 50 mcg/mL. In certain embodiments, for example, the at least one heterophile blocking agent exclusive of human IgG may be present in the sample diluent at a concentration (i.e., the total concentration of all heterophile blocking agents exclusive of human IgG) of between 1 mcg/mL and 100 mcg/mL, for example between 5 mcg/mL and 50 mcg/mL, between 10 mcg/mL and 20 mcg/mL, or the at least one heterophile blocking agent may be present in the sample diluent at a concentration of between 12 mcg/mL and 18 mcg/mL. In certain embodiments, for example, the human IgG may be present in the sample diluent at a concentration of between 1 mg/mL and 10 mg/mL and the at least one heterophile blocking agent exclusive of human IgG may be present at a concentration of at least 10 mcg/mL (for example at least 15 mcg/mL). In certain embodiments, for example, the at least one heterophile blocking agent exclusive of human IgG may be present in the sample diluent at a concentration of 15 mcg/mL. In certain embodiments, for example, the at least one heterophile blocking agent may comprise TRU Block™. In certain embodiments, for example, the TRU Block™ may be present in the sample diluent at a concentration of between 1 mcg/mL and 100 mcg/mL, for example between 2 mcg/mL and 25 mcg/mL, between 5 mcg/mL and 15 mcg/mL, or the TRU Block™ may be present in the sample diluent at a concentration of between 8 mcg/mL and 12 mcg/mL. In certain embodiments, for example, the TRU Block™ may be present in the sample diluent at a concentration of 10 mcg/mL. In certain embodiments, for example, the at least one heterophile blocking agent may comprise Superchemiblock™. In certain embodiments, for example, the Superchemiblock™ may be present in the sample diluent at a concentration of between 0.5 mcg/mL and 25 mcg/mL, for example between 1 mcg/mL and 15 mcg/mL, between 2 mcg/mL and 10 mcg/mL, or the Superchemiblock™ may be present in the sample diluent at a concentration of between 3 mcg/mL and 7 mcg/mL. In certain embodiments, for example, the Superchemiblock™ may be present in the sample diluent at a concentration of 5 mcg/mL. In certain embodiments, for example, the sample diluent may comprise human IgG at a concentration of between 1 mg/mL and 10 mg/mL and at least one heterophile blocking agent at a concentration of between 5 and 25 mcg/mL, for example human IgG at a concentration of between 3 mg/mL and 7 mg/mL and at least one heterophile blocking agent at a concentration of between 10 and 20 mcg/mL, human IgG at a concentration of between 3 mg/mL and 7 mg/mL and at least one heterophile blocking agent at a concentration of between 13 and 17 mcg/mL, or human IgG at a concentration of 5 mg/mL and at least one heterophile blocking agent at a concentration of 15 mcg/mL. In certain embodiments, for example, the sample diluent may comprise human IgG at a concentration of between 1 mg/mL and 10 mg/mL, TRU Block™ at a concentration of 5 mcg/mL and 15 mcg/mL, and Superchemiblock™ at a concentration of 1 mcg/mL and 10 mcg/mL. In certain embodiments, for example, the sample diluent may comprise human IgG at a concentration of between 3 mg/mL and 7 mg/mL, TRU Block™ at a concentration of 5 mcg/mL and 15 mcg/mL, and Superchemiblock™ at a concentration of 1 mcg/mL and 10 mcg/mL. In certain embodiments, for example, the sample diluent may comprise human IgG at a concentration of between 1 mg/mL and 10 mg/mL, TRU Block™ at a concentration of 7 mcg/mL and 12 mcg/mL, and Superchemiblock™ at a concentration of 1 mcg/mL and 10 mcg/mL. In certain embodiments, for example, the sample diluent may comprise human IgG at a concentration of between 1 mg/mL and 10 mg/mL, TRU Block™ at a concentration of 5 mcg/mL and 15 mcg/mL, and Superchemiblock™ at a concentration of 3 mcg/mL and 7 mcg/mL. In certain embodiments, for example, the sample diluent may comprise human IgG at a concentration of 5 mg/mL, TRU Block™ at a concentration of 10 mcg/mL, and Superchemiblock™ at a concentration of 5 mcg/mL. In certain embodiments, for example, the plurality of calibration solutions may be pre-diluted for use to determine a calibration standard curve without further dilution.

B. In certain embodiments, for example, the two or more types of analytes may be four types of analytes consisting of NF-L, GFAP, UCH L1, and Tau. In certain embodiments, for example, the plurality of calibration solutions may be between 6 and 10 calibration solutions, inclusive of an NF-L-free, GFAP-free, UCH L1-free, and Tau-free control solution. In certain embodiments, for example, the plurality of calibration solutions may comprise: i) a first calibration solution comprising NF-L at a concentration of at least 0.5 pg/mL, GFAP at a concentration of at least 1 pg/mL, UCH L1 at a concentration of at least 10 pg/mL, and Tau at a concentration of at least 0.1 pg/mL; ii) a second calibration solution comprising NF-L at a concentration of at least 450 pg/mL, GFAP at a concentration of at least 900 pg/mL, UCH L1 at a concentration of at least 9000 pg/mL, and Tau at a concentration of at least 90 pg/mL; and iii) at least a third calibration solution comprising NF-L at a concentration of between 10 pg/mL and 450 pg/mL, GFAP at a concentration of between 20 pg/mL and 900 pg/mL, UCH L1 at a concentration of between 200 pg/mL and 9000 pg/mL, and Tau at a concentration of between 2 pg/mL and 90 pg/mL.

C. In certain embodiments, for example, at least one of the plurality of capture agents may comprise a paramagnetic bead configured for use in a multiplex digital immunoassay analyzer. In certain embodiments, for example, the plurality of detection agents may comprise: i) an NF-L detection agent configured to bind to NF-L; ii) a GFAP detection agent configured to bind to GFAP; iii) a UCH L1 detection agent configured to bind to UCH L1; and iv) a Tau detection agent configured to bind to Tau.

Certain embodiments may provide, for example, a method to detect a neurological condition. In certain embodiments, for example, the method may comprise: diluting a sample of physiological fluid in a diluent to form a diluted sample. In certain embodiments, for example, the method may comprise: performing a multiplex immunoassay on the diluted sample to obtain a plurality of measured parameters. In certain embodiments, for example, the method may comprise: obtaining concentration values for NF-L, GFAP, UCH L1, and Tau, comprising: inputting at least four of the plurality of measured parameters into a multivariate calibration model.

A. In certain embodiments, for example, the measured parameters may comprise signal readings from a multiplex spotted well immunoassay. In certain embodiments, for example, the measured parameters may be derived from Poisson and/or Gaussian distribution analysis of results of a digital immunoassay.

B. In certain embodiments, for example, the multivariate calibration model may be derived from a results of a series of multiplex calibration immunoassays. In certain embodiments, for example, the multivariate calibration model may be derived from one or more polynomial regressions using the results as inputs. In certain embodiments, for example, the multivariate calibration model may have $R^2$ values of at least 0.95 for two or more of: i) NF-L at a concentration of between 1 pg/mL and 50 pg/mL; ii) Tau at a concentration of between 0.1 pg/mL and 8 pg/mL; iii) GFAP at a concentration of between 5 pg/mL and 100 pg/mL; and iv) UCH L1 at a concentration of between 20 pg/mL and 500 pg/mL. In certain embodiments, for example, the multivariate calibration model may have $R^2$ values of at least 0.95 for two or more of: i) NF-L at a concentration of between 0.1 pg/mL and 10 pg/mL; ii) Tau at a concentration of between 0.1 pg/mL and 8 pg/mL; iii) GFAP at a concentration of between 10 pg/mL and 500 pg/mL; and iv) UCH L1 at a concentration of between 20 pg/mL and 100 pg/mL.

C. In certain embodiments, for example, the series of multiplex calibration immunoassays may comprise: i) a first calibration assay performed on a first calibration solution, the first calibration solution comprising NF-L at a first NF-L concentration, GFAP at a first GFAP concentration, UCH L1 at a first UCH L1 concentration, and Tau at a first Tau concentration; and ii) at least a second calibration assay performed on an at least second calibration solution, the at least second calibration solution comprising NF-L at an at least second NF-L concentration, GFAP at an at least second GFAP concentration, UCH L1 at an at least second UCH L1 concentration, and Tau at an at least second Tau concentration.

D. In certain embodiments, for example, a comparative series of multiplex immunoassays for NF-L, GFAP, UCH L1, and Tau may be performed to obtain a series of comparative measured parameters (for example signal readings or digital assay results) corresponding to at least one of NF-L, GFAP, Tau, and UCH L1 (for example at least two of NF-L, GFAP, Tau, and UCH L1, at least three of NF-L, GFAP, Tau, and UCH L1, or each of NF-L, GFAP, Tau, and UCH L1) that are between 80% and 140% (for example between 80% and 125% or between 90% and 115%) proportional to one another when the sample of physiological fluid (for example a serum sample, plasma sample, or CSF sample) is diluted by between 2 times and 128 times (for example between 4 times and 64 times, such as 4 times, 8 times, 16 times, 32 times, and 64 times diluted) by the sample diluent. In certain embodiments, for example, the multivariate calibration model may be used to obtain a series of comparative concentration values for at least one of NF-L, GFAP, Tau, and UCH L1 (for example at least two of NF-L, GFAP, Tau, and UCH L1, at least three of NF-L, GFAP, Tau, and UCH L1, or each of NF-L, GFAP, Tau, and UCH L1) that are between 80% and 140% (for example between 80% and 125% or between 90% and 115%) proportional to one another when the sample of physiological fluid (for example a serum sample, plasma sample, or CSF sample) is diluted by between 2 times and 128 times (for example between 4 times and 64 times, such as 4 times, 8 times, 16 times, 32 times, and 64 times diluted) by the sample diluent. In certain embodiments, for example, the diluent may comprise between 1 mg/mL and 50 mg/mL human IgG (for example between 1 mg/mL and 10 mg/mL, between 3 mg/mL and 7 mg/mL, or 5 mg/mL human IgG).

Certain embodiments may provide, for example, a test for a neurological condition. In certain embodiments, for example, the test may comprise: providing a liquid sample derived from a sample of physiological fluid. In certain embodiments, for example, the test may comprise: obtaining, via a multiplex immunoassay, concentrations of NF-L, GFAP, UCH L1, and Tau in the liquid sample. In certain embodiments, for example, the test may comprise: calculating at least one classification value based on a multivariate classification model using the concentrations as inputs to the multivariate classification model. In certain embodiments, for example, the test may comprise: assigning a risk of the neurological condition, comprising: comparing the at least one classification value to at least one threshold value.

A. In certain embodiments, for example, the multivariate classification model may predict TBI with an ROC curve having an AUC of at least 0.85. In certain embodiments, for example, the multivariate classification model may predict a TBI with a true positive rate of at least 75% at a false positive rate of less than 25%.

B. In certain embodiments, for example, the test may further comprise: obtaining a CT scan result negative for the neurological condition prior to performing the multiplex immunoassay. In certain embodiments, for example, the multivariate classification model may comprise a neural network.

Certain embodiments may provide, for example, a test for a neurological condition, comprising: i) providing a liquid sample derived from a sample of physiological fluid; ii) obtaining, via a single multiplex immunoassay, concentrations of NF-L, GFAP, UCH L1, and Tau in the liquid sample; iii) calculating at least one classification value based on a multivariate classification model using the concentrations as inputs to the multivariate classification model; and iv) assigning a risk of the neurological condition, comprising: comparing the at least one classification value to at least one threshold value.

Certain embodiments may provide, for example, a single-sample test for a neurological condition, comprising: i) providing a liquid sample derived from a single sample of physiological fluid from a subject; ii) obtaining, via at least one immunoassay, concentrations of NF-L, GFAP, UCH L1, and Tau in the liquid sample; and iii) assigning a risk of the neurological condition in the subject, comprising: determining at least one measure of significance of differences between the concentrations of NF-L, GFAP, UCH L1, and Tau in the liquid sample and concentrations of NF-L, GFAP, UCH L1, and Tau in a group of healthy donors.

Certain embodiments may provide, for example, a protocol indicated by a potential neurological condition, comprising a CT scan positive for a neurological condition; followed by one of the single-sample tests for the neurological condition disclosed herein.

Certain embodiments may provide, for example, a modified protocol indicated by a potential neurological condition, comprising a protocol for detection of the neurological condition comprising a CT scan and in which an MRI scan is replaced by one of the single-sample tests for the neurological condition disclosed herein.

Certain embodiments may provide, for example, a single-assay test for a neurological condition, comprising: i) providing at least one liquid sample derived from a single sample of physiological fluid from a subject; ii) obtaining, via an immunoassay, concentrations of NF-L, GFAP, UCH L1, and Tau in the at least one liquid sample; and iii) assigning a risk of the neurological condition in the subject, comprising: determining at least one measure of significance of differences between the concentrations of NF-L, GFAP, UCH L1, and Tau in the liquid sample and concentrations of NF-L, GFAP, UCH L1, and Tau in a group of healthy donors.

Certain embodiments may provide, for example, a dual-sample test for a neurological condition, comprising: i) providing, from a subject: a) a first liquid sample derived from a sample of a first physiological fluid taken at a first time; and b) a second liquid sample derived from a sample of a second physiological fluid taken at a second time; ii) obtaining, via immunoassay, concentrations of NF-L, GFAP, UCH L1, and Tau in the first liquid sample and in the second liquid sample; iii) assigning a risk of the neurological condition in the subject, comprising: determining at least one measure of significance of differences between the concentrations of NF-L, GFAP, UCH L1, and Tau in the first liquid sample and the concentrations of NF-L, GFAP, UCH L1, and Tau in the second liquid sample.

Certain embodiments may provide, for example, a dual-sample test for a neurological condition, comprising: i) providing, from a subject: a) a first liquid sample derived from a first physiological fluid sample taken at a first time; and b) at least a second liquid sample derived from at least a second physiological fluid sample taken at least a second time; ii) obtaining, via immunoassay, concentrations of NF-L, GFAP, UCH L1, and Tau in the first liquid sample and in the at least the second liquid sample; iii) assigning a risk of the neurological condition in the subject, comprising: determining at least one measure of significance of differences between the concentrations of NF-L, GFAP, UCH L1, and Tau in the first liquid sample and the concentrations of NF-L, GFAP, UCH L1, and Tau in the at least the second liquid sample.

Certain embodiments may provide, for example, a method to distinguish between types of neurological condition, comprising: i) providing a liquid sample derived from a sample of physiological fluid from a subject; ii) obtaining, via at least one immunoassay, concentrations of NF-L, GFAP, UCH L1, and Tau in the liquid sample; iii) distinguishing between types of neurological condition, comprising: a) classifying as statistically significant a difference between at least a first biomarker concentration of the concentrations of NF-L, GFAP, UCH L1, and Tau in the liquid sample and concentrations of NF-L, GFAP, UCH L1, and Tau in a group of healthy donors; and b) determining that a difference between at least a second biomarker concentration of the concentrations of NF-L, GFAP, UCH L1, and Tau in the liquid sample and the concentrations of NF-L, GFAP, UCH L1, and Tau in a group of healthy donors is statistically insignificant.

Certain embodiments may provide, for example, a test for a neurological condition, comprising i) providing a sample of venous blood plasma or serum from a subject; ii) diluting the sample with a diluent to form a liquid sample, the diluent comprising a predetermined concentration of at least one heterophilic interference inhibitor for at least one biomarker selected from the group consisting of NF-L, GFAP, UCH L1, and Tau; iii) obtaining, via digital immunoassay, signal readings for NF-L, GFAP, UCH L1, and Tau in the liquid sample; and iii) computing concentrations for NF-L, GFAP, UCH L1, and Tau in the liquid sample based on a standard curve, the standard curve derived from a plurality of calibration solutions, the calibration solutions exclusive of the heterophilic interference inhibitor.

Certain embodiments may provide, for example, an assay indicated by a traumatic event, comprising: i) providing a first liquid sample, the first liquid sample derived from first physiological fluid taken from a subject within 24 hours of the event; ii) exposing at least a portion of the liquid sample to a plurality of capture objects, the plurality of capture objects comprising binding surfaces having affinity for a plurality of biomarkers, the plurality of biomarkers comprising: NF-L, GFAP, UCH L1, and Tau; iii) binding at least one capture object of the plurality of capture objects to at least one biomarker of the plurality of biomarkers; iv) verifying that a statistically significant proportion of the exposed plurality of capture objects are not bound to any of the at least two biomarkers; v) quantifying first concentrations of the plurality of biomarkers; and vi) applying a statistical test to the first concentrations at a p-value of less than 0.05 to assess a risk of a neurological condition.

Certain embodiments may provide, for example, a method to detect a neurological condition in a subject, comprising: i) performing an assay indicated by a traumatic event, comprising: a) providing a first liquid sample, the first liquid sample derived from first physiological fluid taken from a subject within 24 hours of the event; b) exposing at least a portion of the liquid sample to a plurality of capture objects, the plurality of capture objects comprising binding surfaces having affinity for a plurality of biomarkers, the plurality of biomarkers comprising: NF-L, GFAP, UCH L1, and Tau; c) binding at least one capture object of the plurality of capture objects to at least one biomarker of the plurality of biomarkers; d) verifying that a statistically significant proportion of the exposed plurality of capture objects are not bound to any of the at least two biomarkers; and e) quantifying first concentrations of the plurality of biomarkers; and f) applying a statistical test to the first concentrations at a p-value of less than 0.05 to assess a risk of a neurological condition; ii) calculating at least one classification value based on a classification model of the first concentrations; and iii) assigning a risk of the neurological condition, comprising: comparing the at least one classification value to at least one threshold value.

Certain embodiments may provide, for example, a method for detecting a neurological condition, comprising: i) providing a liquid sample derived from a sample of physiological fluid taken from a subject; ii) diluting the liquid sample to adjust the liquid sample to within a working range in a digital immunoassay, the working range comprising: a) a plurality of biomarkers comprising NF-L, GFAP, UCH L1, and Tau, at least one biomarker of the plurality of biomarkers present at a concentration that is greater than a corresponding at least one limit of quantification of the digital immunoassay; and b) at least one threshold indicative of the neurological condition that is greater than the at least one corresponding limit of quantification; and iii) quantifying concentrations NF-L, GFAP, UCH L1, and Tau via the digital immunoassay.

Certain embodiments may provide, for example, a method for detecting a neurological condition, comprising: i) providing a liquid sample derived from a sample of physiological fluid taken from a subject; ii) diluting a portion of the liquid sample to align concentrations of at least two biomarkers with a classification model for determining a risk of the neurological condition, the at least two biomarkers selected from the group consisting of NF-L, GFAP, UCH L1, and Tau; and iii) quantifying the at least two biomarkers concentrations via a digital immunoassay for NF-L, GFAP, UCH L1, and Tau.

Certain embodiments may provide, for example, a dual-test method to detect a neurological condition, comprising: i) a first assessment for the neurological condition in a subject; and ii) performing, in response to the first assessment, a second assessment for the neurological condition, which second assessment is a multiplex immunoassay for NF-L, GFAP, UCH L1, and Tau on a fluid sample derived from the subject.

Certain embodiments may provide, for example, a method to screen for a neurological condition, comprising: i) providing a liquid sample derived from a sample of physiological fluid taken from a subject; ii) quantifying a first component in a first portion of the liquid sample; iii) computing a dilution factor based on the quantified first component; iv) diluting a second portion of the liquid sample by the dilution factor; and v) quantifying NF-L, GFAP, UCH L1, and Tau in the second portion of the liquid sample.

Certain embodiments may provide, for example, a method to detect a neurological condition, comprising: i) diluting a sample of physiological fluid in a diluent to form a diluted sample; ii) performing a multiplex immunoassay on the diluted sample to obtain a plurality of measured parameters; and iii) obtaining concentration values for NF-L, GFAP, UCH L1, and Tau, comprising: inputting at least four of the plurality of measured parameters into a multivariate calibration model.

Certain embodiments may provide, for example, a kit, comprising: i) a plurality of capture agents configured to separately bind to two or more (for example three or more) types of analytes selected from the group consisting of NF-L, GFAP, UCH L1, and Tau; ii) a plurality of detection agents configured to separately bind to the selected two or more types of analytes; iii) a sample diluent; and iv) at least one calibration solution comprising at least first predetermined concentrations of the selected two or more types of analytes.

Certain embodiments may provide, for example, a kit, comprising: i) a plurality of capture agents configured to separately bind to two or more (for example three or more) types of analytes selected from the group consisting of NF-L, GFAP, UCH L1, and Tau; ii) a plurality of detection agents configured to separately bind to the selected two or more types of analytes; iii) a sample diluent comprising human IgG; and iv) plurality of calibration solutions comprising a plurality of predetermined concentrations of the selected two or more types of analytes.

Certain embodiments may provide, for example, a method to detect a neurological condition, comprising: i) diluting a sample of physiological fluid in a diluent to form a diluted sample; ii) performing a multiplex immunoassay on the diluted sample to obtain a plurality of measured parameters; and iii) obtaining concentration values for NF-L, GFAP, UCH L1, and Tau, comprising: inputting at least four of the plurality of measured parameters into a multivariate calibration model.

Certain embodiments may provide, for example, a test for a neurological condition, comprising: i) providing a liquid sample derived from a sample of physiological fluid; ii) obtaining, via a multiplex immunoassay, concentrations of NF-L, GFAP, UCH L1, and Tau in the liquid sample; iii) calculating at least one classification value based on a multivariate classification model using the concentrations as inputs to the multivariate classification model; and iv) assigning a risk of the neurological condition, comprising: comparing the at least one classification value to at least one threshold value.

Certain embodiments may provide, for example, a kit, comprising: i) a plurality of capture agents configured to separately bind to two or more types of analytes selected from the group consisting of NF-L, GFAP, UCH L1, and Tau; ii) a plurality of detection agents configured to separately bind to the selected two or more types of analytes; iii) a sample diluent comprising human IgG at a concentration of between 1 mg/mL and 10 mg/mL; and iv) a plurality of calibration solutions comprising a plurality of predetermined concentrations of the selected two or more types of analytes.

A. In certain embodiments, for example, the sample diluent further may comprise at least 15 mcg/mL of at least one heterophile blocking agent exclusive of the human IgG. In certain embodiments, for example, the plurality of calibration solutions may be pre-diluted for use to determine a calibration standard curve without further dilution. In certain embodiments, for example, the two or more types of analytes may be four types of analytes consisting of NF-L, GFAP, UCH L1, and Tau. In certain embodiments, for example, the plurality of calibration solutions may be between 6 and 10 calibration solutions, inclusive of an NF-L-free, GFAP-free, UCH L1-free, and Tau-free control solution. In certain embodiments, for example, the plurality of calibration solutions may comprise: i) a first calibration solution comprising NF-L at a concentration of at least 0.5 pg/mL, GFAP at a concentration of at least 1 pg/mL, UCH L1 at a concentration of at least 10 pg/mL, and Tau at a concentration of at least 0.1 pg/mL; ii) a second calibration solution comprising NF-L at a concentration of at least 450 pg/mL, GFAP at a concentration of at least 900 pg/mL, UCH L1 at a concentration of at least 9000 pg/mL, and Tau at a concentration of at least 90 pg/mL; and iii) at least a third calibration solution comprising NF-L at a concentration of between 10 pg/mL and 450 pg/mL, GFAP at a concentration of between 20 pg/mL and 900 pg/mL, UCH L1 at a concentration of between 200 pg/mL and 9000 pg/mL, and Tau at a concentration of between 2 pg/mL and 90 pg/mL. In certain embodiments, for example, at least one of the plurality of capture agents may comprise a paramagnetic bead configured for use in a multiplex digital immunoassay analyzer. In certain embodiments, for example, the plurality of detection agents may comprise: i) an NF-L detection agent configured to bind to NF-L; ii) a GFAP detection agent configured to bind to GFAP; iii) a UCH L1 detection agent configured to bind to UCH L1; and iv) a Tau detection agent configured to bind to Tau.

Certain embodiments may provide, for example, a method to detect a neurological condition, comprising: i) diluting a sample of physiological fluid in a diluent to form a diluted sample; ii) performing a multiplex immunoassay on the diluted sample to obtain a plurality of at least four measured parameters; and iii) obtaining concentration values for NF-L, GFAP, UCH L1, and Tau, comprising: inputting at least four of the plurality of at least four measured parameters into a multivariate calibration model.

A. In certain embodiments, for example, the plurality of the at least four measured parameters may comprise signal readings from a multiplex spotted well immunoassay. In certain embodiments, for example, the plurality of the at least four measured parameters may be derived from Poisson and/or Gaussian distribution analysis of results of a multiplex digital immunoassay. In certain embodiments, for example, the multivariate calibration model may be derived from results of a series of multiplex calibration immunoassays. In certain embodiments, for example, the multivariate calibration model may provide a series of comparative concentration values for at least at least two of NF-L, GFAP, Tau, and UCH L1 that are between 80% and 140% proportional when the sample of physiological fluid is diluted between 4 times and 64 times. In certain embodiments, for example, the multivariate calibration model may have $R^2$ values of at least 0.95 for two or more of: i) NF-L at a concentration of between 1 pg/mL and 50 pg/mL; ii) Tau at a concentration of between 0.1 pg/mL and 8 pg/mL; iii) GFAP at a concentration of between 5 pg/mL and 100 pg/mL; and iv) UCH L1 at a concentration of between 20 pg/mL and 500 pg/mL. In certain embodiments, for example, the series of multiplex calibration immunoassays may comprise: i) a first calibration assay performed on a first calibration solution, the first calibration solution comprising NF-L at a first NF-L concentration, GFAP at a first GFAP concentration, UCH L1 at a first UCH L1 concentration, and Tau at a first Tau concentration; and ii) at least a second calibration assay performed on an at least second calibration solution, the at least second calibration solution comprising NF-L at an at least second NF-L concentration, GFAP at an at least second GFAP concentration, UCH L1 at an at least second UCH L1 concentration, and Tau at an at least second Tau concentration.

Certain embodiments may provide, for example, a test for a neurological condition, comprising: i) providing a liquid sample derived from a sample of physiological fluid; ii) obtaining, via a multiplex immunoassay, concentrations of NF-L, GFAP, UCH L1, and Tau in the liquid sample; iii) calculating at least one classification value based on a multivariate classification model using the concentrations as inputs to the multivariate classification model; and iv) assigning a risk of the neurological condition, comprising: comparing the at least one classification value to at least one threshold value.

A. In certain embodiments, for example, the multivariate classification model may predict a traumatic brain injury with an ROC curve having an AUC of at least 0.85. In certain embodiments, for example, the multivariate classification model may predict a traumatic brain injury with a true positive rate of at least 75% at a false positive rate of less than 25%. In certain embodiments, for example, the test may further comprise: obtaining a CT scan result negative for the neurological condition prior to performing the multiplex immunoassay. In certain embodiments, for example, the multivariate classification model may comprise a neural network.

Methods and kits for determining a measure of the concentration of a panel neurological biomarkers in a sample derived from a patient are generally provided.

The subject matter of the present invention involves, in some cases, interrelated products, alternative solutions to a particular problem, and/or a plurality of different uses of one or more systems and/or articles.

In certain embodiments, for example (for example in one set of embodiments), the methods, tests, assays, kits, or systems (for example methods) may comprise determining a measure of the concentration of a panel of biomarkers in a sample, comprising performing an assay on a sample derived from a human and determining a measure of the concentration of NF-L and at least one other biomarker selected from the group consisting of GFAP, UCH L1, and Tau, in the sample collected from the patient. Certain embodiments, for example, may provide an assay having an LOQ of no greater than 0.1 pg/mL for Tau protein, no greater than 1 pg/mL for NF-L and GFAP, and no greater than 5 pg/mL for UCH L1.

In certain embodiments, for example (for example in another set of embodiments), the methods, tests, assays, kits, or systems (for example kits) may be used for determining a measure of the concentration of a panel of biomarkers in a sample comprises a plurality of capture objects, each having a binding surface comprising a plurality of capture components, a plurality of a first type of binding ligand having affinity for NF-L, and a plurality of a second type of binding ligand and a third type of binding ligand having affinity for at least two other biomarkers selected from the group consisting of GFAP, UCH L1, and Tau.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

DETAILED DESCRIPTION OF THE INVENTION

Figure 1:
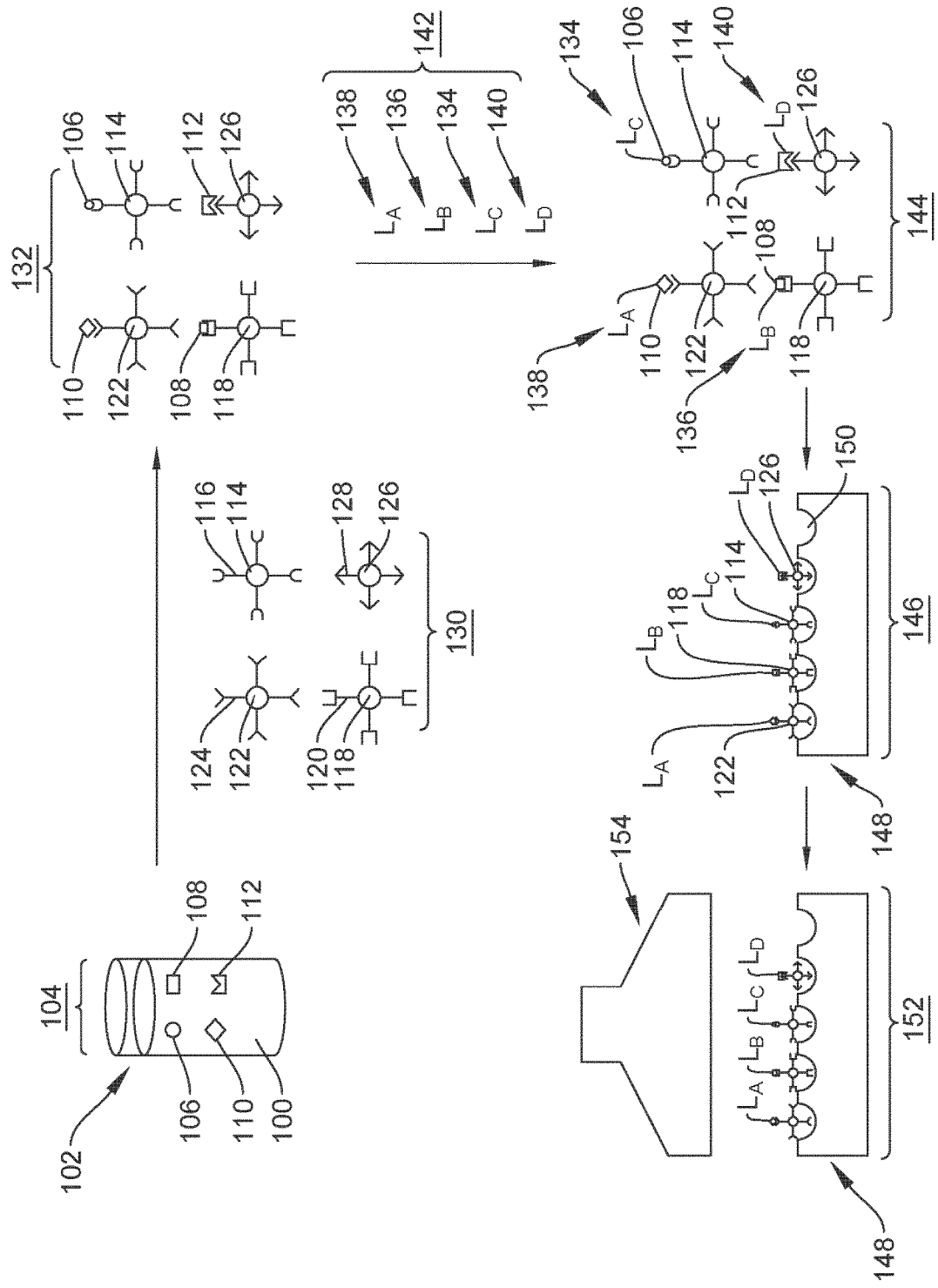
FIG. 1 is a schematic depiction of a multiplex digital assay.

The present disclosure is based, generally, on the discovery that biomarkers collateral to neural function can be rapidly quantified from physiological fluids at very low concentrations (for example femtomolar) and used to help characterize the neural health of a subject, inclusive of detecting a neural condition, excluding a neural condition, predicting onset of a neural condition, and distinguishing between two or more neurological conditions that present similarly. The present disclosure is further specifically based, in part, on the discovery of multi-component calibrators and sample diluent formulations and preparation methods that improve the precision of biomarker measurements. Moreover, these formulations and methods can be applied to a samples obtained from a plurality of individuals (for example a combination of healthy individuals and others suffering from one or more neurological conditions) to obtain data sets from which improved classification models are obtained. Kits based on the formulations and methods disclosed herein enable a subject to benefit from these improved classification models.

Certain embodiments may provide, for example, methods, tests, protocol, assays, kits, and/or systems for detecting, diagnosing, distinguishing, and/or excluding a neurological condition. In certain embodiments, for example, the neurological condition may comprise a disease. In certain embodiments, for example, the disease may be selected from the group consisting of Alzheimer's disease, motor neuron disease, frontotemporal dementia, HIV-associated dementia, progressive supranuclear palsy, Parkinson disease, Huntington's disease, Lewy Body dementia, dementia pugilistica, Creutzfeldt-Jakob disease, amyotrophic lateral sclerosis, transverse myelitis, MS, demyelination occurring after trauma to the brain or spinal cord, or a combination of two or more of the foregoing diseases.

In certain embodiments, for example, the neurological condition may comprise a condition resulting from an injury (for example TBI). In certain embodiments, for example, the condition resulting from an injury may be selected from the group consisting of acute brain injury, spinal cord injury, peripheral nerve injury, ischaemic brain injury, TBI (or head trauma), traumatic spinal cord injury (or spinal cord trauma), stroke related injury, concussion (optionally including post-concussion syndrome), cerebral aneurism related injury, injury from general anoxia, hypoxia, hypoglycemia, hypotension, damage to retinal ganglion cells, a spinal cord injury (optionally including monoplegia, diplegia, paraplegia, hemiplegia and quadriplegia, or a combination of two or more of the foregoing), demyelination occurring after trauma to the brain or spinal cord, brain injuries secondary to seizures (for example seizures induced by radiation, exposure to ionizing or iron plasma, nerve agents, cyanide, toxic concentrations of oxygen, neurotoxicity due to CNS malaria or treatment with anti-malaria agents, trypanosomes, malarial pathogens, other CNS traumas, or a combination of two or more of the foregoing), injuries caused by procedures (for example procedures resulting from embole, hyperfusion, or hypoxia), or a combination of two or more of the foregoing conditions.

In certain embodiments, for example, the neurological condition may comprise a defect. In certain embodiments, for example, the defect may be selected from the group consisting of defects caused by defective tissues or cells of the nervous system, defects caused by defective tissues or cells that affect the nervous system (such as defective spine morphogenesis and defects in dendritic spine morphology), or a combination of two or more of the foregoing defects.

In certain embodiments, for example, the neurological condition may comprise a disorder. In certain embodiments, for example, the disorder may be selected from the group consisting of transverse myelitis, MS, demyelination occurring after trauma to the brain or spinal cord, memory loss, long term and short term memory disorders, learning disorders, autism, depression, benign forgetfulness, children learning disorders, learning disorders, attention deficit disorder, neuronal reaction to viral infection, brain damage, hereditary myelin disorder of the CNS, epilepsy, perinatal asphyxia, asphyxia, anoxia, status epilepticus, and stroke, concussion (including post-concussion syndrome), baldness (such as male pattern baldness), alopecia areata, addiction, clinical depression, neurofibromatosis, tuberous sclerosis, bipolar disorder, posttraumatic stress disorder, anxiety disorder, psychiatric disorders such as bi-polarism, schizophrenia and the like, narcolepsy/sleep disorders (optionally including circadian rhythm disorders, insomnia, narcolepsy, or a combination of two or more of the foregoing); severance of nerves or nerve damage, severance of the cerebrospinal nerve cord and any damage to brain or nerve cells, neurological deficits associated with AIDS, tics (for example Giles de la Tourette's syndrome), Huntington's chorea, schizophrenia, TBI, tinnitus, neuralgia, especially trigeminal neuralgia, neuropathic pain, inappropriate neuronal activity resulting in neurodysthesias in diseases such as diabetes, MS and motor neuron disease, ataxias, muscular rigidity (spasticity), temporomandibular joint dysfunction, atypical parkinsonian disorders, Down's syndrome, or a combination of two or more of the foregoing disorders.

Certain embodiments may provide, for example, methods, tests, protocol, assays, kits, and/or systems for detecting, diagnosing, distinguishing, and/or excluding a neurological condition. In certain embodiments, for example, the neurological condition may comprise MS. In certain embodiments, for example, the MS may comprise relapsing-remitting MS. In certain embodiments, for example, the MS may comprise primary progressive MS. In certain embodiments, for example, the MS may comprise progressive relapsing MS. In certain embodiments, for example, the MS may comprise secondary progressive MS.

Certain embodiments may provide, for example, methods, tests, protocol, assays, kits, and/or systems for detecting, diagnosing, distinguishing, and/or excluding a neurological condition in a subject (for example a subject having symptoms indicative of the neurological condition or a subject having a history of the neurological condition or a related condition). In certain embodiments, for example, the methods, tests, protocol, assays, kits, and/or systems may comprise calculating at least one classification value based on a multivariate classification model of the concentrations of a plurality (for example 2, 3, 4, 5, 6, 7, 8, 9, 10, or more than 10) of biomarkers (for example two or more (for example three or more) of NF-L, Tau, GFAP or UCH L1) in a liquid sample. In certain embodiments, for example, the methods, tests, protocol, assays, kits, and/or systems may comprise assigning a risk of having (or developing) neurological condition, comprising: comparing the at least one classification value to at least one threshold value.

In certain embodiments, for example, the classification model may be a statistical model. In certain embodiments, for example, the classification model may be a regression, linear regression, quadratic regression, polynomial regression, logistic regression, neural network, clustering model, principle component analysis, nearest neighbor classifier analysis, support vector machines, linear discriminant analysis, quadratic discriminant analysis, decision trees, genetic algorithm, classifier optimization using bagging, classifier optimization using boosting, classifier optimization using the Random Subspace Method, a projection pursuit, genetic programming, weighted voting, or a combination of two or more of the foregoing.

In certain embodiments, for example, the classification model may be a regression model (for example a logistic regression model). In certain embodiments, for example, the regression model may include at least one coefficient (for example 1 coefficient, 2 coefficients, or more than 2 coefficients) for at least two (for example each or all) of the biomarkers in a selected set of biomarkers (for example two or more (for example three or more) of NF-L, Tau, GFAP or UCH L1). In certain embodiments, for example, the coefficients for the regression model may be determined using a maximum likelihood algorithm. In certain embodiments, for example, the regression may be a logistic regression. In certain embodiments, for example, the logistic regression may be a binary logistic regression.

In certain embodiments, for example, the classification model may be a neural network. In certain embodiments, for example, the neural network may be constructed for a selected set of biomarkers (for example two or more of NF-L, Tau, GFAP or UCH L1). In certain embodiments, for example, the neural network may be a two-stage regression. In certain embodiments, for example, the neural network may be a two stage classification model. In certain embodiments, for example, the neural network may have a layered structure that includes a layer of input units connected by a layer of weights to a layer of output units. In certain embodiments, for example, the neural network may be a multilayer neural network. In certain embodiments, for example, the multilayer neural network may comprise input layer, at least one hidden layer, and an output layer. In certain embodiments, for example, a single bias layer may be connected to each layer other than the input layer.

In certain embodiments, for example, the classification model may be calibrated to determine the at least one threshold value at least based on one or more data sets. In certain embodiments, for example, at least a portion of the data set (for example at least 10%, at least 20%, at least 30%, or at least 50% of the data set) may be derived from biospecimens from healthy individuals (and/or individuals who do not have a neurological condition nor a history of a neurological condition). In certain embodiments, for example, at least a portion of the data set (for example at least 10%, at least 20%, at least 30%, or at least 50% of the data set) may be derived from biospecimens from individuals who have the neurological condition or a history of the neurological condition. In certain embodiments, for example, at least a portion of the data set (for example at least 10%, at least 20%, at least 30%, or at least 50% of the data set) may comprise diagnostic results from a CT scan and/or an MRI scan. In certain embodiments, for example, the at least a portion of the data set (for example at least 10%, at least 20%, at least 30%, or at least 50% of the data set) may comprise positive diagnostic results for the neural condition (for example CT-positive or MRI-positive results indicative of the neural condition). In certain embodiments, for example, at least a portion of the data set (for example at least 10%, at least 20%, at least 30%, or at least 50% of the data set) may comprise negative diagnostic results for the neural condition (for example CT-negative or MRI-negative results indicative of the absence of the neural condition). In certain embodiments, for example, at least a portion of the data set (for example at least 10%, at least 20%, at least 30%, or at least 50% of the data set) may comprise mixed diagnostic results for the neural condition (for example CT-negative/MRI-positive or CT-positive/MRI-negative results).

In certain embodiments, for example, at least a portion of the data set (for example at least 10%, at least 20%, at least 30%, or at least 50% of the data set) may be obtained from individuals who may have been subject to two or more diagnostic methods (for example a CT scan and an MRI scan). In certain embodiments, for example, at least a portion of the data set (for example at least 10%, at least 20%, at least 30%, or at least 50% of the data set) may be derived from biospecimens from individuals having positive results for the neurological condition in at least one diagnostic method. In certain embodiments, for example, at least a portion of the data set may (for example at least 10%, at least 20%, at least 30%, or at least 50% of the data set) be derived from biospecimens from individuals having a positive CT scan and a positive MRI scan for the neurological condition. In certain embodiments, for example, at least a portion of the data set (for example at least 10%, at least 20%, at least 30%, or at least 50% of the data set) may be derived from biospecimens from individuals having a positive CT scan and a negative MRI scan for the neurological condition. In certain embodiments, for example, at least a portion of the data set (for example at least 10%, at least 20%, at least 30%, or at least 50% of the data set) may be derived from biospecimens from individuals having a negative MRI scan and a positive MRI scan for the neurological condition. In certain embodiments, for example, at least a portion of the data set (for example at least 10%, at least 20%, at least 30%, or at least 50% of the data set) may be derived from biospecimens from individuals having negative results for the neurological condition in the two or more diagnostic methods. In certain embodiments, for example, at least a portion of the data set (for example at least 10%, at least 20%, at least 30%, or at least 50% of the data set) may be derived from biospecimens from individuals having a negative MRI scan and a negative MRI scan for the neurological condition.

In certain embodiments, for example, the data set may be derived from biospecimens from at least 25 healthy controls (for example at least 40 healthy controls, at least 50 healthy controls, at least 75 healthy controls, at least 100 healthy controls, or the data set may be derived from biospecimens from at least 200 healthy controls. In certain embodiments, for example, the data set may be derived from biospecimens from at least 25 subjects exhibiting at least one indication from the neurological condition (for example at least 40 subjects, at least 50 subjects, at least 75 subjects, at least 100 subjects, or the data set may be derived from biospecimens from at least 200 subjects exhibiting at least one indication from the neurological condition.

In certain embodiments, for example, the neurological condition may comprise TBI. In certain embodiments, for example, at least 10% (for example at least 20%, at least 30%, or at least 50%) of the data set may comprise data derived from biospecimens from subjects who have a Glasgow Coma Score of 3-8, a Glasgow Coma Score of 9-12, and/or a Glasgow Coma Score of 13-15. In certain embodiments, for example, the data set may be derived from biospecimens (for example at least 50 biospecimens, at least 75 biospecimens, at least 100 biospecimens, at least 125 biospecimens, at least 150 biospecimens, or at least 200 biospecimens) obtained from the TRACK-TBI pilot study. In certain embodiments, for example, the data set may be derived from biospecimens (for example at least 50 biospecimens, at least 75 biospecimens, at least 100 biospecimens, at least 125 biospecimens, at least 150 biospecimens, or at least 200 biospecimens) obtained from the Traumatic Head Injury Neuroimaging Classification study (NCT01132937).

In certain embodiments, for example, at least a portion of the data set may be derived from biospecimens from the subject. In certain embodiments, for example, at least a portion of the data set may be derived from biospecimens from the subject prior to developing (or prior to the detection of (for example by a healthcare provider)) symptoms indicative of the neurological condition, for example at least 5 minutes prior, at least 15 minutes prior to, at least 30 minutes prior to, at least 45 minutes prior to, at least 1 hour prior to, at least 2 hours prior to, at least 4 hours prior to, at least 6 hours prior to, at least 12 hours prior to, at least 24 hours prior to, at least 48 hours prior to, at least 72 hours prior to, at least 96 hours prior to, at least 1 week prior to, at least 2 weeks prior to, at least 3 weeks prior to, at least 4 weeks prior to, at least 5 weeks prior to, at least 6 weeks prior to, at least 8 weeks prior to, or at least 12 weeks prior to developing (or prior to the detection of (for example by a healthcare provider)) symptoms indicative of the neurological condition. In certain embodiments, for example, at least a portion of the data set may be derived from biospecimens from the subject subsequent to developing (or subsequent to the detection of (for example by a healthcare provider)) symptoms indicative of the neurological condition, for example at least 5 minutes subsequent to, at least 15 minutes subsequent to, at least 30 minutes subsequent to, at least 45 minutes subsequent to, at least 1 hour subsequent to, at least 2 hours subsequent to, at least 4 hours subsequent to, at least 6 hours subsequent to, at least 12 hours subsequent to, at least 24 hours subsequent to, at least 48 hours subsequent to, at least 72 hours subsequent to, at least 96 hours subsequent to, at least 1 week subsequent to, at least 2 weeks subsequent to, at least 3 weeks subsequent to, at least 4 weeks subsequent to, at least 5 weeks subsequent to, at least 6 weeks subsequent to, at least 8 weeks subsequent to, or at least 12 weeks subsequent to developing (or subsequent to the detection of (for example by a healthcare provider)) symptoms indicative of the neurological condition.

In certain embodiments, for example, the classification model may be at least partially characterized by an ROC curve. In certain embodiments, for example, the ROC curve may provide one or more parameters to evaluate the sensitivity and specificity of the results of the methods, tests, protocol, assays, kits, and/or systems for detecting, diagnosing, distinguishing, and/or excluding a neurological condition. In certain embodiments, for example, the classification model may be calibrated to determine the at least one threshold value at least based a preselected true positive rate (i.e., sensitivity) and/or a preselected false positive rate (i.e., 1-specificity). In certain embodiments, for example, the preselected true positive rate and/or preselected false positive rate may be selected from a point on the ROC curve. In certain embodiments, for example, the at least one threshold value may provide a true positive rate (for example a true positive rate measured from the ROC curve) of at least 60%, for example at least 65%, at least 70%, at least 75%, at least 80%, at least 85%, at least 90%, at least 95%, or the at least one threshold value may provide a true positive rate of 100%. In certain embodiments, for example, the at least one threshold value may provide a true positive rate of between 60% and 100%, for example between 60% and 95%, between 70% and 95%, between 70% and 90%, or at least one threshold value may provide a true positive rate of between 80% and 95%. In certain embodiments, for example, the at least one threshold value may provide a false positive rate (for example a false positive rate measured from the ROC curve) of less than 60%, for example less than 50%, less than 40%, less than 30%, less than 20%, or the at least one threshold value may provide a false positive rate of less than 10%. In certain embodiments, for example, the at least one threshold value may provide a false positive rate of between 10% and 80%, for example between 10% and 50%, between 10% and 40%, between 10% and 30%, between 20% and 50%, or the at least one threshold value may provide a false positive rate of between 20% and 40%. In certain embodiments, for example, the at least one threshold value may provide a true positive rate of at least 60% at a false positive rate of less than 20%, for example a true positive rate of at least 65% at a false positive rate of less than 20%, a true positive rate of at least 70% at a false positive rate of less than 20%, a true positive rate of at least 75% at a false positive rate of less than 20%, a true positive rate of at least 80% at a false positive rate of less than 20%, a true positive rate of at least 85% at a false positive rate of less than 20%, or the at least one threshold value may provide a true positive rate of at least a true positive rate of at least 90% at a false positive rate of less than 20%. In certain embodiments, for example, the at least one threshold value may provide a true positive rate of at least 60% at a false positive rate of less than 30%, for example a true positive rate of at least 65% at a false positive rate of less than 30%, a true positive rate of at least 70% at a false positive rate of less than 30%, a true positive rate of at least 75% at a false positive rate of less than 30%, a true positive rate of at least 80% at a false positive rate of less than 30%, a true positive rate of at least 85% at a false positive rate of less than 30%, or the at least one threshold value may provide a true positive rate of at least a true positive rate of at least 90% at a false positive rate of less than 30%. In certain embodiments, for example, the at least one threshold value may provide a true positive rate of at least 60% at a false positive rate of less than 50%, for example a true positive rate of at least 65% at a false positive rate of less than 50%, a true positive rate of at least 70% at a false positive rate of less than 50%, a true positive rate of at least 75% at a false positive rate of less than 50%, a true positive rate of at least 80% at a false positive rate of less than 50%, a true positive rate of at least 85% at a false positive rate of less than 50%, or the at least one threshold value may provide a true positive rate of at least a true positive rate of at least 90% at a false positive rate of less than 50%.

In certain embodiments, for example, the ROC curve may have an AUC of at least 0.95, for example at least 0.50, at least 0.55, at least 0.60, at least 0.65, at least 0.70, at least 0.75, at least 0.80, at least 0.85, at least 0.875, at least 0.90, or the ROC curve may have an AUC of at least 0.925. In certain embodiments, for example, the ROC curve may have an AUC of between 0.6 and 0.95, for example between 0.65 and 0.9, between 0.65 and 0.85, between 0.7 and 0.9, or the ROC curve may have an AUC of between 0.7 and 0.85.

Certain embodiments may provide, for example, methods, tests, assays, kits, or systems to quantify abnormally high (or abnormally depressed) levels of a plurality of biomarkers (for example a panel of biomarkers) indicative of a neurological condition in a subject. In certain embodiments, for example, the one or more biomarkers may be obtained from physiological fluid (for example from a sample of venous or capillary blood). In certain embodiments, for example, the physiological fluid may be limited to a single sample (for example a single sample of blood obtained from the subject proximate the neurological condition). In certain embodiments, for example, the physiological fluid may be at least 2 months old (for example between 2 months and 5 years old). In certain embodiments, for example, the methods, tests, assays, kits, or systems may comprise detecting at least one of the one or more biomarkers at a molar concentration of less than 1 pmol/L. In certain embodiments, for example, concentrations of the plurality of biomarkers may be determined in a series of assays performed on samples of physiological fluids taken from the subject at different times. In certain embodiments, for example, results from the series of assays may be used for diagnosis, prognosis, or monitoring to determine whether a condition resulting from the neurological condition may be improving or worsening.

Any of the methods, tests, assays, kits, or systems disclosed herein may comprise preparing one or more calibration curves to convert an assay result (for example signal readings or average exposed bead measurements) for one or more biomarkers into a measure of concentration of the one or more biomarkers (for example a concentration expressed as pg/mL or pmole/L). In certain embodiments, for example, the one or more calibration curves may comprise a plurality (for example a series) of calibration curves for a multiplex assay (for example a multiplex assay configured to quantify concentrations of a panel of biomarkers, such as a panel of biomarkers indicative of a neurological condition in a subject when present in a venous blood sample obtained from the subject). In certain embodiments, for example, a series of multi-constituent calibrators having known concentrations of multiple biomarkers may be prepared in a solution and assayed, and the resulting assay results correlated (for example by linear or nonlinear regression) to the known concentrations to obtain a calibration curve for each biomarker of the multiple biomarkers.

In certain embodiments, for example, the multi-constituent calibrators may comprise known (for example predetermined) concentrations of one or more (for example all) of NF-L, GFAP, UCH L1, and Tau. In certain embodiments, for example, the multi-constituent calibrators may comprise predetermined concentrations of one or more of purified NF-L, purified Tau, purified GFAP antigen, and purified UCH L1. In certain embodiments, for example, the predetermined concentrations may be between 0.01% and 20%, for example between 0.05% and 15%, or the predetermined concentrations may be at a concentration of between 0.1% and 10% (for example purified NF-L at a concentration of 0.1-10%, purified Tau at a concentration of 0.1-10%, purified GFAP at a concentration of 0.1-10%, and/or or purified UCH L1 at a concentration of 0.1-10%).

In certain embodiments, for example, the biomarker concentrations in the series of multi-constituent calibrators may be selected based on experimental design principles. In certain embodiments, for example, the biomarker concentrations in the series of multi-constituent calibrators may be selected based on an experimental design comprising an orthogonal experimental design. In certain embodiments, for example, the biomarker concentrations in the series of multi-constituent calibrators may be selected based on an experimental design comprising a principal components analysis. In certain embodiments, for example, the biomarker concentrations in the series of multi-constituent calibrators may be selected based on an experimental design comprising a randomized experimental design. In certain embodiments, for example, the biomarker concentrations in the series of multi-constituent calibrators may be selected based on an experimental design comprising a factorial experimental design. In certain embodiments, for example, the biomarker concentrations in the series of multi-constituent calibrators may be selected based on an experimental design comprising a response surface methodology. In certain embodiments, for example, the biomarker concentrations in the series of multi-constituent calibrators may be selected based on an experimental design comprising an optimal experimental design. In certain embodiments, for example, the biomarker concentrations in the series of multi-constituent calibrators may be selected based on known cross-reactivities between one or more of the biomarkers and one or more capture agents for the one or more biomarkers.

In certain embodiments, for example, the series of multi-constituent calibrators may comprise one or more (for example all) of compositions A-H (concentrations expressed as pg/mL):

| Composition | NF-L | GFAP | UCH L1 | Tau |
|---|---|---|---|---|
| A | 0 | 0 | 0 | 0 |
| B | 0.25-0.75 | 0.5-1.5 | 5-15 | 0.05-0.15 |
| C | 1.25-1.75 | 2-5 | 20-40 | 0.2-0.4 |
| D | 4-6 | 6-15 | 75-125 | 0.5-1.5 |
| E | 10-20 | 20-40 | 250-350 | 2-5 |
| F | 25-75 | 75-125 | 800-1200 | 8-12 |
| G | 100-200 | 250-350 | 2000-4000 | 20-40 |
| H | 400-500 | 800-1100 | 8000-10000 | 70-100 |

In certain embodiments, for example, the series of multi-constituent calibrators may comprise one or more (for example all) of compositions I-P (concentrations expressed as pg/mL):

| Composition | NF-L | GFAP | UCH L1 | Tau |
|---|---|---|---|---|
| I | 0 | 0 | 0 | 0 |
| J | 0.25-0.75 | 0.5-1.5 | 5-15 | 0.05-0.15 |
| K | 1.25-1.75 | 2-5 | 20-40 | 0.2-0.4 |
| L | 4-6 | 6-15 | 75-125 | 0.5-1.5 |
| M | 10-20 | 20-40 | 250-350 | 2-5 |
| N | 25-75 | 75-125 | 800-1200 | 8-12 |
| O | 100-200 | 250-350 | 2000-4000 | 20-40 |
| P | 400-500 | 800-1100 | 8000-10000 | 70-100 |

In certain embodiments, for example, the series of multi-constituent calibrators may comprise one or more (for example all) of compositions Q-X (concentrations expressed as pg/mL):

| Composition | NF-L | GFAP | UCH L1 | Tau |
|---|---|---|---|---|
| Q | 0 | 0 | 0 | 0 |
| R | 0.25-0.75 | 0.5-1.5 | 0 | 0.05-0.15 |
| S | 1.25-1.75 | 2-5 | 0 | 0.2-0.4 |
| T | 4-6 | 6-15 | 0 | 0.5-1.5 |
| U | 10-20 | 20-40 | 0 | 2-5 |
| V | 25-75 | 75-125 | 0 | 8-12 |
| W | 100-200 | 250-350 | 0 | 20-40 |
| X | 400-500 | 800-1100 | 0 | 70-100 |

In certain embodiments, for example, the series of multi-constituent calibrators may comprise one or more (for example all) of compositions Y-AF (concentrations expressed as pg/mL):

| Composition | NF-L | GFAP | UCH L1 | Tau |
|---|---|---|---|---|
| Y | 0 | 0 | 0 | 0 |
| Z | 0 | 0.5-1.5 | 0 | 0.05-0.15 |
| AA | 0 | 2-5 | 0 | 0.2-0.4 |
| AB | 0 | 6-15 | 0 | 0.5-1.5 |
| AC | 0 | 20-40 | 0 | 2-5 |
| AD | 0 | 75-125 | 0 | 8-12 |
| AE | 0 | 250-350 | 0 | 20-40 |
| AF | 0 | 800-1100 | 0 | 70-100 |

In certain embodiments, for example, the series of multi-constituent calibrators may comprise one or more (for example all) of compositions AG-AN (concentrations expressed as pg/mL):

| Composition | NF-L | GFAP | UCH L1 | Tau |
|---|---|---|---|---|
| AG | 0 | 0 | 0 | 0 |
| AH | 0.5 | 1 | 10 | 0.1 |
| AI | 1.5 | 3 | 30 | 0.3 |
| AJ | 5 | 10 | 100 | 1 |
| AK | 15 | 30 | 300 | 3 |
| AL | 50 | 100 | 1000 | 10 |
| AM | 150 | 300 | 3000 | 30 |
| AN | 450 | 900 | 9000 | 90 |

In certain embodiments, for example, the series of multi-constituent calibrators may comprise one or more (for example all) of compositions AO-AV (concentrations expressed as pg/mL):

| Composition | NF-L | GFAP | UCH L1 | Tau |
|---|---|---|---|---|
| AO | 0 | 0 | 0 | 0 |
| AP | 0.5 | 1 | 10 | 0.1 |
| AQ | 1.5 | 3 | 30 | 0.3 |
| AR | 5 | 10 | 100 | 1 |
| AS | 15 | 30 | 300 | 3 |
| AT | 50 | 100 | 1000 | 10 |
| AU | 150 | 300 | 3000 | 30 |
| AV | 450 | 900 | 9000 | 90 |

In certain embodiments, for example, the series of multi-constituent calibrators may comprise one or more (for example all) of compositions AW-BD:

| Composition | NF-L | GFAP | UCH L1 | Tau |
|---|---|---|---|---|
| AW | 0 | 0 | 0 | 0 |
| AX | 0.5 | 1 | 0 | 0.1 |
| AY | 1.5 | 3 | 0 | 0.3 |
| AZ | 5 | 10 | 0 | 1 |
| BA | 15 | 30 | 0 | 3 |
| BB | 50 | 100 | 0 | 10 |
| BC | 150 | 300 | 0 | 30 |
| BD | 450 | 900 | 0 | 90 |

In certain embodiments, for example, the series of multi-constituent calibrators may comprise one or more (for example all) of compositions BE-BL (concentrations expressed as pg/mL):

| Composition | NF-L | GFAP | UCH L1 | Tau |
|---|---|---|---|---|
| BE | 0 | 0 | 0 | 0 |
| BF | 0 | 1 | 0 | 0.1 |
| BG | 0 | 3 | 0 | 0.3 |
| BH | 0 | 10 | 0 | 1 |
| BI | 0 | 30 | 0 | 3 |
| BJ | 0 | 100 | 0 | 10 |
| BK | 0 | 300 | 0 | 30 |
| BL | 0 | 900 | 0 | 90 |

In certain embodiment, for example, at least one (for example all) of the multi-constituent calibrators may comprise one or more buffers (or a buffering system) (for example phosphate buffer), one or more ions (for example $Na^+$ and $K^+$), one or more ionic salts (for example NaCl and KCl), one or more blocking agents, one or more surfactants, one or more complexing agents (for example ethylenediaminetetraacetic acid (EDTA) or a salt thereof), one or more anti-microbial agents (for example a mixture of 2-methyl-3(2H)-isothiazolone and 5-chloro-2-methyl-3(2H)-isothiazolone), or a combination of two or more of the foregoing.

In certain embodiments, for example, the multi-constituent calibrators may comprise one or more buffers, or a buffering system (for example one or more of the buffers or buffering systems disclosed herein or in one of the INCORPORATED REFERENCES). In certain embodiments, for example, the one or more buffers may be selected from the group consisting of citrate buffers, phosphate buffers, borate buffers, tris(hydroxymethyl)aminomethane (Tris) buffers, barbital buffers, bicarbonates, as well as Good buffers (non-toxic to cells; not absorbed through cell membranes and feature pKa values at or near physiological pH) such as but not limited to N,N'-bis(2-hydroxyethyl)glycine (BICIN), 2-[bis(2-hydroxyethyl)amino]-2-(hydroxymethyl)-1,3-propanediol (BISTRIS), 2-(cyclohexylamino)ethane-2-sulfonic acid (CHES), N-2-(hydroxyethyl)piperazine-N'-2-ethanesulfonic acid (HEPES), N-(2-hydroxyethyl)piperazine-N'-3-propanesulfonic acid (HEPPS), morpholinoethanesulfonic acid (MES), morpholinopropanesulfonic acid (MOPS), piperazine-N, N'-bis(2-ethanesulfonic acid) (PIPES), N-tris(hydroxymethyl)methyl-2-aminoethanesulfonic acid (TES), N-tris(hydroxymethyl)methyl-3-aminopropanesulfonic acid (TAPS), and N-tris(hydroxymethyl)methylglycine (TRICINE), or a combination of two or more of the foregoing. In certain embodiments, for example, the multi-constituent calibrators may comprise a buffering system comprising a combination of buffers. In certain embodiments, for example, the multi-constituent calibrators may contain a phosphate buffer (for example phosphate at a concentration of between 10 mM and 100 mM, such as phosphate at a concentration of between 30 mM and 70 mM, or at a concentration of 50 mM, or sodium phosphate (dibasic) at a concentration of between 0.1% and 20%, such as sodium phosphate (dibasic) at a concentration of between 0.5% and 15%, or at a concentration of between 1% and 10%, and/or potassium phosphate (monobasic) at a concentration of between 0.01% and 10%, such as potassium phosphate (monobasic) at a concentration of between 0.5% and 5% or at a concentration of between 0.1% and 1%).

In certain embodiments, for example, the one or more ions may comprise one or more ions (for example one or more of the ions disclosed herein or in one of the INCORPORATED REFERENCES). In certain embodiments, for example, the one or more ions may be selected from the group consisting of $Li^+$, $Na^+$, $K^+$, $Mg^{2+}$, $Ca^{2+}$, $Cu^{2+}$, $Mn^{2+}$, $Fe^{2+}$, $Fe^{3+}$, $Cl^-$, $Br^-$, carbonate, hydrogen carbonate, hydrogen sulfate, hydrogen sulfite, sulfate, sulfite, monohydrogen phosphate, dihydrogen phosphate, nitrate, nitrite, permanganate, silicate, sulphates, pyrosulphates, pyrophosphates, citrates, cacodylates, or a combination of two or more of the foregoing. In certain embodiments, for example, the one or more ions may comprise $Cl^-$ (for example $Cl^-$ at a concentration of between 100 mM and 200 mM, such as $Cl^-$ at a concentration of between 120 mM and 160 mM, or at a concentration of 141.7 mM). In certain embodiments, for example, the one or more ions may comprise $Na^+$ (for example $Na^+$ at a concentration of between 100 mM and 200 mM, such as $Na^+$ at a concentration of between 120 mM and 160 mM, or at a concentration of 137 mM). In certain embodiments, for example, the one or more ions may comprise $K^+$ (for example $K^+$ at a concentration of between 1 mM and 5 mM, such as $K^+$ at a concentration of between 2 mM and 3 mM, or at a concentration of 2.7 mM). In certain embodiments, for example, the one or more ions may comprise $Mg^{2+}$ (for example $Mg^{2+}$ at a concentration of between 0.1 mM and 5 mM, such as $Mg^{2+}$ at a concentration of between 0.5 mM and 2.5 mM, or at a concentration of 1 mM). In certain embodiments, for example, the one or more ions may comprise phosphate (for example phosphate at a concentration of between 10 mM and 100 mM, such as phosphate at a concentration of between 30 mM and 70 mM, or at a concentration of 50 mM).

In certain embodiments, for example, the ions may form one or more ionic salts (for example one or more of the ionic salts disclosed herein or in one of the INCORPORATED REFERENCES). In certain embodiments, for example, the one or more ionic salts may be selected from the group consisting of KCl, NaCl, $MgCl_2$, $KH_2PO_4$, $K_2HPO_4$, $NaH_2PO_4$, $Na_2HPO_4$, $NaHCO_3$ and other suitable ionic salts. In certain embodiments, for example, the one or more ionic salts may comprise KCl (for example KCl at a concentration of between 1 mM and 5 mM, such as KCl at a concentration of between 2 mM and 3 mM, or at a concentration of 2.7 mM or KCl at a concentration of between 0.001% and 1%, such as KCl at a concentration of between 0.005% and 0.5%, or at a concentration of between 0.01% and 0.1%). In certain embodiments, for example, the one or more ionic salts may comprise NaCl (for example NaCl at a concentration of between 100 mM and 200 mM, such as NaCl at a concentration of between 120 mM and 160 mM, or at a concentration of 137 mM, or NaCl at a concentration of between 0.05% and 20%, such as NaCl at a concentration of between 0.1% and 10%, or at a concentration of 0.5% and 5%). In certain embodiments, for example, the one or more ionic salts may comprise $MgCl_2$ (for example $MgCl_2$ at a concentration of between 0.1 mM and 5 mM, such as $MgCl_2$ at a concentration of between 0.5 mM and 2.5 mM, or at a concentration of 1 mM).

In certain embodiments, for example, the multi-constituent calibrators may comprise one or more surfactants (for example one or more of the surfactants disclosed herein or in one of the INCORPORATED REFERENCES). In certain embodiments, for example, the one or more surfactants may comprise one or more ionic surfactants. In certain embodiments, for example, the one or more surfactants may comprise one or more nonionic surfactants. In certain embodiments, for example, the one or more surfactants may comprise a glycidyl surfactant (for example 10G surfactant (for example 10G surfactant at a concentration of between 0.01% and 1%, or at a concentration of 0.1%)). In certain embodiments, for example, the one or more surfactants may comprise one or more detergents (for example one or more of the detergents disclosed herein or in one of the INCORPORATED REFERENCES). In certain embodiments, for example, the one or more detergents may be selected from the group consisting of nonionic, cationic, anionic and amphoteric forms. In certain embodiments, for example, the one or more detergents may be selected from the group consisting of polyoxyethylene sorbitan alcohol detergents (i.e., the Tween series), polyoxyethylene alcohols such as the non-ionic, non-denaturing detergent sold under the trademark Nonidet™ P-40 or polyoxyethylene ethers such as Triton™ X-100, or a combination of two or more of the foregoing. In certain embodiments, for example, the one or more detergents may comprise Triton™ X-100 (for example Triton™ X-100 at a concentration of between 0.005% and 2% (for example at a concentration of 0.5%), between 0.1% and 1%, or the multi-constituent calibrators may comprise Triton™ X-100 at a concentration of between 0.25% and 0.75%). In certain embodiments, for example, the surfactant may be at a concentration of between 0.005% and 2%, between 0.01% and 1.5%, or at a concentration of between 0.1% and 1%.

In certain embodiments, multi-constituent calibrators may comprise one or more immunoglobulins (or antibodies or fragments thereof) (for example one of the immunoglobulins (or antibodies or fragments thereof) thereof disclosed herein or in one of the INCORPORATED REFERENCES). In certain embodiments, for example, the one or more immunoglobulins may be selected from the classes consisting of IgA, IgD, IgE, IgG, IgM, a sub-class of one or more of the foregoing, or a combination of two of more of the foregoing. In other embodiments, for example, the one or more immunoglobulins may not belong to any particular class. In certain embodiments, for example, the one or more immunoglobulins may contain different heavy-chain constant domains that correspond to the different classes of immunoglobulins, such as alpha, delta, epsilon, gamma, and mu, respectively. In other embodiments, for example, the one or more immunoglobulins may contain heavy-chain constant domains that do not correspond to any particular class of immunoglobulins. In certain embodiments, for example, the one or more immunoglobulins may comprise but may be not limited to an immunoglobulin of any subclasses (isotypes) in the major classes, such as IgG1, IgG2, IgG3, IgG4, IgA1 and IgA2. In certain embodiments, for example, the one or more immunoglobulins may be not of any subclasses (isotypes) in the major classes. In certain embodiments, for example, the one or more immunoglobulins may be of murine, rat, human, bovine, goat, rabbit, or sheep origin. In certain embodiments, for example, the one or more immunoglobulins may comprise a natural immunoglobulin. In certain embodiments, for example, the one or more immunoglobulins may comprise a genetically modified immunoglobulin. In certain embodiments, for example, the genetically modified immunoglobulin may be a chimeric or humanized immunoglobulin. In certain embodiments, for example, the one or more immunoglobulins may be selected from the group consisting of human IgA, human IgD, human IgE, human IgG, human IgM, murine IgA, murine IgD, murine IgE, murine IgG, murine IgM, rat IgA, rat IgD, rat IgE, rat IgG, rat IgM, bovine IgA, bovine IgD, bovine IgE, bovine IgG, bovine IgM, or a combination of two or more of the foregoing. In certain embodiments, for example, the one or more immunoglobulins may comprise human IgG (for example human IgG at a concentration of between 1 mg/mL and 10 mg/mL, of between 3 mg/mL and 7 mg/mL, or at a concentration of 5 mg/mL).

In certain embodiments, for example, the multi-constituent calibrator may comprise one or more blocking agents (for example one or more of the blocking agents disclosed herein or in one of the INCORPORATED REFERENCES). In certain embodiments, for example, the one or more blocking agents may be configured to prevent non-specific binding to one or more assay surfaces, such as a microtiter well surface. In certain embodiments, for example, the one or more blocking agents may be configured to prevent non-specific binding to one or more target analytes (for example NF-L, GFAP, etc.). In certain embodiments, for example, the one or more blocking agents may be configured to prevent non-specific binding to a capture agent or a detection agent (for example the capture agent or detection agent described herein). In certain embodiments, for example, the one or more blocking agents may be selected from the group consisting of detergents (for example Triton™ X-100 and a Tween), BSA, ovalbumin, glucose, other sugars, polyethylene glycol, dextran, lysozyme, and poly L-lysine, or a combination of two or more of the foregoing. In certain embodiments, for example, the one or more blocking agents may comprise BSA (for example BSA at a concentration of between 0.005% and 0.05% (for example 0.02%), between 0.05% and 0.5%, between 0.5% and 1%, between 1% and 5%, or at a concentration of 2%).

In certain embodiments, for example, one of the one or more immunoglobulins (or antibodies) may be a heterophilic interference inhibitor. In certain embodiments, for example, human IgG may be a heterophilic interference inhibitor. In certain embodiments, for example, one of the one or more immunoglobulins (or antibodies) may be a heterophilic interference molecule. In certain embodiments, for example, human IgG may be a heterophilic interference molecule. In certain embodiments, for example, the multi-constituent calibrators may comprise one or more interference molecules (for example one or more of the interference molecules disclosed herein or in one of the INCORPORATED REFERENCES). In certain embodiments, for example, the one or more interference molecules may be selected from the group consisting of HAGA, HAMA, HARA, HASA, rheumatoid factor, or a combination of two or more of the foregoing.

In certain embodiments, for example, the one or more blocking agents may comprise a component that is a heterophilic interference inhibitor when added to a predetermined type of sample (for example a blood sample, urine sample, CSF sample, etc.). In certain embodiments, for example, the heterophilic interference inhibitor may block one or more heterophilic interference molecules from binding to one or more of the analytes disclosed herein, such as NF-L, GFAP, UCH L1 and/or Tau. In certain embodiments, for example, the heterophilic interference inhibitor may block one or more heterophilic interference molecules from binding a capture agent or a detection agent (for example the capture agents or detection agents described herein). In certain embodiments, for example, at least one of the one or more inhibitors may be selected from the group consisting of BSA, protein L, collagen, PEG4000/6000, whole normal animal serum (for example mouse serum, rat serum, goat serum, rabbit serum, sheep serum), an animal based IgG aggregate (for example mouse IgG, rat IgG, rabbit IgG, goat IgG, sheep IgG), and an antibody derived from goat, mouse, rabbit or sheep that recognizes a HAGA, HAMA, HARA, HASA, rheumatoid factor, Superchemiblock™ heterophile blocking agent (Millipore, Billerica, Massachusetts), TRU Block™ (Meridian Bioscience, Memphis, Tennessee), immunoglobulin-inhibiting reagent (IIR; Bioreclamation, Inc., Westbury, New York), heterophile blocking tubes (Scantibodies Laboratory, Santee, California), StabliGuard immunoassay stabilizer (SurModics, Inc., Eden Prairie, Minnesota), one of the blocking agents disclosed in the INCORPORATED REFERENCES, or a combination of two or more of the foregoing. In certain embodiments, for example, the blocking agent may be an interference blocker at a concentration of between 0.001% and 1%, between 0.005% and 0.5%, or at a concentration of between 0.01% and 0.1%.

In certain embodiments, for example, the heterophilic interference inhibitor may comprise an antibody (for example IgG, IgG, IgM, IgE or IgD), for example of animal (for example mouse, rabbit, sheep, goat, donkey, and other suitable animals) origin. In certain embodiments, for example, the antibody may specifically bind and neutralize one or more heterophilic antibodies, one or more rheumatoid factors, or one or more other interference molecules. For example, the attachment of the immunoglobulin to a heterophilic antibody prevents the heterophilic antibody from binding (capturing) an antibody that may be specific for an analyte or a detection antibody. The one or more heterophilic interference inhibitors may be one or more antibodies that may not bind to one or more analytes or one or more affinity antibodies that may be specific for (for example may specifically bind to) the one or more analytes.

In certain embodiments, for example, the one or more binding agents may comprise one or more heterophile antibody blocking agents (for example one or more of the heterophile antibody blocking agents disclosed herein or in one of the INCORPORATED REFERENCES). In certain embodiments, for example, the one or more binding agents may comprise Superchemiblock™ (for example Superchemiblock™ at a concentration of between 10 pg/mL and 100 pg/mL, such as Superchemiblock™ at a concentration of between 30 pg/mL and 70 pg/mL, at a concentration of 50 pg/mL, between 0.005% and 0.05% (for example 0.02%), between 0.05% and 0.5%, between 0.5% and 1%, between 1% and 5%, or at a concentration of 0.05%).

In certain embodiments, for example, the one or more binding agents may comprise one or more human anti-mouse antibody (HAMA) blockers (for example one of the HAMA blockers disclosed herein or in one of the INCORPORATED REFERENCES). In certain embodiments, for example, the one or more HAMA blockers may comprise TRU Block™ (for example TRU Block™ at a concentration of between 1 mcg/mL and 100 mcg/mL, such as TRU Block™ at a concentration of between 5 mcg/mL and 15 mcg/mL, or at a concentration of 10 mcg/mL).

In certain embodiments, for example, the one or more binding agents may bind to one or more interference molecules. In certain embodiments, for example, more than one type of binding agent may bind to the same interference molecule. In certain embodiments, for example, the one or more blocking agents may comprise a first binding agent and a second binding agent. In certain embodiments, for example, the first binding agent and the second binding agent may bind to the same interference molecule. In certain embodiments, for example, the first binding agent and the second binding agent may not bind to the same interference molecule. In certain embodiments, for example, the one or more blocking agents may comprise a plurality (for example 2, 3, 4, 5, 6, 7, 8, 9, 10, or more than 10) of different types of binding agents. In some embodiments, the one or more binding agents may bind to a plurality (for example 2, 3, 4, 5, 6, 7, 8, 9, 10, or more than 10) of different types of interference molecules.

In certain embodiments, for example, the more than one binding agents may be utilized in a one-to-one ratio. For instance, the first binding agent and the second binding agent may present at equal or approximately equal concentrations (for example molar concentrations). In certain embodiments, for example, the more than one binding agents may be present at different concentrations (for example molar concentrations). In certain embodiments, for example, the first binding agent may be present at a concentration that is at least 1 times greater than the concentration of the second binding agent, for example at least 2 times, at least 3 times, at least 4 times, at least 5 times, or the first binding agent may be present at a concentration that is at least 6 times greater than the concentration of the second binding agent. In certain embodiments, for example, the one or more binding agents may be a plurality of binding agents comprising TRU Block™ and Superchemiblock™ (for example TRU Block™ and Superchemiblock™ at a ratio of between 1:1 and 1:10, such as TRU Block™ and Superchemiblock™ at a ratio of between 1:3 and 1:7, or at a ratio of 1:5).

In certain embodiments, for example, the multi-constituent calibrators may comprise one or more sugars (for example one or more of the sugars disclosed herein or in one of the INCORPORATED REFERENCES). In certain embodiments, for example, the one or more sugars may comprise dextrose (for example dextrose at a concentration of between 0.005% and 0.05% (for example at a concentration of 0.02%), between 0.05% and 0.5%, between 0.5% and 1%, between 1% and 5%, or at a concentration of 0.06%).

In certain embodiments, for example, the multi-constituent calibrators may comprise BgG (for example BgG at a concentration of between 0.005% and 0.05% (for example at a concentration of 0.02%), between 0.05% and 0.5%, between 0.5% and 1%, between 1% and 5%, or at a concentration of 0.01%).

In certain embodiments, for example, the multi-constituent calibrators may comprise urea (for example urea at a concentration of between 0.5 mM and 100 mM (for example at a concentration of 10 mM), between 1 mM and 20 mM, between 1 mM and 10 mM, or at a concentration of between 3 mM and 7 mM, or urea at a concentration of between 0.001% and 1% (for example a concentration of 0.05%), between 0.005% and 0.5%, or at a concentration of 0.01%).

In certain embodiments, for example, the multi-constituent calibrators may comprise one or more complexing agents that are capable of forming a complex with a metal ion (for example one of the complexing agents disclosed herein or in one of the INCORPORATED REFERENCES). In certain embodiments, for example, the one or more complexing agents may be selected from the group consisting of EDTA, deferoxamine (DESFERAL), NTA, β-alaninediacetic acid (β-ADA), diethylenetriaminepentaacetic acid (DTPA), diethylenetriaminepentakis-methylenephosphonic acid (DTPMP), nitrilotriacetic acid (NTA), N-bis[2-1,2-dicarboxyethoxy)ethyl]glycine (BCAS), N-bis[2-1,2-dicarboxyethoxy)ethyl]aspartic acid (BCA6), N-(hydroxyethyl)-ethylenediaminetriacetic acid (HEDTA), gluconic acid and tetracis(2-hydroxypropyl)ethylenediamine (THPED), other suitable complexing agents, or a combination of two or more of the foregoing. In certain embodiments, for example, the complexing agent may comprise EDTA or a salt of EDTA (for example EDTA or salt of EDTA at a concentration of between 1 mM and 50 mM, of between 1 mM and 10 mM, or at a concentration of 5 mM, or EDTA or salt of EDTA at a concentration of 0.02-10%, 0.1-5%, or at a concentration of 0.2-2%). In certain embodiments, for example, the salt of EDTA may be sodium edetate or EDTA disodium salt dihydrate.

In certain embodiments, for example, the multi-constituent calibrators may comprise one or more anti-microbial agents (for example one of the anti-microbial agents disclosed herein or in one of the INCORPORATED REFERENCES). In certain embodiments, for example, the one or more anti-microbial agents may be selected from the group consisting of benzalkonium chloride, sodium azide, sodium fluoride, phenoxyethanol, sodium dehydroacetate, chlorobutanol, phenylethanol, 4-chloroxylenol, 1-hydroxypyridine-2-thione, paraben derivatives, glutaraldehyde, formaldehyde, nalidixic acid, sodium-2-pyridinethiol-1-oxide (sold under the trademark Sodium Omadine™), the bactericidal antimicrobial sold under the trademark Triadine™ 3, the bactericidal antimicrobial sold under the trademark Triadine™ 10, combinations of 5-chloro-2-methyl-4-isothiazolin-2-one, 2-methyl-4-isothiazolin-3-one, 5-bromo-5-nitro-1,3-dioxane, derivatives of each of these compounds, or a combination of two or more of the foregoing. In certain embodiments, for example, the one or more anti-microbial agents may be commercially available and selected from the group consisting of reagents comprising aqueous combinations of 5-chloro-2-methyl-4-methyl-4-isothiazolin-2-one and 2-methyl-4-isothiazolin-3-one (Supelco, under the trademark Proclin), for example, the preservative sold under the trademark ProClin™ 150 reagent (Supelco, an aqueous mixture of 1.15% of 5-chloro-2-methyl-4-isothiazolin-3-one and 0.35% of 2-methyl-4-isothiazolin-3-one), the preservative sold under the trademark ProClin™ 300 reagent (Supelco, a mixture of 2.3% of 5-chloro-2-methyl-4-isothiazolin-3-one and 0.7% of 2-methyl-4-isothiazolin-3-one in a solvent consisting of a modified glycol and alkyl carboxylate), the preservative sold under the trademark Proclin™ 5000 reagent (Supelco, 2-methyl-4-isothiazolin-3-one in a dipropylene glycol solvent), the preservative sold under the trademark Bronidox® L reagent (Cognis Corporation, biocide 5-bromo-5-nitro-1,3-dioxane), or a combination of two or more of the foregoing. In certain embodiments, for example, the multi-constituent calibrators may comprise a combination of two or more anti-microbial agents in any ratio effective to combat microbial growth. In certain embodiments, for example, the one or more anti-microbial agents may comprise benzalkonium chloride. In certain embodiments, for example, the one or more anti-microbial agents may comprise ProClin™ 300 (for example ProClin™ 300 at a concentration of between 0.005% and 0.05% (for example at a concentration of 0.02%), between 0.05% and 0.5%, between 0.5% and 1%, between 1% and 5%, or at a concentration of 2%). In certain embodiments, for example, the one or more anti-microbial agents may comprise a mixture of 2-methyl-3(2H)-isothiazolone and 5-chloro-2-methyl-3(2H)-isothiazolone (for example the mixture having a total concentration of between 0.01% and 5%, between 0.05% and 1%, or having a total concentration of between 0.1% and 0.5%).

In certain embodiments, for example, the multi-constituent calibrators may have a pH of between 2.5 and 10 (for example a pH of between 5 and 9, of between 7 and 8, a pH of 7.4, or an approximately neutral pH).

In certain embodiments, for example, the multi-constituent calibrators may comprise phosphate buffered saline, KCl, BSA, 10G Surfactant, TRU Block™, EDTA, and an anti-microbial agent. In certain embodiments, for example, the multi-constituent calibrators may comprise: phosphate buffered saline, KCl at a concentration of between 3 mM and 5 mM, BSA at a concentration of between 1% and 3%, 10G surfactant at a concentration of between 0.05% and 0.15%, TRU Block™ at a concentration of between 5 mcg/mL and 15 mcg/mL, EDTA or salt of EDTA at a concentration of between 3 mM and 7 mM, and an anti-microbial agent, wherein the multi-constituent calibrators may have a pH of between 7 and 8. In certain embodiments, for example, the multi-constituent calibrators may comprise: phosphate buffered saline, KCl at a concentration of 2.7 mM, BSA at a concentration of 2%, 10G surfactant at a concentration of 0.1%, TRU Block™ at a concentration of 10 mcg/mL, EDTA or salt of EDTA at a concentration of 5 mM, and an anti-microbial agent, wherein the multi-constituent calibrators may have a pH of 7.4. In certain embodiments, for example, the multi-constituent calibrators may comprise: phosphate buffered saline, dextrose at a concentration of 0.06%, BSA at a concentration of 0.02%, BgG at a concentration of 0.01%, urea at a concentration of 5 mM, Triton™ X-100 at a concentration of 0.5%, TRU Block™ at a concentration of 10 mcg/mL, Superchemiblock™ at a concentration of 0.05%, and an anti-microbial agent, wherein the multi-constituent calibrators may have a pH of 7.4.

In certain embodiments, for example, the multi-constituent calibrators may comprise water, sodium phosphate (dibasic), potassium phosphate (monobasic), NaCl, KCl, BSA, a surfactant (for example 10G Surfactant), an interference blocker (for example TRU Block™), EDTA disodium salt dihydrate, and an anti-microbial agent (or a mixture of anti-microbial agents). In certain embodiments, for example, the multi-constituent calibrators may comprise: water at a concentration between 90% and 100%, sodium phosphate (dibasic) at a concentration between 1% to 10%, potassium phosphate (monobasic) at a concentration between 0.1% and 1%, NaCl at a concentration between 0.5% and 5%, KCl at a concentration of between 0.01% and 0.1%, BSA at a concentration of between 0.01% and 0.1%, a surfactant at a concentration of between 0.1% and 1%, an interference blocker at a concentration of between 0.01% and 0.1%, EDTA or salt of EDTA at a concentration of between 0.2% and 2%, and an anti-microbial agent at a concentration between 0.1% and 0.5%, wherein the multi-constituent calibrators may have a pH of between 7 and 8.

In certain embodiments, for example, the multi-constituent calibrators may comprise: phosphate, one or more salts (for example NaCl and/or KCl), BSA, 10G Surfactant, and EDTA. In certain embodiments, for example, the multi-constituent calibrators may comprise: 20-200 mM phosphate, 50-250 mM NaCl, 1-5 mM KCl, 0.5-5% BSA, 0.05-0.25% 10G Surfactant, 1-10 mcg/mL TRU block, 0.005-0.25% ProClin™ 300, and 0.5-20 mM EDTA, wherein the multi-constituent calibrators may have a pH of 6-8.5. In certain embodiments, for example, the multi-constituent calibrators may comprise human IgG (for example human IgG at a concentration of 0.5-20 mg/mL (for example a concentration of 5 mg/mL). In certain embodiments, for example, the multi-constituent calibrators may comprise: 50 mM phosphate, 137 mM NaCl, 2.7 mM KCl, 2% BSA, 0.1% 10G Surfactant, 10 mcg/mL TRU Block™, 0.05% ProClin™ 300, and 5 mM EDTA, wherein the multi-constituent calibrators may have a pH of 7.4.

Any of the methods, tests, assays, kits, or systems disclosed herein may comprise a sample diluent configured to dilute the liquid sample into a working range (for example a working range of analyte concentrations or working range of fluid properties of such as viscosity of the diluted liquid sample) for performing an immunoassay. In certain embodiments, for example, the sample diluent may be mixed with the liquid sample to make a diluted liquid sample (for example a 2× dilution, 4× dilution, 8× dilution, 16× dilution, 32× dilution, 64× dilution, or 128× dilution) suitable for analysis. In certain embodiments, for example, the diluent may be an aqueous diluent.

In certain embodiments, for example, the diluent may comprise a plurality of components selected from the group consisting of one or more buffers (or a buffering system), one or more ions, one or more ionic salts, one or more blocking agents, one or more surfactants, one or more complexing agents, and one or more anti-microbial agents. The diluent may contain any of the buffers (or buffer systems), ions, ionic salts, blocking agents, surfactants, complexing agents, immunoglobulins, and/or anti-microbial agents disclosed herein (for example disclosed in the discussion of the multi-component calibrators) or in one of the INCORPORATED REFERENCES.

In certain embodiments, for example, the diluent may comprise one or more immunoglobulins (or antibodies or fragments thereof) (for example one of the immunoglobulins (or antibodies or fragments thereof) thereof disclosed herein or in one of the INCORPORATED REFERENCES). In certain embodiments, for example, the one or more immunoglobulins may be selected from the classes consisting of IgA, IgD, IgE, IgG, IgM, a sub-class of one or more of the foregoing, or a combination of two of more of the foregoing. In other embodiments, for example, the one or more immunoglobulins may not belong to any particular class. In certain embodiments, for example, the one or more immunoglobulins may contain different heavy-chain constant domains that correspond to the different classes of immunoglobulins, such as alpha, delta, epsilon, gamma, and mu, respectively. In other embodiments, for example, the one or more immunoglobulins may contain heavy-chain constant domains that do not correspond to any particular class of immunoglobulins. In certain embodiments, for example, the one or more immunoglobulins may comprise but may be not limited to an immunoglobulin of any subclasses (isotypes) in the major classes, such as IgG1, IgG2, IgG3, IgG4, IgA1 and IgA2. In certain embodiments, for example, the one or more immunoglobulins may be not of any subclasses (isotypes) in the major classes. In certain embodiments, for example, the one or more immunoglobulins may be of murine, rat, human, bovine, goat, rabbit, or sheep origin. In certain embodiments, for example, the one or more immunoglobulins may comprise a natural immunoglobulin. In certain embodiments, for example, the one or more immunoglobulins may comprise a genetically modified immunoglobulin. In certain embodiments, for example, the genetically modified immunoglobulin may be a chimeric or humanized immunoglobulin. In certain embodiments, for example, the one or more immunoglobulins may be selected from the group consisting of human IgA, human IgD, human IgE, human IgG, human IgM, murine IgA, murine IgD, murine IgE, murine IgG, murine IgM, rat IgA, rat IgD, rat IgE, rat IgG, rat IgM, bovine IgA, bovine IgD, bovine IgE, bovine IgG, bovine IgM, or a combination of two or more of the foregoing. In certain embodiments, for example, the one or more immunoglobulins may comprise human IgG (for example human IgG at a concentration of between 1 mg/mL and 10 mg/mL, of between 3 mg/mL and 7 mg/mL, or at a concentration of 5 mg/mL).

In certain embodiments, for example, the diluent may comprise phosphate buffered saline, KCl, BSA, 10G Surfactant, TRU Block™, EDTA, and an anti-microbial agent. In certain embodiments, for example, the diluent may comprise: phosphate buffered saline, KCl at a concentration of between 3 mM and 5 mM, BSA at a concentration of between 1% and 3%, 10G surfactant at a concentration of between 0.05% and 0.15%, TRU Block™ at a concentration of between 5 mcg/mL and 15 mcg/mL, EDTA or salt of EDTA at a concentration of between 3 mM and 7 mM, and an anti-microbial agent, wherein the diluent may have a pH of between 7 and 8. In certain embodiments, for example, the diluent may comprise: phosphate buffered saline, KCl at a concentration of 2.7 mM, BSA at a concentration of 2%, 10G surfactant at a concentration of 0.1%, TRU Block™ at a concentration of 10 mcg/mL, EDTA or salt of EDTA at a concentration of 5 mM, and an anti-microbial agent, wherein the diluent may have a pH of 7.4. In certain embodiments, for example, the diluent may comprise: phosphate buffered saline, dextrose at a concentration of 0.06%, BSA at a concentration of 0.02%, BgG at a concentration of 0.01%, urea at a concentration of 5 mM, Triton™ X-100 at a concentration of 0.5%, TRU Block™ at a concentration of 10 mcg/mL, Superchemiblock™ at a concentration of 0.05%, and an anti-microbial agent, wherein the diluent may have a pH of 7.4.

In certain embodiments, for example, the sample diluent may comprise: phosphate, one or more ionic salts (for example NaCl, KCl, and/or $MgCl_2$), BSA, a sugar (for example dextrose), BgG, urea, Triton™ X-100, TRU Block™, Superchemiblock™ and ProClin™ 300. In certain embodiments, for example, the sample diluent may comprise an IgG (for example a human IgG). In certain embodiments, for example, the sample diluent may comprise: 20-200 mM phosphate, 50-250 mM NaCl, 1-5 mM KCl, 0.005-0.1% BSA, 0.25-5 mM $MgCl_2$, 0.005-0.25% dextrose, 0.001-0.05% BgG, 0.5-10 mM urea, 0.05-2% Triton™ X-100, 1-100 mcg/mL TRU Block™, 1-100 mcg/mL Superchemiblock™, 0.005-0.25% ProClin™ 300, and 0.5-20 mg/mL human IgG, wherein the sample diluent may have a pH of 6-8.5. In certain embodiments, for example, the sample diluent may comprise: 50 mM phosphate, 137 mM NaCl, 2.7 mM KCl, 0.02% BSA, 1 mM $MgCl_2$, 0.06% dextrose, 0.01% BgG, 5 mM urea, 0.5% Triton™ X-100, 10 mcg/mL TRU Block™, 50 mcg/mL Superchemiblock™, and 0.05% ProClin™ 300, wherein the sample diluent may have a pH of 7.4. In certain embodiments, for example, the sample diluent may comprise: 50 mM phosphate, 137 mM NaCl, 2.7 mM KCl, 0.02% BSA, 1 mM $MgCl_2$, 0.06% dextrose, 0.01% BgG, 5 mM urea, 0.5% Triton™ X-100, 10 mcg/mL TRU Block™, 50 mcg/mL Superchemiblock™, 0.05% ProClin™ 300, and 5 mg/mL human IgG, wherein the sample diluent may have a pH of 7.4.

In certain embodiments, for example, (a) the multi-constituent calibrators may comprise: phosphate, one or more salts (for example NaCl and/or KCl), BSA, 10G Surfactant, and EDTA; and (b) the sample diluent may comprise: phosphate, one or more ionic salts (for example NaCl, KCl, and/or $MgCl_2$), BSA, a sugar (for example dextrose), BgG, urea, Triton™ X-100, TRU Block™, Superchemiblock™, ProClin™ 300, and optionally human IgG. In certain embodiments, for example, (a) the multi-constituent calibrators may comprise: 20-200 mM phosphate, 50-250 mM NaCl, 1-5 mM KCl, 0.5-5% BSA, 0.05-0.25% 10G Surfactant, 1-10 mcg/mL TRU block, 0.005-0.25% ProClin™ 300, and 0.5-20 mM EDTA, wherein the multi-constituent calibrators may have a pH of 6-8.5; and (b) the sample diluent may comprise: 20-200 mM phosphate, 50-250 mM NaCl, 1-5 mM KCl, 0.005-0.1% BSA, 0.25-5 mM $MgCl_2$, 0.005-0.25% dextrose, 0.001-0.05% BgG, 0.5-10 mM urea, 0.05-2% Triton™ X-100, 1-100 mcg/mL TRU Block™, 1-100 mcg/mL Superchemiblock™, 0.005-0.25% ProClin™ 300, and optionally 0.5-20 mg/mL human IgG, wherein the sample diluent may have a pH of 6-8.5. In certain embodiments, for example, (a) the multi-constituent calibrators may comprise: 50 mM phosphate, 137 mM NaCl, 2.7 mM KCl, 2% BSA, 0.1% 10G Surfactant, 10 mcg/mL TRU Block™, 0.05% ProClin™ 300, and 5 mM EDTA, wherein the multi-constituent calibrators may have a pH of 7.4; and (b) the sample diluent may comprise: 50 mM phosphate, 137 mM NaCl, 2.7 mM KCl, 0.02% BSA, 1 mM $MgCl_2$, 0.06% dextrose, 0.01% BgG, 5 mM urea, 0.5% Triton™ X-100, 10 mcg/mL TRU Block™, 50 mcg/mL Superchemiblock™, 0.05% ProClin™ 300, and optionally 5 mg/mL human IgG, wherein the sample diluent may have a pH of 7.4.

Any of the methods, tests, assays, kits, or systems disclosed herein may comprise at least one detection reagent configured to selectively bind with an analyte (for example NF-L, GFAP, UCH L1, or Tau) and support detection of a detectable signal (for example through phosphorescence) in an immunoassay. In certain embodiments, for example, the at least one detection reagent may comprise a first detection reagent, a second detection reagent, and a third detection reagent.

In certain embodiments, for example, the first detection reagent may comprise one or more tagged antibodies (for example, an anti-human NF-L mouse IgG antibody, a Tau antibody coupled with biotin, an anti-human UCH L1 mouse IgG antibody and an anti-human GFAP mouse IgG antibody) that specifically binds to an analyte. In certain embodiments, for example, the first detection reagent may comprise an aqueous solution (for example a solution that may contain 90-100% water) containing the one or more tagged antibodies at a concentration of between 0.01% and 1%, between 0.05% and 0.5%, or at a concentration of between 0.01% and 0.1% (for example, an anti-human NF-L mouse IgG antibody, a Tau antibody coupled with biotin, an anti-human UCH L1 mouse IgG antibody and an anti-human GFAP mouse IgG antibody each at a concentration between 0.01% and 0.1%).

In certain embodiments, for example, the first detection reagent may comprise a plurality (for example 2, 3, 4, 5, 6, 7, 8, 9, 10, or more than 10) of components selected from the group consisting of one or more buffers (or a buffering system) (for example phosphate buffer), one or more ions (for example $Na^+$, $K^+$ and/or $Cl^-$ ions), one or more ionic salts (for example NaCl and KCl), one or more complexing agents (for example EDTA disodium salt dehydrate), BSA, one or more blocking agents (for example interference blocker), and one or more anti-microbial agents (for example a mixture of 2-methyl-3(2H)-isothiazolone and 5-chloro-2-methyl-3(2H)-isothiazolone).

In certain embodiments, for example, the first detection reagent may comprise one or more buffers, or a buffering system (for example one or more of the buffers or buffering systems disclosed herein or in one of the INCORPORATED REFERENCES). In certain embodiments, for example, the one or more buffers may be selected from the group consisting of citrate buffers, phosphate buffers, borate buffers, tris(hydroxymethyl)aminomethane (Tris) buffers, barbital buffers, bicarbonates, as well as Good buffers (non-toxic to cells; not absorbed through cell membranes and feature pKa values at or near physiological pH) such as but not limited to N,N'-bis(2-hydroxyethyl)glycine (BIC IN), 2-[bis(2-hydroxyethyl)amino]-2-(hydroxymethyl)-1,3-propanediol (BISTRIS), 2-(cyclohexylamino)ethane-2-sulfonic acid (CHES), N-2-(hydroxyethyl)piperazine-N'-2-ethanesulfonic acid (HEPES), N-(2-hydroxyethyl)piperazine-N'-3-propanesulfonic acid (HEPPS), morpholinoethanesulfonic acid (MES), morpholinopropanesulfonic acid (MOPS), piperazine-N, N'-bis(2-ethanesulfonic acid) (PIPES), N-tris(hydroxymethyl)methyl-2-aminoethanesulfonic acid (TES), N-tris(hydroxymethyl)methyl-3-aminopropanesulfonic acid (TAPS), and N-tris(hydroxymethyl)methylglycine (TRICINE), or a combination of two or more of the foregoing. In certain embodiments, for example, the first detection reagent may comprise a buffering system comprising a combination of buffers. In certain embodiments, for example, the RGP reagent may contain a phosphate buffer (for example phosphate at a concentration of between 10 mM and 100 mM, such as phosphate at a concentration in the range of between 30 mM and 70 mM, or 50 mM, or sodium phosphate (dibasic) at a concentration of between 0.1% and 30%, such as sodium phosphate (dibasic) at a concentration of between 0.5% and 20%, or at a concentration of between 1% and 10%, and potassium phosphate (monobasic) at a concentration of between 0.001% and 1%, such as potassium phosphate (monobasic) at a concentration of between 0.005% and 0.5% or at a concentration of between 0.01% and 0.1%).

In certain embodiments, for example, the first detection reagent may comprise one or more ions (for example one or more of the ions disclosed herein or in one of the INCORPORATED REFERENCES). In certain embodiments, for example, the one or more ions may be selected from the group consisting of $Li^+$, $Na^+$, $K^+$, $Mg^{2+}$, $Ca^{2+}$, $Cu^{2+}$, $Mn^{2+}$, $Fe^{2+}$, $Fe^{3+}$, $NH4^+$, $Cl^-$, $Br^-$, carbonate, hydrogen carbonate, hydrogen sulfate, hydrogen sulfite, sulfate, sulfite, monohydrogen phosphate, dihydrogen phosphate, nitrate, nitrite, permanganate, silicate, sulphates, pyrosulphates, pyrophosphates, citrates, cacodylates and other suitable ions. In certain embodiments, for example, the one or more ions may comprise $Cl^-$ (for example $Cl^-$ at a concentration of between 100 mM and 200 mM, such as $Cl^-$ at a concentration in the range of between 120 mM and 160 mM, or 141.7 mM). In certain embodiments, for example, the one or more ions may comprise $Na^+$ (for example $Na^+$ at a concentration of between 100 mM and 200 mM, such as $Na^+$ at a concentration in the range of between 120 mM and 160 mM, or 137 mM). In certain embodiments, for example, the one or more ions may comprise $K^+$ (for example $K^+$ at a concentration of between 1 mM and 5 mM, such as $K^+$ at a concentration in the range of between 2 mM and 3 mM, or 2.7 mM).

In certain embodiments, for example, the ions may form one or more ionic salts (for example one or more of the ionic salts disclosed herein or in one of the INCORPORATED REFERENCES). In certain embodiments, for example, the one or more ionic salts may be selected from the group consisting of KCl, NaCl, $MgCl_2$, kh2PO4, K2HPO4, NaH2PO4, Na2HPO4, $NaHCO_3$ and other suitable ionic salts. In certain embodiments, for example, the one or more ionic salts may comprise KCl (for example KCl at a concentration of between 1 mM and 5 mM, such as KCl at a concentration in the range of between 2 mM and 3 mM, or 2.7 mM, or KCl at a concentration of 0.001-1%, such as KCl at a concentration of between 0.005% and 0.5%, or at a concentration of between 0.01% and 0.1%). In certain embodiments, for example, the one or more ionic salts may comprise NaCl (for example NaCl at a concentration of between 100 mM and 200 mM, such as NaCl at a concentration in the range of between 120 mM and 160 mM, or 137 mM, or NaCl at a concentration of between 0.01% and 10%, such as NaCl at a concentration of between 0.05% and 5%, or at a concentration of 0.1% and 1%).

In certain embodiments, for example, the first detection reagent may comprise the nonionic surfactant polyol sold under the trademark Pluronic™ F-127 (for example Pluronic™ F-127 at a concentration of 0.001-1%, such as Pluronic™ F-127 at a concentration of between 0.005% and 0.5%, or at a concentration of between 0.01% and 0.1%).

In certain embodiments, for example, the SBG reagent may comprise one or more complexing agents that are capable of forming a complex with a metal ion (for example one of the complexing agents disclosed herein or in one of the INCORPORATED REFERENCES). In certain embodiments, for example, the one or more complexing agents may be selected from the group consisting of EDTA, deferoxamine (DESFERAL), NTA, β-alaninediacetic acid (β-ADA), diethylenetriaminepentaacetic acid (DTPA), diethylenetriaminepentakis-methylenephosphonic acid (DTPMP), nitrilotriacetic acid (NTA), N-bis[2-1,2-dicarboxyethoxy)ethyl]glycine (BCAS), N-bis[2-1,2-dicarboxyethoxy)ethyl]aspartic acid (BCA6), N-(hydroxyethyl)-ethylenediaminetriacetic acid (HEDTA), gluconic acid and tetracis(2-hydroxypropyl)ethylenediamine (THPED), other suitable complexing agents, or a combination of two or more of the foregoing. In certain embodiments, for example, the complexing agent may comprise EDTA or a salt of EDTA (for example EDTA or salt of EDTA at a concentration of between 1 mM and 50 mM, of between 1 mM and 10 mM, or at a concentration of 5 mM, or EDTA or salt of EDTA at a concentration of between 0.01 and 10%, between 0.05% and 5%, or at a concentration of between 0.1% and 1%). In certain embodiments, for example, the salt of EDTA may be EDTA disodium salt dihydrate.

In certain embodiments, for example, the first detection reagent may comprise BSA (for example BSA at a concentration of between 0.1% and 30%, such as BSA at a concentration of between 0.5% and 20%, or at a concentration of between 0.1% and 10%).

In certain embodiments, for example, the first detection reagent may comprise one or more anti-microbial agents (for example one of the anti-microbial agents disclosed herein or in one of the INCORPORATED REFERENCES). In certain embodiments, for example, the one or more anti-microbial agents may be selected from the group consisting of benzalkonium chloride, sodium azide, sodium fluoride, phenoxyethanol, sodium dehydroacetate, chlorobutanol, phenylethanol, 4-chloroxylenol, 1-hydroxypyridine-2-thione, paraben derivatives, glutaraldehyde, formaldehyde, nalidixic acid, sodium-2-pyridinethiol-1-oxide (sodium Omadine™), Triadine™ 3, Triadine™ 10, various combinations of 5-chloro-2-methyl-4-isothiazolin-2-one, 2-methyl-4-isothiazolin-3-one, 5-bromo-5-nitro-1,3-dioxane, derivatives of each of these compounds, or a combination of two or more of the foregoing. In certain embodiments, for example, the one or more anti-microbial agents may be commercially available and selected from the group consisting of reagents comprising aqueous combinations of 5-chloro-2-methyl-4-methyl-4-isothiazolin-2-one and 2-methyl-4-isothiazolin-3-one (Supelco, under the trademark Proclin), for example, Proclin™ 150 reagent (Supelco, an aqueous mixture of 1.15% of 5-chloro-2-methyl-4-isothiazolin-3-one and 0.35% of 2-methyl-4-isothiazolin-3-one), ProClin™ 300 reagent (Supelco, a mixture of 2.3% of 5-chloro-2-methyl-4-isothiazolin-3-one and 0.7% of 2-methyl-4-isothiazolin-3-one in a solvent consisting of a modified glycol and alkyl carboxylate), Proclin™ 5000 reagent (Supelco, 2-methyl-4-isothiazolin-3-one in a dipropylene glycol solvent), Bronidox® L reagent (Cognis Corporation, biocide 5-bromo-5-nitro-1,3-dioxane), or a combination of two or more of the foregoing. In certain embodiments, for example, the first detection reagent may comprise a combination of two or more anti-microbial agents in any ratio effective to combat microbial growth. In certain embodiments, for example, the one or more anti-microbial agents may comprise benzalkonium chloride. In certain embodiments, for example, the one or more anti-microbial agents may comprise ProClin™ 300 reagent (for example ProClin™ 300 reagent at a concentration of between 0.005% and 0.05% (for example 0.02%), between 0.05% and 0.5%, between 0.5% and 1%, between 1% and 5%, or at a concentration of 2%). In certain embodiments, for example, the one or more anti-microbial agents may comprise a mixture of 2-methyl-3(2H)-isothiazolone and 5-chloro-2-methyl-3(2H)-isothiazolone (for example the mixture at a concentration of between 0.01% and 10%, between 0.05% and 5%, or at a concentration of between 0.1% and 1%).

In certain embodiments, for example, the first detection reagent may comprise one or more blocking agents. In certain embodiments, for example, the blocking agent may be an interference blocker at a concentration of between 0.01% and 10%, between 0.05% and 5%, or at a concentration of between 0.1% and 1%.

In certain embodiments, for example, the first detection reagent may comprise water, sodium phosphate (dibasic), potassium phosphate (monobasic), NaCl, KCl, EDTA disodium salt dihydrate, BSA, an interference blocker, an anti-microbial agent (or a mixture of anti-microbial agents), and one or more first detection reagents (for example one or more tagged antibodies that each is specific to an analyte). In certain embodiments, for example, the first detection reagent may comprise: water at a concentration between 90% and 100%, sodium phosphate (dibasic) at a concentration between 1% to 10%, potassium phosphate (monobasic) at a concentration between 0.01% and 0.1%, NaCl at a concentration between 0.1% and 1%, KCl at a concentration of between 0.01% and 0.1%, EDTA disodium salt dihydrate at a concentration of between 0.1% and 1%, BSA at a concentration of between 1% and 10%, interference blocker at a concentration of between 0.1% and 1.0%, an anti-microbial agent at a concentration between 0.1% and 1%, an anti-human NF-L mouse IgG antibody at a concentration between 0.01% and 0.1%), a Tau antibody coupled with biotin at a concentration between 0.01% and 0.1%), an anti-human UCH L1 mouse IgG antibody at a concentration between 0.01% and 0.1%), and an anti-human GFAP mouse IgG antibody at a concentration between 0.01% and 0.1%).

In certain embodiments, for example the second detection reagent may comprise an enzyme conjugate (for example streptavidin-β-galactosidase (SBG)). In certain embodiments, for example, the second detection reagent may comprise an aqueous solution (for example a solution that may contain 90-100% water). In certain embodiments, for example, the second detection reagent may comprise a plurality (for example 2, 3, 4, 5, 6, 7, 8, 9, 10, or more than 10) of components selected from the group consisting of one or more buffers (or a buffering system) (for example phosphate buffer), one or more ions (for example $Na^+$, $K^+$, $Mg^{2+}$ and/or $Cl^-$ ions), one or more ionic salts (for example NaCl, $MgCl_2$ and KCl), one or more complexing agents (for example ethylenediaminetetraacetic acid (EDTA)), BSA, Tween-20, one or more enzyme conjugates (for example SBG) and one or more anti-microbial agents (for example a mixture of 2-methyl-3(2H)-isothiazolone and 5-chloro-2-methyl-3(2H)-isothiazolone).

In certain embodiments, for example, the second detection reagent may comprise one or more buffers, or a buffering system (for example one or more of the buffers or buffering systems disclosed herein or in one of the INCORPORATED REFERENCES). In certain embodiments, for example, the one or more buffers may be selected from the group consisting of citrate buffers, phosphate buffers, borate buffers, tris(hydroxymethyl)aminomethane (Tris) buffers, barbital buffers, bicarbonates, as well as Good buffers (non-toxic to cells; not absorbed through cell membranes and feature pKa values at or near physiological pH) such as but not limited to N,N'-bis(2-hydroxyethyl)glycine (BIC IN), 2-[bis(2-hydroxyethyl)amino]-2-(hydroxymethyl)-1,3-propanediol (BISTRIS), 2-(cyclohexylamino)ethane-2-sulfonic acid (CHES), N-2-(hydroxyethyl)piperazine-N'-2-ethanesulfonic acid (HEPES), N-(2-hydroxyethyl)piperazine-N'-3-propanesulfonic acid (HEPPS), morpholinoethanesulfonic acid (MES), morpholinopropanesulfonic acid (MOPS), piperazine-N, N'-bis(2-ethanesulfonic acid) (PIPES), N-tris(hydroxymethyl)methyl-2-aminoethanesulfonic acid (TES), N-tris(hydroxymethyl)methyl-3-aminopropanesulfonic acid (TAPS), and N-tris(hydroxymethyl)methylglycine (TRICINE), or a combination of two or more of the foregoing. In certain embodiments, for example, the second detection reagent may comprise a buffering system comprising a combination of buffers. In certain embodiments, for example, the RGP reagent may contain a phosphate buffer (for example phosphate at a concentration of between 10 mM and 100 mM, such as phosphate at a concentration in the range of between 30 mM and 70 mM, or 50 mM, or sodium phosphate (dibasic) at a concentration of between 0.1% and 20%, such as sodium phosphate (dibasic) at a concentration of between 0.5% and 10%, or at a concentration of between 1% and 5%, and potassium phosphate (monobasic) at a concentration of between 0.05% and 20%, such as potassium phosphate (monobasic) at a concentration of between 0.1% and 10% or at a concentration of between 0.5% and 2%).

In certain embodiments, for example, the second detection reagent may comprise one or more ions (for example one or more of the ions disclosed herein or in one of the INCORPORATED REFERENCES). In certain embodiments, for example, the one or more ions may be selected from the group consisting of $Li^+$, $Na^+$, $K^+$, $Mg^{2+}$, $Ca^{2+}$, $Cu^{2+}$, $Mn^{2+}$, $Fe^{2+}$, $Fe^{3+}$, $NH4^+$, $Cl^-$, $Br^-$, carbonate, hydrogen carbonate, hydrogen sulfate, hydrogen sulfite, sulfate, sulfite, monohydrogen phosphate, dihydrogen phosphate, nitrate, nitrite, permanganate, silicate, sulphates, pyrosulphates, pyrophosphates, citrates, cacodylates and other suitable ions. In certain embodiments, for example, the one or more ions may comprise $Cl^-$ (for example $Cl^-$ at a concentration of between 100 mM and 200 mM, such as $Cl^-$ at a concentration in the range of between 120 mM and 160 mM, or 141.7 mM). In certain embodiments, for example, the one or more ions may comprise $Na^+$ (for example $Na^+$ at a concentration of between 100 mM and 200 mM, such as $Na^+$ at a concentration in the range of between 120 mM and 160 mM, or 137 mM). In certain embodiments, for example, the one or more ions may comprise $K^+$ (for example $K^+$ at a concentration of between 1 mM and 5 mM, such as $K^+$ at a concentration in the range of between 2 mM and 3 mM, or 2.7 mM).

In certain embodiments, for example, the ions may form one or more ionic salts (for example one or more of the ionic salts disclosed herein or in one of the INCORPORATED REFERENCES). In certain embodiments, for example, the one or more ionic salts may be selected from the group consisting of KCl, NaCl, $MgCl_2$, $KH2PO4$, $K2HPO4$, $NaH2PO4$, $Na2HPO4$, $NaHCO_3$ and other suitable ionic salts. In certain embodiments, for example, the one or more ionic salts may comprise KCl (for example KCl at a concentration of between 1 mM and 5 mM, such as KCl at a concentration in the range of between 2 mM and 3 mM, or 2.7 mM, or KCl at a concentration of 0.01-10%, such as KCl at a concentration of between 0.05% and 5%, or at a concentration of between 0.1% and 1%). In certain embodiments, for example, the one or more ionic salts may comprise NaCl (for example NaCl at a concentration of between 100 mM and 200 mM, such as NaCl at a concentration in the range of between 120 mM and 160 mM, or 137 mM, or NaCl at a concentration of between 0.01% and 10%, such as NaCl at a concentration of between 0.05% and 5%, or at a concentration of 0.1% and 1%). In certain embodiments, for example, the one or more ionic salts may comprise $MgCl_2$ (for example $MgCl_2$ at a concentration of between 0.1 mM and 5 mM, such as $MgCl_2$ at a concentration in the range of between 0.5 mM and 2.5 mM, or 1 mM, or $MgCl_2$ at a concentration of between 0.01% and 10%, such as $MgCl_2$ at a concentration of between 0.05% and 5%, or at a concentration of 0.1% and 1%).

In certain embodiments, for example, the second detection reagent may comprise one or more complexing agents that are capable of forming a complex with a metal ion (for example one of the complexing agents disclosed herein or in one of the INCORPORATED REFERENCES). In certain embodiments, for example, the one or more complexing agents may be selected from the group consisting of EDTA, deferoxamine (DESFERAL), NTA, β-alaninediacetic acid (β-ADA), diethylenetriaminepentaacetic acid (DTPA), diethylenetriaminepentakis-methylenephosphonic acid (DTPMP), nitrilotriacetic acid (NTA), N-bis[2-1,2-dicarboxyethoxy)ethyl]glycine (BCAS), N-bis[2-1,2-dicarboxyethoxy)ethyl]aspartic acid (BCA6), N-(hydroxyethyl)-ethylenediaminetriacetic acid (HEDTA), gluconic acid and tetracis(2-hydroxypropyl)ethylenediamine (THPED), other suitable complexing agents, or a combination of two or more of the foregoing. In certain embodiments, for example, the complexing agent may comprise EDTA or a salt of EDTA (for example EDTA or salt of EDTA at a concentration of between 1 mM and 50 mM, of between 1 mM and 10 mM, or at a concentration of 5 mM, or EDTA or salt of EDTA at a concentration of between 0.01 and 10%, between 0.05% and 5%, or at a concentration of between 0.1% and 1%). In certain embodiments, for example, the salt of EDTA may be EDTA disodium salt dihydrate.

In certain embodiments, for example, the second detection reagent may comprise BSA (for example BSA at a concentration of between 0.1% and 30%, such as BSA at a concentration of between 0.5% and 20%, or at a concentration of between 0.1% and 10%).

In certain embodiments, for example, the second detection reagent may comprise tween 20 (for example tween 20 at a concentration of between 0.01% and 10%, such as tween 20 at a concentration of between 0.05% and 5%, or at a concentration of between 0.1% and 1%).

In certain embodiments, for example, the second detection reagent may comprise one or more enzyme conjugates. In certain embodiments, for example, the enzyme conjugate may be SBG (for example SBG at a concentration of between 0.001% and 1%, such as SBG at a concentration of between 0.005% and 0.5%, or at a concentration of between 0.01% and 0.1%).

In certain embodiments, for example, the second detection reagent may comprise one or more anti-microbial agents (for example one of the anti-microbial agents disclosed herein or in one of the INCORPORATED REFERENCES). In certain embodiments, for example, the one or more anti-microbial agents may be selected from the group consisting of benzalkonium chloride, sodium azide, sodium fluoride, phenoxyethanol, sodium dehydroacetate, chlorobutanol, phenylethanol, 4-chloroxylenol, 1-hydroxypyridine-2-thione, paraben derivatives, glutaraldehyde, formaldehyde, nalidixic acid, sodium-2-pyridinethiol-1-oxide (sodium Omadine™), Triadine™ 3, Triadine™ 10, various combinations of 5-chloro-2-methyl-4-isothiazolin-2-one, 2-methyl-4-isothiazolin-3-one, 5-bromo-5-nitro-1,3-dioxane, derivatives of each of these compounds, or a combination of two or more of the foregoing. In certain embodiments, for example, the one or more anti-microbial agents may be commercially available and selected from the group consisting of reagents comprising aqueous combinations of 5-chloro-2-methyl-4-methyl-4-isothiazolin-2-one and 2-methyl-4-isothiazolin-3-one (Supelco, under the trademark Proclin), for example, Proclin™ 150 reagent (Supelco, an aqueous mixture of 1.15% of 5-chloro-2-methyl-4-isothiazolin-3-one and 0.35% of 2-methyl-4-isothiazolin-3-one), ProClin™ 300 reagent (Supelco, a mixture of 2.3% of 5-chloro-2-methyl-4-isothiazolin-3-one and 0.7% of 2-methyl-4-isothiazolin-3-one in a solvent consisting of a modified glycol and alkyl carboxylate), Proclin™ 5000 reagent (Supelco, 2-methyl-4-isothiazolin-3-one in a dipropylene glycol solvent), Bronidox® L reagent (Cognis Corporation, biocide 5-bromo-5-nitro-1,3-dioxane), or a combination of two or more of the foregoing. In certain embodiments, for example, the RGP reagent may comprise a combination of two or more anti-microbial agents in any ratio effective to combat microbial growth. In certain embodiments, for example, the one or more anti-microbial agents may comprise benzalkonium chloride. In certain embodiments, for example, the one or more anti-microbial agents may comprise ProClin™ 300 reagent (for example ProClin™ 300 reagent at a concentration of between 0.005% and 0.05% (for example 0.02%), between 0.05% and 0.5%, between 0.5% and 1%, between 1% and 5%, or at a concentration of 2%). In certain embodiments, for example, the one or more anti-microbial agents may comprise a mixture of 2-methyl-3(2H)-isothiazolone and 5-chloro-2-methyl-3(2H)-isothiazolone (for example the mixture at a concentration of between 0.01% and 5%, between 0.05% and 2%, or at a concentration of between 0.1% and 1%).

In certain embodiments, for example, the second detection reagent may comprise water, sodium phosphate (dibasic), potassium phosphate (monobasic), NaCl, KCl, EDTA disodium salt dihydrate, BSA, Tween 20, $MgCl_2$, an enzyme conjugate and an anti-microbial agent (or a mixture of anti-microbial agents). In certain embodiments, for example, the second detection reagent may comprise: water at a concentration between 90% and 100%, sodium phosphate (dibasic) at a concentration between 1% and 5%, potassium phosphate (monobasic) at a concentration between 0.5% and 2%, NaCl at a concentration between 0.1% and 1%, KCl at a concentration of between 0.1% and 1%, $MgCl_2$ at a concentration between 0.1% and 1%, EDTA disodium salt dihydrate at a concentration between 0.1% and 1%, BSA at the concentration of between 1% and 10%, tween 20 at a concentration of between 0.1% and 1%, an enzyme conjugate at a concentration of between 0.01% and 0.1%, and an anti-microbial agent at a concentration between 0.1% and 1%.

In certain embodiments, for example the third detection reagent may comprise a fluorogenic enzyme substrate (for example resorufin b-galactopyranoside (RGP)). In certain embodiments, for example, the third detection reagent may comprise aqueous solution (for example a solution that may contain 90-100% water). In certain embodiments, for example, the third detection reagent may comprise a plurality (for example 2, 3, 4, 5, 6, 7, 8, 9, 10, or more than 10)

of components selected from the group consisting of one or more buffers (or a buffering system) (for example phosphate buffer), one or more ions (for example Na⁺, K⁺ and/or Cl⁻ ions), one or more ionic salts (for example NaCl and KCl), Pluronic™ F-127, resorufin b-galactopyranoside, and one or more anti-microbial agents (for example a mixture of 2-methyl-3(2H)-isothiazolone and 5-chloro-2-methyl-3 (2H)-isothiazolone).

In certain embodiments, for example, the third detection reagent may comprise one or more buffers, or a buffering system (for example one or more of the buffers or buffering systems disclosed herein or in one of the INCORPORATED REFERENCES). In certain embodiments, for example, the one or more buffers may be selected from the group consisting of citrate buffers, phosphate buffers, borate buffers, tris(hydroxymethyl)aminomethane (Tris) buffers, barbital buffers, bicarbonates, as well as Good buffers (non-toxic to cells; not absorbed through cell membranes and feature pKa values at or near physiological pH) such as but not limited to N,N'-bis(2-hydroxyethyl)glycine (BIC IN), 2-[bis(2-hydroxyethyl)amino]-2-(hydroxymethyl)-1,3-propanediol (BISTRIS), 2-(cyclohexylamino)ethane-2-sulfonic acid (CHES), N-2-(hydroxyethyl)piperazine-N'-2-ethanesulfonic acid (HEPES), N-(2-hydroxyethyl)piperazine-N'-3-propanesulfonic acid (HEPPS), morpholinoethanesulfonic acid (MES), morpholinopropanesulfonic acid (MOPS), piperazine-N, N'-bis(2-ethanesulfonic acid) (PIPES), N-tris(hydroxymethyl)methyl-2-aminoethanesulfonic acid (TES), N-tris(hydroxymethyl)methyl-3-aminopropanesulfonic acid (TAPS), and N-tris(hydroxymethyl)methylglycine (TRICINE), or a combination of two or more of the foregoing. In certain embodiments, for example, the third detection reagent may comprise a buffering system comprising a combination of buffers. In certain embodiments, for example, the third detection reagent may contain a phosphate buffer (for example phosphate at a concentration of between 10 mM and 100 mM, such as phosphate at a concentration in the range of between 30 mM and 70 mM, or 50 mM, or sodium phosphate (dibasic) at a concentration of between 0.01% and 5%, such as sodium phosphate (dibasic) at a concentration of between 0.05% and 1%, or at a concentration of between 0.1% and 0.5%, and potassium phosphate (monobasic) at a concentration of between 0.001% and 1%, such as potassium phosphate (monobasic) at a concentration of between 0.005% and 0.5% or at a concentration of between 0.01% and 0.1%).

In certain embodiments, for example, the third detection reagent may comprise one or more ions (for example one or more of the ions disclosed herein or in one of the INCORPORATED REFERENCES). In certain embodiments, for example, the one or more ions may be selected from the group consisting of Li⁺, Na⁺, K⁺, Mg2⁺, Ca2⁺, Cu2⁺, Mn2⁺, Fe2⁺, Fe3⁺, NH4⁺, Cl⁻, Br⁻, carbonate, hydrogen carbonate, hydrogen sulfate, hydrogen sulfite, sulfate, sulfite, monohydrogen phosphate, dihydrogen phosphate, nitrate, nitrite, permanganate, silicate, sulphates, pyrosulphates, pyrophosphates, citrates, cacodylates and other suitable ions. In certain embodiments, for example, the one or more ions may comprise Cl⁻ (for example Cl⁻ at a concentration of between 100 mM and 200 mM, such as Cl⁻ at a concentration in the range of between 120 mM and 160 mM, or 141.7 mM). In certain embodiments, for example, the one or more ions may comprise Na⁺ (for example Na⁺ at a concentration of between 100 mM and 200 mM, such as Na⁺ at a concentration in the range of between 120 mM and 160 mM, or 137 mM). In certain embodiments, for example, the one or more ions may comprise K⁺ (for example K⁺ at a concentration of between 1 mM and 5 mM, such as K⁺ at a concentration in the range of between 2 mM and 3 mM, or 2.7 mM)

In certain embodiments, for example, the ions may form one or more ionic salts (for example one or more of the ionic salts disclosed herein or in one of the INCORPORATED REFERENCES). In certain embodiments, for example, the one or more ionic salts may be selected from the group consisting of KCl, NaCl, MgCl₂, KH2PO4, K2HPO4, NaH2PO4, Na2HPO4, NaHCO₃ and other suitable ionic salts. In certain embodiments, for example, the one or more ionic salts may comprise KCl (for example KCl at a concentration of between 1 mM and 5 mM, such as KCl at a concentration in the range of between 2 mM and 3 mM, or 2.7 mM, or KCl at a concentration of 0.001-1%, such as KCl at a concentration of between 0.005% and 0.5%, or at a concentration of between 0.01% and 0.1%). In certain embodiments, for example, the one or more ionic salts may comprise NaCl (for example NaCl at a concentration of between 100 mM and 200 mM, such as NaCl at a concentration in the range of between 120 mM and 160 mM, or 137 mM, or NaCl at a concentration of between 0.01% and 10%, such as NaCl at a concentration of between 0.05% and 5%, or at a concentration of 0.1% and 1%).

In certain embodiments, for example, the third detection reagent may comprise Pluronic™ F-127 (for example Pluronic™ F-127 at a concentration of 0.001-1%, such as Pluronic™ F-127 at a concentration of between 0.005% and 0.5%, or at a concentration of between 0.01% and 0.1%).

In certain embodiments, for example, the third detection reagent may comprise resorufin b-galactopyranoside (for example resorufin b-galactopyranoside at a concentration of 0.0001-0.1%, such as resorufin b-galactopyranoside at a concentration of between 0.0005% and 0.05%, or at a concentration of between 0.001% and 0.01%).

In certain embodiments, for example, the third detection reagent may comprise one or more anti-microbial agents (for example one of the anti-microbial agents disclosed herein or in one of the INCORPORATED REFERENCES). In certain embodiments, for example, the one or more anti-microbial agents may be selected from the group consisting of benzalkonium chloride, sodium azide, sodium fluoride, phenoxyethanol, sodium dehydroacetate, chlorobutanol, phenylethanol, 4-chloroxylenol, 1-hydroxypyridine-2-thione, paraben derivatives, glutaraldehyde, formaldehyde, nalidixic acid, sodium-2-pyridinethiol-1-oxide (sodium Omadine™), Triadine™ 3, Triadine™ 10, various combinations of 5-chloro-2-methyl-4-isothiazolin-2-one, 2-methyl-4-isothiazolin-3-one, 5-bromo-5-nitro-1,3-dioxane, derivatives of each of these compounds, or a combination of two or more of the foregoing. In certain embodiments, for example, the one or more anti-microbial agents may be commercially available and selected from the group consisting of reagents comprising aqueous combinations of 5-chloro-2-methyl-4-methyl-4-isothiazolin-2-one and 2-methyl-4-isothiazolin-3-one (Supelco, under the trademark Proclin), for example, Proclin™ 150 reagent (Supelco, an aqueous mixture of 1.15% of 5-chloro-2-methyl-4-isothiazolin-3-one and 0.35% of 2-methyl-4-isothiazolin-3-one), ProClin™ 300 reagent (Supelco, a mixture of 2.3% of 5-chloro-2-methyl-4-isothiazolin-3-one and 0.7% of 2-methyl-4-isothiazolin-3-one in a solvent consisting of a modified glycol and alkyl carboxylate), Proclin™ 5000 reagent (Supelco, 2-methyl-4-isothiazolin-3-one in a dipropylene glycol solvent), Bronidox® L reagent (Cognis Corporation, biocide 5-bromo-5-nitro-1,3-dioxane), or a combination of two or more of the foregoing. In certain embodiments, for example, the third detection reagent may comprise a combination of two or more anti-microbial agents in any ratio effective to combat microbial growth. In certain embodiments, for example, the one or more anti-microbial agents may comprise benzalkonium chloride. In certain embodiments, for example, the one or more anti-microbial agents may comprise ProClin™ 300 reagent (for example ProClin™ 300 reagent at a concentration of between 0.005% and 0.05% (for example 0.02%), between 0.05% and 0.5%, between 0.5% and 1%, between 1% and 5%, or at a concentration of 2%). In certain embodiments, for example, the one or more anti-microbial agents may comprise a mixture of 2-methyl-3(2H)-isothiazolone and 5-chloro-2-methyl-3(2H)-isothiazolone (for example the mixture at a concentration of between 0.01% and 5%, between 0.05% and 1%, or at a concentration of between 0.1% and 0.5%).

In certain embodiments, for example, the third detection reagent may comprise water, sodium phosphate (dibasic), potassium phosphate (monobasic), NaCl, KCl, Pluronic™ F-127, resorufin b-galactopyranoside and an anti-microbial agent (or a mixture of anti-microbial agents). In certain embodiments, for example, the third detection reagent may comprise: water at a concentration between 90% and 100%, sodium phosphate (dibasic) at a concentration between 0.1% to 0.5%, potassium phosphate (monobasic) at a concentration between 0.01% and 0.1%, NaCl at a concentration between 0.1% and 1%, KCl at a concentration of between 0.01% and 0.1%, Pluronic™ F-127 at a concentration of between 0.01% and 0.1%, resorufin b-galactopyranoside at a concentration of between 0.001% and 0.01%, and an anti-microbial agent at a concentration between 0.1% and 0.5%.

Certain embodiments may provide, for example, methods, tests, assays (for example digital immunoassays), kits, or systems to quantify abnormal levels of one or more biomarkers present in a sample of physiological fluid taken from a subject. In certain embodiments, for example, the physiological fluid may be plasma or serum obtained from a blood sample (for example a venous blood sample). In certain embodiments, for example, the physiological fluid may be taken from a subject following an event (for example an event comprising a medical procedure, or a potentially neurological condition-inducing event). In certain embodiments, for example, the physiological fluid may be taken within 1 week following the event, for example within 36 hours following the event, within 24 hours, within 12 hours, within 11 hours, within 10 hours, within 9 hours, within 8 hours, within 7 hours, within 6 hours, within 5 hours, within 4 hours, within 3 hours, within 2 hours, within 1 hour, within 45 minutes, within 30 minutes, within 15 minutes, within 10 minutes, within 5 minutes, or the physiological fluid may be taken within 1 minute following the event. In certain embodiments, for example, the physiological fluid may be taken after at least 10 minutes following the event, for example at least 30 minutes following the event, at least 1 hour, at least 2 hours, at least 6 hours, at least 8 hours, at least 12 hours, at least 24 hours, at least 3 days, or the physiological fluid may be taken between after at least 7 days following the event. In certain embodiments, for example, the physiological fluid may be taken between 1 hour and 15 days following the event, for example between 1 hour and 2 days following the event, between 1 hour and 12 hours, between 6 hours and 3 days, or the physiological fluid may be taken between 6 hours and 10 days following the event.

In certain embodiments, for example, the methods, tests, assays, kits, or systems may be limited to testing a single liquid sample derived from the sample of physiological fluid. In certain embodiments, for example, the methods, tests, assays, kits, or systems may comprise testing multiple liquid samples derived from multiple samples of physiological fluid (for example samples taken from the subject at spaced time intervals). In certain embodiments, for example, multiple samples of physiological fluid may be taken from a subject at different times during a predetermined time window. In certain embodiments, for example, between 2 and 10 physiological fluid samples (for example between 3 and 5 physiological fluid samples) may be taken from the subject during a time window of less than 20 days, for example during a time window of less than 10 days, less than 7 days, less than 100 hours, less than 48 hours, or less than 24 hours.

In certain embodiments, for example, the sample of physiological fluid may weigh less than 5 gram, for example less than 2 grams, less than 1 gram, less than 0.5 grams, less than 0.25 grams, less than 0.1 grams, less than 0.01 grams, less than 1 mg, less than 100 mcg, less than 10 mcg, less than 1 mcg, less than 0.1 mcg, or the sample of physiological fluid may weigh less than 0.01 mcg.

In certain embodiments, for example, the sample of physiological fluid may be maintained at −80° C., may be maintained (for example stored) at a temperature of between −80° C. and −60° C., for example at a temperature of between −60° C. and −40° C., between −40° C. and −20° C., −20° C. and 0° C., or the sample of physiological fluid may be maintained at a temperature of between 0° C. and 25° C. In certain embodiments, for example, the sample of physiological fluid may be maintained (for example stored) under ambient conditions (for example ambient temperature and/or humidity). In certain embodiments, for example, the sample of physiological fluid may be maintained at a relative humidity of less than 50%. In certain embodiments, for example, the sample of physiological fluid may be stored for at least 1 month, for example for at least 2 months, at least 3 months, at least 6 months, at least 1 year, at least 2 years, between 1 month and 5 years, between 1 month and 3 months, between 1 month and 1 year, between 1 month and 2 years, between 1 month and 3 years, or between 1 month and 4 years. In certain embodiments, for example, the sample of physiological fluid may be stored for at least 4 years, for example at least 5 years or at least 10 years.

In certain embodiments, for example, the methods, tests, assays, kits, or systems may comprise contacting the sample of physiological fluid with a solution containing assay microbeads (for example the contacting may occur in a reaction vessel). In certain embodiments, for example, the solution contacted with the sample of physiological fluid may be incubated for a period of time (for example for at least 30 minutes, at least 1 hour, at least 2 hours, at least 6 hours, at least 12 hours, at least 24 hours, at least 48 hours, between 1 hour and 2 hours, between 1 hour and 6 hours, between 1 hour and 12 hours, or between 12 hours and 48 hours.

Certain embodiments may provide, for example, methods, tests, assays, kits, or systems for testing a liquid sample derived from a sample of physiological fluid (for example to detect a neurological condition). In certain embodiments, for example, the sample of physiological fluid may be at least 1 week old prior to deriving the liquid sample from the sample of physiological fluid, for example at least 2 weeks old, at least 1 month old, at least 2 months old, at least 3 months old, at least 6 months old, at least 12 months old, at least 2 years old, at least 3 years old, at least 4 years old, at least 5 years old, or the sample of physiological fluid may be at least 10 years old prior to deriving the liquid sample from the sample of physiological fluid. In certain embodiments, for example, the sample of physiological fluid may be between 1 month and 20 years old prior to deriving the liquid sample, for example between 1 month and 6 years old, between 2 months and 3 years old, or the sample of physiological fluid may be between 3 years and 10 years old prior to deriving the liquid sample.

In certain embodiments, for example, the methods, tests, assays, kits, or systems may comprise obtaining or quantifying at least one parameter for at least one biomarker in the liquid sample. In certain embodiments, for example, the at least one biomarker may be a protein biomarker. In certain embodiments, for example, the at least one biomarker may be a phosphorylated protein biomarker. In certain embodiments, for example, the at least one biomarker may comprise a neurofilament. In certain embodiments, for example, the neurofilament may be a type IV intermediate filaments or heteropolymers. In certain embodiments, for example, the neurofilament may be selected from the group consisting of neurofilament heavy chain (NF-H), neurofilament medium chain (NF-M), NF-L, α-internexin, and peripherin. In certain embodiments, for example, the at least one biomarker may comprise NF-L. In certain embodiments, for example, the at least one biomarker may comprise GFAP. In certain embodiments, for example, the at least one biomarker may comprise UCH L1. In certain embodiments, for example, the at least one biomarker may comprise a tau protein (Tau), for example one isoform of tau protein, 2 isoforms of tau protein, 3 isoforms of tau protein, 4 isoforms of tau protein, 5 isoforms of tau protein, 6 isoforms of tau protein, or a phosphorylated tau protein (for example p-tau-181 or p-tau-231). In certain embodiments, for example, the tau protein may be tau 23. In certain embodiments, for example, the tau protein may be tau 24. In certain embodiments, for example, the tau protein may be tau 37. In certain embodiments, for example, the tau protein may be tau 34. In certain embodiments, for example, the tau protein may be tau 39. In certain embodiments, for example, the tau protein may be tau 40. In certain embodiments, for example, the tau protein may be phosphorylated. In certain embodiments, for example, the at least one biomarker may comprise a protein derived from amyloid beta precursor protein (for example a proteolytic product of amyloid beta precursor protein). In certain embodiments, for example, the at least one biomarker may comprise Amyloid beta 40 (A beta 40). In certain embodiments, for example, the at least one biomarker may comprise Amyloid beta 42 (A beta 42). In certain embodiments, for example, the at least one biomarker may comprise S100 calcium-binding protein B (S100B). In certain embodiments, for example, the at least one biomarker may comprise Neuron-specific enolase (NSE). In certain embodiments, for example, the at least one biomarker may comprise β-site aPP-cleaving enzyme 1 (BACe1). In certain embodiments, for example, the at least one biomarker may comprise myelin basic protein (MBP). In certain embodiments, for example, the at least one biomarker may comprise growth associated protein 43. In certain embodiments, for example, the at least one biomarker may comprise glutamine synthetase. In certain embodiments, for example, the at least one biomarker may comprise a glycine transporter (for example at least one of GLYT1 and GLYT2). In certain embodiments, for example, the at least one biomarker may comprise a neuron specific glycoprotein (for example GP50). In certain embodiments, for example, the at least one biomarker may comprise calpain. In certain embodiments, for example, the at least one biomarker may comprise heat shock protein 72. In certain embodiments, for example, the at least one biomarker may comprise a beta-amyloid precursor protein. In certain embodiments, for example, the at least one biomarker may comprise calbindin D-28K. In certain embodiments, for example, the at least one biomarker may comprise a proteolipid protein. In certain embodiments, for example, the at least one biomarker may comprise a myelin associated glycoprotein. In certain embodiments, for example, the at least one biomarker may comprise a creatine kinase protein (for example CK-BB). In certain embodiments, for example, the at least one biomarker may comprise an endothelium membrane protein (for example thrombomodulin).

In certain embodiments, for example, the at least one parameter may be determined from measurements for a selected number and combination of biomarkers associated with a neurological condition. In certain embodiments, for example, the measurements may comprise concentrations of at least 2 biomarkers (for example 2 biomarkers, 3 biomarkers, 4 biomarkers, 5 biomarkers, 6 biomarkers, 7 biomarkers, 8 biomarkers, 9 biomarkers, 10 biomarkers, or more than 10 biomarkers). In certain embodiments, for example, the at least 2 biomarkers may be selected from the group consisting of NF-L, GFAP, UCH L1, and Tau. In certain embodiments, for example, the measurements may comprise concentrations of at least 3 biomarkers. In certain embodiments, for example, the at least 3 biomarkers may be selected from the group consisting of NF-L, GFAP, UCH L1, and Tau. In certain embodiments, for example, the measurements may comprise concentrations of at least 4 biomarkers. In certain embodiments, for example, the at least 4 biomarkers may be selected from the group consisting of NF-L, GFAP, UCH L1, and Tau. In certain embodiments, for example, the measurements may comprise concentrations of at least 5 biomarkers. In certain embodiments, for example, the at least 5 biomarkers may be selected from the group consisting of NF-L, GFAP, UCH L1, and Tau. In certain embodiments, for example, the measurements may comprise concentrations of at least 6 biomarkers. In certain embodiments, for example, the at least 2 biomarkers may be selected from the group consisting of NF-L, GFAP, UCH L1, and Tau. In certain embodiments, for example, the measurements may comprise a concentration of NF-L and a concentration of at least one additional biomarker (for example concentrations of 2 additional biomarkers, 3 additional biomarkers, 4 additional biomarkers, 5 additional biomarkers, 6 additional biomarkers, 7 additional biomarkers, 8 additional biomarkers, 9 additional biomarkers, 10 additional biomarkers, or more than 10 additional biomarkers) selected from the group consisting of GFAP, UCH L1, and Tau. In certain embodiments, for example, the measurements may comprise concentrations of from 2 to 10 biomarkers, for example concentrations of from 2 to 8 biomarkers, from 2 to 5 biomarkers, or the measurements may comprise concentrations of from 2 to 4 biomarkers.

In certain embodiments, for example, the at least one biomarker indicative of the neurological condition may be indicative of the neurological condition at a concentration in the liquid sample of less than 1000 pg/mL, for example less than 100 pg/mL, less than 10 pg/mL, less than 1 pg/mL, less than 0.1 pg/mL, less than 0.01 pg/mL, or the at least one biomarker may be indicative of the neurological condition at a molar concentration in the liquid sample of less than 0.001 pg/mL. In certain embodiments, for example, the at least one biomarker may be indicative of the neurological condition at a concentration in the liquid sample of between 0.001 pg/mL and 0.1 pg/mL. In certain embodiments, for example, the at least one biomarker may be indicative of the neurological condition at a concentration in the liquid sample of between 0.1 pg/mL and 10 pg/mL. In certain embodiments, for example, the at least one biomarker may be indicative of the neurological condition at a concentration in the liquid sample of between 1 pg/mL and 100 pg/mL. In certain embodiments, for example, the at least one biomarker may be indicative of the neurological condition at a concentration in the liquid sample of between 10 pg/mL and 1000 pg/mL.

In certain embodiments, for example, NF-L may be indicative of the neurological condition at a concentration in the liquid sample of less than 1000 pg/mL, for example less than 100 pg/mL, less than 10 pg/mL, less than 1 pg/mL, less than 0.1 pg/mL, less than 0.01 pg/mL, or NF-L may be indicative of the neurological condition at a molar concentration in the liquid sample of less than 0.001 pg/mL. In certain embodiments, for example, NF-L may be indicative of the neurological condition at a concentration in the liquid sample of between 0.001 pg/mL and 0.1 pg/mL. In certain embodiments, for example, NF-L may be indicative of the neurological condition at a concentration in the liquid sample of between 0.1 pg/mL and 10 pg/mL. In certain embodiments, for example, NF-L may be indicative of the neurological condition at a concentration in the liquid sample of between 1 pg/mL and 100 pg/mL. In certain embodiments, for example, NF-L may be indicative of the neurological condition at a concentration in the liquid sample of between 10 pg/mL and 1000 pg/mL.

In certain embodiments, for example, GFAP may be indicative of a neurological condition at a concentration in the liquid sample of less than 1000 pg/mL, for example less than 100 pg/mL, less than 10 pg/mL, less than 1 pg/mL, less than 0.1 pg/mL, less than 0.01 pg/mL, or GFAP may be indicative of the neurological condition at a molar concentration in the liquid sample of less than 0.001 pg/mL. In certain embodiments, for example, GFAP may be indicative of the neurological condition at a concentration in the liquid sample of between 0.001 pg/mL and 0.1 pg/mL. In certain embodiments, for example, GFAP may be indicative of the neurological condition at a concentration in the liquid sample of between 0.1 pg/mL and 10 pg/mL. In certain embodiments, for example, GFAP may be indicative of the neurological condition at a concentration in the liquid sample of between 1 pg/mL and 100 pg/mL. In certain embodiments, for example, GFAP may be indicative of the neurological condition at a concentration in the liquid sample of between 10 pg/mL and 1000 pg/mL.

In certain embodiments, for example, UCH L1 may be indicative of the neurological condition at a concentration in the liquid sample of less than 1000 pg/mL, for example less than 100 pg/mL, less than 10 pg/mL, less than 1 pg/mL, less than 0.1 pg/mL, less than 0.01 pg/mL, or UCH L1 may be indicative of the neurological condition at a molar concentration in the liquid sample of less than 0.001 pg/mL. In certain embodiments, for example, UCH L1 may be indicative of the neurological condition at a concentration in the liquid sample of between 0.001 pg/mL and 0.1 pg/mL. In certain embodiments, for example, UCH L1 may be indicative of the neurological condition at a concentration in the liquid sample of between 0.1 pg/mL and 10 pg/mL. In certain embodiments, for example, UCH L1 may be indicative of the neurological condition at a concentration in the liquid sample of between 1 pg/mL and 100 pg/mL. In certain embodiments, for example, UCH L1 may be indicative of the neurological condition at a concentration in the liquid sample of between 10 pg/mL and 1000 pg/mL.

In certain embodiments, for example, tau protein may be indicative of the neurological condition at a concentration in the liquid sample of less than 1000 pg/mL, for example less than 100 pg/mL, less than 10 pg/mL, less than 1 pg/mL, less than 0.1 pg/mL, less than 0.01 pg/mL, or tau protein may be indicative of the neurological condition at a molar concentration in the liquid sample of less than 0.001 pg/mL. In certain embodiments, for example, tau protein may be indicative of the neurological condition at a concentration in the liquid sample of between 0.001 pg/mL and 0.1 pg/mL. In certain embodiments, for example, tau protein may be indicative of the neurological condition at a concentration in the liquid sample of between 0.1 pg/mL and 10 pg/mL. In certain embodiments, for example, tau protein may be indicative of the neurological condition at a concentration in the liquid sample of between 1 pg/mL and 100 pg/mL. In certain embodiments, for example, tau protein may be indicative of the neurological condition at a concentration in the liquid sample of between 10 pg/mL and 1000 pg/mL.

In certain embodiments, for example, A beta 40 may be indicative of the neurological condition at a concentration in the liquid sample of less than 1000 pg/mL, for example less than 100 pg/mL, less than 10 pg/mL, less than 1 pg/mL, less than 0.1 pg/mL, less than 0.01 pg/mL, or A beta 40 may be indicative of the neurological condition at a molar concentration in the liquid sample of less than 0.001 pg/mL. In certain embodiments, for example, A beta 40 may be indicative of the neurological condition at a concentration in the liquid sample of between 0.001 pg/mL and 0.1 pg/mL. In certain embodiments, for example, A beta 40 may be indicative of the neurological condition at a concentration in the liquid sample of between 0.1 pg/mL and 10 pg/mL. In certain embodiments, for example, A beta 40 may be indicative of the neurological condition at a concentration in the liquid sample of between 1 pg/mL and 100 pg/mL. In certain embodiments, for example, A beta 40 may be indicative of the neurological condition at a concentration in the liquid sample of between 10 pg/mL and 1000 pg/mL.

In certain embodiments, for example, A beta 42 may be indicative of the neurological condition at a concentration in the liquid sample of less than 1000 pg/mL, for example less than 100 pg/mL, less than 10 pg/mL, less than 1 pg/mL, less than 0.1 pg/mL, less than 0.01 pg/mL, or A beta 42 may be indicative of the neurological condition at a molar concentration in the liquid sample of less than 0.001 pg/mL. In certain embodiments, for example, A beta 42 may be indicative of the neurological condition at a concentration in the liquid sample of between 0.001 pg/mL and 0.1 pg/mL. In certain embodiments, for example, A beta 42 may be indicative of the neurological condition at a concentration in the liquid sample of between 0.1 pg/mL and 10 pg/mL. In certain embodiments, for example, A beta 42 may be indicative of the neurological condition at a concentration in the liquid sample of between 1 pg/mL and 100 pg/mL. In certain embodiments, for example, A beta 42 may be indicative of the neurological condition at a concentration in the liquid sample of between 10 pg/mL and 1000 pg/mL.

In certain embodiments, for example, S100B may be indicative of the neurological condition at a concentration in the liquid sample of less than 1000 pg/mL, for example less than 100 pg/mL, less than 10 pg/mL, less than 1 pg/mL, less than 0.1 pg/mL, less than 0.01 pg/mL, or S100B may be indicative of the neurological condition at a molar concentration in the liquid sample of less than 0.001 pg/mL. In certain embodiments, for example, S100B may be indicative of the neurological condition at a concentration in the liquid sample of between 0.001 pg/mL and 0.1 pg/mL. In certain embodiments, for example, S100B may be indicative of the neurological condition at a concentration in the liquid sample of between 0.1 pg/mL and 10 pg/mL. In certain embodiments, for example, S100B may be indicative of the neurological condition at a concentration in the liquid sample of between 1 pg/mL and 100 pg/mL. In certain embodiments, for example, S100B may be indicative of the neurological condition at a concentration in the liquid sample of between 10 pg/mL and 1000 pg/mL.

In certain embodiments, for example, NSE may be indicative of the neurological condition at a concentration in the liquid sample of less than 1000 pg/mL, for example less than 100 pg/mL, less than 10 pg/mL, less than 1 pg/mL, less than 0.1 pg/mL, less than 0.01 pg/mL, or NSE may be indicative of the neurological condition at a molar concentration in the liquid sample of less than 0.001 pg/mL. In certain embodiments, for example, NSE may be indicative of the neurological condition at a concentration in the liquid sample of between 0.001 pg/mL and 0.1 pg/mL. In certain embodiments, for example, NSE may be indicative of the neurological condition at a concentration in the liquid sample of between 0.1 pg/mL and 10 pg/mL. In certain embodiments, for example, NSE may be indicative of the neurological condition at a concentration in the liquid sample of between 1 pg/mL and 100 pg/mL. In certain embodiments, for example, NSE may be indicative of the neurological condition at a concentration in the liquid sample of between 10 pg/mL and 1000 pg/mL.

In certain embodiments, for example, the methods, tests, assays, kits, or systems may require a LOQ of no greater than 0.01 pg/mL (for example no greater than 0.1 pg/mL, no greater than 0.5 pg/mL, no greater than 1 pg/mL, no greater than 2 pg/mL, no greater than 5 pg/mL, no greater than 10 pg/mL, or no greater than 50 pg/mL) for tau protein.

In certain embodiments, for example, the methods, tests, assays, kits, or systems may require a LOQ of no greater than 0.01 pg/mL (for example no greater than 0.1 pg/mL, no greater than 0.5 pg/mL, no greater than 1 pg/mL, no greater than 2 pg/mL, no greater than 5 pg/mL, no greater than 10 pg/mL, or no greater than 50 pg/mL) for NF-L.

In certain embodiments, for example, the methods, tests, assays, kits, or systems may require a LOQ of no greater than 0.01 pg/mL (for example no greater than 0.1 pg/mL, no greater than 0.5 pg/mL, no greater than 1 pg/mL, no greater than 2 pg/mL, no greater than 5 pg/mL, no greater than 10 pg/mL, or no greater than 50 pg/mL) for GFAP.

In certain embodiments, for example, the methods, tests, assays, kits, or systems may require a LOQ of no greater than 0.01 pg/mL (for example no greater than 0.1 pg/mL, no greater than 0.5 pg/mL, no greater than 1 pg/mL, no greater than 2 pg/mL, no greater than 5 pg/mL, no greater than 10 pg/mL, or no greater than 50 pg/mL) for UCH L1.

In certain embodiments, for example, the methods, tests, assays, kits, or systems may require a LOQ of no greater than 0.01 pg/mL (for example no greater than 0.1 pg/mL, no greater than 0.5 pg/mL, no greater than 1 pg/mL, no greater than 2 pg/mL, no greater than 5 pg/mL, no greater than 10 pg/mL, or no greater than 50 pg/mL) for A beta 40.

In certain embodiments, for example, the methods, tests, assays, kits, or systems may require a LOQ of no greater than 0.01 pg/mL (for example no greater than 0.1 pg/mL, no greater than 0.5 pg/mL, no greater than 1 pg/mL, no greater than 2 pg/mL, no greater than 5 pg/mL, no greater than 10 pg/mL, or no greater than 50 pg/mL) for A beta 42.

In certain embodiments, for example, the methods, tests, assays, kits, or systems may require a LOQ of no greater than 0.01 pg/mL (for example no greater than 0.1 pg/mL, no greater than 0.5 pg/mL, no greater than 1 pg/mL, no greater than 2 pg/mL, no greater than 5 pg/mL, no greater than 10 pg/mL, or no greater than 50 pg/mL) for S100B.

In certain embodiments, for example, the methods, tests, assays, kits, or systems may require a LOQ of no greater than 0.01 pg/mL (for example no greater than 0.1 pg/mL, no greater than 0.5 pg/mL, no greater than 1 pg/mL, no greater than 2 pg/mL, no greater than 5 pg/mL, no greater than 10 pg/mL, or no greater than 50 pg/mL) for NSE.

In certain embodiments, for example, the at least one biomarker (or an elevated or reduced concentration of the at least one biomarker) may be indicative of a neurological condition occurring during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or the at least one biomarker may be indicative of a neurological condition occurring during a time of between 1 second and 1 days prior to a date and time on which the physiological fluid was taken from a subject. In certain embodiments, for example, the at least one biomarker may be indicative of a neurological condition being present during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or the at least one biomarker may be indicative of a neurological condition being present during a time of between 1 second and 1 days prior to a date and time on which the physiological fluid was taken from a subject.

In certain embodiments, for example, an increased concentration of NF-L may be indicative of a neurological condition occurring during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of NF-L may be indicative of a neurological condition occurring during a time of between 1 second and 1 days prior to a date and time on which the physiological fluid was taken from a subject. In certain embodiments, for example, an increased concentration of NF-L may be indicative of a neurological condition being present during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of NF-L may be indicative of a neurological condition being present during a time of between 1 second and 1 days prior to a date and time on which the physiological fluid was taken from a subject.

In certain embodiments, for example, an increased concentration of GFAP may be indicative of a neurological condition occurring during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of GFAP may be indicative of a neurological condition occurring during a time of between 1 second and 1 days prior to a date and time on which the physiological fluid was taken from a subject. In certain embodiments, for example, an increased concentration of GFAP may be indicative of a neurological condition being present during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of GFAP may be indicative of a neurological condition being present during a time of between 1 second and 1 days prior to a date and time on which the physiological fluid was taken from a subject.

In certain embodiments, for example, an increased concentration of UCH L1 may be indicative of a neurological condition occurring during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of UCH L1 may be indicative of a neurological condition occurring during a time of between 1 second and 1 days prior to a date and time on which the physiological fluid was taken from a subject. In certain embodiments, for example, an increased concentration of UCH L1 may be indicative of a neurological condition being present during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of UCH L1 may be indicative of a neurological condition being present during a time of between 1 second and 1 days prior to a date and time on which the physiological fluid was taken from a subject.

In certain embodiments, for example, an increased concentration of tau protein may be indicative of a neurological condition occurring during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of tau protein may be indicative of a neurological condition occurring during a time of between 1 second and 1 days prior to a date and time on which the physiological fluid was taken from a subject. In certain embodiments, for example, an increased concentration of tau protein may be indicative of a neurological condition being present during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of tau protein may be indicative of a neurological condition being present during a time of between 1 second and 1 days prior to a date and time on which the physiological fluid was taken from a subject.

In certain embodiments, for example, an increased concentration of A beta 40 may be indicative of a neurological condition occurring during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of A beta 40 may be indicative of a neurological condition occurring during a time of between 1 second and 1 days prior to a date and time on which the physiological fluid was taken from a subject. In certain embodiments, for example, an increased concentration of A beta 40 may be indicative of a neurological condition being present during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of A beta 40 may be indicative of a neurological condition being present during a time of between 1 second and 1 days prior to a date and time on which the physiological fluid was taken from a subject.

In certain embodiments, for example, an increased concentration of A beta 42 may be indicative of a neurological condition occurring during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of A beta 42 may be indicative of a neurological condition occurring during a time of between 1 second and 1 days prior to a date and time on which the physiological fluid was taken from a subject. In certain embodiments, for example, an increased concentration of A beta 42 may be indicative of a neurological condition being present during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of A beta 42 may be indicative of a neurological condition being present during a time of between 1 second and 1 days prior to a date and time on which the physiological fluid was taken from a subject.

In certain embodiments, for example, an increased concentration of S100B may be indicative of a neurological condition occurring during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of S100B may be indicative of a neurological condition occurring during a time of between 1 second and 1 days prior to a date and time on which the physiological fluid was taken from a subject. In certain embodiments, for example, an increased concentration of S100B may be indicative of a neurological condition being present during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of S100B may be indicative of a neurological condition being present during a time of between 1 second and 1 days prior to a date and time on which the physiological fluid was taken from a subject.

In certain embodiments, for example, an increased concentration of NSE may be indicative of a neurological condition occurring during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of NSE may be indicative of a neurological condition occurring during a time of between 1 second and 1 days prior to a date and time on which the physiological fluid was taken from a subject. In certain embodiments, for example, an increased concentration of NSE may be indicative of a neurological condition being present during a time of between 1 second and 5 years prior to a date and time on which the physiological fluid was taken from a subject, for example during a time of between 1 second and 2 years, at time of between 1 second and 1 year, a time of between 1 second and 6 months, a time of between 1 second and 3 months, a time of between 1 second and 1 month, a time of between 1 second and 10 days, or an increased concentration of NSE may be indicative of a neurological condition being present during a time of between 1 second and 1 days prior to a date and time on which the physiological fluid was taken from a subject.

In certain embodiments, for example, the at least one parameter may comprise a ratio of a concentration of a first biomarker to a concentration of a second component (for example a non-CNS protein or a second biomarker (for example a second biomarker comprising a CNS protein)) of the fluid sample. In certain embodiments, for example, the ratio may be indicative of the neurological condition at a value of at least 1% (for example at least 2%, at least 4%, at least 6%, at least 8%, at least 10%, at least 12%, at least 14%, at least 15%, at least 20%, at least 25%, at least 30%, at least 35%, at least 40%, at least 45%), at least 50%, at least 55%, at least 60%, at least 65%, at least 70%, at least 75%, at least 80%, at least 85%, at least 90%, at least 95%, at least 99%, at least 100%, at least 110%, at least 115%, at least 120%, at least 140%, at least 150%, at least 200%, at least 250%, at least 300%, at least 350%, at least 400%, or between 1% and 400%, between 1% and 300%, between 1% and 200%, between 1% and 100%, between 1% and 50%, between 1% and 25%, between 1% and 10%, between 10% and 400%, between 10% and 300%, between 10% and 200%, between 10% and 100%, between 10% and 50%, between 50% and 400%, between 50% and 300%, between 50% and 200%, between 50% and 100%, between 50% and 75%, between 75% and 100%, or 1%, 2%, 4%, 5%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 250%, 300%, 350%, or 400%. In certain embodiments, for example, the ratio may be indicative of the neurological condition at a value of between 1% and 500%, between 1% and 450%, between 1% and 400%, between 1% and 350%, between 1% and 300%, between 1% and 250%, between 1% and 200%, between 1% and 150%, between 1% and 100%, between 1% and 50%, between 1% and 25%, between 1% and 20%, between 1% and 15%, between 1% and 10%, between 1% and 5%, between 2% and 500%, between 2% and 450%, between 2% and 400%, between 2% and 350%, between 2% and 300%, between 2% and 250%, between 2% and 200%, between 2% and 150%, between 2% and 100%, between 2% and 50%, between 2% and 25%, between 2% and 20%, between 2% and 15%, between 2% and 10%, between 5% and 500%, between 5% and 450%, between 5% and 400%, between 5% and 350%, between 5% and 300%, between 5% and 250%, between 5% and 200%, between 5% and 150%, between 5% and 100%, between 5% and 50%, between 5% and 25%, between 5% and 20%, between 5% and 15%, between 5% and 10%, between 10% and 500%, between 10% and 450%, between 10% and 400%, between 10% and 350%, between 10% and 300%, between 10% and 250%, between 10% and 200%, between 10% and 150%, between 10% and 100%, between 10% and 50%, between 10% and 25%, between 10% and 20%, between 10% and 15%, between 15% and 500%, between 15% and 450%, between 15% and 400%, between 15% and 350%, between 15% and 300%, between 15% and 250%, between 15% and 200%, between 15% and 150%, between 15% and 100%, between 15% and 50%, between 15% and 25%, between 15% and 20%, between 20% and 500%, between 20% and 450%, between 20% and 400%, between 20% and 350%, between 20% and 300%, between 20% and 250%, between 20% and 200%, between 20% and 150%, between 20% and 100%, between 20% and 50%, between 20% and 25%, between 25% and 500%, between 25% and 450% between 25% and 400%, between 25% and 350%, between 25% and 300%, between 25% and 250%, between 25% and 200%, between 25% and 150%, between 25% and 100%, between 25% and 50%, between 50% and 500%, between 50% and 450%, between 50% and 400%, between 50% and 350%, between 50% and 300%, between 50% and 250%, between 50% and 200%, between 50% and 150%, between 50% and 100%, between 100% and 500%, between 100% and 450%, between 100% and 400%, between 100% and 350%, between 100% and 300%, between 100% and 250%, between 100% and 200%, between 100% and 150%, between 150% and 500%, between 150% and 450%, between 150% and 400%, between 150% and 350%, between 150% and 300%, between 150% and 250%, between 150% and 200%, between 200% and 500%, between 200% and 450%, between 200% and 400%, between 200% and 350%, between 200% and 300%, between 200% and 250%, between 250% and 500%, between 250% and 450%, between 250% and 400%, between 250% and 350%, between 250% and 300%, between 300% and 500%, between 300% and 450%, between 300% and 400%, between 300% and 350%, between 350% and 500%, between 350% and 450%, between 350% and 400%, between 400% and 500%, between 400% and 450%, or between 450% and 500%.

In certain embodiments, for example, the at least one parameter may comprise an increase (for example a percentage increase) in the concentration of a biomarker, for example a percentage increase of at least 1% (for example at least 2%, at least 4%, at least 6%, at least 8%, at least 10%, at least 12%, at least 14%, at least 15%, at least 20%, at least 25%, at least 30%, at least 35%, at least 40%, at least 45%), at least 50%, at least 55%, at least 60%, at least 65%, at least 70%, at least 75%, at least 80%, at least 85%, at least 90%, at least 95%, at least 99%, at least 100%, at least 110%, at least 115%, at least 120%, at least 140%, at least 150%, at least 200%, at least 250%, at least 300%, at least 350%, at least 400%, or between 1% and 400%, between 1% and 300%, between 1% and 200%, between 1% and 100%, between 1% and 50%, between 1% and 25%, between 1% and 10%, between 10% and 400%, between 10% and 300%, between 10% and 200%, between 10% and 100%, between 10% and 50%, between 50% and 400%, between 50% and 300%, between 50% and 200%, between 50% and 100%, between 50% and 75%, between 75% and 100%, or 1%, 2%, 4%, 5%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 250%, 300%, 350%, or 400%. In certain embodiments, for example, the at least one parameter may comprise a percentage increase in the concentration of a biomarker of between 1% and 500%, between 1% and 450%, between 1% and 400%, between 1% and 350%, between 1% and 300%, between 1% and 250%, between 1% and 200%, between 1% and 150%, between 1% and 100%, between 1% and 50%, between 1% and 25%, between 1% and 20%, between 1% and 15%, between 1% and 10%, between 1% and 5%, between 2% and 500%, between 2% and 450%, between 2% and 400%, between 2% and 350%, between 2% and 300%, between 2% and 250%, between 2% and 200%, between 2% and 150%, between 2% and 100%, between 2% and 50%, between 2% and 25%, between 2% and 20%, between 2% and 15%, between 2% and 10%, between 5% and 500%, between 5% and 450%, between 5% and 400%, between 5% and 350%, between 5% and 300%, between 5% and 250%, between 5% and 200%, between 5% and 150%, between 5% and 100%, between 5% and 50%, between 5% and 25%, between 5% and 20%, between 5% and 15%, between 5% and 10%, between 10% and 500%, between 10% and 450%, between 10% and 400%, between 10% and 350%, between 10% and 300%, between 10% and 250%, between 10% and 200%, between 10% and 150%, between 10% and 100%, between 10% and 50%, between 10% and 25%, between 10% and 20%, between 10% and 15%, between 15% and 500%, between 15% and 450%, between 15% and 400%, between 15% and 350%, between 15% and 300%, between 15% and 250%, between 15% and 200%, between 15% and 150%, between 15% and 100%, between 15% and 50%, between 15% and 25%, between 15% and 20%, between 20% and 500%, between 20% and 450%, between 20% and 400%, between 20% and 350%, between 20% and 300%, between 20% and 250%, between 20% and 200%, between 20% and 150%, between 20% and 100%, between 20% and 50%, between 20% and 25%, between 25% and 500%, between 25% and 450%, between 25% and 400%, between 25% and 350%, between 25% and 300%, between 25% and 250%, between 25% and 200%, between 25% and 150%, between 25% and 100%, between 25% and 50%, between 50% and 500%, between 50% and 450%, between 50% and 400%, between 50% and 350%, between 50% and 300%, between 50% and 250%, between 50% and 200%, between 50% and 150%, between 50% and 100%, between 100% and 500%, between 100% and 450%, between 100% and 400%, between 100% and 350%, between 100% and 300%, between 100% and 250%, between 100% and 200%, between 100% and 150%, between 150% and 500%, between 150% and 450%, between 150% and 400%, between 150% and 350%, between 150% and 300%, between 150% and 250%, between 150% and 200%, between 200% and 500%, between 200% and 450%, between 200% and 400%, between 200% and 350%, between 200% and 300%, between 200% and 250%, between 250% and 500%, between 250% and 450%, between 250% and 400%, between 250% and 350%, between 250% and 300%, between 300% and 500%, between 300% and 450%, between 300% and 400%, between 300% and 350%, between 350% and 500%, between 350% and 450%, between 350% and 400%, between 400% and 500%, between 400% and 450%, or between 450% and 500%, for example as compared to a reference level.

In certain embodiments, for example, the at least one parameter may comprise a reduction (for example a percentage reduction) in the concentration of a biomarker of between 1% and 99%, for example between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 15%, between 1% and 10%, between 1% and 5%, between 5% and 99%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 99%, between 10% and 95%, between 10% and 90%, between 10% and 85%, between 10% and 80%, between 10% and 75%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 15% and 99%, between 15% and 95%, between 15% and 90%, between 15% and 85%, between 15% and 80%, between 15% and 75%, between 15% and 70%, between 15% and 65%, between 15% and 60%, between 15% and 55%, between 15% and 50%, between 15% and 45%, between 15% and 40%, between 15% and 35%, between 15% and 30%, between 15% and 25%, between 15% and 20%, between 20% and 99%, between 20% and 95%, between 20% and 90%, between 20% and 85%, between 20% and 80%, between 20% and 75%, between 20% and 70%, between 20% and 65%, between 20% and 60%, between 20% and 55%, between 20% and 50%, between 20% and 45%, between 20% and 40%, between 20% and 35%, between 20%) and 30%, between 20% and 25%, between 25% and 99%, between 25% and 95%, between 25% and 90%, between 25% and 85%, between 25% and 80%, between 25% and 75%, between 25% and 70%, between 25% and 65%, between 25% and 60%, between 25% and 55%, between 25% and 50%, between 25% and 45%, between 25% and 40%, between 25% and 35%, between 25% and 30%, between 30% and 99%, between 30% and 95%, between 30% and 90%, between 30% and 85%, between 30% and 80%, between 30% and 75%, between 30% and 70%, between 30% and 65%, between 30% and 60%, between 30% and 55%, between 30% and 50%, between 30% and 45%, between 30% and 40%, between 30% and 35%, between 35% and 99%, between 35% and 95%, between 35% and 90%, between 35% and 85%, between 35% and 80%, between 35% and 75%, between 35% and 70%, between 35% and 65%, between 35% and 60%, between 35% and 55%, between 35% and 50%, between 35% and 45%, between 35% and 40%, between 40% and 99%, between 40% and 95%, between 40% and 90%, between 40% and 85%, between 40% and 80%, between 40% and 75%, between 40% and 70%, between 40% and 65%, between 40% and 60%, between 40% and 55%, between 40% and 50%, between 40% and 45%, between 45% and 99%, between 45% and 95%, between 45% and 90%, between 45% and 85%, between 45% and 80%, between 45% and 75%, between 45% and 70%, between 45% and 65%, between 45% and 60%, between 45% and 55%, between 45% and 50%, between 50% and 99%, between 50% and 95%, between 50% and 90%, between 50% and 85%, between 50% and 80%, between 50% and 75%, between 50% and 70%, between 50% and 65%, between 50% and 60%, between 50% and 55%, between 55% and 99%, between 55% and 95%, between 55% and 90%, between 55% and 85%, between 55% and 80%, between 55% and 75%, between 55% and 70%, between 55% and 65%, between 55% and 60%, between 60% and 99%, between 60% and 95%, between 60% and 90%, between 60% and 85%, between 60% and 80%, between 60% and 75%, between 60% and 70%, between 60% and 65%, between 65% and 99%, between 65% and 95%, between 65% and 90%, between 65% and 85%, between 65% and 80%, between 65% and 75%, between 65% and 70%, between 70% and 99%, between 70% and 95%, between 70% and 90%, between 70% and 85%, between 70% and 80%, between 70% and 75%, between 75% and 99%, between 75% and 95%, between 75% and 90%, between 75% and 85%, between 75% and 80%, between 80% and 99%, between 80% and 95%, between 80% and 90%, between 80% and 85%, between 85% and 99%, between 85% and 95%, between 85% and 90%, between 90% and 99%, between 90% and 95%, or between 95% and 99%.

A schematic depiction of a method to quantify concentrations of four analytes (for example NF-L, GFAP, UCH L1, and Tau) in a liquid sample via digital assay is shown in FIG. 1. The liquid sample 100 (in vessel 102) is provided 104 containing first type of analyte molecule (for example a first analyte molecule 106 such as NF-L), a second type of analyte molecule (for example a second analyte molecule 108 such as GFAP), a third type of analyte molecule (for example a third analyte molecule 110 such as UCH L1), and a fourth type of analyte molecule (for example a fourth analyte molecule 112 such as Tau). For example, the first type of analyte molecule may be NF-L, the second type of analyte molecule may be GFAP, the third type of analyte molecule may be UCH L1, and the fourth type of analyte molecule may be Tau. Capture objects including a first capture object 114 having a first anti-analyte immobilization agent 116, a second capture object 118 having a second anti-analyte immobilization agent 120, a third capture object 122 having a third anti-analyte immobilization agent 124, and a fourth capture object 126 having a fourth anti-analyte immobilization agent 128 are combined 130 with the liquid sample 100, wherein the first anti-analyte immobilization agent 116 is specific to the first type of analyte molecule, the second anti-analyte immobilization agent 120 is specific to the second type of analyte molecule, the third anti-analyte immobilization agent 124 is specific to the third type of analyte molecule, and the fourth anti-analyte immobilization agent 128 is specific to the fourth type of analyte molecule. The added capture objects are incubated 132 with the liquid sample 100 for a period of time, resulting in the first capture object 114 binding with the first analyte molecule 106, the second capture object 118 binding with the second analyte molecule 108, the third capture object 122 binding with the third analyte molecule 110, and the fourth capture object 126 binding with the fourth analyte molecule 112. Some of the capture objects (not shown) do not bind with any analyte. An excess number of capture objects (not shown) is provided whereby the fraction of capture objects binding with more than one analyte is statistically insignificant. After the capture objects have immobilized at least a portion of the analyte molecules (not all analyte molecules are shown), a first type of detectable agent (for example a first detectable agent 134) configured to bind with the first type of analyte, a second type of detectable agent (for example a second detectable agent 136) configured to bind with the second type of analyte, a third type of detectable agent (for example a third detectable agent 138) configured to bind with the third type of analyte, and a fourth type of detectable agent (for example a fourth detectable agent 140) configured to bind with the fourth type of analyte are contacted 142 with the capture objects and incubated 144, resulting in the first detectable agent 134 binding to the first analyte molecule 106, the second detectable agent 136 binding to the second analyte molecule 108, the third detectable agent 138 binding to the third analyte molecule 110, and the fourth detectable agent 140 binding to the fourth analyte molecule 112. Detectable agents do not bind to a capture object unless the capture object has immobilized an analyte molecule (not all detectable agents are shown). The capture objects are spatially separated 146 into a plurality of reaction vessels (for example femtoliter-sized reaction vessels etched in a plate) on a substrate 148. As shown, the first capture object 114, the second capture object 118, the third capture object 122, and the fourth capture object 126 (along with additional capture objects not shown) are present in separate reaction vessels while some of the reaction vessels such as the reaction vessel 150 may not contain any capture objects. The substrate 148 may then be analyzed 152 by an optical-based analyzer 154 to determine the number of reaction vessels containing an analyte bound to a capture object, wherein in the number of the first type of analyte molecule, the number of the second type of analyte molecule, the number of the third type of analyte molecule, and the number of the fourth type of analyte molecule may be related to a measures of the concentration of each type of analyte in the liquid sample 100 (for example by a standard curve).

Figure 2:
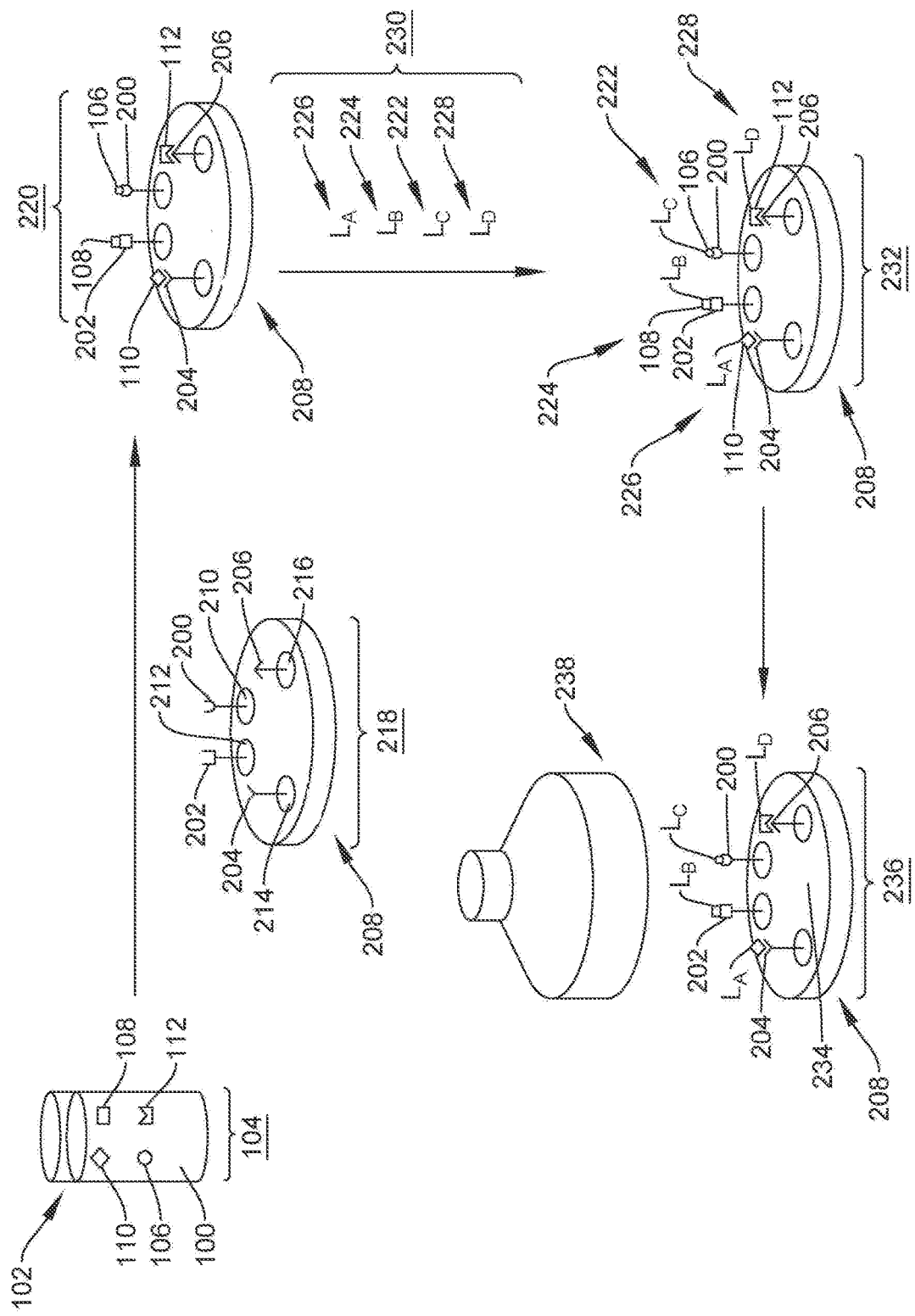
FIG. 2 is a schematic depiction of a multiplex spotted well assay.

A schematic depiction of a method to quantify concentrations of four analytes (for example NF-L, GFAP, UCH L1, and Tau) in a liquid sample via a multi-spotted reaction well (for example one well of a plurality of such wells) is shown in FIG. 2. The liquid sample 100 (in vessel 102) is provided 100 containing first type of analyte molecule (for example a first analyte molecule 106), a second type of analyte molecule (for example a second analyte molecule 108), a third type of analyte molecule (for example a third analyte molecule 110), and a fourth type of analyte molecule (for example a fourth analyte molecule 112). For example, the first type of analyte molecule may be NF-L, the second type of analyte molecule may be GFAP, the third type of analyte molecule may be UCH L1, and the fourth type of analyte molecule may be Tau. Anti-analyte immobilization agents including a first type of anti-analyte immobilization agent (for example the anti-analyte immobilization agent 200), a second type of anti-analyte immobilization agent (for example the anti-analyte immobilization agent 202), a third type of anti-analyte immobilization agent (for example the anti-analyte immobilization agent 204), and a fourth type of anti-analyte immobilization agent (for example the anti-analyte immobilization agent 206), that are immobilized in a plurality of spatially separated zones (or "spots") in a reaction well 208. For example a first spot 210 contains a plurality of the first type of anti-analyte immobilization agent exclusive of the other types of anti-analyte immobilization agents; a second spot 212 contains a plurality of the second type of anti-analyte immobilization agent exclusive of the other types of anti-analyte immobilization agents; a third spot 214 contains a plurality of the third type of anti-analyte immobilization agent exclusive of the other types of anti-analyte immobilization agents; and a fourth spot 216 contains a plurality of the fourth type of anti-analyte immobilization agent exclusive of the other types of anti-analyte immobilization agents. The liquid sample 100 is added 218 to the reaction well 208, wherein the first anti-analyte immobilization agent 200 is specific to the first type of analyte molecule, the second anti-analyte immobilization agent 202 is specific to the second type of analyte molecule, the third anti-analyte immobilization agent 204 is specific to the third type of analyte molecule, and the fourth anti-analyte immobilization agent 206 is specific to the fourth type of analyte molecule. The anti-analyte immobilization agents are incubated 220 with the liquid sample 100 for a period of time, resulting in the first anti-analyte immobilization agent 200 binding with the first analyte molecule 106, the second anti-analyte immobilization agent 202 binding with the second analyte molecule 108, the third anti-analyte immobilization agent 204 binding with the third analyte molecule 110, and the fourth anti-analyte immobilization agent 206 binding with the fourth analyte molecule 112. In certain embodiments, for example, the reaction well may be agitated according to a predetermined scheme to increase fluid flow of the liquid sample relative to the one or more spatially separated zones and thereby achieve one or more of increased sensitivity (for example lower LOQ), reduced assay time, and assay reproducibility. After the anti-analyte immobilization agents have immobilized at least a portion of the analyte molecules (not all analyte molecules are shown), a first type of detectable agent (for example a first detectable agent 222) configured to bind with the first type of analyte, a second type of detectable agent (for example a second detectable agent 224) configured to bind with the second type of analyte, a third type of detectable agent (for example a third detectable agent 226) configured to bind with the third type of analyte, and a fourth type of detectable agent (for example a fourth detectable agent 228) configured to bind with the fourth type of analyte are contacted 230 with the plurality of spatially separated zones and incubated 232 in the reaction well 208, resulting in the first detectable agent 222 binding to the first analyte molecule 106, the second detectable agent 224 binding to the second analyte molecule 108, the third detectable agent 226 binding to the third analyte molecule 110, and the fourth detectable agent 228 binding to the fourth analyte molecule 112. Detectable agents do not bind to an anti-analyte immobilization agent unless the anti-analyte immobilization agent has immobilized an analyte molecule (not all detectable agents molecules are shown). The substrate 234 may then be analyzed 236 by an optical-based analyzer 238 to determine the signal levels in spatially separated reaction vessels containing an analyte bound to an anti-analyte immobilization agent, wherein in the signal level of the first type of analyte molecule, the signal level of the second type of analyte molecule, the signal level of the third type of analyte molecule, and the signal level of the fourth type of analyte molecule may be related to a measures of the concentration of each type of analyte in the liquid sample 100. For example, the signal may comprise a chemilluminecent signal. In certain embodiments, for example, analyte quantification via the described detection of analytes in the spotted reaction well may provide one or more of the same level of sensitivity, LOQ, and LOD as one or more of the digital assays described herein or in one of the INCORPORATED REFERENCES.

Any of the disclosed methods, tests, assays, kits, or systems may comprising processing the results of one or more assays (for example the concentrations of one or more biomarkers) into useful information regarding a risk, diagnosis, prognosis, or state of a neurological condition in a subject (for example a human subject such as a neonate) by passing the results through a classification model to compute at least one classification value which can be compared to at least one threshold value.

In certain embodiments, for example, the at least one threshold value may correspond to a predetermined sensitivity level for a multivariate statistical model of the expression levels of one or more biomarkers in a plurality (for example 2, 3, 4, 5, 6, 7, 8, 9, 10, or more than 10) of training samples from individuals diagnosed as having an indicated neurological condition (for example TBI) and control samples from individuals without the indicated neurological condition. In certain embodiments, for example, the subject's classification value may be calculated using the multivariate statistical model. In certain embodiments, for example, the multivariate statistical model may comprise a binary logistic regression, a linear regression, a quadratic regression, a polynomial regression, a logistic regression, results of a principal component analysis, results of a maximum likelihood analysis, a neural network, results of a linear discriminant analysis, a decision tree, or a combination of two or more of the foregoing.

Certain embodiments, for example, may provide methods, tests, assays, kits, or systems to measure NF-L, GFAP, UCH L1, and Tau. In certain embodiments, for example, NF-L, GFAP, UCH L1, and Tau may be detected by a multiplex assay. In certain embodiments, for example, the multiplex assay may comprise adding portions of a liquid sample (for example a liquid sample obtained by diluting a sample of human physiological fluid such as human blood serum or plasma) to a plurality of reaction wells (for example a 96-well assay plate). In certain embodiments, for example, each of the reaction wells may comprise a plurality of zones (or spots). In certain embodiments, for example, the plurality of zones (or spots) may be spatially separated. In certain embodiments, for example, the zones by be radially disposed (for example symmetrically disposed at a fixed radius about a central position in each reaction well). In certain embodiments, for example, each of the reaction wells may be sized to contain, in total, between 20 mcL and 100 mcL (for example 50 mcL) of liquid sample and assay reagents. In certain embodiments, for example, each of the zones may be coated (or covalently conjugated to) a plurality (for example 2, 3, 4, 5, 6, 7, 8, 9, 10, or more than 10) of an anti-analyte agent that is specific to one of NF-L, GFAP, UCH L1, and Tau, whereby a first zone of each reaction well will preferentially immobilize NF-L, a second zone of each reaction well will preferentially immobilize GFAP, a third zone of each reaction well will preferentially immobilize UCH L1, and a fourth zone of each reaction well will preferentially immobilize Tau. In certain embodiments, for example, the multi-well plate may be coupled to a digital nanofluidic deposition system for controlled addition of sample, washing reagents, and detection agents. In certain embodiments, for example, detectable agents (for example four different detectable agents having different colors or the same color) may be added to each of the reaction wells to bind with immobilized NF-L, GFAP, UCH L1, and Tau and produce a detectable signal. In certain embodiments, for example, the multi-well plate may made of translucent plastic. In certain embodiments, for example, imaging of detectable signals may be performed through the bottom of the translucent multi-well plate. In certain embodiments, for example, the multi-well plate may be coupled to an agitation system. In certain embodiments, for example, the agitation system may be configured to agitate the multi-well plate to form a vortex of fluid in each reaction well.

In certain embodiments, for example, the multiplex assay may comprise agitating the liquid sample, for example agitating the liquid sample for up to 1 hour, up to 1.5 hours, up to 2 hours, up to 2.5 hours, up to 3 hours, up to 3.5 hours, up to 4 hours, up to 4.5 hours, up to 5 hours, up to 6 hours, up to 8 hours, up to 10 hours, up to between 1 hour and 3 hours, up to between 1.5 hours and 2.5 hours, for 2 hours, or for greater than 10 hours. In certain embodiments, for example the multiplex assay may comprise adding biotinylated detection antibodies, followed by an additional 30 minutes of shaking. In certain embodiments, for example, the detection antibodies may bind to form an amino complex. In certain embodiments, for example, horseradish peroxidase (HRP)-conjugated streptavidin may be added, followed by an additional 30 minute agitation cycle, substrate added, and the zones containing NF-L, GFAP, UCH L1, and Tau detected via chemiluminescent signal. In certain embodiments, for example, a machine learning algorithm may optimize exposure times in the number of images for each sample to maximize sensitivity and dynamic range. In certain embodiments, for example, the multiplex assay may be performed within 6 hours inclusive of preparation of a the liquid sample from a sample of physiological fluid, for example within 5 hours, within 4 hours, within 3 hours within 2 hours, within 1 hour, within 30 minutes, within between 1 hour and 6 hours, within between 2 hours and 4 hours, within between 2.5 hours and 3.5 hours, or within 3 hours.

Certain embodiments may provide, for example, methods, tests, assays, kits, or systems for determining a measure of the concentration of a panel of neurological biomarkers in a sample derived from a human are disclosed. In certain embodiments, for example, the methods, tests, assays, kits, or systems may involve determining the concentration of two or more biomarkers associated with brain injury and/or neurodegeneration in a human sample. In certain embodiments, for example, the method may comprise determining a measure of the concentration of NF-L and at least one other biomarker selected from the group consisting of GFAP, UCH L1, and Tau. An exemplary method and kit may be directed to determination of a measure of the concentration of a biomarker panel comprising at least NF-L, GFAP, UCH L1, and Tau. In certain embodiments, for example, a measure of the concentration of the biomarkers may be determined using a single assay. In some such cases, the assay may utilize certain assay conditions that allow for the determination of each biomarker with a relatively high specificity and sensitivity. The methods, tests, assays, kits, and systems described herein may be used to assess a variety of brain injuries and neurodegenerative conditions, including TBI.

A cascade of biomarkers, such as NF-L, GFAP, UCH L1, and Taus, may be generated in the brain in response to and/or in proportion to the extent of a brain injury. NF-L, a cytoskeletal intermediate filament protein, may combine with other proteins to form neurofilaments in neurons and may be released in significant quantity following axonal damage or neuronal degeneration. Tau protein, a microtubule-stabilizing protein primarily localized in CNS neurons, may be observed in the cerebrospinal fluid (CSF) of patients with neurodegenerative disease and head injuries, suggesting its extracellular release during neuronal damage and a role as a biomarker with specificity for brain injury. GFAP, a class-III intermediate filament involved in many central nervous system processes including cell communication and the functioning of the blood brain barrier, may be associated with multiple diseases such as TBI, stroke, brain tumors, etc. UCH L1, which hydrolyzes small C-terminal adducts of ubiquitin to generate the ubiquitin monomer and is expressed predominantly in neurons, may be released from injured neurons and flow into the cerebrospinal fluid and circulating blood. Such biomarkers could in turn diffuse across the blood brain barrier and into the blood in response to and/or in proportion to the extent of the injury, and may be generally found in low abundance. In certain embodiments, for example, the ability to determine a measure of the concentration of two or more biomarkers (for example three or more biomarkers, four or more biomarkers) in a patient sample (or a plurality samples) obtained following a suspected injury event may be used to determine whether brain injury occurred and/or otherwise assess the injury. For example, a measure of the concentration of two or more biomarkers may be used to assess the severity of the brain injury.

In certain embodiments, for example, sample(s) of the patient's cerebrospinal fluid (CSF) may be obtained and analyzed to determine a measure of the concentration of the biomarkers. In certain embodiments, for example, it may be advantageous to determine the level of biomarkers in the blood of a patient as compared to CSF, as blood sampling may be generally less invasive and may result in fewer complications as compared to CSF sampling. However, many of the biomarkers that are present in the CSF have a slow rate of transmission across and/or a high barrier of transportation across the blood-brain barrier (BBB) and thus, a measure of the concentration of the biomarkers in the patient's blood may be generally sufficiently lower as compared to a measure of the concentration in CSF, which can make it difficult or impossible to accurately determine using typically employed conventional immunoassays. Certain embodiments may provide, for example, methods, tests, assays, kits, or systems that have very low limits of quantification (LOQ) and/or limits of detection (LOD) can facilitate determination of a measure of the concentration of such biomarkers in the patient's blood with sufficient accuracy and repeatability to provide statistically significant and/or meaningful results. In certain embodiments, for example, the methods, tests, assays, kits, or systems may have very low LODs and/or LOQs (for example in the low pg/mL range) to determine a measure of the concentration of two or more biomarkers in a sample obtained from a patient following a suspected injury event. In certain embodiments, for example, one or more parameters related to the concentrations of the biomarkers in the sample (for example blood sample) may be correlated with the diagnosis of brain injury, the assessment of the extent of brain injury, and/or a method of treatment following the injury event.

It should be noted, that while many of the embodiments described herein focus on brain injuries caused by traumatic events, this is by no way limiting, and In certain embodiments, for example, the brain injury may be caused by other events, for example, a biochemical event, such as oxygen deprivation (hypoxia). Hypoxia generally refers to a deficiency in the amount of oxygen reaching body tissues or a condition of insufficient levels of oxygen in issue or blood. Oxygen deprivation to the brain results in neuronal damage and death, which may be in turn related to the extent of long term brain dysfunction.

In certain embodiments, for example, the methods, tests, assays, kits, or systems may comprise determining a measure of the concentration of two or more biomarkers selected from the group consisting of GFAP, UCH L1, Tau, and NF-L. In certain embodiments, for example, the methods, tests, assays, kits, or systems may comprise determining a measure of the concentration of NF-L protein and at least one other biomarker selected from the group consisting of GFAP, UCH L1, and Tau. In certain embodiments, for example, the methods, tests, assays, kits, or systems may comprise determining a measure of the concentration of NF-L and GFAP. In certain embodiments, for example, the method may comprise determining a measure of the concentration of NF-L and UCH L1. In certain embodiments, for example, the methods, tests, assays, kits, or systems may comprise determining a measure of the concentration of NF-L and Tau protein. In certain embodiments, for example, the methods, tests, assays, kits, or systems may comprise determining a measure of the concentration of NF-L and A beta 40. In certain embodiments, for example, the methods, tests, assays, kits, or systems may comprise determining a measure of the concentration of NF-L and A beta 42. In certain embodiments, for example, the methods, tests, assays, kits, or systems may comprise determining a measure of the concentration of NF-L and S100B. In certain embodiments, for example, the methods, tests, assays, kits, or systems may comprise determining a measure of the concentration of NF-L and NSE.

In certain embodiments, for example, the methods, tests, assays, kits, or systems may comprise determining a measure of the concentration of GFAP and at least one other biomarker selected from the group consisting of UCH L1, Tau, A beta 40, A beta 42, S100B, and NSE. In certain embodiments, for example, the methods, tests, assays, kits, or systems may comprise determining a measure of the concentration of GFAP and UCH L1. In certain embodiments, for example, the methods, tests, assays, kits, or systems may comprise determining a measure of the concentration of GFAP and Tau. In certain embodiments, for example, the methods, tests, assays, kits, or systems may comprise determining a measure of the concentration of GFAP and A beta 40. In certain embodiments, for example, the methods, tests, assays, kits, or systems may comprise determining a measure of the concentration of GFAP and A beta 42. In certain embodiments, for example, the methods, tests, assays, kits, or systems may comprise determining a measure of the concentration of GFAP and S100B. In certain embodiments, for example, the methods, tests, assays, kits, or systems may comprise determining a measure of the concentration of GFAP and NSE.

In certain embodiments, for example, the methods, tests, assays, kits, or systems may comprise determining a measure of the concentration of UCH L1 and at least one other biomarker selected from the group consisting of Tau, A beta 40, A beta 42, S100B, and NSE. In certain embodiments, for example, the methods, tests, assays, kits, or systems may comprise determining a measure of the concentration of UCH L1 and Tau. In certain embodiments, for example, the methods, tests, assays, kits, or systems may comprise determining a measure of the concentration of UCH L1 and A beta 40. In certain embodiments, for example, the methods, tests, assays, kits, or systems may comprise determining a measure of the concentration of UCH L1 and A beta 42. In certain embodiments, for example, the methods, tests, assays, kits, or systems may comprise determining a measure of the concentration of UCH L1 and S100B. In certain embodiments, for example, the methods, tests, assays, kits, or systems may comprise determining a measure of the concentration of UCH L1 and NSE.

In certain embodiments, for example, the methods, tests, assays, kits, or systems may comprise determining a measure of the concentration of Tau and at least one other biomarker selected from the group consisting of A beta 40, A beta 42, S100B, and NSE. In certain embodiments, for example, the methods, tests, assays, kits, or systems may comprise determining a measure of the concentration of Tau and A beta 40. In certain embodiments, for example, the methods, tests, assays, kits, or systems may comprise determining a measure of the concentration of Tau and A beta 42. In certain embodiments, for example, the methods, tests, assays, kits, or systems may comprise determining a measure of the concentration of Tau and S100B. In certain embodiments, for example, the methods, tests, assays, kits, or systems may comprise determining a measure of the concentration of Tau and NSE.

In certain embodiments, for example, the methods, tests, assays, kits, or systems may comprise determining a measure of the concentration of A beta 40 and at least one other biomarker selected from the group consisting of A beta 42, S100B, and NSE. In certain embodiments, for example, the methods, tests, assays, kits, or systems may comprise determining a measure of the concentration of A beta 40 and A beta 42. In certain embodiments, for example, the methods, tests, assays, kits, or systems may comprise determining a measure of the concentration of A beta 40 and S100B. In certain embodiments, for example, the methods, tests, assays, kits, or systems may comprise determining a measure of the concentration of A beta 40 and NSE.

In certain embodiments, for example, the methods, tests, assays, kits, or systems may comprise determining a measure of the concentration of A beta 42 and at least one other biomarker selected from the group consisting of S100B, and NSE. In certain embodiments, for example, the methods, tests, assays, kits, or systems may comprise determining a measure of the concentration of A beta 42 and S100B. In certain embodiments, for example, the methods, tests, assays, kits, or systems may comprise determining a measure of the concentration of A beta 42 and NSE.

In certain embodiments, for example, the methods, tests, assays, kits, or systems may comprise determining a measure of the concentration of S100B and NSE.

In certain embodiments, for example, the methods, tests, assays, kits, or systems may comprise measuring a selected number and combination of biomarkers associated with brain injury and/or neurodegeneration. In certain embodiments, for example, the methods, tests, assays, kits, or systems may comprise determining the concentration of two biomarkers. In certain embodiments, for example, the methods, tests, assays, kits, or systems may comprise determining the concentration of three biomarkers. In certain embodiments, for example, the methods, tests, assays, kits, or systems may comprise determining a measure of the concentration of at least the following four biomarkers: Tau, GFAP, UCH L1, and NF-L. In certain embodiments, for example, the methods, tests, assays, kits, or systems may comprise determining the concentration of at least about 1 biomarker, at least about 2, at least about 3, at least about 4, at least about 5, at least about 6, at least about 7, at least about 8, at least about 9, or at least about 10 biomarkers. In certain embodiments, for example, the number of biomarkers, whose concentration may be determined, may range from 2 to 10, from 2 to 8, ranges from 2 to 6, or from 2 to 5 (for example from 2 to 4).

In certain embodiments, for example, an immunoassay may be used to determine a measure of the concentration of two or more biomarkers. In certain embodiments, for example, the immunoassay may be a multiplex assay in which the concentration of more than one biomarker may be measured in a single performance of the assay. In such cases, at least some (for example all) of the biomarkers may be measured at one time. Certain embodiments may provide, for example, systems and methods that allow for the selective and sensitive detection and quantification of biomarkers (for example in a multiplex assay).

In many conventional assay systems, multiplexing may be hindered by non-specific binding, cross-reactivity (for example between detection molecules for a first biomarker and a second biomarker), the relative concentrations of the biomarkers, and/or incompatibility between the assay conditions (for example dilution, detection molecules, pH, solvent, reagents) for a first biomarker and the assay conditions for a second biomarker. For instance, certain conventional reagents necessary for ultrasensitive detection of a first analyte (for example Tau) may not allow for accurate detection of a second analytes (for example UCH L1). For example, certain conventional detergents while beneficial for the detection of Tau may induce conformational changes (for example due to physicochemical alterations in solvation activity) in other analytes (for example biomarkers), such as UCH L1, that adversely affect presentation of the portion (for example antigenic epitope) of the analyte utilized for detection. For instance, a conventional detergent may cause the antigenic epitope of an analyte to be less available or overly available for binding to a detection molecule (for example antibody) resulting in inaccurate quantification and/or a relatively high LOQ and/or LOD. As another example, certain detection molecules utilized for ultrasensitive detection of a biomarker may cross-react or non-specifically bind with another biomarker or detection molecule resulting in inaccurate quantification of the biomarker. For instance, detection molecules for certain biomarkers (for example NF-L, GFAP, and/or Tau) may cross-react or non-specifically bind with UCH L1 resulting in inaccurate quantification of the biomarker(s). As yet another example, molecules used to calibrate the multiplex assay may non-specifically bind resulting in inaccurate quantification. For instance, a biomarker standard (for example GFAP standard) used for calibration of the biomarker may non-specifically bind to assay components (for example molecules, beads) necessary for the detection (for example quantification) of other biomarkers.

In certain embodiments, for example, the concentration of detection molecules that affords relatively low LODs and LOQs in a non-multiplex assay may result in cross-reactivity or non-specific binding in a multiplex assay. In certain embodiments, for example, a high sensitivity assay may be provided which requires relatively low background levels, such that signal-to-noise may be adequate at low analyte (for example biomarker) concentrations to permit reliable measurement. Non-specific binding between assay components for a biomarker and assay components for another biomarker increases background levels resulting in a reduced signal-to-noise ratio and accordingly reduced sensitivity. In certain embodiments, for example, certain conventional diluents that produce acceptable dilution linearity and spike recovery for the detection of a biomarker may result in dilution non-linearity and/or unpredictable spike recovery for another biomarker. In many assays, one or more blocker reagents may be included in a sample diluent to mimic the physicochemical properties of the native sample in order to allow for acceptable dilution linearity. Diluents, and accordingly the blocker reagents comprised therein, that do not result in linear dilution may be unsuitable for use in the assay. In multiplex assays, suitable diluents should produce acceptable dilution linearity for each analyte (for example biomarkers). Many conventional diluents generally employed may be unsuitable for multiplexing. The problems associated with multiplexing often amplify as the number of biomarkers to be multiplexed increases. Thus, for many conventional assay systems, multiplexing of certain biomarkers may be difficult and/or not possible.

Certain embodiments may provide, for example, methods, tests, assays, kits, or systems that do not suffer from one or more limitations of conventional immunoassays with respect to multiplexing biomarkers, and thus can provide an improved way to measure biomarkers associated with brain injury and/or neurodegeneration. In certain embodiments, for example, the methods, tests, assays, kits, or systems provide ultra-sensitive detection of two or more biomarkers selected from the group consisting of NF-L, GFAP, UCH L1, and Tau. In certain embodiments, for example, the methods, tests, assays, kits, or systems may comprise certain assay conditions (for example detection molecules, blockers, detergents, concentrations) that allow for sub-femtomolar detection of at least some (for example each) of the biomarkers.

In certain embodiments, for example, the methods, tests, assays, kits, or systems may utilize one or more reagents and/or techniques that reduce and/or eliminate cross-reactivity, non-specific binding, dilution non-linearity, unpredictable spike recovery, and/or adverse analyte (for example protein) confirmation. In certain embodiments, for example, the methods, tests, assays, kits, or systems may utilize a detergent that promotes favorable biomarker confirmation for at least some (for example two or more, three or more, all) of the biomarkers in the multiplex assay. In certain embodiments, for example, the methods, tests, assays, kits, or systems may utilize a detergent that promotes a confirmation of NF-L and another biomarker (for example UCH L1, GFAP, and/or Tau) that may be favorable for accurate detection (for example quantification). In certain embodiments, for example, use of the detergents described herein may allow for the detection of multiple biomarkers in a single assay that may not be measured using conventional detergents generally employed. In certain embodiments, for example, use of the detergents described herein may allow for the detection of both Tau and UCH-LI in the multiplexed assay. Conversely, some conventional detergents that allow for the detection of tau proteins cause UCH L1 to be undetectable. Non-limiting examples of suitable detergents include non-ionic detergents, such as Triton™ X-100, the non-ionic surfactant sold under the trademark Triton™ X-114, Tween-20, Tween-80, and combinations thereof.

In certain embodiments, for example, the detergent may be used during one or more assay steps and/or present in one or more assay compositions (for example diluent composition). In certain embodiments, for example, the detergent may be present during the detection step. In certain embodiments, for example, the detergent may be present in the diluent composition. In certain embodiments, for example, the methods, tests, assays, kits, or systems may utilize a diluent comprising a detergent (for example Triton™ X-100 or Triton™ X-114) at a concentration of between about 0.1 wt. % and about 1.0 w.t % (for example about 0.5 wt. %). In certain embodiments, for example, the presence of the detergent in the diluent composition may allow for the accurate detection (for example quantification) of the biomarkers in the multiplex assay and/or a relatively low LOD and/or LOQ. In certain embodiments, for example, the absence of a detergent in one or more assay steps and/or assay compositions may result in one or more biomarkers (for example UCH L1) being undetectable.

In certain embodiments, for example, the methods, tests, assays, kits, or systems may utilize one or more reagents that reduce and/or eliminate cross-reactivity or non-specific binding between assay components (for example detection molecules, calibration molecules, biomarker) for one biomarker and assay components for another biomarker. In certain embodiments, for example, the methods, tests, assays, kits, or systems may utilize detection and/or calibration molecules that have relatively low non-specific binding and/or cross-reactivity with other components in the multiplex assay. In certain embodiments, for example, use of the detection and/or calibration molecules described herein allowed for the detection of multiple biomarkers in a single assay that could not be accurately measured, measured with acceptable clinical discrimination, and/or measured with low LOQ and/or LOD using certain conventional detection and/or calibration molecules. In certain embodiments, for example, the methods, tests, assays, kits, or systems may utilize certain combinations of UCH L1 clones (for example human recombinant protein, UCH L1 clones 10D1 and 1033) that provide relatively high clinical discrimination, relatively low non-specific binding, and relatively low cross-reactivity with other assay components (for example other biomarkers). Conversely, conventional combinations of UCH L1 clones that provide relatively low LOD for UCH L1 may produce poor clinical discrimination for other biomarkers, have high non-specific binding with assay components for other biomarkers, or otherwise adversely affect the detection of other biomarkers in the multiplex assay. In certain embodiments, for example, the methods, tests, assays, kits, or systems may utilize certain GFAP standards (for example Hytest native human GFAP) for calibration that do not cross-react and/or non-specifically bind with the assay components for the NF-L, UCH L1, and/or Tau assays, whereby the cross-reactivity between the GFAP calibration standard that results in a non-specific signal in non-GFAP assays (for example NF-L, UCH-L1, and/or Tau assays) with increasing doses of GFAP antigen may be reduced and/or eliminated.

In certain embodiments, for example, the concentration of one or more binding ligands used in the multiplex assay may be less than the concentration utilized in a single biomarker assay. In certain embodiments, for example, the binding ligand may be a molecule, particle, or the like which specifically binds to or otherwise specifically associates with a biomarker molecule to aid in the detection of the biomarker molecule. In certain embodiments, for example, the binding ligand may comprise an antibody for the biomarker that may be directly or indirectly detected. Other embodiments are contemplated herein. In certain embodiments, for example, the concentration of one or more binding ligands used in the multiplex assay may range from about 2 to about 10 (for example from about 2 to about 8, from about 4 to about 10, from about 4 to about 8) times less than the concentration utilized in a single biomarker assay. In certain embodiments, for example, the concentration of binding ligands used in a single biomarker assay may result in cross-reactivity and/or non-specific binding with assay components for another assay. In certain embodiments, for example, the UCH L1 binding ligand (for example clone 1033) concentrations for a single biomarker assay may result in a relatively high amount of non-specific binding. In certain embodiments, for example, the concentration of the UCH L1 binding ligand in the multiplex assay may be at least about 2 times (for example at least about 4 times, about 6 times) less than the concentration utilized in the single biomarker assay. In certain embodiments, for example, the concentration of one or more binding ligands in the multiplex assay may be in the range of from about 0.1 to about 2 pg/mL, whereby cross reactivity and/or non-specific binding may be reduced or eliminated.

In certain embodiments, for example, the methods, tests, assays, kits, or systems may utilize one or more reagents and/or techniques that reduce and/or eliminate dilution non-linearity and unpredictable spike recovery for each biomarker (for example NF-L, GFAP, UCH L1, and/or Tau). In certain embodiments, for example, the methods, tests, assays, kits, or systems may utilize one or more blockers that promote dilution linearity (for example of a tested sample when diluted with a sample diluent) and predictable spike recovery. In certain embodiments, for example, the one or more blockers may serve to reduce and/or eliminate sample matrix effects that adversely affect linearity, spike recovery, and/or quantification. In certain embodiments, for example, the term "blocker" may refer to a reagent (for example protein-containing reagent) designed to competitively block non-specific binding. In certain embodiments, for example, the blocker may comprise one or more proteins. In certain embodiments, for example, the blocker reagent may contain multiple proteins (for example IgG), to block non-specific interactions between monoclonal antibodies (for example mouse monoclonal antibodies). In certain embodiments, for example, the blocker reagents may comprise proteins or antibodies from different animal species (for example mouse, bovine, human). Non-limiting examples of suitable blockers include globulin (for example bovine gamma globulin), albumin (for example BSA), TRU Block™ Superchemiblock™, and combinations thereof. In certain embodiments, for example, the methods, tests, assays, kits, or systems may utilize (for example in a diluent) two or more blockers (for example three or more, four). In certain embodiments, for example, a diluent may comprise a globulin (for example bovine gamma globulin, in the range of about 0.005 wt. % to about 0.2 wt. %), an albumin (for example BSA, in the range of about 0.01 wt. % to about 0.1%), TRU Block™ (for example in the range of about 5 pg/mL to about 20 pg/mL), and/or Superchemiblock™ (for example in the range of about 10 pg/mL to about 100 pg/mL, in the range of about 10 pg/mL to about 100 pg/mL). In certain embodiments, for example, the diluent may comprise a carbohydrate (for example dextrose, in a range of about 0.005 wt. % to about 0.05 wt. %), a nitrogen containing small molecule (for example urea, in a range of about 1 mM to about 10 mM), and/or a detergent (for example Triton™ X-100, in a range of about 0.2 wt. % to about 1 wt. %).

In certain embodiments, for example, the concentration of one or more blockers used in the multiplex assay may be greater than the concentration utilized in a single biomarker assay. In certain embodiments, for example, the concentration of one or more blockers and/or all blockers used in the multiplex assay may range from about 5 to about 100 times (for example from about 10 to about 100, from about 20 to about 100, from about 5 to about 50) greater than the concentration utilized in a single biomarker assay. In certain embodiments, for example, the concentration of one or more blockers (for example TRU™ block, Superchemiblock™) and/or all blockers in an assay composition (for example diluent, detection composition) may be at least about 10 pg/mL, at least about 15 pg/mL, at least about 20 pg/mL, at least about 30 pg/mL, at least about 40 pg/mL, at least about 50 pg/mL, at least about 60 pg/mL, at least about 70 pg/mL, at least about 80 pg/mL, at least about 90 pg/mL, at least about 100 pg/mL, at least about 125 pg/mL, at least about 150 pg/mL, at least about 175 pg/mL, or at least about 200 pg/mL. In certain embodiments, for example, the concentration of one or more blockers (for example TRU™ block, Superchemiblock™) and/or all blockers in an assay composition may ranges from about 10 pg/mL to about 200 pg/mL (for example 10 pg/mL to about 100 pg/mL, 5 pg/mL to about 20 pg/mL, 50 pg/mL to about 100 pg/mL).

Certain embodiments may provide, for example, methods, tests, assays, kits, or systems that are ultrasensitive and have very low limits of quantification and/or limits of detection (for example in the low pg/mL range). In certain embodiments, for example, the methods, tests, assays, kits, or systems may be used to provide statistically significant and/or meaningful results regarding a measure of the concentration of the panels of two or more biomarkers associated with brain injury and/or neurodegeneration. In certain embodiments, for example, the methods, tests, assays, kits, or systems may have a limit of detection and/or a limit of quantification of less than about or about 500 pg/mL, less than about or about 250 pg/mL, less than about or about 100 pg/mL, less than about or about 50 pg/mL, less than about or about 40 pg/mL, less than about or about 30 pg/mL, less than about or about 20 pg/mL, less than about or about 10 pg/mL, less than about or about 8 pg/mL, less than about or about 6 pg/mL, less than about or about 5 pg/mL, less than about or about 4 pg/mL, less than about or about 3 pg/mL, less than about or about 2 pg/mL, less than about or about 1 pg/mL, less than about or about 0.8 pg/mL, less than about or about 0.7 pg/mL, less than about or about 0.6 pg/mL, less than about or about 0.5 pg/mL, less than about or about 0.4 pg/mL, less than about or about 0.3 pg/mL, less than about or about 0.2 pg/mL, less than about or about 0.1 pg/mL, less than about or about 0.08 pg/mL, less than about or about 0.06 pg/mL, less than about or about 0.05 pg/mL, less than about or about 0.04 pg/mL, less than about or about 0.02 pg/mL, less than about or about 0.01 pg/mL, or less than about or about 0.005 pg/mL for at least some (for example each) of the biomarkers. In certain embodiments, for example, the methods, tests, assays, kits, or systems may have a limit of quantification and/or a limit of detection between about 100 pg/mL and about 0.01 pg/mL, between about 50 pg/mL and about 0.02 pg/mL, or between about 25 pg/mL and about 0.02 pg/mL, between about 10 pg/mL and about 0.02 pg/mL for at least some (for example each) of the biomarkers.

In certain embodiments, for example, an LOQ and/or LOD may differ for one or more (for example each) of the biomarkers determined with the same assay and/or when two or more biomarkers are determined together in a single assay and/or from a single sample. In certain embodiments, for example, the LOD for Tau may be equal to or less than about 0.02 pg/mL and/or the LOQ for Tau may be equal to or less than about 0.1 pg/mL (for example equal to or less than about 0.06 pg/mL), for example when measured with one or more other biomarkers. In certain embodiments, for example, the LOD for NF-L may be equal to or less than about 0.2 pg/mL (for example equal to or less than about 0.1 pg/mL) and/or the LOQ for NF-L may be equal to or less than about 1.0 pg/mL (for example equal to or less than about 0.4 pg/mL, equal to or less than about 0.3 pg/mL), for example when measured with one or more other biomarkers. In certain embodiments, for example, the LOD for GFAP may be equal to or less than about 0.3 pg/mL and/or the LOQ for GFAP may be equal to or less than about 1.0 pg/mL (for example equal to or less than about 0.5 pg/mL), for example when measured with one or more other biomarkers. In certain embodiments, for example, the LOD for UCH L1 may be equal to or less than about 5 pg/mL (for example equal to or less than about 2 pg/mL) and/or the LOQ for UCH-L1 may be equal to or less than about 10 pg/mL (for example equal to or less than about 5 pg/mL), for example when measured with one or more other biomarkers.

The terms "limit of detection" (or LOD) and "limit of quantification" (or LOQ) are given their ordinary meaning in the art. The LOD refers to the lowest analyte concentration likely to be reliably distinguished from background noise and at which detection is feasible. The LOD as used herein may be defined as three standard deviations (SD) above background noise. The LOQ refers to the lowest concentration at which the analyte can not only be reliably detected but at which some predefined goals for bias and imprecision are met. Generally, as is used herein, the LOQ refers to the lowest concentration above the LOD wherein the coefficient of variation (CV) of the measured concentrations less than about 20%.

In certain embodiments, for example, the methods, tests, assays, kits, or systems may comprise comparing the levels of the one or more biomarkers with levels of the biomarkers obtained from a certain population of individuals. In certain embodiments, for example, the methods, tests, assays, kits, or systems may comprise comparing the levels of the one or more biomarkers with levels of the biomarkers obtained from a population of individuals having a certain gender, age, ethnicity, health status, disease, phenotype, and/or genotype. In certain embodiments, for example, the methods, tests, assays, kits, or systems may comprise comparing the levels of the one or more biomarkers with levels of the biomarkers obtained from a population of healthy individuals. In certain embodiments, for example, the methods, tests, assays, kits, or systems may comprise comparing the levels of the one or more biomarkers with levels of the biomarkers obtained from a population of individuals with a history of one/or more brain injury events. In certain embodiments, for example, the methods, tests, assays, kits, or systems may comprise collecting a sample from the patient (for example a venous or capillary blood sample). In certain embodiments, for example, the sample may be collected after a suspected brain injury. In certain embodiments, for example, the sample may be collected after an event creating a risk (for example a heightened risk) of brain injury (for example child birth or detonation of an explosive) or an event prone to causing brain injury. In certain embodiments, for example, the sample may be collected within a certain timeframe of the brain injury or suspected brain injury. In certain embodiments, for example, the timeframe may be selected such that a measure of the concentration of the biomarkers in the sample becomes statistically significant. In certain embodiments, for example, the period of time between the brain injury or suspected brain injury and collection of the blood sample from the patient may account for any lag time required for the biomarkers to cross the blood brain barrier (BBB). Non-limiting examples of suitable periods of time in which a sample may be obtained from the patient include 1 hour, 2 hours, 3 hours, 4 hours, 6 hours, 8 hours, 10 hours, 12 hours, 18 hours, 24 hours, 36 hours, 48 hours, 60 hours, 72 hours, 4 days, 5 days, 6 days, 7 days, or more. In certain embodiments, for example, the duration of time between suspected brain injury and sample collection may be at least 60 hours or at least 72 hours. In certain embodiments, for example, the duration of time may be between 12 hours and 7 days, between 24 hours and 4 days, between 2 days and 4 days, or between 3 days and 4 days. In certain embodiments, for example, the sample may be obtained from the patient within a short timeframe following the brain injury or suspected brain injury. For example, the sample may be obtained from the patient within 1 hour, 2 hours, 3 hours, 4 hours, 5 hours, 6 hours, 8 hours, 10 hours, or 12 hours of the brain injury. In certain embodiments, for example, the sample may be obtained within 6 hours of the brain injury. In certain embodiments, for example, the sample collection may occur months following the brain injury in order to assess long-term effects. In certain embodiments, for example, the samples may be collected 14 days, 1 month, 3 month, 6 months, 9 months, or more, following brain injury.

In certain embodiments, for example, the sample obtained from the patient may be from any suitable bodily source. In certain embodiments, for example, the sample may be a CSF fluid sample. In certain embodiments, for example, the sample may be exclusive of CSF fluid. In certain embodiments, for example, the sample may be blood (for example venous blood or capillary blood) or a blood product (for example whole blood, plasma, serum, etc.). In certain embodiments, for example, the sample may be a urine or a saliva sample. In certain embodiments, for example, the sample may be analyzed directly (for example without the need for extraction of the biomarker from the fluid sample) and/or with dilution (for example addition of a buffer or agent to the sample). Those of ordinary skill in the art will be aware of suitable systems and methods for obtaining a sample from a patient. In addition to the biomarkers specifically mentioned herein, those of ordinary skill will be aware of other suitable biomarkers to use in connection with the methods described herein. In certain embodiments, for example, biomarkers detected and/or quantified by the methods, tests, assays, kits, or systems may comprise, without limitation, neuron specific neuronal enolase (NSE), β-site aPP-cleaving enzyme 1 (BACe1), S100B, myelin basic protein (MBP), growth associated protein 43, glutamine synthetase, GFAP, glycine transporter (for example GLYT1, GLYT2), neuron specific glycoprotein (for example GP50), calpain, neurofibrillary protein, heat shock protein 72, beta-amyloid precursor proteins, calbindin D-28K, proteolipid protein, myeline associated glycoprotein, neurofilament H, creatine kinase protein (for example CK-BB), tau proteins (including phosphorylated taus such as p-tau-181 or p-tau-231), and endothelium membrane proteins (for example thrombomodulin).

In certain embodiments, for example, the methods, tests, assays, kits, or systems may comprise detecting and/or quantifying a panel of biomarkers. In certain embodiments, for example, the panel of biomarkers may include at least one species of tau protein. Various forms and/or combinations of tau proteins are contemplated for use as a target biomarker with the methods described herein, including isoforms and short isoforms, for example, ranging from tau 23 (352a.a, "0N3R", wherein R indicates the number of repeats and N indicates the number or amino terminal inserts, as will be understood by those of ordinary skill in the art) to tau 40 (441a.a, "2N4R"). There are six known naturally-occurring tau proteins, the sequences of which are well known in the art. The six tau proteins include tau 23 (352, 0N3R), tau 24 (383, 0N4R), tau 37 (381, 1N3R), tau 34 (412, 1N4R), tau 39 (410, 2N3R), tau 40 (441, 2N4R), and/or combinations thereof. In certain embodiments, for example, at least some of the tau proteins may be phosphorylated.

Those of ordinary skill in the art will understand that determination of a biomarker in a sample may comprise determining a measure of the concentration a single isoform of a biomarker, or alternatively, may comprise determining a measure of the concentration of a plurality (for example 2, 3, 4, 5, 6, 7, 8, 9, 10, or more than 10) of isoforms of the biomarker. In certain embodiments, for example, a measure of the concentration of tau protein employed in the methods described herein may be a measure of the concentration of a single isoform of tau protein in the sample, or alternatively, a measure of the concentration of tau protein employed in the algorithms and methods described herein may be a measure of the concentration of a plurality of forms of tau proteins in the sample.

In certain embodiments, for example, the methods, tests, assays, kits, or systems may comprise using an immunoassay to determine a measure of the concentration of two or more biomarkers. In certain embodiments, for example, the immunoassay may utilize an antibody as a detection molecule. In general, any suitable antibodies that differentially and/or selectively binds a biomarker may be used.

An immunoassay is a biochemical test that measures the presence or concentration of a molecule of interest (for example a macromolecule such as a protein) in a sample through the use of an antibody or immunoglobulin. Typically, an antibody specific to the molecule of interest interacts with the molecule in an immunoassay. The antibody can be labeled, directly or indirectly such that those bound to the molecule could release a detectable signal. Presence or concentration of the molecule of interest can be determined based on the level of the detectable signal. Certain embodiments may provide, for example, an immunoassay using one or more types of labels including, without limitation, enzymes, radioactive isotopes, DNA reporters, fluorogenic reporters, electrochemiluminescent tags, all of which are well known in the art. In certain embodiments, for example, the immunoassay may amplify a signal via a catalyst (for example an enzyme). In certain embodiments, for example, the immunoassay may be exclusive of a label.

In certain embodiments, for example, the immunoassay may be used to detect an antigen of interest (for example NF-L, tau protein, GFAP, UCH L1, etc.). In certain embodiments, for example, the immunoassay may comprise a protocol that comprises certain standard techniques known in the art. In certain embodiments, for example, the immunoassay may be a competitive immunoassay. In certain embodiments, for example, the immunoassay may be a one-site non-competitive assay. In certain embodiments, for example, the immunoassay may be a two-site noncompetitive assay (for example a sandwich assay). In certain embodiments, for example, the immunoassay may comprise multiple steps with reagents being added and washed away or separated at different points in the assay (for example a heterogeneous immunoassay). In certain embodiments, for example, the immunoassay may be carried out simply by mixing the reagents and sample and making a physical measurement (for example a homogenous immunoassay).

In a preferred embodiment, for example, the immunoassay may be an enzyme-linked immunosorbent assay (ELISA). In certain embodiments, for example, the immunoassay may be a digital assay (for example a digital ELISA). In certain embodiments, for example, the digital ELISA may incorporate single molecule array technology (for example digital immunoassay technology sold under the Simoa trademark) as described herein. Additional details regarding single molecule array technologies are described herein.

The basic nature of the ELISA format is generally well known in the art. The inventive ELISA type assays used in certain embodiments of the detection methods described herein can incorporate a variety of formats known in the art, including direct ELISA, Sandwich ELISA, competitive ELISA, and multiple and ready-to-use ELISA. In a typical "indirect" ELISA, an antibody having specificity for the antigen of interest is immobilized on a solid surface (for example the wells of a standard microtiter assay plate, or the surface of a microbead or a microarray) and a sample comprising, for example bodily fluid or substances extracted from stool samples, to be tested for the presence of the antigen is brought into contact with the immobilized antibody. Any antigen of interest in the sample will bind to the immobilized antibody. The bound antibody/antigen complexes may then be detected using any suitable method. In one embodiment, a second antibody, which specifically recognizes an epitope of the antigen, which may be different from the epitope recognized by the immobilized antibody, is used to detect the antibody/antigen complexes. The second antibody may be usually labelled with a detectable marker (directly or indirectly). In some examples, the maker can be an enzyme such as peroxidase, alkaline phosphatase, or galactosidase, allowing quantitative detection by the addition of a substrate for the enzyme which generates a detectable product, for example a colored, chemiluminescent or fluorescent product. Other types of detectable labels known in the art may be used with equivalent effect. In other examples, the second antibody may be labeled with a member of a receptor/ligand pair, for example, biotin. An enzyme conjugate comprising an enzyme conjugated with the other member of the receptor/ligand pair, for example streptavidin, can be brought into contact with the second antibody. A substrate of the enzyme may be then added to produce a product that releases a detectable signal.

Generally, the methods employed have low limits of detection and/or limits of quantification as compared to bulk analysis techniques (for example ELISA methods). The use of assay methods that have low limits of detection and/or limits of quantification allows for correlations to be made between the various parameters discussed above and a method of treatment and/or diagnostic indication that may otherwise not be determinable and/or apparent.

An antibody (interchangeably used in plural form) may be an immunoglobulin molecule capable of specific binding to a target, such as NF-L, Tau, GFAP, and UCH L1, through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, linear antibodies, single chain antibodies, multispecific antibodies (for example bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. The antibodies described herein can be murine, rat, human, or any other origin (including chimeric or humanized antibodies).

In certain embodiments, for example, the analyte antibodies described herein may have a suitable binding affinity to the antigen. As used herein, "binding affinity" refers to the apparent association constant or $K_A$. The $K_A$ is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target relative to the second target. Differences in binding affinity (for example for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (for example using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) may be related to the concentration of free target protein ([Free]) and the concentration of binding sites for the binding protein on the target where (N) may be the number of binding sites per target molecule by the following equation:

$$[Bound]=[N][Free]/(K_D+[Free])$$

It is not always necessary to make an exact determination of $K_A$, though, since sometimes it may be sufficient to obtain a quantitative measurement of affinity, for example determined using a method such as ELISA or FACS analysis, which is proportional to $K_d$, and thus can be used for comparisons, such as determining whether a higher affinity is, for example 2-fold higher, to obtain a qualitative measurement of affinity, or to obtain an inference of affinity, for example by activity in a functional assay, for example an in vitro or in vivo assay.

In certain embodiments, for example, the antibodies used in the detection assays described herein may differentially bind one biomarker associated with brain injury and/or neurodegeneration over another such biomarker. An antibody that "differentially binds" to a first target or a first epitope as relative to a second target or a second epitope refers to an antibody that has different binding affinities to the first and second targets or different binding affinities to the first and second epitopes. In certain embodiments, for example, an antibody may have a much higher binding affinity to the first target/epitope as relative to the second target/epitope, or vice versa, for example at least 2-fold higher, 5-fold higher, 10-fold higher, 50-fold higher, 100-fold higher, 200-fold higher, 500-fold higher, 1,000-fold higher, or 10,000-fold higher. In other examples, the antibody may have a much lower binding affinity to the first target/epitope as relative to the second target/epitope, or vice versa, for example at least 2-fold lower, 5-fold lower, 10-fold lower, 50-fold lower, 100-fold lower, 200-fold lower, 500-fold lower, 1,000-fold lower, or 10,000-fold lower.

In certain embodiments, for example, the antibodies used in the detection assays described herein may specifically bind one biomarker associated with brain injury and/or neurodegeneration over another such biomarker. An antibody "specifically binds" to a target antigen if it binds with greater affinity, avidity, more readily, and/or with greater duration than it binds to other substances. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

Antibodies capable of binding biomarkers associated with brain injury and/or neurodegeneration can be made by any method known in the art and/or are commercially available. See, for example, Harlow and Lane, (1988) Antibodies: A Laboratory Manual, Cold Spring Harbor Laboratory, New York.

In certain embodiments, for example, the methods, tests, assays, kits, or systems may comprise determining a measure of the concentration of a panel of at least one biomarker in one or more samples obtained from a patient following a suspected brain injury. In certain embodiments, for example, a diagnosis, prognostic indication of the patient's recovery, and/or determining a course of treatment may be based at least in part on the measure of the concentration of the at least one biomarker present in the one or more samples. In certain embodiments, for example, following determining the measure of the concentration of the biomarkers, the measure of the concentration may be compared with a predefined level of the biomarker from a population of healthy individuals. In certain embodiments, for example, the methods, tests, assays, kits, or systems may comprise comparing the measure of the concentration of NF-L and at least one other biomarker (for example one or more of GFAP, UCH L1, and Tau) with levels of NF-L and the at least one other biomarker (for example levels based on measurements taken from samples obtained from a population of healthy individuals).

Certain embodiments may provide, for example, kits for use in determining a measure of the concentration of at least one biomarker in a sample. In certain embodiments, for example, the at least one biomarker may be at least two biomarkers, wherein a first biomarker of the at least two biomarkers may be NF-L and at least a second of the at least two biomarkers may be at least one other biomarker selected from the group consisting of GFAP, UCH L1, and Tau. In certain embodiments, for example, the kit may be for measuring concentration of a biomarker panel comprising at least Tau, GFAP, UCH L1, and NF-L (for example comprising GFAP, UCH L1, and Tau). In certain embodiments, for example, the kit may comprise a plurality of capture objects (for example beads, optionally magnetic beads), each having a binding surface comprising a plurality of capture components. In certain embodiments, for example, the plurality of capture components may comprise a plurality of an antibodies having specific affinity for the one or more biomarkers being detected. In certain embodiments, for example, each capture object (for example bead) may comprise a plurality of types of capture objects, each type of capture object having specific affinity for a particular biomarker (for example a plurality of antibodies having specific affinity for NF-L and a plurality of antibodies having specific affinity for at least one other biomarker selected from the group consisting of, GFAP, UCH L1, and Tau). In certain embodiments, for example, the kit may comprise a plurality of types of binding ligands having specific affinity for the at least one biomarker. In certain embodiments, for example, the binding ligands may be directly or indirectly detectable. In certain embodiments, for example, the kit may comprise a plurality of a first type of binding ligand having affinity for NF-L and a plurality of a second type of binding ligand having affinity for at least one other biomarker selected from the group consisting of, GFAP, UCH L1, and Tau. In certain embodiments, for example, the kit may comprise i) a plurality of capture objects, each having a binding surface comprising a plurality of capture components; ii) a plurality of a first type of binding ligand having affinity for NF-L; and iii) a plurality of a second type of binding ligand and a third type of binding ligand having affinity for at least two other biomarker selected from the group consisting of, GFAP, UCH L1, and Tau. In certain embodiments, for example, the kit may comprise i) a plurality of capture objects, each having a binding surface comprising a plurality of capture components; ii) a plurality of a first type of binding ligand having affinity for NF-L; iii) a plurality of a second type of binding ligand having affinity for GFAP; iv) a plurality of a third type of binding ligand having affinity for UCH L1; and v) a plurality of a fourth type of binding ligand having affinity for Tau. In certain embodiments, for example, the kit may comprise one or more components for performing the assays. In certain embodiments, for example, the kit may comprise an enzyme label substrate for indirect detection of a binding ligand. In certain embodiments, for example, the kit may comprise an instruction manual providing guidance for using the kit to perform any one of the detection assay provided herein.

Exemplary Assay Methods and Systems

Certain embodiments, for example, may provide methods, tests, assays, kits, or systems having low limits of detection and/or limits of quantification as compared to bulk analysis techniques (for example modified ELISA methods). In certain embodiments, for example, use of the provided methods, tests, assays, kits, or systems may enable one or more methods of treatment and/or diagnostic indication that may otherwise not be determinable and/or apparent.

In certain embodiments, for example, a measure of the concentration of biomarker molecules in the fluid sample that may be substantially accurately determined may be less than about or about 5000 fM, less than about or about 3000 fM, less than about or about 2000 fM, less than about or about 1000 fM, less than about or about 500 fM, less than about or about 300 fM, less than about or about 200 fM, less than about or about 100 fM, less than about or about 50 fM, less than about or about 25 fM, less than about or about 10 fM, less than about or about 5 fM, less than about or about 2 fM, less than about or about 1 fM, less than about or about 0.5 fM, less than about or about 0.1 fM, or less. In certain embodiments, for example, a measure of the concentration of biomarker molecules in the fluid sample that may be substantially accurately determined may be between about 5000 fM and about 0.1 fM, between about 3000 fM and about 0.1 fM, between about 1000 fM and about 0.1 fM, between about 1000 fM and about 1 fM, between about 100 fM and about 1 fM, between about 100 fM and about 0.1 fM, or the like. In certain embodiments, for example, a measure of the concentration of analyte molecules or particles in a fluid sample may be considered to be substantially accurately determined if the measured concentration of the biomarker molecules in the fluid sample may be within about 10% of the actual (for example true) concentration of the biomarker molecules in the fluid sample. In certain embodiments, for example, the measured concentration of the biomarker molecules in the fluid sample may be within about 5%, within about 4%, within about 3%, within about 2%, within about 1%, within about 0.5%, within about 0.4%, within about 0.3%, within about 0.2% or within about 0.1%, of the actual concentration of the biomarker molecules in the fluid sample. In certain embodiments, for example, a measure of the concentration determined may differ from the true (for example actual) concentration by no greater than about 20%, no greater than about 15%, no greater than 10%, no greater than 5%, no greater than 4%, no greater than 3%, no greater than 2%, no greater than 1%, or no greater than 0.5%. In certain embodiments, for example, the accuracy of the assay method may be determined by determining a measure of the concentration of biomarker molecules in a fluid sample of a known concentration using the selected assay method.

Certain embodiments may provide, for example, an assay method comprising: spatially segregating biomarker molecules into a plurality of locations to facilitate detection/quantification, such that each location comprises/contains either zero or one or more biomarker molecules. In certain embodiments, for example, the locations may be configured in a manner such that each location can be individually addressed. In certain embodiments, for example, a measure of the concentration of biomarker molecules in a fluid sample may be determined by detecting biomarker molecules immobilized with respect to a binding surface having affinity for at least one type of biomarker molecule. In certain embodiments, for example, the binding surface may form (for example a surface of a well/reaction vessel on a substrate) or be contained within (for example a surface of a capture object, such as a bead, contained within a well) one of a plurality of locations (for example a plurality of wells/reaction vessels) on a substrate (for example plate, dish, chip, optical fiber end, etc.). In certain embodiments, for example, at least a portion of the locations may be addressed and a measure indicative of the number/percentage/fraction of the locations containing at least one biomarker molecule may be made. In certain embodiments, for example, based upon the number/percentage/fraction, a measure of the concentration of biomarker molecules in the fluid sample may be determined. In certain embodiments, for example, the measure of the concentration of biomarker molecules in the fluid sample may be determined by a digital analysis method/system. In certain embodiments, for example, the measure of the concentration of biomarker molecules in the fluid sample may be determined by a digital analysis method/system employing Poisson distribution adjustment. In certain embodiments, for example, the measure of the concentration of biomarker molecules in the fluid sample may be determined by a digital analysis method/system based at least in part on a measured intensity of a signal. In certain embodiments, for example, the assay method (or apparatus or systems performing at least a portion of the assay method) may be automated.

Any of the methods, tests, assays, kits, or systems may employ one or more of the methods and systems for spatially segregating analyte molecules (for example biomarkers) described in U.S. Patent Application Publication No. US-2007-0259448 (Ser. No. 11/707,385), filed Feb. 16, 2007, entitled "METHODS AND ARRAYS FOR TARGET ANALYTE DETECTION AND DETERMINATION OF TARGET ANALYTE CONCENTRATION IN SOLUTION," by Rissin et al.; U.S. Patent Application Publication No. US-2007-0259385 (Ser. No. 11/707,383), filed Feb. 16, 2007, entitled "METHODS AND ARRAYS FOR DETECTING CELLS AND CELLULAR COMPONENTS IN SMALL DEFINED VOLUMES," by Rissin et al.; U.S. Patent Application Publication No. US-2007-0259381 (Ser. No. 11/707,384), filed Feb. 16, 2007, entitled "METHODS AND ARRAYS FOR TARGET ANALYTE DETECTION AND DETERMINATION OF REACTION COMPONENTS THAT AFFECT A REACTION," by Rissin et al.; International Patent Publication No. WO 2009/029073 (International Patent Application No. PCT/US2007/019184), filed Aug. 30, 2007, entitled "METHODS OF DETERMINING THE CONCENTRATION OF AN ANALYTE IN SOLUTION," by Walt et al.; U.S. Patent Application Publication No. US-2010-0075862 (Ser. No. 12/236,484), filed Sep. 23, 2008, entitled "HIGH SENSITIVITY DETERMINATION OF THE CONCENTRATION OF ANALYTE MOLECULES OR PARTICLES IN A FLUID SAMPLE," by Duffy et al.; U.S. Patent Application Publication No. US-2010-0075407 (Ser. No. 12/236,486), filed Sep. 23, 2008, entitled "ULTRA-SENSITIVE DETECTION OF MOLECULES ON SINGLE MOLECULE ARRAYS," by Duffy et al.; U.S. Patent Application Publication No. US-2010-0075439 (Ser. No. 12/236,488), filed Sep. 23, 2008, entitled "ULTRA-SENSITIVE DETECTION OF MOLECULES BY CAPTURE-AND-RELEASE USING REDUCING AGENTS FOLLOWED BY QUANTIFICATION," by Duffy et al.; International Patent Publication No. WO2010/039179 (International Patent Application No. PCT/US2009/005248), filed Sep. 22, 2009, entitled "ULTRA-SENSITIVE DETECTION OF MOLECULES OR ENZYMES," by Duffy et al.; U.S. Patent Application Publication No. US-2010-0075355 (Ser. No. 12/236,490), filed Sep. 23, 2008, entitled "ULTRA-SENSITIVE DETECTION OF ENZYMES BY CAPTURE-AND-RELEASE FOLLOWED BY QUANTIFICATION," by Duffy et al.; U.S. patent application Ser. No. 12/731,130, filed Mar. 24, 2010, published as US-2011-0212848 on Sep. 1, 2011, entitled "ULTRA-SENSITIVE DETECTION OF MOLECULES OR PARTICLES USING BEADS OR OTHER CAPTURE OBJECTS," by Duffy et al.; International Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS," by Duffy et al.; International Patent Application No. PCT/US2011/026657, filed Mar. 1, 2011, published as WO 2011/109372 on Sep. 9, 2011, entitled "ULTRA-SENSITIVE DETECTION OF MOLECULES USING DUAL DETECTION METHODS," by Duffy et al.; U.S. patent application Ser. No. 12/731,135, filed Mar. 24, 2010, published as US-2011-0212462 on Sep. 1, 2011, entitled "ULTRA-SENSITIVE DETECTION OF MOLECULES USING DUAL DETECTION METHODS," by Duffy et al.; International Patent Application No. PCT/US2011/026665, filed Mar. 1, 2011, published as WO 2011/109379 on Sep. 9, 2011, entitled "METHODS AND SYSTEMS FOR EXTENDING DYNAMIC RANGE IN ASSAYS FOR THE DETECTION OF MOLECULES OR PARTICLES," by Rissin et al.; U.S. patent application Ser. No. 12/731,136, filed Mar. 24, 2010, published as US-2011-0212537 on Sep. 1, 2011, entitled "METHODS AND SYSTEMS FOR EXTENDING DYNAMIC RANGE IN ASSAYS FOR THE DETECTION OF MOLECULES OR PARTICLES," by Duffy et al.; U.S. patent application Ser. No. 13/035,472, filed Feb. 25, 2011, published as US 2012-0196774, entitled "SYSTEMS, DEVICES, AND METHODS FOR ULTRA-SENSITIVE DETECTION OF MOLECULES OR PARTICLES," by Fournier et al.; or U.S. patent application Ser. No. 13/037,987, filed Mar. 1, 2011, published as US-2011-0245097 on Oct. 6, 2011, entitled "METHODS AND SYSTEMS FOR EXTENDING DYNAMIC RANGE IN ASSAYS FOR THE DETECTION OF MOLECULES OR PARTICLES," by Rissin et al.; each herein incorporated by reference.

Certain embodiments may provide, for example, methods, tests, assays, kits, or systems comprising spatially segregating biomarker molecules for detecting and/or quantifying the biomarker molecules (for example in a sample). In certain embodiments, for example, the methods, tests, assays, kits, or systems may comprise immobilizing a plurality of biomarker molecules with respect to a plurality of capture objects (for example beads) that each include a binding surface having affinity for at least one type of biomarker. In certain embodiments, for example, the capture objects may comprise a plurality of beads comprising a plurality of capture components (for example an antibody having specific affinity for a biomarker of interest, etc.). In certain embodiments, for example, at least a portion of the capture objects (for example at least a portion that is associated with at least one biomarker molecule) may be spatially separated/segregated into a plurality of locations, and at least some of the locations may be addressed/interrogated (for example using an imaging system). In certain embodiments, for example, a measure of the concentration of biomarker molecules in the fluid sample may be determined based on the information received when addressing the locations (for example using the information received from the imaging system and/or processed using a computer implemented control system). In certain embodiments, for example, a measure of the concentration may be based at least in part on the number of locations determined to contain a capture object that is or was associated with at least one biomarker molecule. In certain embodiments, for example, a measure of the concentration may be based at least in part on an intensity level of at least one signal indicative of the presence of a plurality of biomarker molecules and/or capture objects associated with a biomarker molecule at one or more of the addressed locations.

In certain embodiments, for example, a number/percentage/fraction of locations containing a capture object but not containing a biomarker molecule may also be determined and/or the number/percentage/fraction of locations not containing any capture object may also be determined. In certain embodiments, for example, a measure of the concentration of biomarker molecules in the fluid sample may be based at least in part on a ratio of the number of locations determined to contain a capture object associated with a biomarker molecule to the total number of locations determined to contain a capture object not associated with a biomarker molecule. In certain embodiments, for example, a measure of the concentration of biomarker molecules in the fluid sample a measure of the concentration of biomarker molecule in the fluid sample may be based at least in part on the ratio of the number of locations determined to contain a capture object associated with a biomarker molecule to the number of locations determined to not contain any capture objects. In certain embodiments, for example, a measure of the concentration of biomarker molecules in the fluid sample, a measure of the concentration of biomarker molecule in the fluid sample may be based at least in part on the ratio of the number of locations determined to contain a capture object associated with a biomarker molecule to the number of locations determined to contain a capture object. In certain embodiments, for example, a measure of the concentration of biomarker molecules in the fluid sample, a measure of the concentration of biomarker molecule in the fluid sample may be based on a combination of two or more of the foregoing measures. In certain embodiments, for example, a measure of the concentration of biomarker molecules in the fluid sample, a measure of the concentration of biomarker molecule in the fluid sample may be based may be based at least in part on the ratio of the number of locations determined to contain a capture object and a biomarker molecule to the total number of locations addressed and/or analyzed. In certain embodiments, for example, a measure of the concentration of biomarker molecules in the fluid sample, a measure of the concentration of biomarker molecule in the fluid sample may be based on a combination of two or more of the foregoing measures.

In certain embodiments, for example, at least some of the plurality of capture objects (for example at least some associated with at least one biomarker molecule) may be spatially separated into a plurality of locations, for example, a plurality of reaction vessels in an array format. The plurality of reaction vessels may be formed in, on and/or of any suitable material. In certain embodiments, for example, the reaction vessels may be sealed or may be formed upon the mating of a substrate with a sealing component. In certain embodiments, for example, (for example where quantization of the capture objects associated with at least one biomarker molecule is desired), the partitioning of the capture objects may be performed such that at least some (for example a statistically significant fraction; for example as described in International Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS," by Duffy et al., herein incorporated by reference) of the reaction vessels comprise at least one or, in certain cases, only one capture object associated with at least one biomarker molecule and at least some (for example a statistically significant fraction) of the reaction vessels comprise an capture object not associated with any biomarker molecules. In certain embodiments, for example, the capture objects associated with at least one biomarker molecule may be quantified, thereby allowing for the detection and/or quantification of biomarker molecules in the fluid sample by any of the techniques described herein.

Certain embodiments may provide, for example, an assay method, wherein: a sample fluid containing or suspected of containing biomarker molecules is provided; and an assay consumable comprising a plurality of assay sites is exposed to the sample fluid. In certain embodiments, for example, the biomarker molecules may be provided in a manner (for example at a concentration) such that a statistically significant fraction of the assay sites contain a single biomarker molecule and a statistically significant fraction of the assay sites do not contain any biomarker molecules. In certain embodiments, for example, the assay sites may be exposed to a variety of reagents (for example using a reagent loader) and or rinsed. In certain embodiments, for example, the assay sites may then optionally be sealed and imaged (see, for example, U.S. patent application Ser. No. 13/035,472, filed Feb. 25, 2011, published as US 2012-0196774, entitled "SYSTEMS, DEVICES, AND METHODS FOR ULTRA-SENSITIVE DETECTION OF MOLECULES OR PARTICLES," by Fournier et al.). In certain embodiments, for example, the images may be analyzed (for example using a computer implemented control system) such that a measure of the concentration of the biomarker molecules in the fluid sample may be obtained, based at least in part, by determination of the number/fraction/percentage of assay sites which contain a biomarker molecule and/or the number/fraction/percentage of sites which do not contain any biomarkers molecules. In certain embodiments, for example, the biomarker molecules may be provided in a manner (for example at a concentration) such that at least some assay sites comprise more than one biomarker molecule. In certain embodiments, for example, a measure of the concentration of biomarker molecules in the fluid sample may be obtained at least in part on an intensity level of at least one signal indicative of the presence of a plurality of biomarkers molecules at one or more of the assay sites.

In certain embodiments, for example, the methods, tests, assays, kits, or systems may comprise exposing the fluid sample to a plurality of capture objects (for example beads). In certain embodiments, for example, at least a portion of the biomarker molecules may be immobilized with respect to a bead. In certain embodiments, for example, the biomarker molecules may be provided in a manner (for example at a concentration) such that a statistically significant fraction of the beads associate with a single biomarker molecule and a statistically significant fraction of the beads do not associate with any biomarker molecules. In certain embodiments, for example, at least a portion of the plurality of beads (for example those associated with a single biomarker molecule or not associated with any biomarker molecules) may then be spatially separated/segregated into a plurality of assay sites (for example of an assay consumable). In certain embodiments, for example, the assay sites may optionally be exposed to a variety of reagents and/or rinsed. In certain embodiments, for example, at least a portion of the assay sites may then be addressed to determine the number of assay sites containing a biomarker molecule. In certain embodiments, for example, the number of assay sites containing a bead not associated with a biomarker molecule, the number of assay sites not containing a bead and/or the total number of assay sites addressed may also be determined. In certain embodiments, for example, the determined total number of assay sites may then be used to determine a measure of the concentration of biomarker molecules in the fluid sample. In certain embodiments, for example, more than one biomarker molecule may associate with a bead and/or more than one bead may be present in an assay site. In certain embodiments, for example, the plurality biomarker molecules may be exposed to at least one additional reaction component prior to, concurrent with, and/or following spatially separating at least some of the biomarker molecules into a plurality of locations.

In certain embodiments, for example, the biomarker molecules may be directly detected or indirectly detected. In certain embodiments, for example, one or more of the biomarker molecules may be directly detected via a molecule or moiety that is directly interrogated and/or detected (for example by one or more fluorescent entities attached to the one or more biomarker molecules). In certain embodiments, for example, one or more of the biomarker molecules may be indirectly detected by the presence of an additional component. In certain embodiments, for example, the biomarker molecules (for example optionally associated with a bead) may be exposed to at least one type of binding ligand. In certain embodiments, for example, the at least one type of binding ligand may be adapted to be directly detected (for example the at least one type of binding ligand may comprise a detectable molecule or moiety) or may be adapted to be indirectly detected (for example the at least one type of binding ligand may including a component that can convert a precursor labeling agent into a labeling agent). In certain embodiments, for example, a component of the at least one type of binding ligand may be adapted to be directly detected via a measurable property (for example a fluorescence emission, a color, etc.). In certain embodiments, for example, a component a component of the at least one type of binding ligand may facilitate indirect detection, for example, by converting a precursor labeling agent into a labeling agent (for example an agent that is detected in an assay). A "precursor labeling agent" is any molecule, particle, or the like, that can be converted to a labeling agent upon exposure to a suitable converting agent (for example an enzymatic component). A "labeling agent" is any molecule, particle, or the like, that facilitates detection, by acting as the detected entity, using a chosen detection technique. In certain embodiments, for example, the at least one type of binding ligand may comprise an enzymatic component (for example horseradish peroxidase, beta-galactosidase, alkaline phosphatase, etc.). In certain embodiments, for example, a first type of binding ligand may or may not be used in conjunction with one or more additional types of binding ligands (for example second type, etc.).

In certain embodiments, for example, the at least one type of binding ligand may comprise a plurality of types of binding ligands (for example a first type of binding ligand and at least a second type of binding ligand). In certain embodiments, for example, a first type of binding ligand may be configured to associate with a first type of biomarker molecule and a second type of binding ligand may be configured to associate with the first binding ligand. In certain embodiments, for example, both a first type of binding ligand and a second type of binding ligand may associate with the same or different epitopes of a single biomarker molecule. In certain embodiments, for example, at least one binding ligand may comprise an enzymatic component.

In certain embodiments, for example, a binding ligand and/or a biomarker may comprise an enzymatic component. In certain embodiments, for example, the enzymatic component may convert a precursor labeling agent (for example an enzymatic substrate) into a labeling agent (for example a detectable product). In certain embodiments, for example, a measure of the concentration of biomarker molecules in the fluid sample may be determined based at least in part by determining the number of locations containing a labeling agent (for example by relating the number of locations containing a labeling agent to the number of locations containing a biomarker molecule (or number of capture objects associated with at least one biomarker molecule to total number of capture objects)). Non-limiting examples of enzymes or enzymatic components include horseradish peroxidase, beta-galactosidase, and alkaline phosphatase. Other non-limiting examples of systems or methods for detection include embodiments where nucleic acid precursors are replicated into multiple copies or converted to a nucleic acid that can be detected readily, such as the polymerase chain reaction (PCR), rolling circle amplification (RCA), ligation, Loop-Mediated Isothermal Amplification (LAMP), etc. Such systems and methods will be known to those of ordinary skill in the art, for example, as described in "DNA Amplification: Current Technologies and Applications," Vadim Demidov et al., 2004.

In certain embodiments, for example, the biomarker molecules may be exposed to a precursor labeling agent (for example enzymatic substrate) and the enzymatic substrate may be converted to a detectable product (for example fluorescent molecule) upon exposure to a biomarker molecule.

Certain embodiments may provide, for example, methods, tests, assays, kits, or systems that employ a variety of different components, steps, and/or other aspects that will be known and understood by those of ordinary skill in the art. In certain embodiments, for example, the methods, tests, assays, kits, or systems may comprise determining at least one background signal determination. In certain embodiments, for example, the methods, tests, assays, kits, or systems may further comprise subtracting the background signal from other determinations. In certain embodiments, for example, the methods, tests, assays, kits, or systems may comprise one more washings of capture objects to remove excess sample, reagents, and the like.

In certain embodiments, for example, the methods, tests, assays, kits, or systems may include the use of at least one binding ligand. In certain embodiments, for example, a measure of the concentration of biomarker molecules in a fluid sample may be based at least in part on comparison of a measured parameter to a calibration curve. In certain embodiments, for example, the calibration curve may be formed at least in part by determination at least one calibration factor.

In certain embodiments, for example, precursor labeling agents suspended and/or solubilized in a liquid may be employed. In certain embodiments, for example, the precursor labeling agents may be converted to labeling agents which are insoluble in the liquid. In certain embodiments, for example, the precursor labeling agents may be converted to labeling agents which become immobilized proximate a location (for example within the reaction vessel in which the labeling agent is formed). Such precursor labeling agents and labeling agents and their use are described in commonly owned U.S. Patent Application Publication No. US-2010-0075862 (Ser. No. 12/236,484), filed Sep. 23, 2008, entitled "HIGH SENSITIVITY DETERMINATION OF THE CONCENTRATION OF ANALYTE MOLECULES OR PARTICLES IN A FLUID SAMPLE," by Duffy et al., incorporated herein by reference.

Figure 3A:
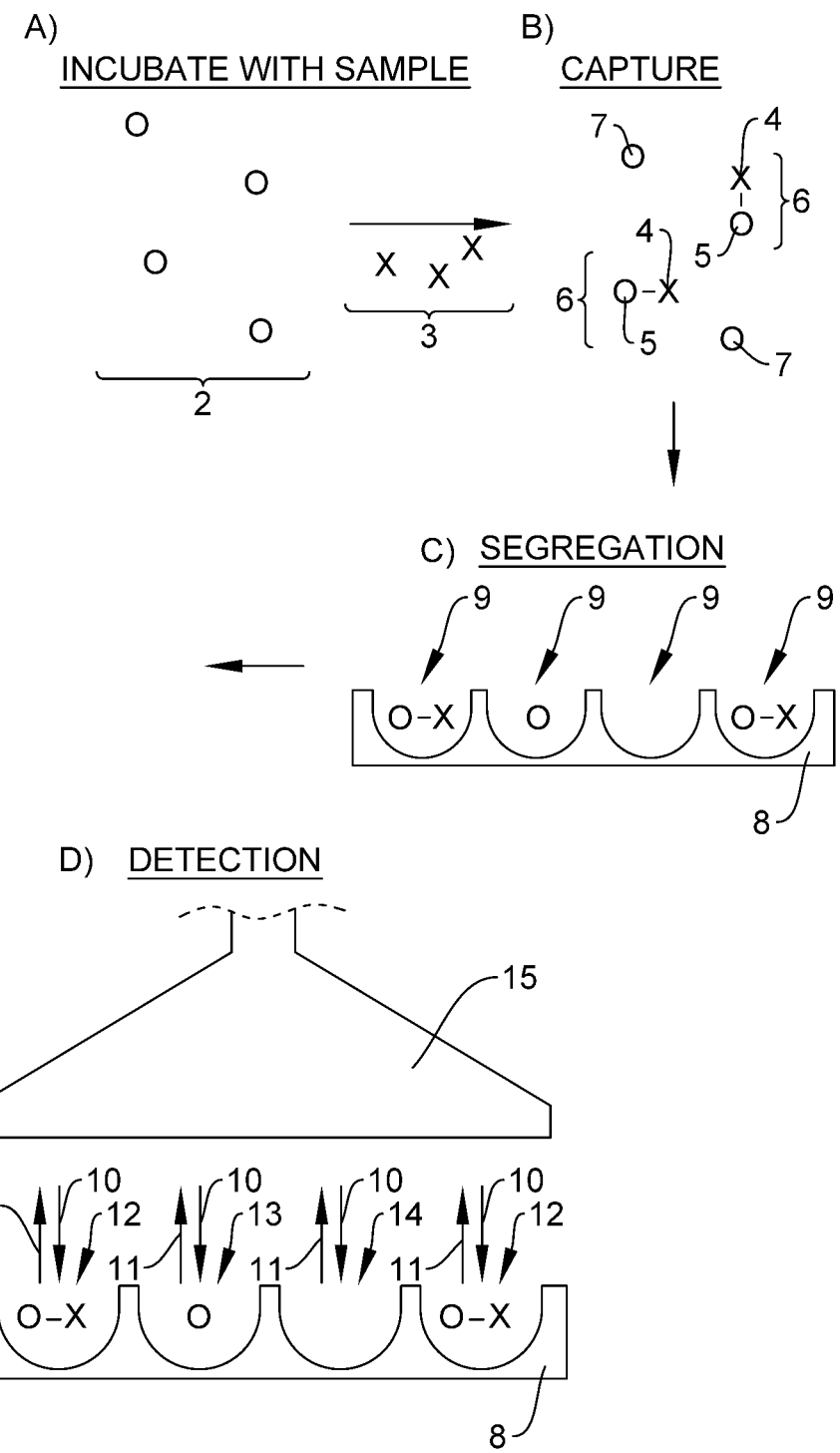
FIG. 3A is a schematic flow diagram depicting a detection method, according to certain embodiments.

An exemplary embodiment of an assay method that may be used in certain embodiments of the invention is illustrated in FIG. 3A. A plurality of capture objects 2, are provided (step (A)). In this particular example, the plurality of capture objects comprises a plurality of beads. The beads are exposed to a fluid sample containing a plurality of biomarker molecules 3 (for example beads 2 are incubated with biomarker molecules 3). At least some of the biomarker molecules are immobilized with respect to a bead. In this example, the biomarker molecules are provided in a manner (for example at a concentration) such that a statistically significant fraction of the beads associate with a single biomarker molecule and a statistically significant fraction of the beads do not associate with any biomarker molecules. For example, as shown in step (B), biomarker molecule 4 is immobilized with respect to bead 5, thereby forming complex 6, whereas some beads 7 are not associated with any biomarker molecules. It should be understood, in some embodiments, more than one biomarker molecule may associate with at least some of the beads, as described herein. At least some of the plurality of beads (for example those associated with a single biomarker molecule or not associated with any biomarker molecules) may then be spatially separated/segregated into a plurality of locations. As shown in step (C), the plurality of locations is illustrated as substrate 8 comprising a plurality of wells/reaction vessels 9. In this example, each reaction vessel comprises either zero or one beads. At least some of the reaction vessels may then be addressed (for example optically or via other detection means) to determine the number of locations containing a biomarker molecule. For example, as shown in step (D), the plurality of reaction vessels are interrogated optically using light source 15, wherein each reaction vessel is exposed to electromagnetic radiation (represented by arrows 10) from light source 15. The light emitted (represented by arrows 11) from each reaction vessel is determined (and/or recorded) by detector 15 (in this example, housed in the same system as light source 15). The number of reaction vessels containing a biomarker molecule (for example reaction vessels 12) is determined based on the light detected from the reaction vessels. In some cases, the number of reaction vessels containing a bead not associated with a biomarker molecule (for example reaction vessel 13), the number of wells not containing a bead (for example reaction vessel 14) and/or the total number of wells addressed may also be determined. Such determination(s) may then be used to determine a measure of the concentration of biomarker molecules in the fluid sample.

Figure 3B:
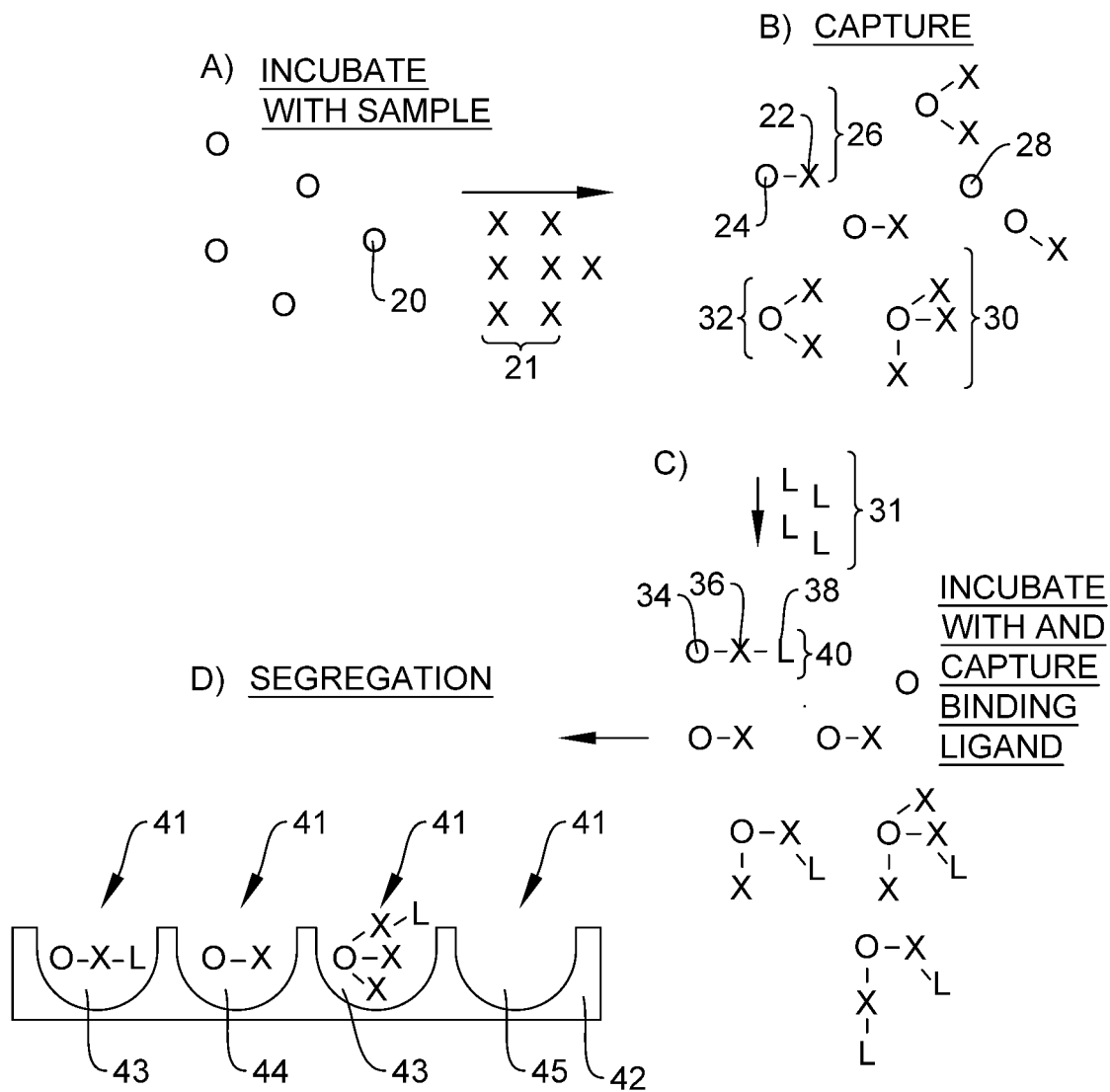
FIG. 3B is a schematic flow diagram depicting a detection method, according to certain embodiments.

A non-limiting example of an embodiment where a capture object is associated with more than one biomarker molecule is illustrated in FIG. 3B. A plurality of capture objects 20 are provided (step (A)). In this example, the plurality of capture objects comprises a plurality of beads. The plurality of beads is exposed to a fluid sample containing plurality of biomarker molecules 21 (for example beads 20 are incubated with biomarker molecules 21). At least some of the biomarker molecules are immobilized with respect to a bead. For example, as shown in step (B), biomarker molecule 22 is immobilized with respect to bead 24, thereby forming complex 26. Also illustrated is complex 30 comprising a bead immobilized with respect to three biomarker molecules and complex 32 comprising a bead immobilized with respect to two biomarker molecules. Additionally, in some cases, some of the beads may not associate with any biomarker molecules (for example bead 28). The plurality of beads from step (B) is exposed to a plurality of binding ligands 31. As shown in step (C), a binding ligand associates with some of the biomarker molecules immobilized with respect to a bead. For example, complex 40 comprises bead 34, biomarker molecule 36, and binding ligand 38. The binding ligands are provided in a manner such that a statistically significant fraction of the beads comprising at least one biomarker molecule become associated with at least one binding ligand (for example one, two, three, etc.) and a statistically significant fraction of the beads comprising at least one biomarker molecule do not become associated with any binding ligands. At least a portion of the plurality of beads from step (C) are then spatially separated into a plurality of locations. As shown in step (D), in this example, the locations comprise a plurality of reaction vessels 41 on a substrate 42. The plurality of reaction vessels may be exposed to the plurality of beads from step (C) such at each reaction vessel contains zero or one beads. The substrate may then be analyzed to determine the number of reaction vessels containing a binding ligand (for example reaction vessels 43), wherein in the number may be related to a measure of the concentration of biomarker molecules in the fluid sample. In some cases, the number of reaction vessels containing a bead and not containing a binding ligand (for example reaction vessel 44), the number of reaction vessels not containing a bead (for example reaction vessel 45), and/or the total number of reaction vessels addressed/analyzed may also be determined. Such determination(s) may then be used to determine a measure of the concentration of biomarker molecules in the fluid sample.

In certain embodiments, for example, a plurality of locations may be addressed and/or a plurality of capture objects and/or species/molecules/particles of interest may be detected substantially simultaneously. "Substantially simultaneously" when used in this context, refers to addressing/detection of the locations/capture objects/species/molecules/particles of interest at approximately the same time such that the time periods during which at least two locations/capture objects/species/molecules/particles of interest are addressed/detected overlap, as opposed to being sequentially addressed/detected, where they would not. Simultaneous addressing/detection may be accomplished by using various techniques, including optical techniques (for example CCD detector). In certain embodiments, for example, capture objects/species/molecules/particles may be spatially segregated into a plurality of discrete, resolvable locations. In certain embodiments, for example, the spatially segregated capture objects/species/molecules/particles may be detected substantially simultaneously by allowing multiple locations to be addressed substantially simultaneously. In certain embodiments, for example, individual species/molecules/particles may be associated with capture objects that are spatially segregated with respect to the other capture objects into a plurality of discrete, separately resolvable locations during detection. In certain embodiments, for example, the plurality of discrete, individual capture objects (and thus individual species/molecules/particles (for example biomarker molecules)) are separately resolved in the separately resolvable locations. In certain embodiments, for example, individual molecules/particles of a plurality of molecules/particles may be partitioned across a plurality of reaction vessels such that each reaction vessel contains zero or only one species/molecule/particle. In certain embodiments, for example, at least about 80%, at least about 85%, at least about 90%, at least about 95%, at least about 96%, at least about 97%, at least about 98%, at least about 99%, at least about 99.5% of all species/molecules/particles may be spatially separated with respect to other species/molecules/particles during detection. In certain embodiments, for example, a plurality of species/molecules/particles may be detected substantially simultaneously within a time period of less than about 1 second, less than about 500 milliseconds, less than about 100 milliseconds, less than about 50 milliseconds, less than about 10 milliseconds, less than about 1 millisecond, less than about 500 microseconds, less than about 100 microseconds, less than about 50 microseconds, less than about 10 microseconds, less than about 1 microsecond, less than about 0.5 microseconds, less than about 0.1 microseconds, or less than about 0.01 microseconds, less than about 0.001 microseconds, or less. In certain embodiments, for example, the plurality of species/molecules/particles may be detected substantially simultaneously within a time period of between about 100 microseconds and about 0.001 microseconds, between about 10 microseconds and about 0.01 microseconds, or less.

In certain embodiments, for example, the locations may be optically interrogated. In certain embodiments, for example, locations exhibiting changes in their optical signature may be identified by a conventional optical train and optical detection system. Depending on the detected species (for example type of fluorescence entity, etc.) and the operative wavelengths, optical filters designed for a particular wavelength may be employed for optical interrogation of the locations. In certain embodiments, for example, a system for optical interrogation may comprise more than one light source and/or a plurality of filters to adjust the wavelength and/or intensity of the more than one light source. In certain embodiments, for example, the optical signal from a plurality of locations may be captured using a CCD camera.

In certain embodiments, for example, the plurality of reaction vessels may be sealed (for example after the introduction of the biomarker molecules, binding ligands, and/or precursor labeling agent). In certain embodiments, for example, the plurality of reaction vessels may be sealed by mating of the second substrate with a sealing component. In certain embodiments, for example, the plurality of reaction vessels may be sealed with a sealing fluid (for example a silicone oil sealing fluid). In certain embodiments, for example, the sealing of the reaction vessels may be such that the contents of each reaction vessel cannot escape the reaction vessels during performance of an assay. In certain embodiments, for example, the reaction vessels may be sealed after the addition of the biomarker molecules and, optionally, at least one type of precursor labeling agent to facilitate detection of the biomarker molecules. In certain embodiments, for example, by sealing the contents in some or each reaction vessel, a reaction to produce the detectable labeling agents may proceed within the sealed reaction vessels, thereby producing a detectable amount of labeling agents that is retained in the reaction vessel for detection purposes.

In certain embodiments, for example, the plurality of locations may be formed using a variety of methods and/or materials. In certain embodiments, for example, the plurality of locations may comprise a plurality of reaction vessels/wells on a substrate. In certain embodiments, for example, the plurality of reaction vessel may be formed as an array of depressions on a first surface. In certain embodiments, for example, the plurality of reaction vessels may be formed by mating a sealing component comprising a plurality of depressions with a substrate that may either have a featureless surface or include depressions aligned with those on the sealing component. Any of the device components, for example, the substrate or sealing component, may be fabricated from a compliant material, for example an elastomeric polymer material, to aid in sealing. The surfaces may be or made to be hydrophobic or contain hydrophobic regions to minimize leakage of aqueous samples from the microwells. In certain embodiments, for example, the reactions vessels may be configured to receive and contain only a single capture object (for example a single bead such as a paramagnetic bead).

In certain embodiments, for example, the reaction vessels may all have approximately the same volume. In certain embodiments, for example, the reaction vessels may have differing volumes. In certain embodiments, for example, the volume of each individual reaction vessel may be selected to be appropriate to facilitate an assay protocol. In certain embodiments, for example, the number of capture objects used for biomarker capture contained in each vessel may be limited to a small number. In certain further embodiments, for example, the volumes of the reaction vessels may range from 1 attoliter (or smaller) to 100 nanoliters (or larger). In certain further embodiments, for example, the volumes of the reaction vessels may be selected depending upon one or more of the nature of the capture objects, the detection technique and equipment employed, the number and density of the wells on the substrate, and the expected concentration of capture objects in the fluid applied to the substrate containing the wells. In certain embodiments, for example, the size of one or more of the reaction vessels may be selected such only a single capture object used for biomarker capture can be fully contained within the reaction vessel. In certain embodiments, for example, the size of one or more of the reaction vessels may be selected according to one or more of the embodiments disclosed in U.S. patent application Ser. No. 12/731,130, filed Mar. 24, 2010, published as US-2011-0212848 on Sep. 1, 2011, entitled "ULTRA-SENSITIVE DETECTION OF MOLECULES OR PARTICLES USING BEADS OR OTHER CAPTURE OBJECTS," by Duffy et al.; or International Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS," by Duffy et al., each herein incorporated by reference.

In certain embodiments, for example, the reaction vessels may have a volume between about 1 femtoliter and about 1 picoliter, between about 1 femtoliters and about 100 femtoliters, between about 10 attoliters and about 100 picoliters, between about 1 picoliter and about 100 picoliters, between about 1 femtoliter and about 1 picoliter, or between about 30 femtoliters and about 60 femtoliters. In certain embodiments, for example, the reaction vessels have a volume of less than about 1 picoliter, less than about 500 femtoliters, less than about 100 femtoliters, less than about 50 femtoliters, or less than about 1 femtoliter. In certain embodiments, for example, the reaction vessels have a volume of about 10 femtoliters, about 20 femtoliters, about 30 femtoliters, about 40 femtoliters, about 50 femtoliters, about 60 femtoliters, about 70 femtoliters, about 80 femtoliters, about 90 femtoliters, or about 100 femtoliters.

In certain embodiments, for example, the total number of locations and/or density of the locations employed in an assay. In certain embodiments, for example, the total number of locations and/or density of the locations of reaction vessels in an array of reaction vessels can depend on the composition and end use of the array. In certain embodiments, for example, the number of reaction vessels employed may depend on the number of types of biomarker molecule and/or binding ligand employed, the suspected concentration range of the assay, the method of detection, the size of the capture objects, the type of detection entity (for example free labeling agent in solution, precipitating labeling agent, etc.). In certain embodiments, for example, arrays containing from about 2 to more than 1 billion reaction vessels (or total number of reaction vessels) may be made by utilizing any one of a variety of techniques and materials. In certain embodiments, for example, increasing the number of reaction vessels in the array may be used to increase the dynamic range of an assay or to allow multiple samples or multiple types of biomarker molecules to be assayed in parallel. In certain embodiments, for example, the array may comprise between one thousand and one million reaction vessels per sample to be analyzed. In certain embodiments, for example, the array may comprise greater than one million reaction vessels. In certain embodiments, for example, the array may comprise between about 1,000 and about 50,000, between about 1,000 and about 1,000,000, between about 1,000 and about 10,000, between about 10,000 and about 100,000, between about 100,000 and about 1,000,000, between about 100,000 and about 500,000, between about 1,000 and about 100,000, between about 50,000 and about 100,000, between about 20,000 and about 80,000, between about 30,000 and about 70,000, between about 40,000 and about 60,000 reaction vessels. In certain embodiments, for example, the array may comprise about 10,000, about 20,000, about 50,000, about 100,000, about 150,000, about 200,000, about 300,000, about 500,000, about 1,000,000, or more, reaction vessels.

In certain embodiments, for example, the array of reaction vessels may be arranged on a substantially planar surface or in a non-planar three-dimensional arrangement. In certain embodiments, for example, the reaction vessels may be arrayed in a regular pattern or may be randomly distributed. In certain embodiments, for example, the array may be a regular pattern of sites on a substantially planar surface permitting the sites to be addressed in an X-Y coordinate plane.

In certain embodiments, for example, the reaction vessels may be formed in a solid material. Suitable materials in which the reaction vessels can be formed includes, but is not limited to, glass (including modified and/or functionalized glass), plastics (including acrylics, polystyrene and copolymers of styrene and other materials, polypropylene, polyethylene, polybutylene, polyurethanes, cyclic olefin copolymer (COC), cyclic olefin polymer (COP), Teflon®, polysaccharides, nylon or nitrocellulose, etc.), elastomers (such as poly(dimethyl siloxane) and poly urethanes), composite materials, ceramics, silica or silica-based materials (including silicon and modified silicon), carbon, metals, optical fiber bundles, or the like. In certain embodiments, for example, the substrate material may be selected to allow for optical detection without appreciable autofluorescence. In certain embodiments, for example, the reaction vessels may be formed in a flexible material.

A reaction vessel in a surface (for example a substrate or a sealing component) may be formed using a variety of techniques known in the art, including, but not limited to, photolithography, stamping techniques, molding techniques, etching techniques, or the like. As will be appreciated by those of the ordinary skill in the art, the technique used can depend on the composition and shape of the supporting material and the size and number of reaction vessels. In a particular embodiment, an array of reaction vessels is formed by creating microwells on one end of a fiber optic bundle and utilizing a planar compliant surface as a sealing component.

In certain embodiments, for example, the methods and assays may be carried out using commercially available systems, for example, the Simoa HD-1 Analyzer and Quanterix SR-X (Quanterix™, Lexington, Massachusetts) and the systems described in U.S. patent application Ser. No. 13/035,472, filed Feb. 25, 2011, published as US 2012-0196774, entitled "SYSTEMS, DEVICES, AND METHODS FOR ULTRA-SENSITIVE DETECTION OF MOLECULES OR PARTICLES," by Fournier et al., herein incorporated by reference.

In certain embodiments, for example, the array of reaction vessels may be fabricated using other methods and materials that do not utilize the ends of an optical fiber bundle as a substrate. In certain embodiments, for example, the array may be a spotted, printed or photolithographically fabricated substrate produced by techniques known in the art such as those disclosed in WO95/25116; WO95/35505; PCT US98/09163; U.S. Pat. Nos. 5,700,637, 5,807,522, 5,445,934, 6,406,845, and 6,482,593, which are hereby incorporated, in their entirety, by reference. In certain embodiments, for example, the array may be produced using molding, embossing, and/or etching techniques as will be known to those of ordinary skill in the art.

In certain embodiments, for example, the plurality of locations may not comprise a plurality of reaction vessels/wells. In certain embodiments, for example, a patterned substantially planar surface may be employed and the patterned areas form a plurality of locations for receiving the capture objects. In certain embodiments, for example, the patterned areas may comprise substantially hydrophilic surfaces which are substantially surrounded by substantially hydrophobic surfaces. In certain embodiments, for example, a plurality of capture objects (for example beads) may be substantially surrounded by a substantially hydrophilic medium (for example comprising water), and the beads may be exposed to the patterned surface such that the beads associate in the patterned areas (for example the hydrophilic locations on the surface), thereby spatially segregating the plurality of beads. In certain embodiments, for example, a substrate may be or include a gel or other material able to provide a sufficient barrier to mass transport (for example convective and/or diffusional barrier) to prevent capture objects used for biomarker capture and/or precursor labeling agent and/or labeling agent from moving from one location on or in the material to another location so as to cause interference or cross-talk between spatial locations containing different capture objects during the time frame required to address the locations and complete the assay. In certain embodiments, for example, a plurality of capture objects may be spatially separated by dispersing the capture objects on and/or in a hydrogel material. In certain embodiments, for example, a precursor labeling agent may be already present in the hydrogel, thereby facilitating development of a local concentration of the labeling agent (for example upon exposure to a binding ligand or biomarker molecule carrying an enzymatic component). In certain embodiments, for example, the capture objects may be confined in one or more capillaries. In certain embodiments, for example, the plurality of capture objects may be absorbed or localized on a porous or fibrous substrate (for example filter paper). In certain embodiments, for example, the capture objects may be spatially segregated on a uniform surface (for example a planar surface), and the capture objects may be detected using precursor labeling agents which are converted to substantially insoluble or precipitating labeling agents that remain localized at or near the location of where the corresponding capture object is localized. The use of such substantially insoluble or precipitating labeling agents is described herein. In certain embodiments, for example, single biomarker molecules may be spatially segregated into a plurality of droplets. In certain embodiments, for example, single biomarker molecules may be substantially contained in a droplet containing a first fluid. In certain embodiments, for example, the droplet may be substantially surrounded by a second fluid, wherein the second fluid is substantially immiscible with the first fluid.

Certain embodiments may provide, for example, methods and assays comprising at least one washing. In certain embodiments, for example, a wash solution for the washing is selected so that it does not cause appreciable change to the configuration of the capture objects. In certain embodiments, for example, a wash solution for the washing is selected so that it does not cause appreciable change to the biomarker molecules. In certain embodiments, for example, a wash solution for the washing is selected so that it does not disrupt any specific binding interaction between at least two components (for example between a capture component and a biomarker molecule component). In certain embodiments, for example, the wash solution may be a solution that is selected to chemically interact with one or more assay components. As will be understood by those of ordinary skill in the art, a wash step may be performed at any appropriate time point during the methods and assays. In certain embodiments, for example, a plurality of capture objects may be washed after exposing the capture objects to one or more solutions comprising biomarker molecules, binding ligands, precursor labeling agents, or the like. In certain embodiments, for example, following immobilization of the biomarker molecules with respect to a plurality of capture objects, the plurality of capture objects may be subjected to a washing step thereby removing any biomarker molecules not specifically immobilized with respect to a capture object.

Other assay methods in addition to those described herein are known in the art and may be used in connection with the inventive methods. In certain embodiments, for example, various analyzers are commercially available for the determination of the concentration of biomarkers. The assay methods employed should meet the algorithm requirements for LOD and LOQ.

INCORPORATION BY REFERENCE

Without limitation, the following documents are hereby incorporated, in their entirety, by reference: U.S. Patent Application Publication Nos. 2002/0122612, 2003/0016897, 2003/0027126, 2005/0130188, 2006/0013543, 2007/0040095, 2007/0122861, 2007/0259448, 2007/0259385, 2007/0259381, 2008/0032324, 2009/0101175, 2009/0149341, 2009/0156425, 2009/0170728, 2010/0075862, 2010/0075407, 2010/0075439, 2010/0075355, 2011/0195852, 2011/0212848, 2011/0212462, 2011/0212537, 2011/0245097, 2011/0251105, 2012/0135154, 2012/0196774, 2012/0277114, 2013/0034284, 2013/0142710, 2013/0266969, 2014/0094386, 2014/0134652, 2014/0227720, 2014/0302532, 2015/0038355, 2015/0353997, 2016/0123969, 2017/0160292, 2018/0003703, 2018/0037614, and 2018/0339296; U.S. Pat. No. 6,706,526; U.S. Provisional Application Nos. 62/655,738 and 62/789,067; International Patent Publication Nos. WO 2009/029073, WO 2010/039179, WO 2011/109364, WO 2011/109372, WO 2011/109379, WO 2016/115256, WO 2016/130923, and WO2018/222585; Kuhle, J. et al., "Comparison of three analytical platforms for quantification of the neurofilament light chain in blood samples: ELISA, electrochemiluminescence immunoassay and Simoa," *Clin Chem Lab Med* 54:10 (2016) 1655-1661; Rissin, D. M. et al., "Simultaneous Detection of Single Molecules and Singulated Ensembles of Molecules Enables Immunoassays with Broad Dynamic Range," *Anal Chem* 83:6 (2011) 2279-2285; Armbruster, D. A. et al., "Limit of Blank, Limit of Detection and Limit of Quantitation," *Clin Biochem Rev* 29(Suppl 1) (2008) S49-S52; Quanterix, "Neuro 4-Plex A Kit: Material Safety Data Sheet," (May 25, 2017), available at https://www.quanterix.com/sites/default/files/safety_data_sheets/Neuro%204-Plex%20A%20Kit%20102153.pdf; Harlow and Lane, (1988) Antibodies: A Laboratory Manual, Cold Spring Harbor Laboratory, New York; Demidov, V. et al., "DNA Amplification: Current Technologies and Applications," *J Antimicrobial Chemotherapy* 54:6 (2004); Depoorter et al., "Neurofilament Light Chain: Blood Biomarker of Neonatal Neuronal Injury" Front. Neurol. (20 Nov. 2018), available at https://www.frontiersin.org/articles/10.3389/fneur.2018.00984/full; Gill, J. et al., "Glial fibrillary acidic protein elevations relate to neuroimaging abnormalities after mild TBI," *Neurology* 91:15 (Oct. 9, 2018) e1385-e1389; Korley, F. K., "Performance Evaluation of a Multiplex Assay for Simultaneous Detection of Four Clinically Relevant Traumatic Brain Injury Biomarkers," *J. Neurotrauma* 36 (Jan. 1, 2019) 182-187; Hossain, I. et al., "Early Levels of Glial Fibrillary Acidic Protein and Neurofilament Light Protein in Predicting the Outcome of Mild Traumatic Brain Injury," *J. Neurotrauma* 36 (2019) 1-10; Good, N. E. et al., "Hydrogen Ion Buffers for Biological Research," *Biochemistry* 5:2 (1966) 467-477; Crowther, J R., "ELISA: Theory and Practice Methods," Mol. Biol. 42 (1995) 1-218; Davies, C., "Concepts," In the Immunoassay Handbook, D. Wild, ed., Stockton Press, New York (1994) 83-115; Hornbeck, P., "Enzyme-Linked Immunosorbent Assays," In Current Protocols in Immunology, Unit 2.1, ed., R. Coico, John Wiley & Sons, Hoboken, N.J. (2001); and Pirkanniemi, K. "Complexing Agents Long-term Toxicity, Catalytic Oxidative Degradation and Concentrations in Industrial Waste Water," Doctoral Dissertation, University of Kuopio (2007) (collectively, the "INCORPORATED REFERENCES").

EXAMPLES

In the following Examples:
"AEB" means "average enzyme per bead";
">" means "greater than";
"<" means "less than";
"LOB" means "limit of blank";
"LOD" means "limit of detection";
"LOQ" means "limit of quantification";
"q.s." refers to a quantity of buffer sufficient to bring the listed components to the concentrations indicated;
"n.a." means "not applicable"; and
"---" indicates no data presented.
"no." means "number";
"SD" means "standard deviation";
"NSI" means "Neurobehavioral Symptom Inventory";
"MVA" means "motor vehicle accident";
"+" means positive indication of brain injury;
"−" means negative indication of brain injury;
"S" means "statistically significant difference"; and
"NS" means "nonsignificant difference".

Example 1

The following non-limiting example describes a human multiplex assay that measured four important neurology biomarkers in both cerebrospinal fluid (CSF) and blood. The four targets were NF-L, total tau protein, glial GFAP, and UCH L1. All four biomarkers have been studied as indicators of TBI severity. Recent reports indicate serum NF-L is a biomarker for mild TBI in amateur boxers and professional hockey players1, that plasma tau is related to concussion severity, and that serum GFAP and UCH L1 can detect mild to moderate TBI. The four targets were measured in a single performance of the assay. Each assay of the multiplex assay is described below.

NF-L is a 68 kDa cytoskeletal intermediate filament protein that is expressed in neurons. It associates with the 125 kDa Neurofilament medium (NF-M) and the 200 kDa Neurofilament heavy (NF-H) to form neurofilaments. They are major components of the neuronal cytoskeleton, and are believed to function primarily to provide structural support for the axon and to regulate axon diameter. Neurofilaments can be released in significant quantity following axonal damage or neuronal degeneration. NF-L has been shown to associate with TBI, MS, frontotemporal dementia and other neurodegenerative diseases. The NF-L assay was a digital immunoassay for the quantitative determination of NF-L in serum, plasma and CSF. The antibodies also cross reacted with murine, bovine, and macaque NF-L epitopes, and the assay could be used for research with these species.

Figure 4A:
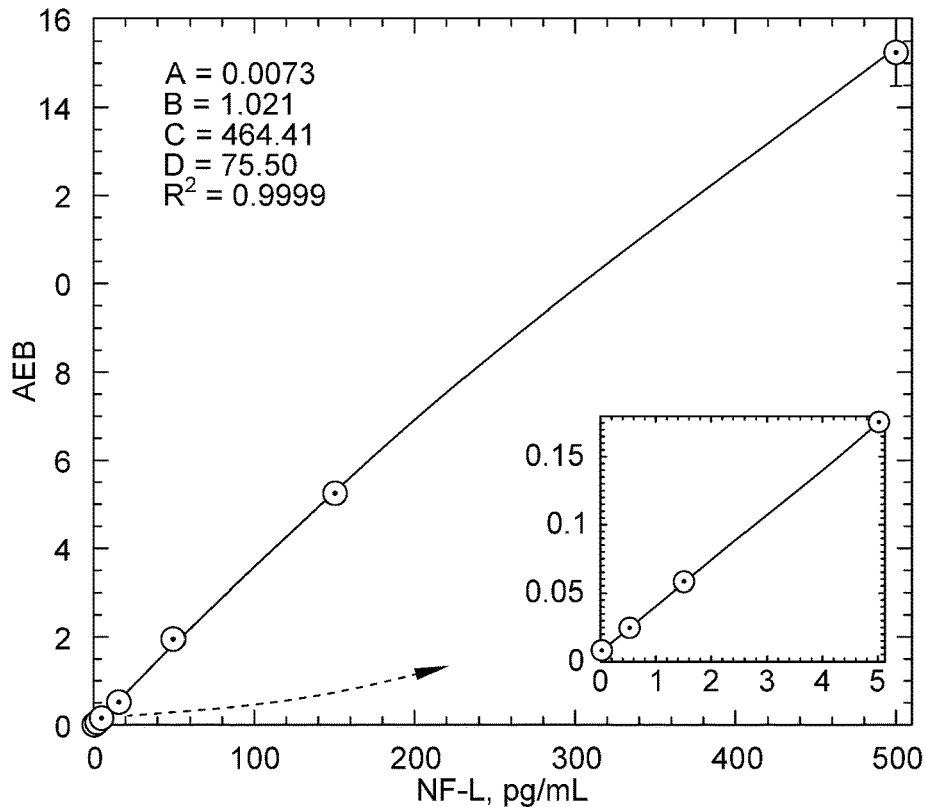
FIG. 4A is a NF-L immunoassay dose-response curve, according to certain embodiments.
Figure 4B:
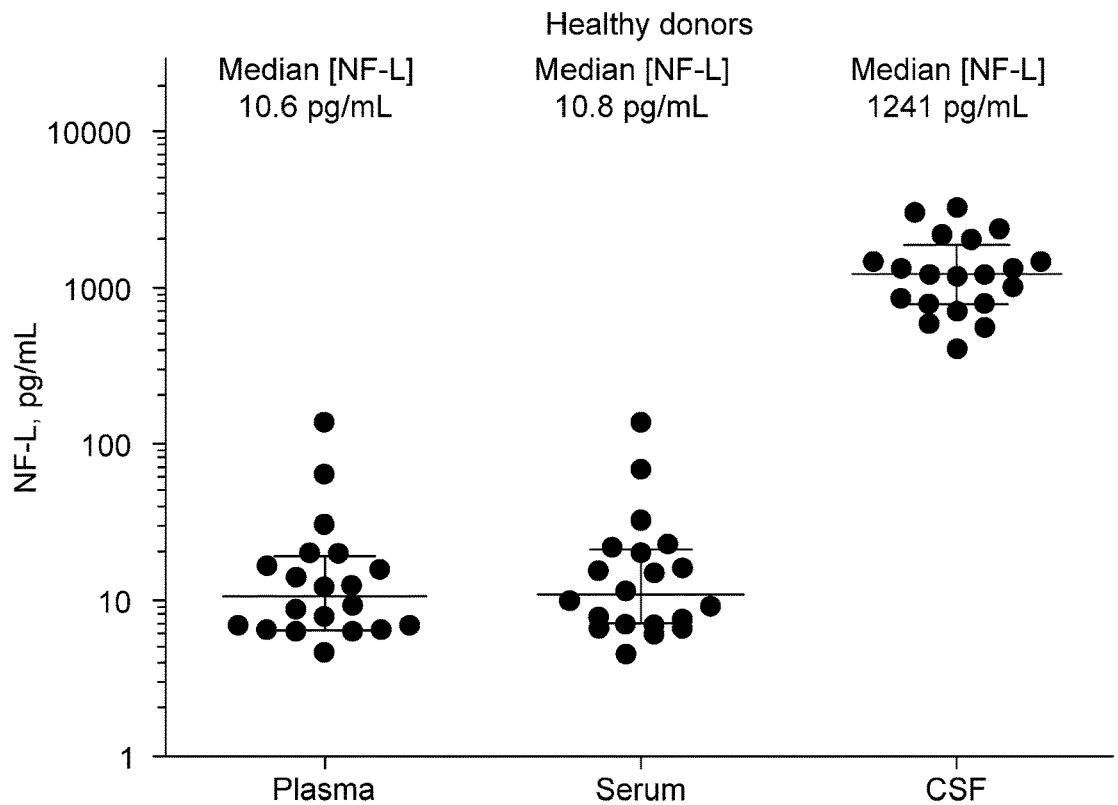
FIG. 4B is NF-L concentration in plasma, matched serum, and CSF from healthy donors.

FIG. 4A shows the NF-L immunoassay dose-response curve. Calibrators were assayed in replicates of three. Four-parameter curve fit parameters are depicted. The analytical performance characteristics of the NF-L portion of the multiplex assay were characterized as summarized in Table 1 below. Table 1 shows the reproducibility of the NF-L immunoassay portion of the multiplex assay. FIG. 4B shows the NF-L concentration in EDTA plasma (n=20), matched serum (n=20) and CSF (n=20) from healthy donors. Error bars depict mean and interquartile ranges.

TABLE 1

General characteristics of NF-L immunoassay portion of the multiplex assay.

| | |
|---|---|
| Calibration range | 0-500 pg/mL |
| Dynamic range[1] | 0-2000 pg/mL |
| Lower limit of detection (2.5 SD; 3 reps × 24 estimates across 12 runs, 3 instruments, 2 lots; mean LoD[2]) | 0.104 pg/mL |
| Lower limit of quantification[3] (12 runs, 3 instruments, 2 reagent lots, mean LoQ) | 0.241 pg/mL |
| Spike-recovery: serum/plasma (NF-L spiked into 3 serum, 3 plasma samples at 15 and 150 pg/mL, mean[4]) | 90.1% |

TABLE 1-continued

General characteristics of NF-L immunoassay portion of the multiplex assay.

| | |
|---|---|
| Spike-recovery: CSF (NF-L spiked into 4 CSF samples at 500 and 5000 pg/mL, mean[5]) | 107.7% |
| Linearity (high NF-L plasma sample fractionally admixed with low NF-L serum sample, mean of 10 levels[6]) | 94.9% |
| Dilution linearity: serum (spiked serum diluted 2X serially from MRD to 128-fold w/ Sample Diluent; mean recovery[7]) | 118.8% |
| Dilution linearity: CSF (CSF diluted 2X serially from MRD to 128-fold w/ Sample Diluent; mean recovery[8]) | 99.9% |
| Inter lot CV (Pool of CVs from 5 samples[9] tested with 2 reagent lots across 2 runs × 3 instruments) | 3.5% |
| Inter instrument CV (Pool of CVs from 5 samples[9] tested with 3 instruments across 2 runs × 2 reagent lots) | 2.5% |
| Typical serum/plasma sample volume (Includes dead volume; see Package Insert for details) | 46 µL |
| CSF sample volume (Includes dead volume; See Package Insert for details) | 4.6 µL |

[1]Samples auto-diluted 4X; note: ranges may vary between calibrator lots.
[2]SD 0.067 pg/ml; range 0.025-0.276 pg/mL.
[3]≤20%CV, 80-120% recovery; pooled CV 12.0%, mean recovery 109.8%; not corrected for pre-dilutions; 4X LoQ 0.964 pg/mL.
[4]Recovery range 67.7-125.7%.
[5]Recovery range 88.8-124.9%.
[6]Recovery range 87.6-101.3.
[7]Recovery range 101.0-155.2%; minimum recommended dilution (MRD) 1:4.
[8]Recovery range 92.6-109.9%; MRD 1:40.
[9]Range 9.28-320 pg/mL.

TABLE 2

Reproducibility precision of NF-L immunoassay across instruments and reagent lots. Reproducibility was determined with guidance from CLSI Protocol EP5-A. Five samples consisting of two serum panels, one plasma panel, and two NF-L controls were assayed in replicates of three for two runs on each of three instruments and two reagent lots. Analysis of variance (nested ANOVA) results are summarized in the following table.

| Sample | Mean NF-L pg/mL | Between Instrument % CV, n = 3 | Between Lot % CV, n = 2 | Between Run % CV, n = 12 | Within Run % CV, n = 30 |
|---|---|---|---|---|---|
| Control 1 | 9.31 | 0.9 | 3.4 | 5.8 | 6.2 |
| Control 2 | 925 | 0.0 | 6.1 | 4.6 | 4.4 |
| Serum Panel 1 | 16.8 | 0.0 | 0.0 | 5.1 | 5.4 |
| Plasma Panel 2 | 60.1 | 0.0 | 0.0 | 5.6 | 4.7 |
| Serum Panel 3 | 332 | 0.0 | 3.7 | 5.0 | 4.7 |

Tau is a microtubule-stabilizing protein primarily localized in central nervous system neurons, but also expressed at low levels in astrocytes and oligodendrocytes. Tau consists of six isoforms in the human brain, with molecular weights of 48,000 to 67,000 Daltons depending on isoform. Tau elevation is observed in the cerebrospinal fluid (CSF) of patients with neurodegenerative disease and head injuries, suggesting its extracellular release during neuronal damage and a role as a biomarker with specificity for brain injury. Potential movement of elevated CSF tau protein across the blood-brain barrier presents a possibility that measurements of tau protein in blood could provide a convenient peripheral window into brain/CSF status. Studies of tau protein in serum and plasma have been hampered by its low abundance (typically low pg/mL), and there are relatively few reports characterizing the appearance of tau protein in blood or evaluating the usefulness of this biomarker for brain injury assessment. Recent reports using digital immunoassay technology have shown elevation in peripheral tau protein associated with hypoxic brain injury, concussed hockey players, and repetitive minimal head injury in Olympic boxing. The total tau portion of the multiplex assay used a combination of monoclonal antibodies that react with both normal and phosphorylated tau. With an epitope in the midregion of the molecule, the assay recognizes all tau isoforms.

Figure 5A:
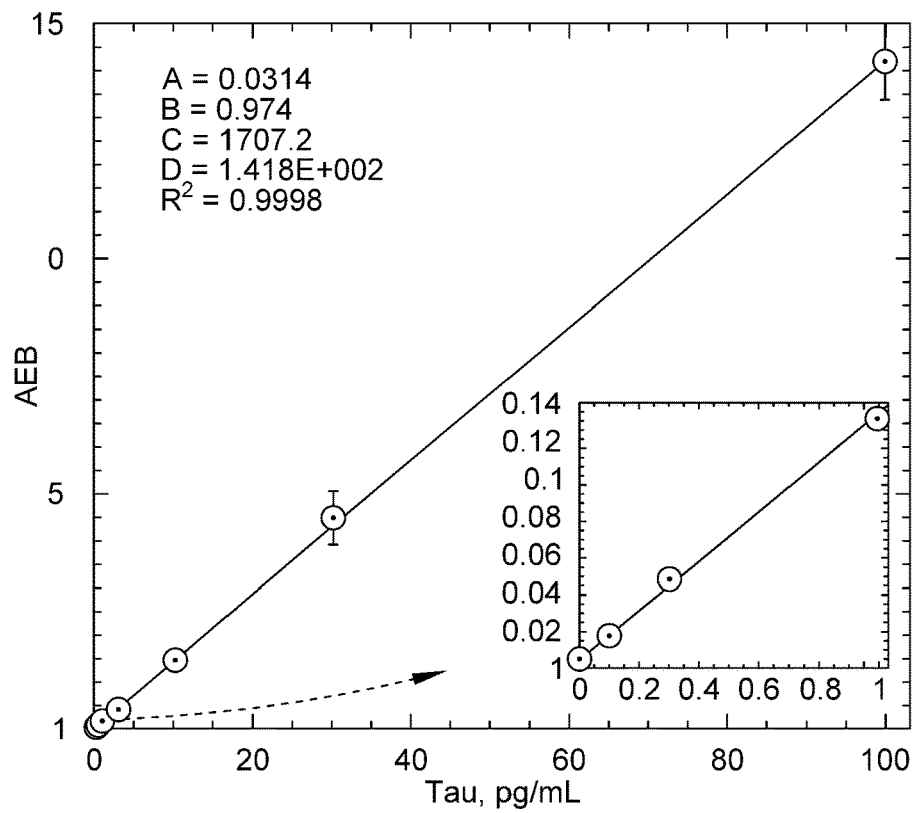
FIG. 5A is a Tau protein immunoassay dose-response curve.
Figure 5B:
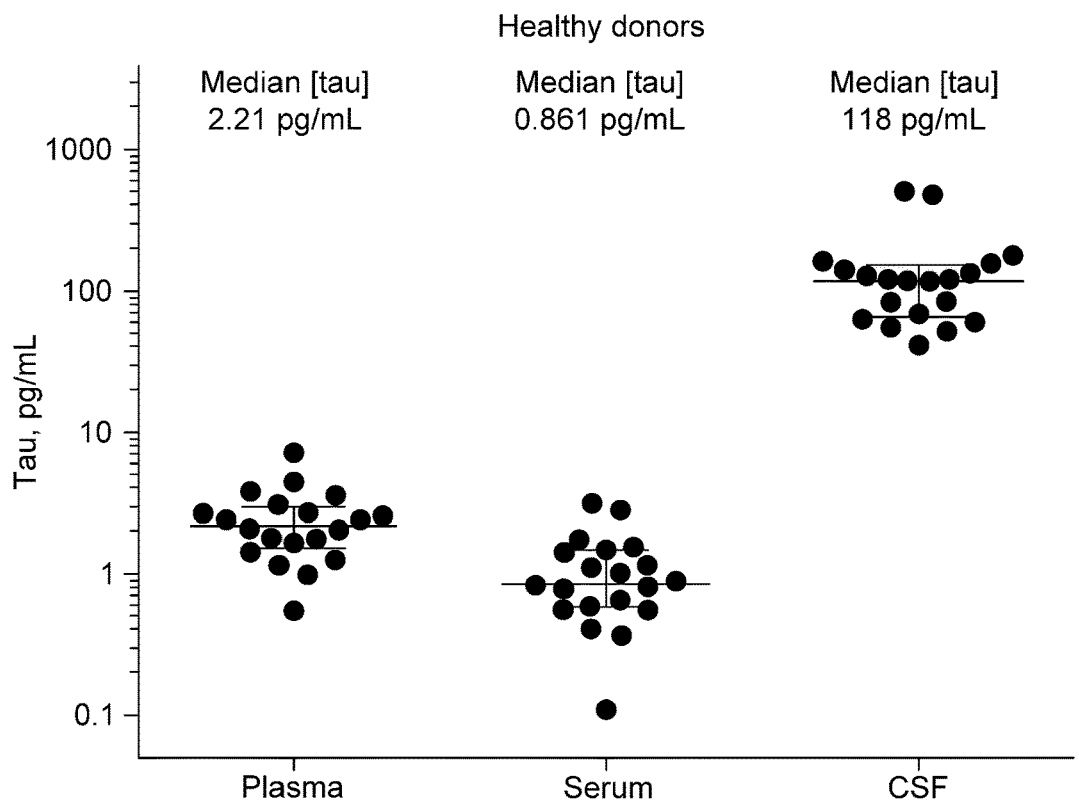
FIG. 5B is Tau protein concentration in plasma, matched serum, and CSF from healthy donors.

FIG. 5A shows the tau immunoassay dose-response curve. Calibrators were assayed in replicates of three. Four-parameter curve fit parameters are depicted. The analytical performance characteristics of the tau portion of the multiplex assay were characterized as summarized in Table 3 below. Table 4 shows the reproducibility of the NF-L immunoassay portion of the multiplex assay. FIG. 5B shows the tau concentration in EDTA plasma (n=20), matched serum (n=20) and CSF (n=20) from healthy donors. Error bars depict mean and interquartile ranges.

TABLE 3

General characteristics of tau immunoassay portion of the multiplex assay.

| | |
|---|---|
| Calibration range | 0-100 pg/mL |
| Dynamic range[1] | 0-400 pg/mL |
| Lower limit of detection (2.5 SD; 3 reps × 24 estimates across 12 runs, 3 instruments, 2 lots; mean LoD[2]) | 0.024 pg/mL |
| Lower limit of quantification[3] (12 runs, 3 instruments, 2 reagent lots, mean LoQ) | 0.053 pg/mL |

TABLE 3-continued

General characteristics of tau immunoassay portion of the multiplex assay.

| | |
|---|---|
| Spike-recovery: serum/plasma (tau 441 spiked into 3 serum, 3 plasma samples at 5 and 50 pg/mL, mean[4]) | 117.8% |
| Spike-recovery: CSF (tau 411 spiked into 4 CSF samples at 100 and 1000 pg/mL, mean[5]) | 116.3% |
| Linearity (high tau serum sample fractionally admixed with low tau plasma sample, mean of 10 levels[6]) | 94.3% |
| Dilution linearity: serum (spiked serum diluted 2X serially from MRD to 128-fold w/ Sample Diluent; mean recovery[7]) | 115.0% |
| Dilution linearity: CSF (CSF diluted 2X serially from MRD to 128-fold w/ Sample Diluent; mean recovery[8]) | 91.6% |
| Inter lot CV (Pool of CVs from 5 samples[9] tested with 2 reagent lots across 2 runs × 3 instruments) | 3.0% |
| Inter instrument CV (Pool of CVs from 5 samples[9] tested with 3 instruments across 2 runs × 2 reagent lots) | 3.6% |
| Typical serum/plasma sample volume (Includes dead volume; see Package Insert for details) | 46 μL |
| CSF sample volume (Includes dead volume; See Package Insert for details) | 4.6 μL |

[1]Samples auto-diluted 4X; note: ranges may vary between calibrator lots.
[2]SD 0.011 pg/ml; range 0.007-0.059 pg/mL.
[3]≤20%CV, 80-120% recovery; pooled CV 12.2%, mean recovery 108.9%; not corrected for pre-dilutions; 4X LoQ 0.212 pg/mL.
[4]Recovery range 52.2-192.9%.
[5]Recovery range 96.7-137.8%.
[6]Recovery range 83.4-105.6.
[7]Recovery range 106.1-125.5%; minimum recommended dilution (MRD) 1:4.
[8]Recovery range 78.16-121.2%; MRD 1:40.
[9]Range 2.76-202.6 pg/mL.

TABLE 4

Reproducibility precision of tau immunoassay across instruments and reagent lots. Reproducibility was determined with guidance from CLSI Protocol EP5-A. Five samples consisting of two serum panels, one plasma panel, and two tau controls were assayed in replicates of three for two runs on each of three instruments and two reagent lots. Analysis of variance (nested ANOVA) results are summarized in the following table.

| Sample | Mean Tau pg/mL | Between Instrument % CV, n = 3 | Between Lot % CV, n = 2 | Between Run % CV, n = 12 | Within Run % CV, n = 30 |
|---|---|---|---|---|---|
| Control 1 | 3.71 | 7.1 | 2.6 | 1.6 | 7.6 |
| Control 2 | 200 | 0.0 | 6.7 | 4.5 | 4.5 |
| Serum Panel 1 | 2.66 | 0.0 | 0.0 | 5.7 | 6.7 |
| Plasma Panel 2 | 20.2 | 1.5 | 0.0 | 6.6 | 4.9 |
| Serum Panel 3 | 148 | 5.2 | 0.0 | 3.0 | 5.2 |

GFAP is a class-III intermediate filament majorly expressed in astrocytic glial cells in the central nervous system. Astrocytes play a variety of key roles in supporting, guiding, nurturing, and signaling neuronal architecture and activity. Monomeric GFAP is about 55 kD. It is capable of forming both homodimers and heterodimers; GFAP can polymerize with other type III proteins or with neurofilament protein, such as NF-L. GFAP is involved in many important CNS processes, including cell communication and the functioning of the blood brain barrier. GFAP, as a potential biomarker has been shown to associate with multiple diseases such as TBI, stroke, brain tumors, etc. Decreases in GFAP expression have been reported in Down's syndrome, schizophrenia, bipolar disorder, and depression.

Figure 6A:
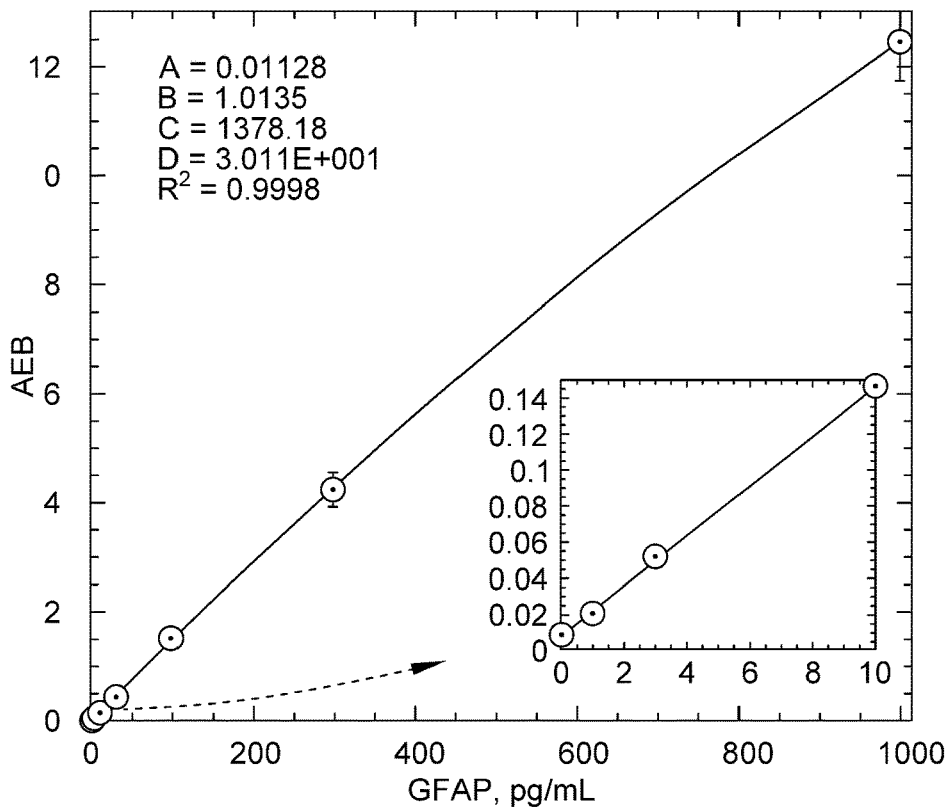
FIG. 6A is a GFAP immunoassay dose-response curve.
Figure 6B:
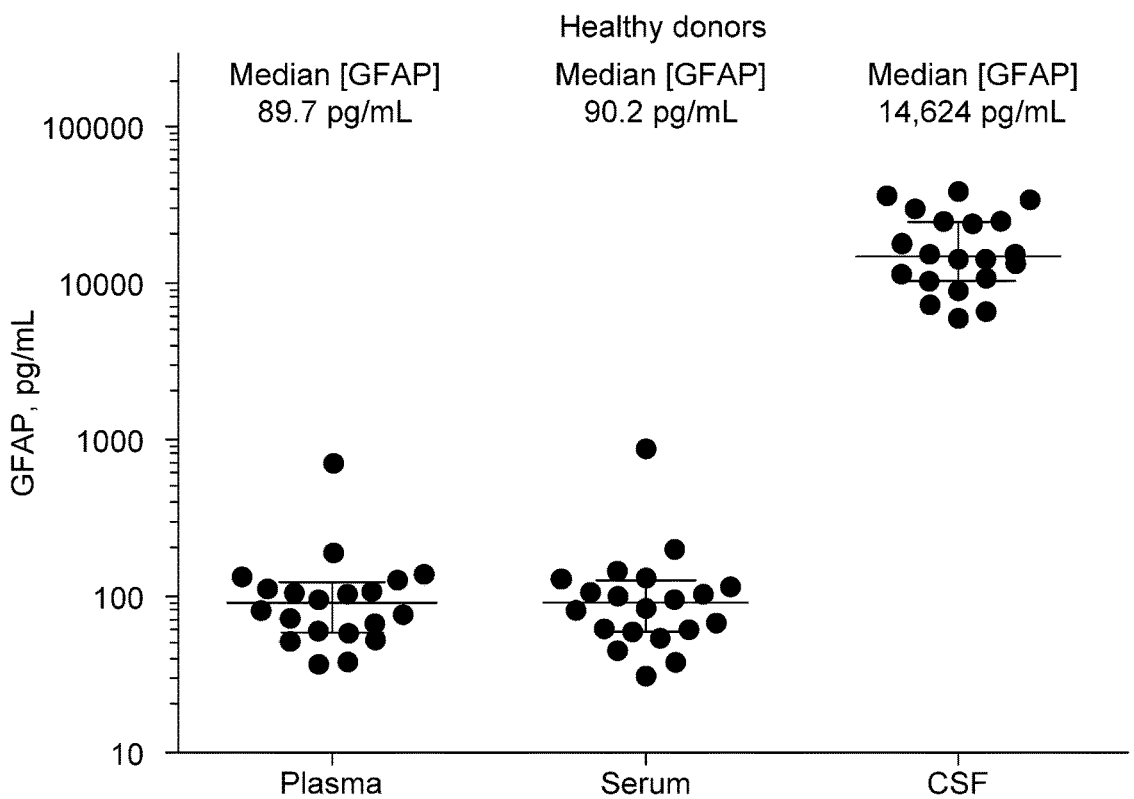
FIG. 6B is GFAP concentration in plasma, matched serum, and CSF from healthy donors.

FIG. 6A shows the tau immunoassay dose-response curve. Calibrators were assayed in replicates of three. Four-parameter curve fit parameters are depicted. The analytical performance characteristics of the GFAP portion of the multiplex assay were characterized as summarized in Table 5 below. Table 6 shows the reproducibility of the GFAP immunoassay portion of the multiplex assay. FIG. 6B shows the GFAP concentration in EDTA plasma (n=20), matched serum (n=20) and CSF (n=20) from healthy donors. Error bars depict mean and interquartile ranges.

TABLE 5

General characteristics of GFAP immunoassay portion of the multiplex assay.

| | |
|---|---|
| Calibration range | 0-1000 pg/mL |
| Dynamic range[1] | 0-4000 pg/mL |
| Lower limit of detection (2.5 SD; 3 reps × 24 estimates across 12 runs, 3 instruments, 2 lots; mean LoD[2]) | 0.221 pg/mL |
| Lower limit of quantification[3] (12 runs, 3 instruments, 2 reagent lots, mean LoQ) | 0.467 pg/mL |
| Spike-recovery: serum/plasma (GFAP spiked into 3 serum, 3 plasma samples at 75 and 750 pg/mL, mean[4]) | 105.0% |
| Spike-recovery: CSF (GFAP spiked into 4 CSF samples at 1,500 and 15,000 pg/mL, mean[5]) | 118.9% |

TABLE 5-continued

General characteristics of GFAP immunoassay portion of the multiplex assay.

| | |
|---|---|
| Linearity (high GFAP serum sample fractionally admixed with low tau plasma sample, mean of 10 levels[6]) | 100.6% |
| Dilution linearity: serum (spiked serum diluted 2X serially from MRD to 128-fold w/ Sample Diluent; mean recovery[7]) | 108.3% |
| Dilution linearity: CSF (CSF diluted 2X serially from MRD to 128-fold w/ Sample Diluent; mean recovery[8]) | 98.1% |
| Inter lot CV (Pool of CVs from 5 samples[9] tested with 2 reagent lots across 2 runs × 3 instruments) | 4.4% |
| Inter instrument CV (Pool of CVs from 5 samples[9] tested with 3 instruments across 2 runs × 2 reagent lots) | 4.7% |
| Typical serum/plasma sample volume (Includes dead volume; see Package Insert for details) | 46 µL |
| CSF sample volume (Includes dead volume; See Package Insert for details) | 4.6 µL |

[1]Samples auto-diluted 4X; note: ranges may vary between calibrator lots
[2]SD 0.108 pg/mL; range 0.042-0.481 pg/mL.
[3]≤20% CV, 80-120% recovery; pooled CV 12.9%, mean recovery 102.8%; not corrected for pre-dilutions; 4X LoQ 1.87 pg/mL.
[4]Recovery range 54.2-146.3%.
[5]Recovery range 87.5-176.7%.
[6]Recovery range 88.9-112.2%.
[7]Recovery range 102.3-120.9%; minimum recommended dilution (MRD) 1:4.
[8]Recovery range 95.5-103.6%; MRD 1:40.
[9]Range 27.3-2062 pg/mL.

TABLE 6

Reproducibility precision of GFAP immunoassay across instruments and reagent lots. Reproducibility was determined with guidance from CLSI Protocol EPS-A. Five samples consisting of two serum panels, one plasma panel, and two GFAP controls were assayed in replicates of three for two runs on each of three instruments and two reagent lots. Analysis of variance (nested ANOVA) results are summarized in the following table.

| Sample | Mean GFAP pg/mL | Between Instrument % CV, n = 3 | Between Lot % CV, n = 2 | Between Run % CV, n = 12 | Within Run % CV, n = 30 |
|---|---|---|---|---|---|
| Control 1 | 27.6 | 0.0 | 3.9 | 3.0 | 7.7 |
| Control 2 | 1492 | 0.0 | 2.2 | 7.1 | 4.2 |
| Serum Panel 1 | 59.4 | 0.0 | 8.5 | 3.8 | 3.9 |
| Plasma Panel 2 | 226 | 0.0 | 3.0 | 6.2 | 3.6 |
| Serum Panel 3 | 2095 | 0.0 | 6.5 | 3.8 | 4.5 |

The UCH L1, hydrolyze small C-terminal adducts of ubiquitin to generate the ubiquitin monomer. It is also called PARK5 or neuronal-specific protein gene product 9.5, expressed predominantly in neurons, UCH L1 is one of the most abundant brain protein, representing 1 to 2% of total soluble brain protein. In vivo, UCH L1 has been shown to be involved in the regulation of the ubiquitin pool, apoptosis, learning and memory, and its absence in mice because of spontaneous intragenic deletions yields phenotypes with neurological defects. A point mutation (193M) and a polymorphism (S18Y) in this gene have been shown to associate with Parkinson's disease. Recently, UCH L1 has been proposed as a candidate biomarker for brain injury. UCH L1 can be released from injured neurons and flow into the cerebrospinal fluid and circulating blood.

Figure 7A:
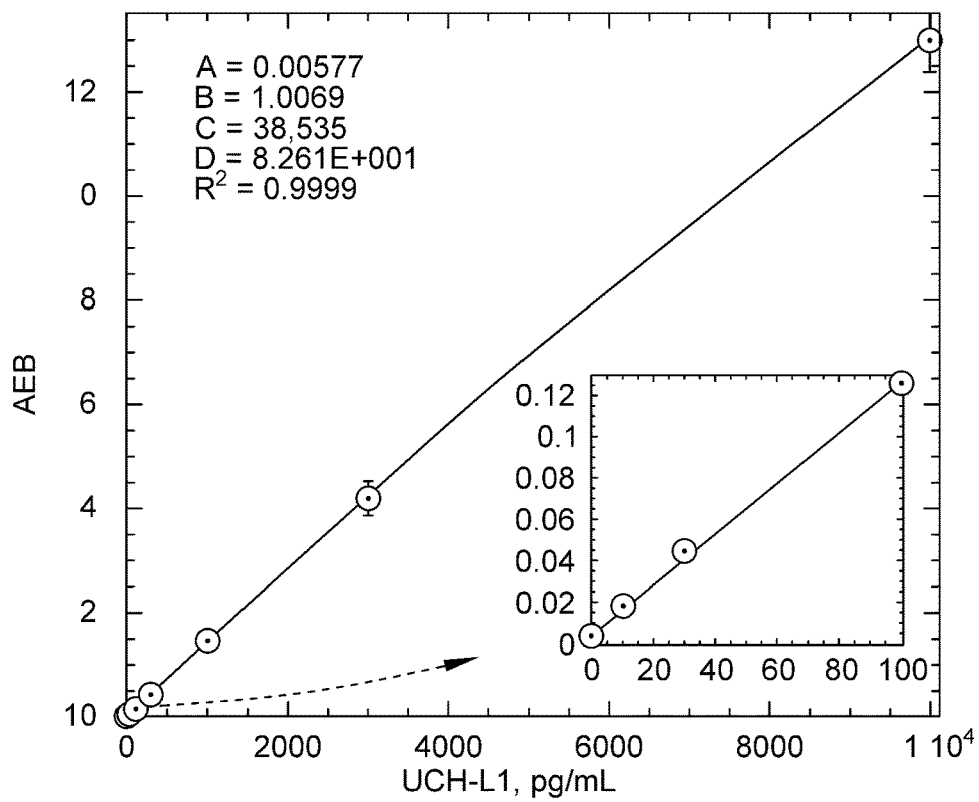
FIG. 7A is a UCH L1 immunoassay dose-response curve.
Figure 7B:
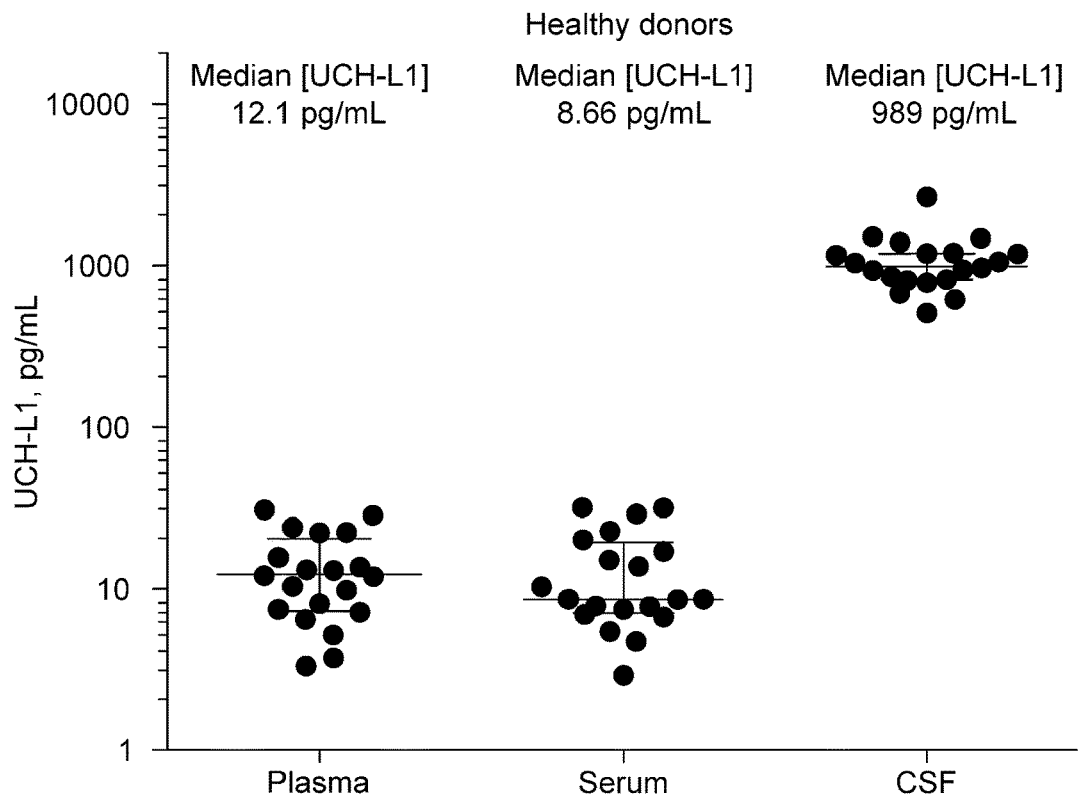
FIG. 7B is UCH L1 concentration in plasma, matched serum, and CSF from healthy donors.
Figure 8:
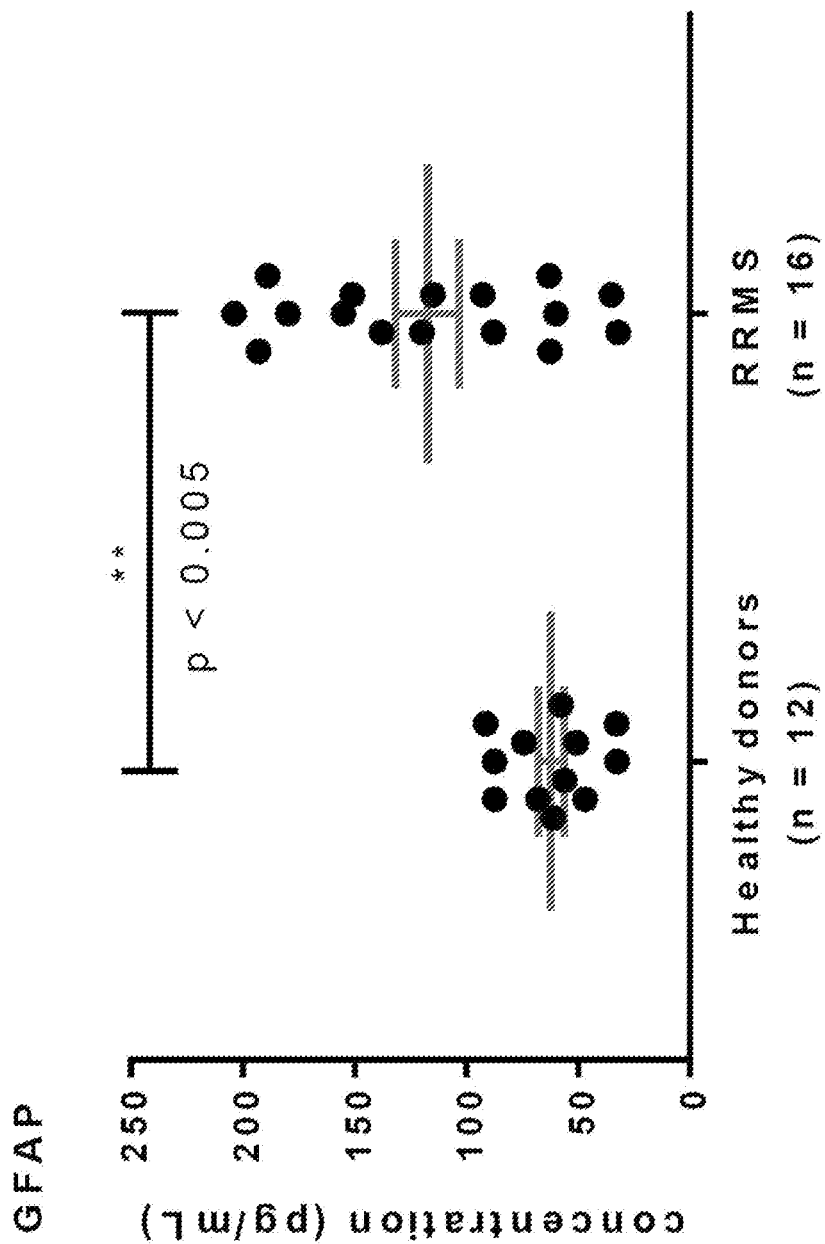
FIG. 8 is a diagram of GFAP concentration.
Figure 9:
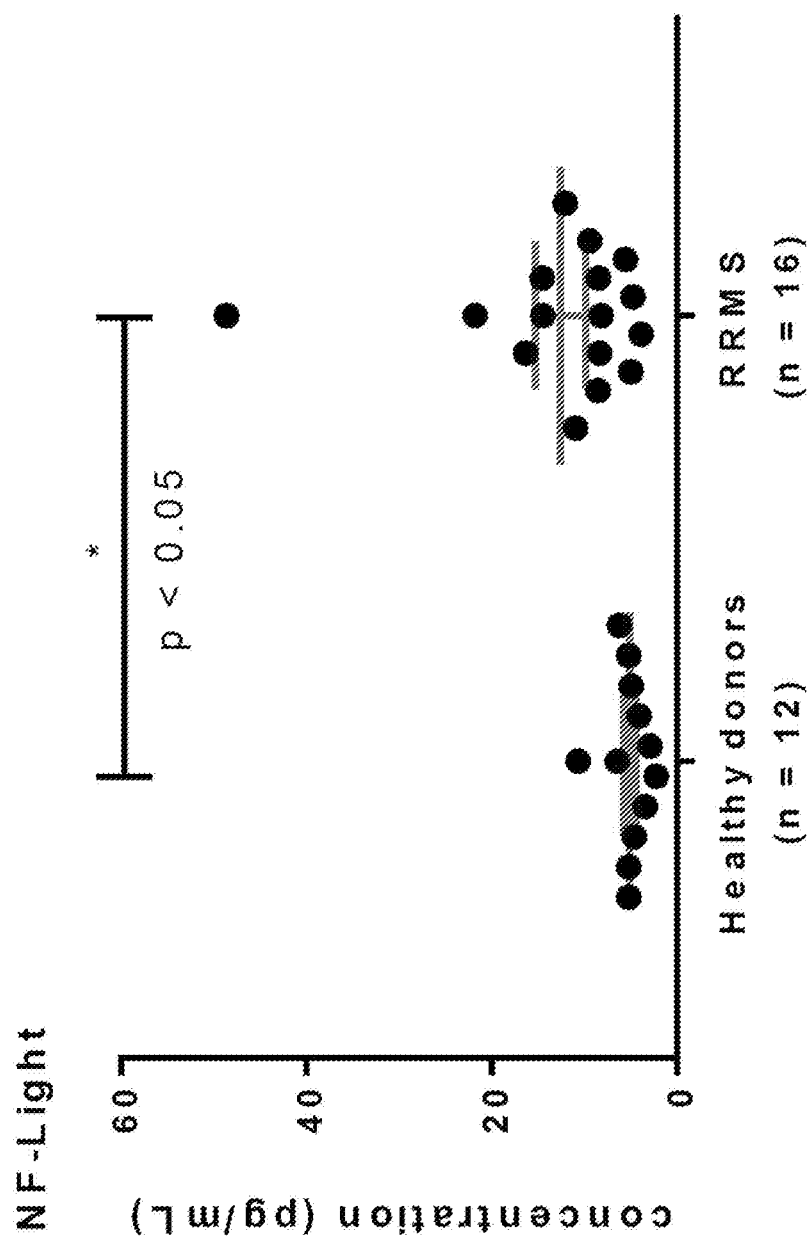
FIG. 9 is a diagram of NF-L concentration.
Figure 10:
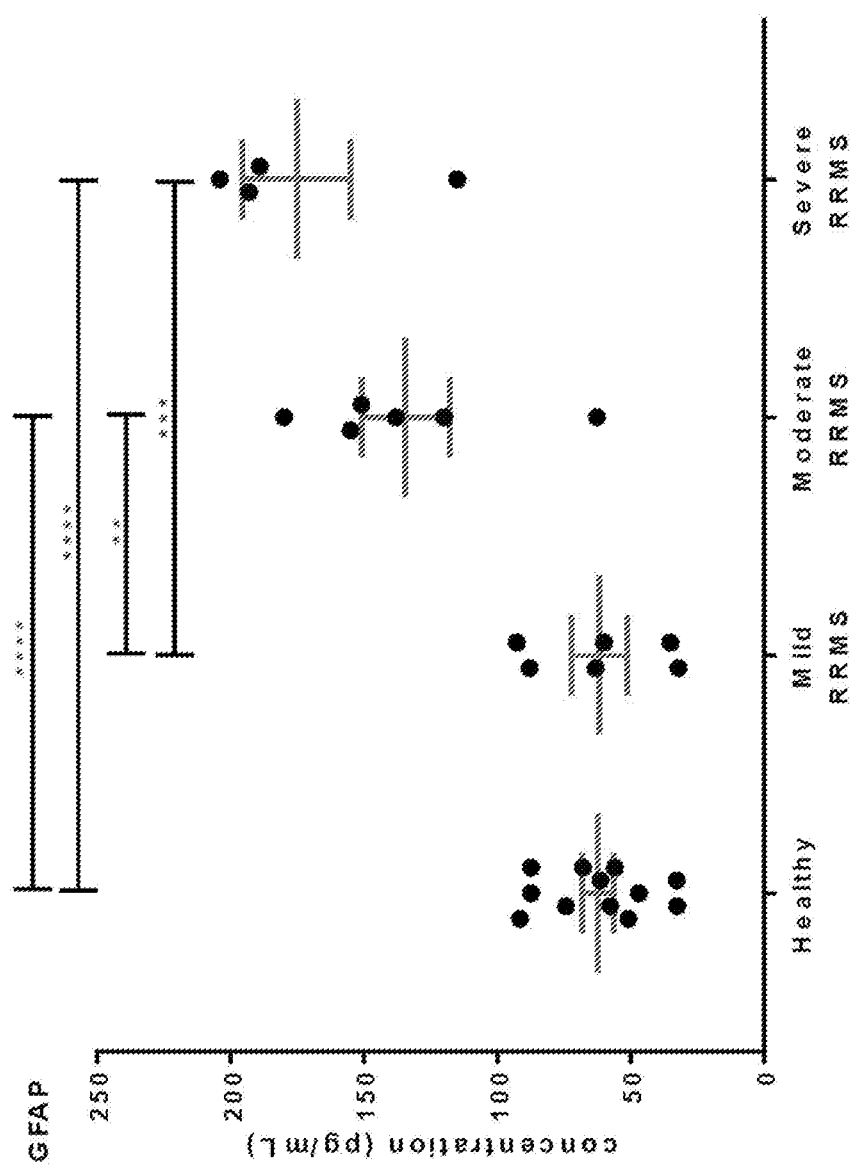
FIG. 10 is a diagram of GFAP concentration.
Figure 11:
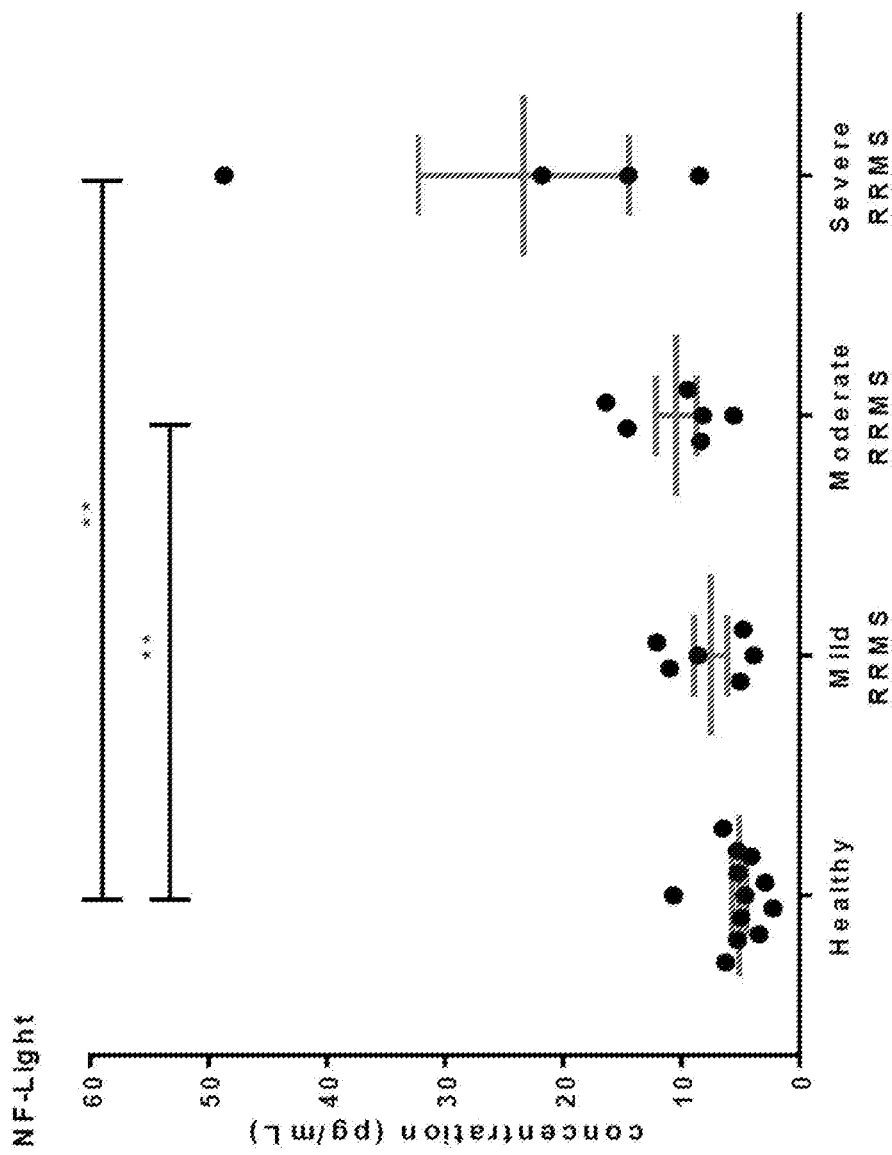
FIG. 11 is a diagram of NF-L concentration.

FIG. 7A shows the tau immunoassay dose-response curve. Calibrators were assayed in replicates of three. Four-parameter curve fit parameters are depicted. The analytical performance characteristics of the UCH L1 portion of the multiplex assay were characterized as summarized in Table 7 below. Table 8 shows the reproducibility of the UCH L1 immunoassay portion of the multiplex assay. FIG. 7B shows the UCH L1 concentration in EDTA plasma (n=20), matched serum (n=20) and CSF (n=20) from healthy donors. Error bars depict mean and interquartile ranges.

TABLE 7

General characteristics of UCH L1 immunoassay portion of the multiplex assay.

| | |
|---|---|
| Calibration range | 0-10 ng/ml |
| Dynamic range[1] | 0-40 ng/ml |
| Lower limit of detection (2.5 SD; 3 reps × 24 estimates across 12 runs, 3 instruments, 2 lots; mean LoD[2]) | 1.74 pg/mL |
| Lower limit of quantification[3] (12 runs, 3 instruments, 2 reagent lots, mean LoQ) | 5.45 pg/mL |
| Spike-recovery: serum/plasma (UCH-L1 spiked into 3 serum, 3 plasma samples at 750 and 7500 pg/mL, mean[4]) | 95.3% |
| Spike-recovery: CSF (UCH-L1 spiked into 4 CSF samples at 15,000 and 150,000 pg/mL, mean[5]) | 118.9% |
| Linearity (high UCH-L1 serum sample fractionally admixed with low tau serum sample, mean of 10 levels[6]) | 95.4% |
| Dilution linearity: serum (spiked serum diluted 2X serially from MRD to 128-fold w/ Sample Diluent; mean recovery[7]) | 90.1% |

TABLE 7-continued

General characteristics of UCH L1 immunoassay portion of the multiplex assay.

| | |
|---|---|
| Dilution linearity: CSF (CSF diluted 2X serially from MRD to 128-fold w/ Sample Diluent; mean recovery[8]) | 95.8% |
| Inter lot CV (Pool of CVs from 5 samples[9] tested with 2 reagent lots across 2 runs × 3 instruments) | 3.9% |
| Inter instrument CV (Pool of CVs from 5 sampls[9] tested with 3 instruments across 2 runs × 2 reagent lots) | 4.5% |
| Typical serum/plasma sample volume (Includes dead volume; see Package Insert for details) | 46 µL |
| CSF sample volume (Includes dead volume; See Package Insert for details) | 4.6 µL |

[1]Samples auto-diluted 4X; note: ranges may vary between calibrator lots
[2]SD 0.917 pg/mL; range 0.120-3.48 pg/mL.
[3]≤20% CV, 80-120% recovery; pooled CV 15.0%, mean recovery 108.9%; not corrected for pre-dilutions; 4X LoQ 1.87 pg/mL.
[4]Recovery range 57.9-131.4%.
[5]Recovery range 96.0-167.2%.
[6]Recovery range 85.1-104.0%.
[7]Recovery range 79.0-103.0%; minimum recommended dilution (MRD) 1:4.
[8]Recovery range 93.5-98.0%; MRD 1:40.
[9]Range 22.6-389 pg/mL.

TABLE 8

Reproducibility precision of UCH L1 immunoassay across instruments and reagent lots.
Reproducibility was determined with guidance from CLSI Protocol EP5-A. Five samples consisting of two serum panels, one plasma panel, and two UCH-L1 controls were assayed in replicates of three for two runs on each of three instruments and two reagent lots. Analysis of variance (nested ANOVA) results are summarized in the following table.

| Sample | Mean UCH-L1 pg/mL | Between Instrument % CV, n = 3 | Between Lot % CV, n = 2 | Between Run % CV, n = 12 | Within Run % CV, n = 30 |
|---|---|---|---|---|---|
| Control 1 | 129 | 1.8 | 0.0 | 2.9 | 9.3 |
| Control 2 | 13145 | 0.0 | 2.8 | 4.9 | 5.4 |
| Serum Panel 1 | 71.9 | 5.0 | 0.0 | 6.4 | 11.3 |
| Plasma Panel 2 | 381 | 4.8 | 0.0 | 4.9 | 5.6 |
| Serum Panel 3 | 6663 | 0.0 | 4.2 | 5.9 | 4.2 |

Example 3

This example describes the materials and methods used in Example 3.

Instrumentation

The multiplex assay in Example 3 was formulated for use on either Quanterix Simoa HD-1 Analyzer or Simoa SR-X (Quanterix™, Lexington, Massachusetts). The Simoa HD-1 is a fully automated digital immunoassay analyzer that utilizes single molecule array (Simoa) technology for isolation and counting of single molecules. The instrument pipettes sample directly from sample tubes (capacity 96 tubes) and processes immunoassays and data reduction with a steady state throughput of 66 tests/hour. The Simoa SR-X is a semi-automated digital immunoassay detection system that functions like the HD-1 system except that samples and reagents are added manually to a 96-well ELISA plate for the assay-processing step. Following completion of the immunoassay processing, the ELISA plates are imaged automatically by the plate loading system, and processed in similar fashion to the HD-1. The multiplex assay in Example 3 was run on Simoa SR-X.

Reagents

The following four reagents were developed: paramagnetic capture beads, biotinylated detector molecules, streptavidin: β-galactosidase (SβG) conjugate, and sample diluent. The capture beads comprised a mixture of paramagnetic microbeads conjugated separately with anti-NF-L mouse monoclonal antibodies, anti-tau mouse monoclonal antibodies, anti-GFAP mouse monoclonal antibodies, and anti-UCH L1 mouse monoclonal antibodies. For multiplexing, the beads were pre-coated with four separate fluorescent dyes, one dye for each analyte. Each fluorescently labeled bead type was assigned to one particular analyte (488 nm dye to NF-L, 750 nm dye to tau, 647 nm dye GFAP, and 700 nm dye to UCH L1. The beads were not co-coated with all four antibodies, but were coated separately in independent batches, then mixed together in equal portions. The antibodies were covalently attached to the beads by standard carbodiimide coupling chemistry to 2.7-µm carboxy paramagnetic microbeads (Agilent Technologies). The antibody-coated beads were diluted to a concentration of $7\times10^6$ beads/mL in a diluent composed of 50 mM Tris (pH 7.8), 50 mM NaCl, 10 mM EDTA, 1% BSA, 0.1% Tween 20, and an antimicrobial preservative (for example ProClin™ 300). Biotinylated detector reagent comprised a mixture of four biotinylated mouse monoclonal antibodies directed to epitopes on NF-L, tau, GFAP, and UCH L1. The antibodies were separately biotinylated using standard methods known in the art (for example EZ-Link NHS-PEG4-Biotin, Life Technologies), prior to mixing. Antibodies were diluted in such a way as to maximize signal while minimizing non-specific binding. Detector concentrations for the 4-plex differed significantly from what was utilized for single assays, and the range of detector concentrations was 0.1 mcg/mL (NF-L) to 1.8 mcg/mL (tau). Dilutions were performed in a diluent of phosphate-buffered saline (pH 7.4), 2% BSA, 0.1% Tween 20 and an anti-microbial preservative. SβG reagent was prepared by covalent conjugation of purified streptavidin (Thermo Scientific) and RG (Sigma) using standard coupling chemistry and diluted to 150 pM in phosphate buffered saline (pH 7.4) with 1% sucrose, 3% BSA, 0.1% Tween 20, and 1 mM $MgCl_2$ with an anti-microbial preservative. Sample diluent was formulated in phosphate buffered saline (pH 7.4) with dextrose (0.06%), BSA (0.02%), BgG (0.01%), urea (5 mM), Triton™ X-100 (0.5%), TRU Block™ (10 mcg/mL), Superchemiblock™ (0.05%), and an anti-microbial preservative. This unique and complex formulation resulted in good analytical characteristics for the multiplex assay.

Calibration

Multi-constituent calibrators were prepared in a diluent of phosphate buffered saline, pH 7.4, with 2.7 mM KCl, 2% BSA, 0.1% 10G Surfactant, 10 mcg/mL TRU Block™, 5 mM EDTA, and of an anti-microbial (ProClin™ 300). The following antigens used were:
  NF-light: Encor, recombinant human full length NF-L, Vendor Part #Prot-r-NF-L
  Tau: Millipore Tau 381 (AG952)
  GFAP: Hytest, native human GFAP, Vendor Part #8GF23
  UCH L1: Origene, recombinant human UCHL1, Vendor Part #TP301803. As described in the next section, the choice of GFAP antigen was important in reducing cross reactivity with the other three assays. Calibrator levels were:
  NF-light: 0, 0.5, 1.5, 5, 15, 50, 150, 500 pg/mL,
  Tau: 0, 0.1, 0.3, 1, 3, 10, 30, 100 pg/mL;
  GFAP: 0, 1, 3, 10, 30, 100, 300, 1000 pg/mL;
  UCH L1: 0, 10, 30, 100, 300, 1000, 3000, 10000 pg/mL.

Protocol

The multiplex assay in Example 3 was a 2-step digital immunoassay. In the first step, assay specific antibody coated paramagnetic capture beads, sample, and biotinylated detector antibody were combined. These beads were labeled with different dyes. NF-L, tau, GFAP, and UCH L1 molecules present in the sample were captured by the correspondent antibody coated capture beads and labeled with biotinylated detector antibodies. After washing, a conjugate of streptavidin-ß-galactosidase (SBG) is mixed with the capture beads. SBG binds to the biotinylated detector antibodies, resulting in enzyme labeling of captured targets. Following a second wash, the capture beads are resuspended in a resorufin ß-D-galactopyranoside (RGP) substrate solution and transferred to the Simoa Disc. Individual capture beads are then sealed within microwells in the array. If target has been captured and labeled, the ß-galactosidase hydrolyzes the RGP substrate into a fluorescent product that provides the signal for measurement. A single labeled target molecule results in sufficient fluorescent signal to be detected and counted by the Simoa optical system. The dye signal on each bead is decoded to determine which target it captured. At low target concentration, the percentage of bead-containing wells in the array that have a positive signal is proportional to the amount of target present in the sample. At higher target concentration, when most of the bead-containing wells have one or more labeled target molecules, the total fluorescence signal is proportional to the amount of target present in the sample. The concentration of NF-L, Tau, GFAP, and UCH L1 in unknown samples is interpolated from a standard curve.

When running the described reagents for the 4-plex on the HD-1, the above protocol was executed automatically by the instrument. When utilizing the SR-X instrument, the above protocol was performed outside of the instrument with manual pipetting by the user. The following sequence of steps were used to perform the testing manually in preparation for detection with the SR-X system. First, sample dilutions were prepared were diluted 4× in sample diluent. Then, aliquots of diluted samples were pipetted into ELISA plate wells. Third, capture beads were pipetted into each ELISA plate well (20 µl per well). Next, detector molecules were pipetted into each ELISA well (20 µl per well). Then, the sample plate was incubated on a microplate shaker for 30 minutes, 800 rpm, 30° C. Next, the sample plate was washed using a microplate washer (for example BioTek washer) with 3 cycles with Tris wash buffer. The total wash time was 5 minutes. Then SBG reagent was added (100 µl per well). Next, a second wash was performed using a microplate washer (for example BioTek washer) with 2 cycles with sucrose-containing wash buffer. The total wash time was 2 minutes. Then, the plate was incubated on magnet for 10 minutes to dry pellet. Once, the assay prep was complete, the plate was transferred to SR-X and start run.

Example 4

The following non-limiting example describes the non-specific binding of certain GFAP antigen used for calibration. Table A shows the average enzyme per bead (AEB) and the S/B for a calibration curve using GFAP Vendor An antigen and GFAP Hytest antigen.

TABLE A

| Antigen Beads Detector | | Tau Det Mix | | Ab42 Det Mix | | GFAP Det Mix | | UCHL1 Det Mix | |
|---|---|---|---|---|---|---|---|---|---|
| Calibrator | pg/mL | AEB | S/B | AEB | S/B | AEB | S/B | AEB | S/B |
| | | | | | GFAP Vendor A | | | | |
| Cal A | 0 | 0.035 | | 0.020 | | 0.012 | | 0.007 | |
| Cal B | 0.122 | 0.033 | 1.0 | 0.025 | 1.3 | 0.019 | 1.6 | 0.009 | 1.2 |
| Cal C | 0.488 | 0.034 | 1.0 | 0.028 | 1.4 | 0.046 | 3.9 | 0.011 | 1.6 |
| Cal D | 1.95 | 0.051 | 1.5 | 0.029 | 1.5 | 0.138 | 11.8 | 0.014 | 2.0 |
| Cal E | 7.81 | 0.112 | 3.2 | 0.039 | 2.0 | 0.121 | 10.3 | 0.037 | 5.3 |
| Cal F | 31.3 | 0.339 | 9.7 | 0.103 | 5.3 | 1.938 | 165.1 | 0.101 | 14.2 |
| Cal G | 125 | 1.079 | 31.0 | 0.221 | 11.3 | 7.245 | 617.2 | 0.406 | 57.0 |
| Cal H | 500 | 3.132 | 89.9 | 0.667 | 34.0 | 21.285 | 1813.1 | 1.594 | 223.7 |
| | | | | | GFAP Hytest vendor | | | | |
| Cal A | 0 | 0.015 | | 0.025 | | 0.008 | | 0.008 | |
| Cal B | 0.122 | 0.020 | 1.3 | 0.024 | 0.9 | 0.020 | 2.5 | 0.013 | 1.5 |
| Cal C | 0.488 | 0.021 | 1.4 | 0.024 | 0.9 | 0.034 | 4.2 | 0.010 | 1.2 |
| Cal D | 1.95 | 0.022 | 1.5 | 0.026 | 1.0 | 0.076 | 9.4 | 0.011 | 1.3 |
| Cal E | 7.81 | 0.020 | 1.3 | 0.024 | 0.9 | 0.281 | 34.4 | 0.012 | 1.5 |

TABLE A-continued

| Antigen Beads Detector | | Tau Det Mix | | Ab42 Det Mix | | GFAP Det Mix | | UCHL1 Det Mix | |
|---|---|---|---|---|---|---|---|---|---|
| Calibrator | pg/mL | AEB | S/B | AEB | S/B | AEB | S/B | AEB | S/B |
| Cal F | 31.3 | 0.015 | 1.0 | 0.025 | 1.0 | 1.123 | 137.6 | 0.012 | 1.5 |
| Cal G | 125 | 0.020 | 1.3 | 0.025 | 1.0 | 4.672 | 572.7 | 0.012 | 1.5 |
| Cal H | 500 | 0.023 | 1.5 | 0.032 | 1.3 | 14.939 | 1831.5 | 0.013 | 1.6 |

Example 5

The following non-limiting example describes the cross-reactivity and/or non-specific binding of certain UCH L1 clones with NF-L capture beads. UCH L1 clones 2D3 and 1016 produced a relatively high non-specific binding signal and were incompatible with the multiplex format as shown in Table B-1. Conversely, UCH L1 clones 10D1 and 1033 did not produce a detectable non-specific signal as shown in Table B2.

TABLE B-1

UCHL1 antibody pair 2D3-1016 causing crosstalk

| Antigen Beads Detector | | Tau | | | | Antigen Beads Detector | | NF-L | | | |
|---|---|---|---|---|---|---|---|---|---|---|---|
| | | Tau Det Mix | | NF-L Det Mix | | | | Tau Det Mix | | NF-L Det Mix | |
| Calibrator | pg/mL | AEB | S/B | AEB | S/B | Calibrator | pg/mL | AEB | S/B | AEB | S/B |
| Cal A | 0 | 0.031 | | 0.400 | | Cal A | 0 | 0.034 | | 0.548 | |
| Cal B | 0.024 | 0.039 | 1.3 | 0.436 | 1.1 | Cal B | 0.014 | 0.037 | 1.1 | 0.522 | 1.0 |
| Cal C | 0.098 | 0.051 | 1.7 | 0.444 | 1.1 | Cal C | 0.055 | 0.030 | 0.9 | 0.542 | 1.0 |
| Cal D | 0.391 | 0.106 | 3.5 | 0.418 | 1.0 | Cal D | 0.218 | 0.033 | 1.0 | 0.608 | 1.1 |
| Cal E | 1.56 | 0.302 | 9.8 | 0.449 | 1.1 | Cal E | 0.87 | 0.028 | 0.8 | 0.717 | 1.3 |
| Cal F | 6.25 | 0.461 | 15.0 | 0.461 | 1.2 | Cal F | 3.49 | 0.029 | 0.9 | #DIV/0! | #DIV/0! |
| Cal G | 25.0 | 2.882 | 93.9 | 0.489 | 1.2 | Cal G | 14.0 | 0.031 | 0.9 | #DIV/0! | #DIV/0! |
| Cal H | 100 | 9.314 | 303.3 | 0.587 | 1.5 | Cal H | 55.9 | 0.032 | 1.0 | #DIV/0! | #DIV/0! |

| Antigen Beads Detector | | GFAP Vendor A | | | | Antigen Beads Detector | | UCHL1 Vendor B | | | |
|---|---|---|---|---|---|---|---|---|---|---|---|
| | | Tau Det Mix | | NF-L Det Mix | | | | Tau Det Mix | | NF-L Det Mix | |
| Calibrator | pg/mL | AEB | S/B | AEB | S/B | Calibrator | pg/mL | AEB | S/B | AEB | S/B |
| Cal A | 0 | 0.035 | | 0.515 | | Cal A | 0 | 0.029 | | 0.516 | |
| Cal B | 0.122 | 0.033 | 1.0 | 0.468 | 0.9 | Cal B | 1.22 | 0.032 | 1.1 | 0.539 | 1.0 |
| Cal C | 0.488 | 0.034 | 1.0 | 0.477 | 0.9 | Cal C | 4.88 | 0.033 | 1.2 | 0.511 | 1.0 |
| Cal D | 1.95 | 0.051 | 1.5 | 0.499 | 1.0 | Cal D | 19.5 | 0.034 | 1.2 | 0.494 | 1.0 |
| Cal E | 7.81 | 0.112 | 3.2 | 0.570 | 1.1 | Cal E | 78.1 | 0.035 | 1.2 | 0.515 | 1.0 |
| Cal F | 31.3 | 0.339 | 9.7 | 0.589 | 1.1 | Cal F | 313 | 0.032 | 1.1 | 0.433 | 0.8 |
| Cal G | 125 | 1.079 | 31.0 | 0.726 | 1.4 | Cal G | 1250 | 0.032 | 1.1 | 0.458 | 0.9 |
| Cal H | 500 | 3.132 | 89.9 | #DIV/0! | #DIV/0! | Cal H | 5000 | 0.041 | 1.4 | 0.471 | 0.9 |

TABLE B2

UCHL1 antibody pair 1001-1033 had minimal crosstalk

| Antigen Beads Detector | | Tau Det Mix | | Ab42 Det Mix | | GFAP Det Mix | | UCHL1 Det Mix | |
|---|---|---|---|---|---|---|---|---|---|
| Calibrator | pg/mL | AEB | S/B | AEB | S/B | AEB | S/B | AEB | S/B |
| | | Tau | | | | | | | |
| Cal A | 0 | 0.011 | | 0.028 | | 0.014 | | 0.010 | |
| Cal B | 0.024 | 0.013 | 1.2 | 0.028 | 1.0 | 0.015 | 1.0 | 0.011 | 1.1 |
| Cal C | 0.098 | 0.026 | 2.4 | 0.026 | 0.9 | 0.012 | 0.8 | 0.010 | 0.9 |

TABLE B2-continued

UCHL1 antibody pair 1001-1033 had minimal crosstalk

| Antigen Beads Detector | | Tau Det Mix | | Ab42 Det Mix | | GFAP Det Mix | | UCHL1 Det Mix | |
|---|---|---|---|---|---|---|---|---|---|
| Calibrator | pg/mL | AEB | S/B | AEB | S/B | AEB | S/B | AEB | S/B |
| Cal D | 0.391 | 0.050 | 4.7 | 0.026 | 0.9 | 0.013 | 0.9 | 0.014 | 1.3 |
| Cal E | 1.56 | 0.178 | 16.5 | 0.028 | 1.0 | 0.015 | 1.1 | 0.012 | 1.1 |
| Cal F | 6.25 | 0.673 | 62.7 | 0.025 | 0.9 | 0.017 | 1.2 | 0.018 | 1.7 |
| Cal G | 25.0 | 2.184 | 203.6 | 0.031 | 1.1 | 0.030 | 2.1 | 0.036 | 3.5 |
| Cal H | 100 | 8.638 | 805.0 | 0.037 | 1.3 | 0.076 | 5.3 | 0.109 | 10.5 |
| Ab42 | | | | | | | | | |
| Cal A | 0 | 0.015 | | 0.029 | | 0.012 | | 0.010 | |
| Cal B | 0.014 | 0.012 | 0.8 | 0.029 | 1.0 | 0.013 | 1.0 | 0.015 | 1.4 |
| Cal C | 0.055 | 0.016 | 1.1 | 0.051 | 1.8 | 0.014 | 1.1 | 0.012 | 1.1 |
| Cal D | 0.218 | 0.012 | 0.8 | 0.104 | 3.6 | 0.014 | 1.2 | 0.014 | 1.4 |
| Cal E | 0.87 | 0.017 | 1.1 | 0.310 | 10.7 | 0.012 | 1.0 | 0.011 | 1.1 |
| Cal F | 3.49 | 0.015 | 1.0 | 1.187 | 40.8 | 0.014 | 1.1 | 0.013 | 1.3 |
| Cal G | 14.0 | 0.014 | 1.0 | 3.648 | 125.5 | 0.014 | 1.1 | 0.014 | 1.3 |
| Cal H | 56 | 0.017 | 1.2 | 14.216 | 489.1 | 0.013 | 1.1 | 0.013 | 1.3 |
| UCHL | | | | | | | | | |
| Cal A | 0 | 0.029 | | 0.029 | | 0.014 | | 0.013 | |
| Cal B | 1.22 | 0.032 | 1.1 | 0.033 | 1.1 | 0.014 | 1.0 | 0.018 | 1.4 |
| Cal C | 4.88 | 0.033 | 1.2 | 0.030 | 1.0 | 0.016 | 1.1 | 0.025 | 2.0 |
| Cal D | 19.5 | 0.034 | 1.2 | 0.030 | 1.0 | 0.014 | 1.0 | 0.056 | 4.4 |
| Cal E | 78.1 | 0.035 | 1.2 | 0.031 | 1.1 | 0.014 | 1.0 | 0.182 | 14.5 |
| Cal F | 313 | 0.032 | 1.1 | 0.032 | 1.1 | 0.016 | 1.1 | 0.638 | 50.8 |
| Cal G | 1250 | 0.032 | 1.1 | 0.032 | 1.1 | 0.022 | 1.6 | 2.051 | 163.1 |
| Cal H | 5000 | 0.041 | 1.4 | 0.040 | 1.4 | 0.039 | 2.7 | 9.591 | 762.7 |
| GFAP | | | | | | | | | |
| Cal A | 0 | 0.015 | | 0.025 | | 0.008 | | 0.008 | |
| Cal B | 0.122 | 0.020 | 1.3 | 0.024 | 0.9 | 0.020 | 2.5 | 0.013 | 1.5 |
| Cal C | 0.488 | 0.021 | 1.4 | 0.024 | 0.9 | 0.034 | 4.2 | 0.010 | 1.2 |
| Cal D | 1.95 | 0.022 | 1.5 | 0.026 | 1.0 | 0.076 | 9.4 | 0.011 | 1.3 |
| Cal E | 7.81 | 0.020 | 1.3 | 0.024 | 0.9 | 0.281 | 34.4 | 0.012 | 1.5 |
| Cal F | 31.3 | 0.015 | 1.0 | 0.025 | 1.0 | 1.123 | 137.6 | 0.012 | 1.5 |
| Cal G | 125 | 0.020 | 1.3 | 0.025 | 1.0 | 4.672 | 572.7 | 0.012 | 1.5 |
| Cal H | 500 | 0.023 | 1.5 | 0.032 | 1.3 | 14.939 | 1831.5 | 0.013 | 1.6 |

Example 6

The following non-limiting example describes the use of certain detergents in the sample diluent. Triton™ X-100 was found to be suitable for both Tau and UCH L1 assays as shown in Table C.

TABLE C

| Sample Diluent | Detergent | UCHL1 Zero signal | UCHL1 Normal sample signal | CSF Tau conc (pg/mL) | Normalized by Tau sample diluent |
|---|---|---|---|---|---|
| Sample diluent 1 | 1% 3-(Decyldimethyl) | 0.0030 | 0.0188 | 2.58 | 2% |
| Sample diluent 2 | 1% N-Dodecyl | | 0.0038 | 84.37 | 50% |
| Sample diluent 3 | 0.5% 3-(Decyldimethyl) | | 0.0060 | 20.75 | 12% |
| Sample diluent 4 | 0.5% N-Dodecyl | | 0.0043 | 83.84 | 50% |
| Sample diluent 5 | 0.5% Triton | | 0.0069 | 160.10 | 95% |
| Sample diluent 6 | 0.5% Tw20 | | 0.0078 | 147.59 | 88% |
| Sample diluent 7 | 0.5% ASB14 | | 0.0033 | 160.43 | 95% |
| Tau sample diluent | 1% ASB14 | | 0.0029 | 168.10 | 100% |

Example 7

The following non-limiting example describes the use of blockers in the sample diluent to impart dilution linearity and predictable spike recovery. Superchemiblock™ produced linear dilutions and predictable spike recovery as shown in Table D.

TABLE D

| Sample ID | Spiking Level | w/o Superchemiblock | w Superchemiblock |
|---|---|---|---|
| NF-L Buffer Corrected Recovery | | | |
| Buffer | 10 pg/mL | 100% | 100% |
|  | 100 pg/mL | 100% | 100% |
| Serum 1 | 10 pg/mL | 43% | 76% |
|  | 100 pg/mL | 34% | 74% |
| Serum 2 | 10 pg/mL | 61% | 92% |
|  | 100 pg/mL | 52% | 104% |
| Average |  | 48% | 87% |

| Dilution | w/o Superchemiblock | w Superchemiblock |
|---|---|---|
| NF-L Spiked Serum Dilution Linearity | | |
| 1:4 | 100% | 100% |
| 1:8 | 106% | 96% |
| 1:16 | 139% | 112% |
| 1:32 | 156% | 117% |
| 1:64 | 181% | 116% |
| 1:128 | 212% | 99% |
| Average | 159% | 108% |
| NF-L Endogenous CSF Dilution Linearity | | |
| 1:4 | 100% | 100% |
| 1:8 | 102% | 123% |
| 1:16 | 112% | 115% |
| 1:32 | 129% | 113% |
| 1:64 | 143% | 104% |
| 1:128 | 192% | 119% |
| 1:256 | 301% | 127% |
| 1:512 | 602% | 108% |
| Average | 210% | 114% |
| Tau Spiked Serum Dilution Linearity | | |
| 1:4 | 100% | 100% |
| 1:8 | 100% | 96% |
| 1:16 | 115% | 89% |
| 1:32 | 152% | 82% |
| 1:64 | 171% | 82% |
| 1:128 | 186% | 88% |
| 1:256 | 217% | 82% |
| 1:512 | 236% | 102% |
| Average | 160% | 90% |

Example 8

The following non-limiting example describes the effect of detection molecule concentration on non-specific binding. Table E shows AEB and S/B for NF-L for different concentrations of UCH L1 detector. The concentration of UCH L1 detection molecules used in a single assay (i.e., 5 pg/mL) and the concentration used in the multiplex assay (i.e., 0.5 pg/mL) were investigated.

TABLE E

| Plex | | 4-plex- NFL | | | |
|---|---|---|---|---|---|
| [UCHL1 Det] | | 5 ug/mL | | 0.5 ug/mL | |
| Calibrator | pg/mL | AEB | S/B | AEB | S/B |
| Cal A | 0 | 0.014 |  | 0.008 |  |
| Cal B | 1 | 0.017 | 1.3 | 0.016 | 1.9 |
| Cal C | 5 | 0.108 | 7.8 | 0.100 | 12.0 |
| Cal D | 50 | 0.864 | 62.4 | 0.884 | 106.1 |
| Cal E | 500 | 9.213 | 664.8 | 8.874 | 1065.0 |

For description of various details associate with this assay, see, for example, U.S. patent application Ser. No. 12/731,130, filed Mar. 24, 2010, published as US-2011-0212848 on Sep. 1, 2011, entitled "ULTRA-SENSITIVE DETECTION OF MOLECULES OR PARTICLES USING BEADS OR OTHER CAPTURE OBJECTS," by Duffy et al.; International Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS," by Duffy et al.; International Patent Application No. PCT/US2011/026657, filed Mar. 1, 2011, published as WO 2011/109372 on Sep. 9, 2011, entitled "ULTRA-SENSITIVE DETECTION OF MOLECULES USING DUAL DETECTION METHODS," by Duffy et al.; U.S. patent application Ser. No. 12/731,135, filed Mar. 24, 2010, published as US-2011-0212462 on Sep. 1, 2011, entitled "ULTRA-SENSITIVE DETECTION OF MOLECULES USING DUAL DETECTION METHODS," by Duffy et al.; International Patent Application No. PCT/US2011/026665, filed Mar. 1, 2011, published as WO 2011/109379 on Sep. 9, 2011, entitled "METHODS AND SYSTEMS FOR EXTENDING DYNAMIC RANGE IN ASSAYS FOR THE DETECTION OF MOLECULES OR PARTICLES," by Rissin et al.; U.S. patent application Ser. No. 12/731,136, filed Mar. 24, 2010, published as US-2011-0212537 on Sep. 1, 2011, entitled "METHODS AND SYSTEMS FOR EXTENDING DYNAMIC RANGE IN ASSAYS FOR THE DETECTION OF MOLECULES OR PARTICLES," by Duffy et al.; U.S. patent application Ser. No. 13/035,472, filed Feb. 25, 2011, published as US 2012-0196774, entitled "SYSTEMS, DEVICES, AND METHODS FOR ULTRA-SENSITIVE DETECTION OF MOLECULES OR PARTICLES," by Fournier et al.; U.S. patent application Ser. No. 13/037,987, filed Mar. 1, 2011, published as US-2011-0245097 on Oct. 6, 2011, entitled "METHODS AND SYSTEMS FOR EXTENDING DYNAMIC RANGE IN ASSAYS FOR THE DETECTION OF MOLECULES OR PARTICLES," by Rissin et al.; each herein incorporated by reference.

Examples 9-11

Analysis of plasma samples from patients with mild traumatic brain injury. A series of assay experiments for NF-L, Tau, GFAP, and UCH L1 were performed on blood samples obtained from donors suspected for mild TBI and from a control group. Donor characteristics are shown in Table 9 and results are shown in Tables 10-11. See Gill, J. et al., "Glial fibrillary acidic protein elevations relate to neuroimaging abnormalities after mild TBI," *Neurology* 91:15 (Oct. 9, 2018) e1385-e1389.

TABLE 9

Donor Characteristics in Examples 9-11

| Example[1] | Number of Donors | Demographic Characteristics[2] | | | | Injury Mechanisms | | | |
|---|---|---|---|---|---|---|---|---|---|
| | | Age | GCS | NSI | Male | Vehicular Accident | Fall | Assault | Struck by Object |
| Example 9 | 69 | 52.0 | 14.07 | 15.80 | 65% | 40% | 21% | 17% | 13% |
| Example 10 | 28 | 46.0 | 14.42 | 14.89 | 60% | 46% | 32% | 25% | 7% |
| Example 11 | 177 | 41.5 | 14.33 | 14.51 | 57% | 54% | 28% | 18% | 9% |
| Comparative Example A | 49 | 48.6 | n.a. | n.a. | 61% | n.a. | n.a. | n.a. | n.a. |

[1] Donors in Examples 9-11 were participants in Traumatic Head Injury Neuroimaging Classification study (NCT01132937). EDTA blood samples (venous) were collected within 48 hours of injury, plasma obtained, and stored at −80° C. Donors in Comparative Example A were healthy donors without a history of TBI or neurologic disease.
[2] Mean age ("Age"), Glasgow Coma Scale ("GCS"), Neurobehavioral Symptom Inventory ("NSI"), and percentage male ("Male") presented.

TABLE 10

Assay and Imaging Results

| Example | Assay Results[1] | | | | Imaging Results[2] | |
|---|---|---|---|---|---|---|
| | NF-L | Tau | GFAP | UCH L1 | MRI | CT |
| Example 9 | 23.20 (11.82-44.78) | 2.84 (1.86-4.17) | 2853 (768.2-5724) | 53.62 (30.60-149.5) | + | + |
| Example 10 | 17.94 (11.68-32.56) | 2.32 (1.7-7.33) | 2098 (253.7-8382) | 42.16 (16.63-96.20) | + | − |
| Example 11 | 7.62 (4.56-16.09) | 1.76 (1.1-2.88) | 266.2 (101.8-857.2) | 23.06 (13.44-44.06) | − | − |
| Comparative Example A | 4.87 (3.04-7.11) | 1.25 (0.71-2.09) | 56.18 (45.98-69.84) | 9.59 (6.01-19.86) | n.a. | n.a. |
| Statistical Significance[3] | $x^2 = 80.99$ $p < 0.00011$ | $x^2 = 36.94$ $p < 0.00011$ | $x^2 = 143.8$ $p < 0.00011$ | $x^2 = 45.99$ $p < 0.00011$ | n.a. | n.a. |

[1] Analytes were quantified in plasma samples by multiplex assay using the Simoa (Single Molecule Array) Neurology 4-plex assay kit (Quanterix, Lexington, MA). Median and interquartile ranges presented in pg/mL
[2] MRI and CT performed within 48 hours of injury. MRI protocol comprised diffusion-tensor imaging, T2*-weighted imaging, T2-fluid-attenuated inversion recovery (FLAIR), high-resolution 3D-T1, dynamic susceptibility contrast perfusion-weighted imaging, and post-contrast T1 and T2-FLAIR.
[3] Differences between the Examples and Comparative Example were calculated using the Kruskal-Wallis and the Mann-Whitney tests, and correlation analyses were performed using the Spearman rank test, with p-values adjusted for multiple comparisons with the Benjamini-Hochberg procedure. All tests were 2-tailed; $p < 0.05$ was considered significant.

TABLE 11

AUC's for Age-Adjusted ROC Curves in Examples 9-11

| ROC Curve | Donors Used | | AUC | | |
|---|---|---|---|---|---|
| | True Negative Condition | True Positive Condition | NF-L | Tau | GFAP |
| Healthy donors vs. donors suspected for mild traumatic brain injury (control vs. mTBI) | Comparative Example A | Examples 9-11 | 0.7668 | 0.6777 | 0.9283 |
| Donors with positive vs. negative computed CT indication of brain injury (CT⁺ vs. CT⁻) | Examples 10-11 | Example 9 | 0.6539 | 0.6572 | 0.7722 |
| Donors with positive vs. negative MRI indication of brain injury (MRI⁺ vs. MRI⁻) | Example 11 | Examples 9-10 | 0.6628 | 0.7170 | 0.8032 |
| Donors with negative CT and negative MRI indication of brain injury vs. negative CT and positive MRI indications of brain injury (CT⁻ MRI⁻ vs. CT⁻ MRI⁺) | Example 11 | Example 10 | 0.6399 | 0.6836 | 0.7402 |

Example 12

Analysis of plasma samples from patients with traumatic brain injury. A series of assay experiments for NF-L, Tau, GFAP, and UCH L1 were performed on venous blood samples obtained from donors suspected for TBI. Donor characteristics are shown in Table 12 and results are shown in Tables 13-14. See Korley, F. K., "Performance Evaluation of a Multiplex Assay for Simultaneous Detection of Four Clinically Relevant Traumatic Brain Injury Biomarkers," *J. Neurotrauma* 36 (Jan. 1, 2019) 182-187.

TABLE 12

Donor Characteristics in Examples 12-13

| Example[1] | Number of Donors | Age | GCS 3-8 | GCS 9-12 | GCS 13-15 | Male | Vehicular Accident | Pedestrian Vehicular Accident | Fall | Assault | Struck by Object | Post-traumatic Amnesia Yes | Suspected | No | Unknown |
|---|---|---|---|---|---|---|---|---|---|---|---|---|---|---|---|
| Example 12 | 63 | 39.0 | 0% | 1.6% | 98.4% | 63.5% | 27.0% | 6.3% | 49.2% | 12.7% | 4.8% | 55.6% | 1.6% | 33.3% | 9.5% |
| Example 13 | 44 | 44.0 | 25.0% | 9.1% | 65.9% | 86.4% | 39.5% | 2.3% | 44.2% | 14.0% | 0.0% | 43.2% | 18.2% | 18.2% | 20.5% |

[1]Donors in Example 12 and Comparative Example B were participants in the Transforming Research and Clinical Knowledge in TBI Pilot (TRACK-TB Pilot Study). Venous blood samples were collected within 24 hours of injury. Donors in Example 12 showed no intracranial abnormality on head CT (CT⁺) while donors in Comparative Example B showed no intracranial abnormality on head CT (CT⁻). Samples were centrifuged and plasma aliquots were stored at −80° C.
[2]Median age ("Age"), Glasgow Coma Scale ("GCS"), and percentage male ("Male") presented.

TABLE 13

Assay and CT Scan Results

| Example | NF-L | Tau | GFAP | UCH L1 | CT[2] |
|---|---|---|---|---|---|
| Example 12 | 8.8 (5.6-13.8) | 3.5 (2.2-6.5) | 540.0 (104.5-1265.9) | 38.8 (22.4-62.5) | − |
| Example 13 | 20.4 (15.2-39.1) | 11.0 (4.9-17.2) | 4406.3 (2677.5-13630.7) | 120.6 (70.7-226.4) | + |
| Statistical Significance[3] | $p < 0.001$ | $p < 0.001$ | $p < 0.001$ | $p < 0.001$ | n.a. |

[1]Analytes were quantified in plasma samples by multiplex assay using the Simoa (Single Molecule Array) Neurology 4-plex assay kit (Quanterix, Lexington, MA). Median and interquartile ranges presented in pg/mL. Digital assay results were examined for normality with distributional plots and the Shapiro-Wilk test.
[2]Head CT performed within 24 hours of injury.
[3]The Mann-Whitney U test was used to assess for between-group differences in the digital assay results.

TABLE 14

AUC's for Age-Adjusted ROC Curves in Examples 12-13

| ROC Curve | Donors Used True Negative Condition | True Positive Condition | AUC NF-L | Tau | GFAP | UCH L1 |
|---|---|---|---|---|---|---|
| Donors with normal vs. abnormal CT scans (CT⁻ vs. CT⁺) | Example 12 | Examples 13 | 0.84 | 0.77 | 0.88 | 0.86 |

Examples 14-16

Analysis of plasma samples from patients with RRMS. A series of digital assay experiments for NF-L, Tau, GFAP, and UCH L1 were performed on blood samples obtained from donors diagnosed with RRMS. Results are shown in Table 15 and FIGS. 8-11.

TABLE 15

Assay Results in Examples 14-16

| Example[1] | Number of Donors | Assay Results[2] | | | | Relapsing-remitting Multiple Sclerosis Severity[3] |
|---|---|---|---|---|---|---|
| | | NF-L | Tau | GFAP | UCH L1 | |
| Example 14 | 6 | 7.57 ± 1.43 | 1.0 ± 0.459 | 61.9 ± 10.4 | 10.5 ± 1.09 | Mild |
| Example 15 | 6 | 10.4 ± 1.7 | 1.09 ± 0.218 | 135 ± 16.5 | 12.9 ± 3.75 | Moderate |
| Example 16 | 4 | 23.4 ± 8.87 | 2.08 ± 0.864 | 175 ± 20.3 | 46.0 ± 33.7 | Severe |
| Comparative Example B[4] | 12 | 5.14 ± 0.623 | 2.02 ± 0.277 | 62.2 ± 5.82 | 8.96 ± 1.93 | n.a. |

[1]EDTA blood samples (venous) were obtained from Bioreclamation. Samples from patients diagnosed with RRMS were actively receiving medical treatment.
[2]Analytes were quantified in plasma samples by multiplex assay using the Simoa (Single Molecule Array) Neurology 4-plex assay kit (Quanterix, Lexington, MA). Mean concentration is presented in pg/mL.
[3]RRMS severity was categorized based on a physician's diagnosis. Mild: Expanded Disability Status Scale (EDSS) scores less than 3; moderate: EDSS scores between 3 and 5; severe: EDSS scores greater than 5.
[4]Donors in Comparative Example B were healthy donors.

Prophetic Examples

Prophetic Examples 17-19

Assay analysis of samples diluted with sample diluent containing added human IgG. A series of assay experiments would be performed on samples at various levels of dilution and with and without added human IgG. Diluent compositions are shown in Table 16. The results shown in Tables 17-19 would be obtained.

TABLE 16

Diluent Compositions in Example 17-19

| | |
|---|---|
| Examples 17-19 | 50 mM phosphate, 137 mM NaCl, 2.7 mM KCl, 0.02% BSA, 1 mM MgCl$_2$, 0.06% dextrose, 0.01% BgG, 5 mM urea, 0.5% Triton ™ X-100, 10 mcg/mL TRU block ™, 50 mcg/mL Superchemiblock ™, 5 mg/mL human IgG, and 0.05% ProClin 300 ™ at pH 7.4. |
| Comparative Examples C-E | 50 mM phosphate, 137 mM NaCl, 2.7 mM KCl, 0.02% BSA, 1 mM MgCl$_2$, 0.06% dextrose, 0.01% BgG, 5 mM urea, 0.5% Triton ™ X-100, 10 mcg/mL TRU block ™, 50 mcg/mL Superchemiblock ™, and 0.05% ProClin 300 ™ at pH 7.4. |

TABLE 17

Assay Results for Spiked Samples in Example 17[1]

| Matrix[2] | NF-L | | Tau | | GFAP | | UCH L1 | |
|---|---|---|---|---|---|---|---|---|
| | Example 17 | Comparative Example C | Example 17 | Comparative Example C | Example 17 | Comparative Example C | Example 17 | Comparative Example C |
| Serum | 80-120% | <70% | 80-120% | <70% | 80-120% | <70% | 80-120% | <70% |
| Plasma | 80-120% | <70% | 80-120% | <70% | 80-120% | <70% | 80-120% | <70% |
| Plasma | 80-120% | <70% | 80-120% | <70% | 80-120% | <70% | 80-120% | <70% |
| Plasma | 80-120% | <70% | 80-120% | <70% | 80-120% | <70% | 80-120% | <70% |
| Serum | 80-120% | <70% | 80-120% | <70% | 80-120% | <70% | 80-120% | <70% |
| Serum | 80-120% | <70% | 80-120% | <70% | 80-120% | <70% | 80-120% | <70% |

[1]Samples would be spiked with 100 pg/mL each of NF-L, Tau, GFAP, and UCH L1. Spike recovery is the ratio of observed concentration following subtraction of endogenous NF-L to expected concentration expressed as a percentage.
[2]Samples would be diluted 4x with the sample diluent indicated in Table 16.

TABLE 18

Assay Results for Unspiked Samples[1]

Ratio of Concentration of Indicated Analyte in Example 18 to Comparative Example D

| Matrix[2] | NF-L | Tau | GFAP | UCH L1 |
|---|---|---|---|---|
| Serum | 0.9-1.1 | 0.9-1.1 | 0.9-1.1 | 0.9-1.1 |
| Plasma | 0.9-1.1 | 0.9-1.1 | 0.9-1.1 | 0.9-1.1 |
| Plasma | 0.9-1.1 | 0.9-1.1 | 0.9-1.1 | 0.9-1.1 |
| Plasma | 0.9-1.1 | 0.9-1.1 | 0.9-1.1 | 0.9-1.1 |
| Serum | 0.9-1.1 | 0.9-1.1 | 0.9-1.1 | 0.9-1.1 |
| Serum | 0.9-1.1 | 0.9-1.1 | 0.9-1.1 | 0.9-1.1 |

[1]Concentration is presented in pg/mL.
[2]Samples would be diluted 4× with the sample diluent indicated in Table 16.

TABLE 19

Assay Results of Plasma at Different Levels of Dilution[1]

Ratio of Observed to Expected Concentration for Each of NF-L, Tau, GFAP, and UCH L1 Based on 4× Dilution

| Dilution[2] | Example 19 | Comparative Example E |
|---|---|---|
| 4× | 100% | 100% |
| 8× | 100-115% | 120-150% |
| 16× | 105-130% | 150-180% |
| 32× | 110-140% | 190-220% |
| 64× | 120-150% | 210-240% |

[1]Spike recovery is the ratio of observed concentration following subtraction of endogenous NF-L to expected concentration expressed as a percentage.

Prophetic Example 20

Multiplex assay calibration experiments. A series of calibration solutions with and without added non-analyte proteins would be assayed for the following biomarkers: NF-L, GFAP, UCH L1, and Tau. The results reported in Table 20 would be attained.

TABLE 20

Assay[1] Calibration Results in Example 20

| Calibration Solution[2] | | | | Measured concentration | | | |
|---|---|---|---|---|---|---|---|
| NF-L | GFAP | UCH L1 | Tau | NF-L | GFAP | UCH L1 | Tau |
| 0 | 0 | 0 | 0 | LOB | LOB | LOB | LOB |
| 0.5 | 1 | 10 | 0.1 | >LOQ | >LOQ | >LOQ | >LOQ |
| 1.5 | 3 | 30 | 0.3 | >LOQ | >LOQ | >LOQ | >LOQ |
| 5 | 10 | 100 | 1 | >LOQ | >LOQ | >LOQ | >LOQ |
| 15 | 30 | 300 | 3 | >LOQ | >LOQ | >LOQ | >LOQ |
| 50 | 100 | 1000 | 10 | >LOQ | >LOQ | >LOQ | >LOQ |
| 150 | 300 | 3000 | 30 | >LOQ | >LOQ | >LOQ | >LOQ |
| 450 | 900 | 9000 | 90 | >LOQ | >LOQ | >LOQ | >LOQ |

[1]Separate portions of carboxy-terminated, 2.7 micron-diameter magnetic beads (Agilent Technologies) would be prepared by conjugating with anti-NF-L mouse monoclonal antibodies, anti-GFAP mouse monoclonal antibodies, anti-UCH L1 mouse monoclonal antibodies, anti-Tau protein mouse monoclonal antibodies, anti-Amyloid beta 42/40 mouse monoclonal antibodies, anti-S100B mouse monoclonal antibodies, and anti-NSE mouse monoclonal antibodies (via carbodiimide coupling), blocking, and mixing the magnetic beads together. The mixed antibody-coated beads would be diluted in a buffer solution. 100 mcL calibration solution would be mixed with a volume of the bead solution to provide $10^9$ beads and incubated, the beads washed post-incubation, resuspended and incubated with biotinylated detector reagent, washed, resuspended and incubated with streptavidin-β-galactosidase, loaded into microwell arrays, and NF-L, GFAP, UCH L1, Tau, A beta 40, S100B, and NSE quantified using a Quanterix Simoa HD-1 Analyzer (Quanterix ™, Lexington, Massachusetts).
[2]Calibration solution at indicated concentrations of NF-L, GFAP, UCH L1, and Tau (pg/mL), 50 mM phosphate, 137 mM NaCl, 2.7 mM KCl, 2% BSA, 0.1% 10 G Surfactant, 10 mcg/mL TRU block ™, 0.05% ProClin ™ 300, and 5 mM EDTA.

Calibration curves for the Examples would be obtained to express the biomarker concentrations (pg/mL) as a function of AEB by third-order polynomial fitted to the AEB data.

Prophetic Examples 21-26

Analysis of plasma samples from patients suspected of traumatic brain injury. A series of multiplex digital assays would be conducted on samples obtained from venous blood and AEB's obtained using a Quanterix Simoa HD-1 Analyzer (Quanterix™, Lexington, Massachusetts). The results reported in Table 21 would be obtained.

TABLE 21

Biomarker Assay Results[1-2]

| Prophetic Example | Donor | Sample Timing | NF-L | GFAP | UCH L1 | Tau |
|---|---|---|---|---|---|---|
| Example 21 | Suspected of mild traumatic brain injury | Within 12 hours of event | >LOQ | >LOQ | >LOQ | >LOQ |
| Example 22 | | 7 days post event | >LOQ | >LOQ | >LOQ | >LOQ |
| Example 23 | | 14 days post event | >LOQ | >LOQ | >LOQ | >LOQ |
| Example 24 | Suspected of traumatic brain injury | Within 12 hours of event | >LOQ | >LOQ | >LOQ | >LOQ |
| Example 25 | | 7 days post event | >LOQ | >LOQ | >LOQ | >LOQ |
| Example 26 | | 14 days post event | >LOQ | >LOQ | >LOQ | >LOQ |

[1]Plasma obtained from venous blood samples obtained at the indicated timing would be diluted in sample diluent and assayed. The sample diluent would comprise 50 mM phosphate, 137 mM NaCl, 2.7 mM KCl, 0.02% BSA, 1 mM $MgCl_2$, 0.06% dextrose, 0.01% BgG, 5 mM urea, 0.5% Triton™ X-100, 10 mcg/mL TRU block™, 50 mcg/mL Superchemiblock™, and 0.05% ProClin™ 300.
[2]Biomarker concentrations (pg/mL) would be obtained using the calibration curve obtained for Example 20.

Example 27

Assay analysis of samples diluted with sample diluent containing added IgG. A series of digital assay experiments would performed on samples diluted with added human IgG, mouse IgG or bovine IgG. Diluent compositions are shown in Table 22. The results shown in Table 23 would be obtained.

TABLE 22

Diluent Compositions in Example 27

| | |
|---|---|
| Example 27 | 50 mM Phosphate, 137 mM NaCl, 2.7 mM KCl, 0.02% BSA, 1 mM $MgCl_2$, 0.06% dextrose, 0.01% BgG, 5 mM urea, 0.5% Triton™ X-100, 10 mcg/mL TRU block™, 50 mcg/mL Superchemiblock™, 5 mg/mL human IgG, and 0.05% ProClin 300™ at pH 7.4. |
| Comparative Example F | 50 mM Phosphate, 137 mM NaCl, 2.7 mM KCl, 0.02% BSA, 1 mM $MgCl_2$, 0.06% Dextrose, 0.01% BgG, 5 mM Urea, 0.5% Triton X-100, 10 mcg/mL TRU block™, 50 mcg/mL Superchemiblock™, 5 mg/mL mouse IgG, and 0.05% ProClin 300 at pH 7.4 |
| Comparative Example G | 50 mM Phosphate, 137 mM NaCl, 2.7 mM KCl, 0.02% BSA, 1 mM $MgCl_2$, 0.06% Dextrose, 0.01% BgG, 5 mM Urea, 0.5% Triton X-100, 10 mcg/mL TRU block™, 50 mcg/mL Superchemiblock™, 5 mg/mL bovine IgG, and 0.05% ProClin 300 at pH 7.4 |

TABLE 23

Assay Results for Spiked Samples in Example 27[1]

Spike Recovery for Each of NF-L, Tau, GFAP, and UCH L1

| Matrix[2] | Example 27 | Each of Comparative Examples F and G |
|---|---|---|
| Plasma | 80-120% | <70% |
| Serum | 80-120% | <70% |
| Serum | 80-120% | <70% |

[1]Spike recovery is the ratio of observed concentration following subtraction of endogenous NF-L to expected concentration expressed as a percentage.
[2]Samples would be diluted 4x with the sample diluent indicated in Table 22.

All publications and patent applications mentioned in this specification are herein incorporated by reference to the same extent as if each individual publication or patent application was specifically and individually indicated to be incorporated by reference.

While preferred embodiments of the present invention have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A kit, comprising:
    i) a plurality of capture agents comprising:
        a) a first capture agent comprising a first antibody capable of specifically binding tau protein (Tau); and
        b) a second capture agent comprising a second antibody capable of specifically binding neurofilament light chain (NF-L);
    ii) a plurality of detection agents comprising:
        a) a first detection agent comprising a first antibody capable of specifically binding the Tau; and
        b) a second detection agent comprising a second antibody capable of specifically binding the NF-L;
    iii) a sample diluent comprising human IgG at a concentration of between 1 mg/mL and 10 mg/mL; and
    iv) a plurality of calibration solutions comprising a plurality of predetermined concentrations of the Tau and the NF-L.

2. The kit of claim 1, wherein the sample diluent further comprises at least 15 mcg/mL of at least one heterophile blocking agent exclusive of the human IgG.

3. The kit of claim 1, wherein the plurality of calibration solutions comprises a set of pre-diluted solutions for use in determining a calibration standard curve.

4. The kit of claim 3, wherein the kit further comprises a third capture agent, said third capture agent comprising a third antibody capable of specifically binding glial fibrillary acidic protein (GFAP).

5. The kit of claim 4, wherein the kit further comprises a fourth capture agent, said fourth capture agent comprising a fourth antibody capable of specifically binding ubiquitin carboxyl-terminal hydrolase L1 (UCH L1).

6. The kit of claim 3, wherein the kit further comprises a third capture agent, said third capture agent comprising a third antibody capable of specifically binding ubiquitin carboxyl-terminal hydrolase L1 (UCH L1).

7. The kit of claim 3, wherein the plurality of calibration solutions is between 6 and 10 calibration solutions, and further comprises a Tau-free and a NF-L-free control solution.

8. The kit of claim 7, wherein the plurality of calibration solutions comprises:
    i) a first calibration solution comprising Tau at a concentration of at least 0.1 pg/mL and NF-L at a concentration of at least 0.5 pg/mL;
    ii) a second calibration solution comprising Tau at a concentration of at least 90 pg/mL and NF-L at a concentration of at least 450 pg/mL; and
    iii) at least a third calibration solution comprising Tau at a concentration of between 2 pg/mL and 90 pg/mL and NF-L at a concentration of between 10 pg/mL and 450 pg/mL.

9. The kit of claim 5, wherein the plurality of calibration solutions is between 6 and 10 calibration solutions, and further comprises a Tau-free, a NF-L-free, a GFAP-free, and a UCH L1-free control solution.

10. The kit of claim 9, wherein the plurality of calibration solutions comprises:
    i) a first calibration solution comprising Tau at a concentration of at least 0.1 pg/mL, NF-L at a concentration of at least 0.5 pg/mL, GFAP at a concentration of at least 1 pg/mL, and UCH L1 at a concentration of at least 10 pg/mL;
    ii) a second calibration solution comprising Tau at a concentration of at least 90 pg/mL, NF-L at a concentration of at least 450 pg/mL, GFAP at a concentration of at least 900 pg/mL, and UCH L1 at a concentration of at least 9000 pg/mL; and
    iii) at least a third calibration solution comprising Tau at a concentration of between 2 pg/mL and 90 pg/mL, NF-L at a concentration of between 10 pg/mL and 450 pg/mL, GFAP at a concentration of between 20 pg/mL and 900 pg/mL, and UCH L1 at a concentration of between 200 pg/mL and 9000 pg/mL.

11. The kit of claim 1, wherein the first antibody capable of specifically binding Tau is attached to a first paramagnetic bead; and the second antibody capable of specifically binding NF-L is attached to a second paramagnetic bead.

12. The kit of claim 11, wherein at least some a portion of the Tau and the NF-L are immobilized with respect to the first capture agent and the second capture agent, respectively.

13. The kit of claim 11, wherein a portion of the first paramagnetic beads and the second paramagnetic beads do not form a complex with the Tau and the NF-L, respectively.

14. The kit of claim 1, wherein the isoform of Tau protein is a phosphorylated Tau protein.

15. The kit of claim 14, wherein the phosphorylated Tau protein is phosphorylated Tau 181 (p-Tau-181) or phosphorylated Tau 231 (p-Tau-231).

16. The kit of claim 14, wherein the isoform of Tau protein is Tau 23, Tau 24, Tau 37, Tau 34, Tau 39, or Tau 40.

* * * * *

UNITED STATES PATENT AND TRADEMARK OFFICE
CERTIFICATE OF CORRECTION

PATENT NO. : 12,130,294 B2
APPLICATION NO. : 17/046119
DATED : October 29, 2024
INVENTOR(S) : Edward Kevin Hrusovsky et al.

Page 1 of 1

It is certified that error appears in the above-identified patent and that said Letters Patent is hereby corrected as shown below:

In the Claims

Claim 12:
Column 128, Line 39, "wherein at least some a portion" should read --wherein a portion--.

Signed and Sealed this
Twenty-first Day of January, 2025

Coke Morgan Stewart
*Acting Director of the United States Patent and Trademark Office*